US012698309B2

(12) United States Patent
Garcia Montojo et al.

(10) Patent No.: US 12,698,309 B2
(45) Date of Patent: Aug. 4, 2026

(54) HERV-K (HML-2) Env ANALOG FUSION PROTEINS FOR ANTIGEN SPECIFIC IMMUNOTHERAPY AND METHODS OF USE

(71) Applicant: TWILIGHT BIOSCIENCE, INC., Topsfield, MA (US)

(72) Inventors: Marta Garcia Montojo, Silver Spring, MD (US); Ajay Verma, Rehoboth, MA (US); Thomas M. Lancaster, Wenham, MA (US)

(73) Assignee: TWILIGHT BIOSCIENCE, INC., Topsfield, MA (US)

( * ) Notice: Subject to any disclaimer, the term of this patent is extended or adjusted under 35 U.S.C. 154(b) by 0 days.

(21) Appl. No.: 19/287,448

(22) Filed: Jul. 31, 2025

(65) Prior Publication Data

US 2026/0035414 A1     Feb. 5, 2026

Related U.S. Application Data

(63) Continuation of application No. PCT/US2025/040120, filed on Jul. 31, 2025.

(60) Provisional application No. 63/678,337, filed on Aug. 1, 2024, provisional application No. 63/678,293, filed on Aug. 1, 2024.

(51) Int. Cl.
| | |
|---|---|
| *C07K 14/005* | (2006.01) |
| *A61K 9/00* | (2006.01) |
| *A61K 38/00* | (2006.01) |
| *A61K 39/00* | (2006.01) |
| *A61P 37/04* | (2006.01) |

(52) U.S. Cl.
CPC .......... *C07K 14/005* (2013.01); *A61K 9/0019* (2013.01); *A61P 37/04* (2018.01); *A61K 38/00* (2013.01); *A61K 39/00* (2013.01); *C07K 2319/30* (2013.01); *C12N 2740/12022* (2013.01); *C12N 2740/12034* (2013.01)

(58) Field of Classification Search
CPC C07K 14/005; C07K 2319/30; A61K 9/0019; A61K 38/00; A61K 39/00; A61P 37/04; C12N 2740/12022; C12N 2740/12034
See application file for complete search history.

(56) References Cited

U.S. PATENT DOCUMENTS

| | | | | |
|---|---|---|---|---|
| 2009/0252729 | A1* | 10/2009 | Farrington | A61P 35/00 |
| | | | | 435/69.6 |
| 2013/0139274 | A1* | 5/2013 | Sanders | C07K 14/535 |
| | | | | 435/235.1 |
| 2020/0079831 | A1* | 3/2020 | Schreiber | A61K 47/60 |
| 2020/0140527 | A1* | 5/2020 | Kobie | A61K 39/42 |

FOREIGN PATENT DOCUMENTS

| | | |
|---|---|---|
| WO | 2003106634 | 12/2003 |
| WO | 2019043127 | 3/2019 |
| WO | 2021207599 | 10/2021 |
| WO | 2023118508 | 6/2023 |

OTHER PUBLICATIONS

Shubin Z, Li W, Poonia B, Ferrari G, LaBranche C, Montefiori D, Zhu X, Pauza CD. An HIV Envelope gp 120-Fc Fusion Protein Elicits Effector Antibody Responses in Rhesus Macaques. Clin Vaccine Immunol. Jun. 5, 2017;24(6):e00028-17. (Year: 2017).*
Zhang MY, Wang Y, Mankowski MK, Ptak RG, Dimitrov DS. Cross-reactive HIV-1-neutralizing activity of serum IgG from a rabbit immunized with gp41 fused to IgG1 Fc: possible role of the prolonged half-life of the immunogen. Vaccine. Feb. 5, 2009;27(6):857-63. Epub Dec. 10, 2008. (Year: 2008).*
Garcia-Montojo M, Doucet-O'Hare T, Henderson L, Nath A. Human endogenous retrovirus-K (HML-2): a comprehensive review. Crit Rev Microbiol. Nov. 2018;44(6):715-738. Epub Oct. 14, 2018. (Year: 2018).*
International Search Report and Written Opinion in corresponding PCT/US2025/40120, dated Nov. 11, 2025.
Kraus, et al., "Vaccination directed against the human endogenous retrovirus-k envelope protein inhibits tumor growth in a murine model system", PLOS ONE, Aug. 30, 2013, 8(8), e72756.
Hosseiniporgham, et al., "Anti-HERV-K Drugs and Vaccines, Possible Therapies against Tumors", Vaccines, Mar. 28, 2023, 11(4), p. 751.
Lu Dai, et al., "Development of human endogenous retrovirus type K-related treatments for human diseases", J of Med Virology, Mar. 18, 2024, 96(3), 6 pages.
Xue Bei, et al., "Human endogenous retrovirus K (HML-2) in health and disease", Frontiers in Micro, Jul. 17, 2020, 11 (1690), 13 pages.
Garcia-Montojo, et al., "Human endogenous retrovirus-K (HML-2): A comprehensive review", Crit Rev Microbiol., Nov. 2018, 44(6), 715-735.
Czajkowsky, et al., "Fc-fusion proteins: new developments and future perspectives", EMBO Mol Med., Oct. 1, 2012, 4(10), 1015-1028.

(Continued)

*Primary Examiner* — Rachel B Gill
(74) *Attorney, Agent, or Firm* — Hovey Williams LLP; Crissa A. Cook

(57) ABSTRACT
Recombinantly manufactured fusion proteins comprising a HERV-K (HML-2) Env protein fragment or an analog thereof linked to a human Fc fragment are described. The fusion proteins may be administered to patients having a disease or a disorder with the intention of mitigating and/or reducing the duration of symptoms associated with the condition or disease (for example but not limited to muscular weakness, paralysis and respiratory failure), and/or preventing symptoms associated with the condition or disease, for example, by preventing motor neuron degeneration and cell death in amyotrophic lateral sclerosis (ALS) patients associated with the condition or disease. Improvement after treatment may be manifested as a decrease or elimination of such symptoms, for example, by a decrease or elimination of symptoms associated with ALS, and/or by a decrease in the duration of such symptoms.

20 Claims, 52 Drawing Sheets
Specification includes a Sequence Listing.

(56) References Cited

OTHER PUBLICATIONS

Richel, et al., "Antigen-dependent modulation of immune responses to antigen-Fc fusion proteins by Fc-effector functions", Frontiers in Immun., Oct. 5, 2023, 14, 16 pages.

Garcia-Montojo, et al., "Development of an Fc-fusion HERV-K vaccine to treat amyotrophic lateral sclerosis and frontotemporal dementia", Neurotherapeutics: The J of Amer Soc Expir Neuro., Jul. 1, 2025, 22(4), p. e00657 (abstract attached).

* cited by examiner

SEQ ID NO: 4    MNPSEMQRKAPPRRRRHRNRAPLTHKMNKMVTSEEQMKLPSTKKAEPPTWAQIKKLTQLA    60
SEQ ID NO: 5    ------------------------------------------------------------    0
SEQ ID NO: 6    ------------------------------------------------------------    0
SEQ ID NO: 7    ------------------------------------------------------------    0
SEQ ID NO: 8    MNPSEMQRKAPPRRRRHRNRAPLTHKMNKMVTSEEQMKLPSTKKAEPPTWAQIKKLTQLA    60

SEQ ID NO: 4    TKYLENTKVTQTPESMLLAALMIVSMVVS-------------------------------    89
SEQ ID NO: 5    -------------------------LPMPAGAAANYTYWAYVPFPPLIRAVTWMD    31
SEQ ID NO: 6    ------------------------------------------------------------    0
SEQ ID NO: 7    ------------------------------------------------------------    0
SEQ ID NO: 8    TKYLENTKVTQTPESMLLAALMIVSMVVSLPMPAGAAANYTYWAYVPFPPLIRAVTWMD    120

SEQ ID NO: 4    ------------------------------------------------------------    89
SEQ ID NO: 5    NPIEVYVNDSVWVPGPIDDRCPAKPEEEGMMINISIGYRYPPICLGRAPGCLMPAVQNWL    91
SEQ ID NO: 6    ------------------------------------------------------------    0
SEQ ID NO: 7    ------------------------------------------------------------    0
SEQ ID NO: 8    NPIEVYVNDSVWVPGPIDDRCPAKPEEEGMMINISIGYRYPPICLGRAPGCLMPAVQNWL    180

FIG. 3A

```
SEQ ID NO: 4   ----------------------------------------------------------   89
SEQ ID NO: 5   VEVPTVSPISRFTYHMVSGMSLRPRVNYLQDFSYQRSLKFRPKGKPCPKEIPKESKNTEV  151
SEQ ID NO: 6   ----------------------------------------------------------   0
SEQ ID NO: 7   ----------------------------------------------------------   0
SEQ ID NO: 8   VEVPTVSPISRFTYHMVSGMSLRPRVNYLQDFSYQRSLKFRPKGKPCPKEIPKESKNTEV  240

SEQ ID NO: 4   ----------------------------------------------------------   89
SEQ ID NO: 5   LVWEECVANSAVILQNNEFGTIIDWAPRGQFYHNCSGQTQSCPSAQVSPAVDSDLTESLD  211
SEQ ID NO: 6   ----------------------------------------------------------   0
SEQ ID NO: 7   ----------------------------------------------------------   0
SEQ ID NO: 8   LVWEECVANSAVILQNNEFGTIIDWAPRGQFYHNCSGQTQSCPSAQVSPAVDSDLTESLD  300

SEQ ID NO: 4   ----------------------------------------------------------   89
SEQ ID NO: 5   KHKHKKLQSFYPWEWGEKGISTPRPKIISPVSGPEHPELWRLTVASHHIRIWSGNQTLET  271
SEQ ID NO: 6   ----------------------------------------------------------   0
SEQ ID NO: 7   ----------------------------------------------------------   0
SEQ ID NO: 8   KHKHKKLQSFYPWEWGEKGISTPRPKIISPVSGPEHPELWRLTVASHHIRIWSGNQTLET  360
```

FIG. 3B

SEQ ID NO: 4 ------------------------------------------------- 89

SEQ ID NO: 5 MSLEHRFQLQCDWNTSDFCITPQIYNESEHHWDMVRRHLQGREDNLTLDISKLKEQIFEA 511

SEQ ID NO: 6 ------------------------------------------------- 0

SEQ ID NO: 7 ------------------------------------------------- 0

SEQ ID NO: 8 MSLEHRFQLQCDWNTSDFCITPQIYNESEHHWDMVRRHLQGREDNLTLDISKLKEQIFEA 600

SEQ ID NO: 4 ------------------------------------------------- 89

SEQ ID NO: 5 SKAHLNLVPGTEAIAGVADGLANLNPVTWVKT----------------------------- 543

SEQ ID NO: 6 ------------------------IGSTTIINLILILVCLFCLLL--------------- 21

SEQ ID NO: 7 --------------------------------------------VCRCTQQ 7

SEQ ID NO: 8 SKAHLNLVPGTEAIAGVADGLANLNPVTWVKTIGSTTIINLILILVCLFCLLLVCRCTQQ 660

SEQ ID NO: 4 ------------------------------------------------- 89

SEQ ID NO: 5 ------------------------------------------------- 543

SEQ ID NO: 6 ------------------------------------------------- 21

SEQ ID NO: 7 LRRDSDHRERAMMTMAVLSKRKGGNVGKSKRDQIVTVSV 46

SEQ ID NO: 8 LRRDSDHRERAMMTMAVLSKRKGGNVGKSKRDQIVTVSV 699

FIG. 3D

```
SEQ ID NO: 8   MNPSEMQRKAPPRRRRHRNRAPLTHKMNKMVTSEEQMKLPSTKKAEPPTWAQLKKLTQLA   60
SEQ ID NO: 9   MNPSEMQRKAPPRRRRHRNRAPLTHKMNKMVTSEEQMKLPSTKKAEPPTWAQLKKLTQLA   60
SEQ ID NO: 10  MNPSEMQRKAPPRRRRHRNRAPLTHKMNKMVTSEEQMKLPSTKKAEPPTWAQLKKLTQLA   60
SEQ ID NO: 11  MNPSEMQRKAPPRRRRHRNRAPLTHKMNKMVTSEEQMKLPSTKKAEPPTWAQLKKLTQLA   60
SEQ ID NO: 12  MNPSEMQRKAPPRRRRHRNRAPLTHKMNKMVTSEEQMKLPSTKKAEPPTWAQLKKLTQLA   60
SEQ ID NO: 13  MHPSEMQRKAPPRRRRHRNRAPLTHKMNKMVTSEEQMKLPSTKKAEPPTWAQLKKLTQLA   59
SEQ ID NO: 14  MNPSEMQRKAPPRRRRHRNRAPLTHKMNKMVTS-EQMKLPSTKKAEPPTWAQLKKLTQLA   60
SEQ ID NO: 15  MNPSEMQRKAPPRRRRHRNRAPLTHKMNKMVTSEEQMKLPSTKKAEPPTWAQLKKLTQLA   60
SEQ ID NO: 16  ------------------------------------------------------------    0

SEQ ID NO: 8   TKYLENTKVTQTPESMLLAALMIVSMVVSLPMPAGAAAANYTYWAYVPFPPLIRAVTWMD  120
SEQ ID NO: 9   TKYLENTKVTQTPESMLLAALMIVSMVVSLPMPAGAAAANYTNWAYVPFPPLIRAVTWMD  120
SEQ ID NO: 10  TKYLENTKVTQTPESMLLAALMIVSMVVSLPMPAGAAAANYTNWAYVPFPPLIRAVTWMD  120
SEQ ID NO: 11  TKYLENTKVTQTPESMLLAALMIVSMVVSLPMPAGAAAANYTNWAYVPFPPLIRAVTWMD  120
SEQ ID NO: 12  TKYLENTKVTQTPESMLLAALMIVSMVVSLPMPAGAAVANYTNWAYVPFPPLIRAVTWMD  120
SEQ ID NO: 13  TKYLENTKVTQTPESMLLAALMIVSMVVSLPMPAGAAAANYTNWAYVPFPPLIRAVTWMD  119
SEQ ID NO: 14  TKYLENTKVTQTPESMLLAALMIVSMVVSLPMPAGAAAANYTNWAYVPFPPLIRAVTWMD  120
SEQ ID NO: 15  TKYLENTKVTQTPESMLLAALMIVSMVVSLPMPAGAAAANYTYWAYVPFPPLIRAVTWMD  120
SEQ ID NO: 16  -----------------------------------------------------MVTPVTWMD    9
                                                                    ::    *****
```

FIG. 4A

```
SEQ ID NO: 8   NPIEVYVNDSVWVPGPIDDRCPAKPEEEGMMINISIGYRYPPICLGRAPGCLMPAVQNWL   180
SEQ ID NO: 9   NPIEVYVNDSVWVPGPIDDRCPAKPEEEGMMINISIGYRYP-ICLGRAPGCLMPAVQNWL   179
SEQ ID NO: 10  NPTEVYVNDSVWVPGPIDDRCPAKPEEEGMMINISIGYHYPPICLGRAPGCLMPAVQNWL   180
SEQ ID NO: 11  NPIEVYVNDSVWVPGPIDDRCPAKPEEEGMMINISIGYRYPPICLGRAPGCLMPAVQNWL   180
SEQ ID NO: 12  NPIEVYVNDSVWVPGPIDDRCPAKPEEEGMMINISIGYRYPPICLGTAPGCLMPAVQNWL   180
SEQ ID NO: 13  NPIEVYVNDSVWVHGPIDDRCPAKPEEEGMMINISIGYHYPPICLGRAPGCLMPAVQNWL   179
SEQ ID NO: 14  NPIEIYVNDSVWVPGPTDDCCPAKPEEEGMMINISIGYRYPPICLGRAPGCLMPAVQNWL   180
SEQ ID NO: 15  NPIEVYVNDSVWVPGPTDDHCPAKPEEEGMMINISIGYRYPPICLGRAPGCLMPAVQNWL   180
SEQ ID NO: 16  NPIEVYVNDSVWVPGPTDDRCPAKPEEEGMMINISIGYHYPPICLGRAPGCLMPAVQNWL    69
               * ** *:***** ** ** *********************:** ****  *  *

SEQ ID NO: 8   VEVPTVSPISRFTYHMVSGMSLRPRVNYLQDFSYQRSLKFRPKGKPCPKEIPKESKNTEV   240
SEQ ID NO: 9   VEVPIVSPICRFTYHMVSGMSLRPRVNYLQDFSYQRSLKFRPKGKPCPKEIPKESKNTEV   239
SEQ ID NO: 10  VEVPTVSPICRFTYHMVSGMSLRPRVNYLQDFSYQRSLKFRPKGKPCPKEIPKESKNTEV   240
SEQ ID NO: 11  VEVPTVSPISRFTYHMVSGMSLRPRVNYLQDFSYQRSLKFRPKGKPCPKEIPKESKNTEV   240
SEQ ID NO: 12  VEVPIVSPISRFTYHMVSGMSLRPRVNYLQDFSYQRSLKFRPKGKPCPKEIPKESKNTEV   240
SEQ ID NO: 13  VEVPTVSPISRFTYNMVSGMSLRPRVNYLQDFSYQRSLKFRPKGKPCPKEIPKESKNTEV   239
SEQ ID NO: 14  VEVPTVSPISRFTYHMVSGMSLRPRVNYLQDFSYQRSLKFRPKGKPCPKEIPKESKNTEV   240
SEQ ID NO: 15  VEVPTVSPISRFTYHMVSGMSLRPRVNYLQDFSYQRSFKFRPKGKPCPKEIPKESKNTEV   240
SEQ ID NO: 16  VEVPTVSPNSRFTYHMVSGMSLRPRVNCLQDFSYQRSLKFRPKGKTCPKEIPKGSKNTEV   129
               **** *** . :****.:********** *********:****** ****** *******
```

FIG. 4B

```
SEQ ID NO: 8   LVWEECVANSAVILQNNEFGTIIDWAPRGQFYHNCSGQTQSCPSAQVSPAVDSDLTESLD   300
SEQ ID NO: 9   LVWEECVANSAVILQNNEFGTIIDWTPQGQFYHNCSGQTQSCPSAQVSPAVDSDLTESLD   299
SEQ ID NO: 10  LVWEECVANSAVILQNNEFGTIIDWAPRGQFYHNCSGQTQSCPSAQVSPAVDSDLTESLD   300
SEQ ID NO: 11  LVWEECVANSAVILQNNEFGTIIDWAPRGQFYHNCSGQTQSCPSAQVSPAVDSDLTESLD   300
SEQ ID NO: 12  LVWEECVANSAVILQNNEFGTIIDWAPRGQFYHNCSGQTQSCPSAQVSPAVDSDLTESLD   300
SEQ ID NO: 13  LVWEECVANSVVILQNNEFGTIIDWAPRGQFYHNCSGQTQSCPSAQVSPAVDSDLTESLD   299
SEQ ID NO: 14  LVWEECVANSAVILQNNEFGTLIDWAPRGQFYHNCSGQTQSCPSAQVSPAVDSDLTESLD   300
SEQ ID NO: 15  LVWEECVANSAVILQNNEFGTIIDWAPRGQFYHNCSGQTQSCPSAQVSPAVDSDLTESLD   300
SEQ ID NO: 16  LVWEECVANSVVILQNNEFGTIIDWAPRGQFYHNCSGQTQSCPSAQVSPAVDSDLTESLD   189
               ***********.*******:***.:*** :.***:.************************

SEQ ID NO: 8   KHKHKKLQSFYPWEWGEKGISTPRPKIISPVSGPEHPELWRLTVASHHIRIWSGNQTLET   360
SEQ ID NO: 9   KHKHKKLQSFYPWEWGEKGISTPRPKIISPVSGPEHPELWRLTVASHHIRIWSGNQTLET   359
SEQ ID NO: 10  KHKHKKLQSFYPWEWGEKGISTPRPKIVSPVSGPEHPELWRLTVASHHIRIWSGNQTLET   360
SEQ ID NO: 11  KHKHKKLQSFYPWEWGEKRISTPRPKIVSPVSGPEHPELWRLTVASHHIRIWSGNQTLET   360
SEQ ID NO: 12  KHKHKKLQSFYPWEWGEKGISTPRPKIVSPVSGPEHPELWRLTVASHHIRIWSGNQTLET   360
SEQ ID NO: 13  KHKHKKLQSFYPWEWGEKGISTPRPKIISPVSGPEHPELWRLTVASHHIRIWSGNQTLET   359
SEQ ID NO: 14  KHKHKKLQSFYPWEWGEKGISTARPKIISPVSGPEHPELWRLTVASHHIRIWSGNQTLET   360
SEQ ID NO: 15  KHKHKKLQSFYPWEWGEKGISTPRPKIISPVSGPEHPELWRLTVASHHIRIWSGNQTLET   360
SEQ ID NO: 16  KHKHKKLQSFYLWEWEEKGISTPRPKIISPVSGPEHPELWRLTVASHHIRIWSGNQTLET   249
               ***********  *** **** *.***.************************
```

FIG. 4C

```
SEQ ID NO: 8    RDRKPFYTVDLNSSLTVPLQSCVKPPYMLVVGNIVIKPDSQTITCENCRLLTCIDSTFNW    420
SEQ ID NO: 9    RDRKPFYTVDLNSSLTLPLQSCVKPPYMLVVGNIVIKPDSQTITCENCRLLTCIDSTFNW    419
SEQ ID NO: 10   RDRKPFYTIDLNSSLTVPLQSCVKPPYMLVVGNIVIKPDSQTITCENCRLLTCIDSTFNW    420
SEQ ID NO: 11   RDRKPFYTVDLNSSLTLPLQSCVKPPYMLVVGNIVIKPDSQTITCENCRLLTCIDSTFNW    420
SEQ ID NO: 12   RDRKPFYTVDLNSSLTVPLQSCVKPPYMLVVGNIVIKPDSQTITCENCRLLTCIDSTFNW    420
SEQ ID NO: 13   RDRKPFYTVDLNSSLTVPLQSCVKPPYMLVVGNIVIKPDSQTITCENCRLLTCIDSTFNW    419
SEQ ID NO: 14   RDRKPFYTVDLNSSLTVPLQSCVKPPYMLVVGNIVIKPDSQTITCENCRLLTCIDSTFNW    420
SEQ ID NO: 15   RDRKPFYTVDLNSSVTVPLQSCIKPPYMLVVGNIVIKPDSQTITCENCRLLTCIDSTFNW    420
SEQ ID NO: 16   RYRKPFYTIDLNSILTVPLQSCVKPPYMLVVGNIVIKPASQTITCENCRLFTCIDSTFNW    309
                * *******:**** :*:****:****************** ********:*********

SEQ ID NO: 8    QHRILLVRAREGVWIPVSMDRPWEASPSIHILTEVLKGVLNRSKRFIFTLIAVIMGLIAV    480
SEQ ID NO: 9    QHRILLVRAREGVWIPVSMDRPWEASPSIHILTEVLKGVLNRSKRFIFTLIAVIMGLIAV    479
SEQ ID NO: 10   QHRILLVRAREGVWIPVSMDRPWEASPSVHILTEVLKGVLNRSKRFIFTLIAVIMGLIAV    480
SEQ ID NO: 11   QHRILLVRAREGVWIPVSMDRPWEASPSVHILTEVLKGVLNRSKRFIFTLIAVIMGLIAV    480
SEQ ID NO: 12   QHRILLVRAREGVWIPVSMDRPWEASPSIHILTEVLKGVLNRSKRFIFTLIAVIMGLIAV    480
SEQ ID NO: 13   QHRILLVRAREGVWIPVSMDRPWEASPSIHILTEVLKGVLNRSKRFIFTLIAVIMGLIAV    480
SEQ ID NO: 14   QHRILLVRAREGVWIPVSMDRPWEASPSVHILTEVLKGVLNRSKRFIFTLIAVIMGLIAV    479
SEQ ID NO: 15   QHRILLVRAREGVWIPVSMDRPWETSPSIHTLTEVLKGVLNRSKRFIFTLIAVIMGLIAV    480
SEQ ID NO: 16   QHRILLVRAREGMWIPVSTDRPWEASPSIHILTEILKGVLNRSKRFIFTLIAVIMGLIAV    369
                ************:****** *****:***** :**** :*************************
```

FIG. 4D

```
SEQ ID NO: 8    TATAAVAGVALHSSVVQSVNFVNDWQKNSTRLWNSQSSIDQKLANQINDLRQTVIWMGDRL   540
SEQ ID NO: 9    TATAAVAGVALHSSVVQSVNFVNDGQKNSTRLWNSQSSIDQKLANQINDLRQTVIWMGDRL   539
SEQ ID NO: 10   TATAAVAGVALHSSVVQSVNFVNDWQKNSTRLWNSQSSIDQKLANQINDLRQTVIWMGDRL   540
SEQ ID NO: 11   TATAAVAGVALHSSVVQSVNFVNDGQKNSTRLWNSQSSIDQKLANQINDLRQTVIWMGDRL   540
SEQ ID NO: 12   TATGAVAGVALHSSVVQSVNFVNDWQKNSTRLWNSQSSIDQKLANQINDLRQTVIWMGDRL   540
SEQ ID NO: 13   TAMAAVAGVALHSFVVQSVNFVNDWQKNSTRLWNSQSSIDQKLANQINDLRQTVIWMGDRL   539
SEQ ID NO: 14   TATAAVAGVALHSSVVQSVNFVNDWQNNSTRLWNSQSSIDQKLANQINDLRQTVIWMGDRL   540
SEQ ID NO: 15   TATAAVAGVALHSSVVQSVNFVNDWQKNSTRLWNSQSSIDQKLANQINDLRQTVIWMGDRL   540
SEQ ID NO: 16   TATAAVAGVALHSSVVQSVNFVNYWQKNSTRLWNSQSSIDQKLASQINDLRQTVIWMGDRL   429
                ** .******** ********* *:.*********************** *

SEQ ID NO: 8    MSLEHRFQLQCDWNTSDFCITPQIYNESEHHWDMVRRHLQGREDNLTLDISKLKEQIFEA   600
SEQ ID NO: 9    MSLEHRFQLQCDWNTSDFCITPQIYNESEHHWDMVRRHLQGREDNLTLDISKLKEQIFEA   599
SEQ ID NO: 10   MSLEHRFQLQCDWNTSDFCITPQIYNESEHHWDMVRRHLQGREDNLTLDISKLKEQIFEA   600
SEQ ID NO: 11   MSLEHRFQLQCDWNTSDFCITPQIYNDSEHHWDMVRRHLQGREDNLTLDISKLKEQIFEA   600
SEQ ID NO: 12   MSLEHRFQLQCDWNTSDFCITPQIYNESEHHWDMVRRHLQGREDNLTLDISKLKEQIFKA   600
SEQ ID NO: 13   MSLEHRFQLQCDWNTSDFCITPQIYNESEHHWDMVRRHLQGREDNLTLDISKLKEQIFEA   599
SEQ ID NO: 14   MSLEHRFQLQCDWNTSDFCITPQIYNESEHHWDMVRCHLQGREDNLTLDISKLKEQIFEA   600
SEQ ID NO: 15   MSLEHRFQLQCDWNTSDFSITPQIYNESEHHWDMVRRHLQGREDNLTLDISKLKEQIFEA   600
SEQ ID NO: 16   MTLEHHFQLQCDWNTSDFCITPQIYNESEHHWDMVRRHLQGREDNLTLDISKLKEQIFEA   489
                *:***:*********** *********:*********** *************** *
```

FIG. 4E

```
SEQ ID NO: 8   SKAHLNLVPGTEAIAGVADGLANLNPVTWVKTIGSTTIINLILILVCLFCLLLVCRCTQQ   660
SEQ ID NO: 9   SKAHLNLVPGTEAIAGVADGLANLNPVTWVKTIGSTTIINLILILVCLFCLLLVCRCTQQ   659
SEQ ID NO: 10  SKAHLNLVPGTEAIAGVADGLANLNPVTWVKTIGSTTIINLILILVCLFCLLLVCRCTQQ   660
SEQ ID NO: 11  SKAHLNLVPGTEAIAGVADGLANLNPVTWVKTIGSTTIINLILILVCLFCLLLVCRCTQQ   660
SEQ ID NO: 12  SKAHLNLVPGTEAIAGVADGLANLNPVTWVKTIGSTTIINLILILVCLFCLLLVCRCTQQ   660
SEQ ID NO: 13  SKAHLNLVPGTEAIAGVADGLANLNPVTWVKTIGSTTIINLILILVCLFCLLLVCRCTQQ   659
SEQ ID NO: 14  SKAHLNLVPGTEAIAGVADGLANLNTVTWVKTIGSTTIINLILILVCLFCLLLVYRCTQQ   660
SEQ ID NO: 15  SKAHLNLVPGTEAIAGVADGLANLNPVTWVKTIGSTTIINLILILVCLFCLLLVCRCTQQ   660
SEQ ID NO: 16  SKAHLNLVPGTEAIAGVADGLANLNPVTWIKTIRSTMIINLILIVVCLFCLLLVCRCTQQ   549
               **********************.********:.******** *** :*** ** *****

SEQ ID NO: 8   LRRDSDHRERAMMTMAVLSKRKGGNVGKSKRDQIVTVSV   699
SEQ ID NO: 9   LRRDSDHRERAMMTMAVLSKRKGGNVGKSKRDQIVTVSV   698
SEQ ID NO: 10  LRRDSDHRERAMMTMAVLSKRKGGNVGKSKRDQIVTVSV   699
SEQ ID NO: 11  LRRDSDHRERAMMTMAVLSKRKGGNVGKSKRDQIVTVSV   699
SEQ ID NO: 12  L--------------------------------------   661
SEQ ID NO: 13  LRRDSDHRERAMMTMVVLSKRKGGNVGKSKRDQIVTVSV   698
SEQ ID NO: 14  LRRDSDHRERAMMTMVVLSKRKGGNVGKSKRDQIVTVSV   699
SEQ ID NO: 15  LRRDSDHRERAMMTMAVLSKRKGGNVGKSKRDQIVTVSV   699
SEQ ID NO: 16  LRRDSDIENGP----------------------------   560
               *
```

FIG. 4F

SEQ ID NO: 8    LVWEECVANSAVILQNNEEGTIIDWAPRGQFYHNCSGQTQSCPSAQVSPAVDSDLTESLD    300
SEQ ID NO: 18   ----    63
SEQ ID NO: 19   ----    19
SEQ ID NO: 20   ----    22
SEQ ID NO: 21   ----    18
SEQ ID NO: 22   ----    19
SEQ ID NO: 23   ----    17
SEQ ID NO: 24   --------GQFYHNCSGQTQSCPSAQVSPAVDSDLTESLD    32
SEQ ID NO: 25   ----    0

SEQ ID NO: 8    KHKHKKLQSFYPWEWGEKGISTPRPKIISPVSGPEHPELWRLTVASHHIRIWSGNQTLET    360
SEQ ID NO: 18   ----    63
SEQ ID NO: 19   ----    19
SEQ ID NO: 20   ----    22
SEQ ID NO: 21   ----    18
SEQ ID NO: 22   ----    19
SEQ ID NO: 23   ----    17
SEQ ID NO: 24   KHKHKKLQSFYPWEWGEK--------    50
SEQ ID NO: 25   ------------SPVSGPEHPELWRLTVASHHIRIWSGNQTLET    32

FIG. 5C

```
SEQ ID NO: 16   MVTPVTWMDNPIEVYVNDSVWVPGPTDDRCPAKPEEEGMMINISIGYHYPPICLGRAPGC   60
SEQ ID NO: 22   ------------------------VWVPGPTDDRCPAKPEEEG-----------------   19
                                        ********************

SEQ ID NO: 16   LMPAVQNWLVEVPTVSPNSRFTYHMVSGMSLRPRVNCLQDFSYQRSLKFRPKGKTCPKEI  120
SEQ ID NO: 22   ------------------------------------------------------------   19

SEQ ID NO: 16   PKGSKNTEVLVWEECVANSVVILQNNEFGTIIDWAPRGQFYHNCSGQTQSCPSAQVSPAV  180
SEQ ID NO: 22   ------------------------------------------------------------   19

SEQ ID NO: 16   DSDLTESLDKHKHKKLQSFYLWEWEEKGISTPRPKIISPVSGPEHPELWRLTVASHHIRI  240
SEQ ID NO: 22   ------------------------------------------------------------   19

SEQ ID NO: 16   WSGNQTLETRYRKPFYTIDLNSILTVPLQSCVKPPYMLVVGNIVIKPASQTITCENCRLF  300
SEQ ID NO: 22   ------------------------------------------------------------   19
```

FIG. 6A

SEQ ID NO: 16   TCIDSTFNWQHRILLVRAREGMWIPVSTDRPWEASPSIHILTEILKGVLNRSKRFIFTLI   360
SEQ ID NO: 22   ------------------------------------------------------------   19

SEQ ID NO: 16   AVIMGLIAVTATAAVAGVALHSSVQSVNFVNYWQKNSTRLWNSQSSIDQKLASQINDLRQ   420
SEQ ID NO: 22   ------------------------------------------------------------   19

SEQ ID NO: 16   TVIWMGDRLMTLEHHFQLQCDWNTSDFCITPQIYNESEHHWDMVRRHLQGREDNLTLDIS   480
SEQ ID NO: 22   ------------------------------------------------------------   19

SEQ ID NO: 16   KLKEQIFEASKAHLNLVPGTEAIAGVADGLANLNPVTWIKTIRSTMIINLILIVVCLFCL   540
SEQ ID NO: 22   ------------------------------------------------------------   19

SEQ ID NO: 16   LLVCRCTQQLRRDSDIENGP   560
SEQ ID NO: 22   --------------------   19

FIG. 6B

SEQ ID NO: 8      MNPSEMQRKAPPRRRRHRNRAPLTHKMNKMVTSEEQMKLPSTKKAEPPTWAQLKKLTQLA      60
SEQ ID NO: 17     ------------------------------------------------------------      0

SEQ ID NO: 8      TKYLENTKVTQTPESMLLAALMIVSMVVSLPMPAGAAAANYTYWAYVPFPPLIRAVTWMD      120
SEQ ID NO: 17     ------------------------------------------------------------      0

SEQ ID NO: 8      NPIEVYVNDSVWVPGPIDDRCPAKPEEEGMMINISIGYRYPPICLGRAPGCLMPAVQNWL      180
SEQ ID NO: 17     ------------------------------------------------------------      0

SEQ ID NO: 8      VEVPTVSPISRFTYHMVSGMSLRPRVNYLQDFSYQRSLKFRPKGKPCPKEIPKESKNTEV      240
SEQ ID NO: 17     ------------------------------------------------------------      0

FIG. 7A

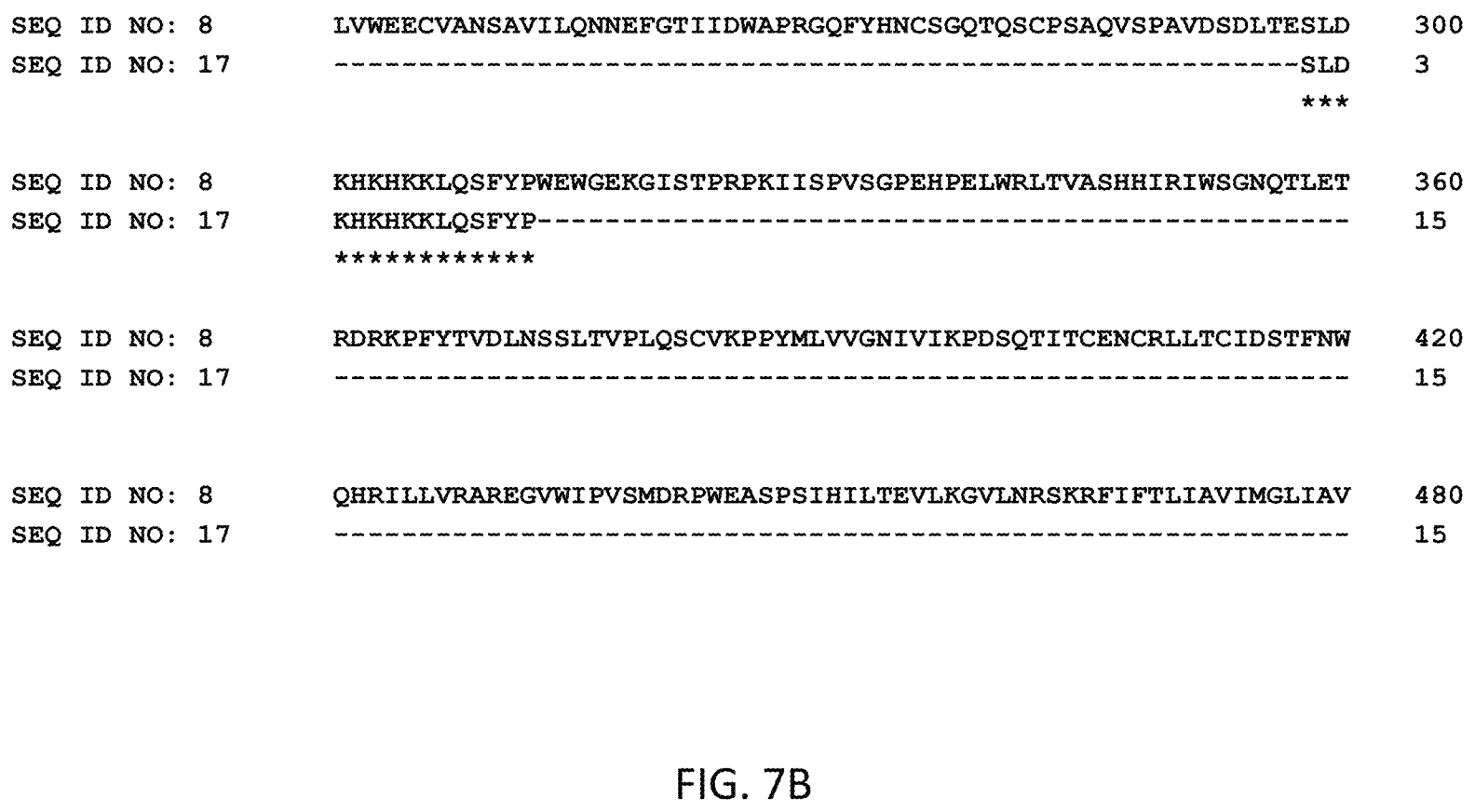

SEQ ID NO: 8    LVWEECVANSAVILQNNEFGTIIDWAPRGQFYHNCSGQTQSCPSAQVSPAVDSDLTESLD    300
SEQ ID NO: 17   ------------------------------------------------------SLD    3
                                                                      ***

SEQ ID NO: 8    KHKHKKLQSFYPWEWGEKGISTPRPKIISPVSGPEHPELWRLTVASHHIRIWSGNQTLET    360
SEQ ID NO: 17   KHKHKKLQSFYP------------------------------------------------    15
                ***********

SEQ ID NO: 8    RDRKPFYTVDLNSSLTVPLQSCVKPPYMLVVGNIVIKPDSQTITCENCRLLTCIDSTFNW    420
SEQ ID NO: 17   ------------------------------------------------------------    15

SEQ ID NO: 8    QHRILLVRAREGVWIPVSMDRPWEASPSIHILTEVLKGVLNRSKRFIFTLIAVIMGLIAV    480
SEQ ID NO: 17   ------------------------------------------------------------    15

FIG. 7B

```
SEQ ID NO:  8    TATAAVAGVALHSSVQSVNFVNDWQKNSTRLWNSQSSIDQKLANQINDLRQTVIWMGDRL   540
SEQ ID NO: 17    -----------------------------------------------------------    15

SEQ ID NO:  8    MSLEHRFQLQCDWNTSDFCITPQIYNESEHHWDMVRRHLQGREDNLTLDISKLKEQIFEA   600
SEQ ID NO: 17    -----------------------------------------------------------    15

SEQ ID NO:  8    SKAHLNLVPGTEAIAGVADGLANLNPVTWVKTIGSTTIINLILILVCLFCLLLVCRCTQQ   660
SEQ ID NO: 17    -----------------------------------------------------------    15

SEQ ID NO:  8    LRRDSDHRERAMMTMAVLSKRKGGNVGKSKRDQIVTVSV   699
SEQ ID NO: 17    ---------------------------------------    15
```

FIG. 7C

```
SEQ ID NO: 19    WAYVPFPPLIRAVTWMDNP    19
SEQ ID NO: 29    --------LIRAVTWMDNP    11
                         ***********
```

FIG. 9

SEQ ID NO: 20     MVSGMSLRPRVNYLQDFSYQRS     22

SEQ ID NO: 30     ------LRPRVNYLQDFSYQRS     16

```
SEQ ID NO: 21   CPAKPEEGMMINISIGY         18
SEQ ID NO: 31   CPAKPEEGM--------         10
                *********
```

FIG. 11

```
SEQ ID NO: 22    VWVPGPTDDRCPAKPEEEG         19
SEQ ID NO: 32    ------DDRCPAKPEEEG          12
                       ***********
```

FIG. 12

```
SEQ ID NO: 25    SPVSGPEHPELWRLTVASHHIRIWSGNQTLETRDRKPFYT    40
SEQ ID NO: 34    SPVSGPEHPE------------------------------    10
SEQ ID NO: 35    ----------------IRIWSGNQTLETRDRKPFYT       20
```

FIG. 13

```
SEQ ID NO: 25   SPVSGPEHPELWRLTVASHHIRIWSGNQTLETRDRKPFYT   40
SEQ ID NO: 36   ------------------------------DRKPFY-     6
SEQ ID NO: 37   ----------------SHHIRIWS-------------     8
```

SEQ ID NO: 24    GQFYHNCSGQTQSCPSAQVSPAVDSDLTESLDKHKHKKLQSFYPWEWGEK    50

SEQ ID NO: 33    --------------------------------------------SFYPWE---    6

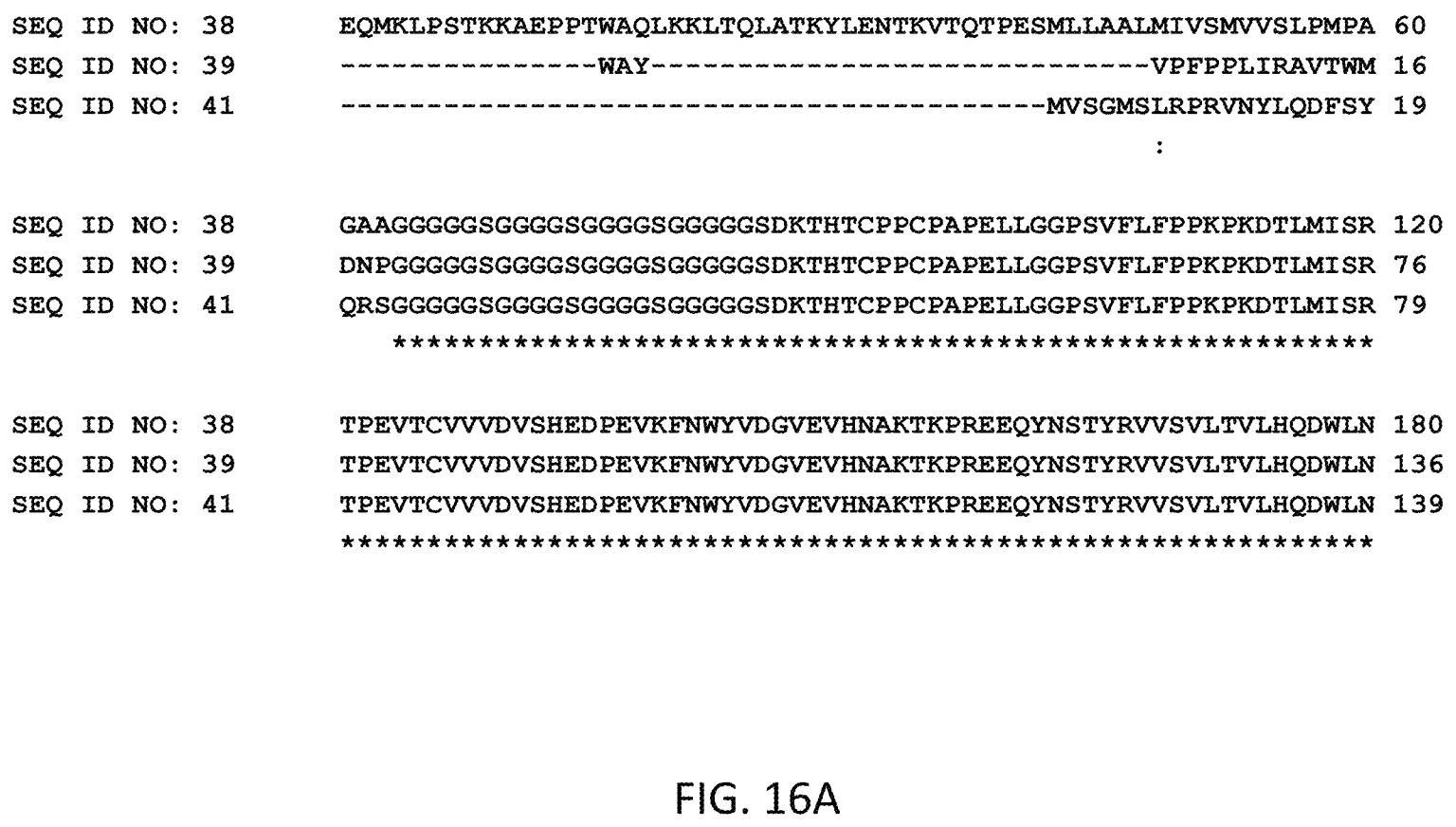

```
SEQ ID NO: 38    EQMKLPSTKKAEPPTWAQLKKLLTQLATKYLENTKVTQTPESMLLAALMIVSMVVSLPMPA  60
SEQ ID NO: 39    ----------WAY-------------------------------------VPFPPLIRAVTWM  16
SEQ ID NO: 41    ----------MVSGMSLRPRVNYLQDFSY  19
                                                                           ..

SEQ ID NO: 38    GAAGGGGGSGGGGSGGGGSGGGGSGGGGSDKTHTCPPCPAPELLGGPSVFLFPPKPKDTLMISR  120
SEQ ID NO: 39    DNPGGGGGSGGGGSGGGGSGGGGSGGGGSDKTHTCPPCPAPELLGGPSVFLFPPKPKDTLMISR  76
SEQ ID NO: 41    QRSGGGGGSGGGGSGGGGSGGGGSGGGGSDKTHTCPPCPAPELLGGPSVFLFPPKPKDTLMISR  79
                    ********************************************************

SEQ ID NO: 38    TPEVTCVVVDVSHEDPEVKFNWYVDGVEVHNAKTKPREEQYNSTYRVVSVLTVLHQDWLN  180
SEQ ID NO: 39    TPEVTCVVVDVSHEDPEVKFNWYVDGVEVHNAKTKPREEQYNSTYRVVSVLTVLHQDWLN  136
SEQ ID NO: 41    TPEVTCVVVDVSHEDPEVKFNWYVDGVEVHNAKTKPREEQYNSTYRVVSVLTVLHQDWLN  139
                    ************************************************************
```

FIG. 16A

```
SEQ ID NO: 38   GKEYKCKVSNKALPAPIEKTISKAKGQPREPQVYTLPPSRDELTKNQVSLTCLVKGFYPS 240
SEQ ID NO: 39   GKEYKCKVSNKALPAPIEKTISKAKGQPREPQVYTLPPSRDELTKNQVSLTCLVKGFYPS 196
SEQ ID NO: 41   GKEYKCKVSNKALPAPIEKTISKAKGQPREPQVYTLPPSRDELTKNQVSLTCLVKGFYPS 199
                ************************************************************

SEQ ID NO: 38   DIAVEWESNGQPENNYKTTPPVLDSDGSFFLYSKLTVDKSRWQQGNVFSCSVMHEALHNH 300
SEQ ID NO: 39   DIAVEWESNGQPENNYKTTPPVLDSDGSFFLYSKLTVDKSRWQQGNVFSCSVMHEALHNH 256
SEQ ID NO: 41   DIAVEWESNGQPENNYKTTPPVLDSDGSFFLYSKLTVDKSRWQQGNVFSCSVMHEALHNH 259
                ************************************************************

SEQ ID NO: 38   YTQKSLSLSPG 311
SEQ ID NO: 39   YTQKSLSLSPG 267
SEQ ID NO: 41   YTQKSLSLSPG 270
                ***********
```

FIG. 16B

```
SEQ ID NO: 40   HEDPEVKFNWYVDGVEVHNAKTKPREEQYNSTYRVVSVLTVLHQDWLNGKEYKCKVSNKA   134
SEQ ID NO: 42   HEDPEVKFNWYVDGVEVHNAKTKPREEQYNSTYRVVSVLTVLHQDWLNGKEYKCKVSNKA   137
SEQ ID NO: 43   HEDPEVKFNWYVDGVEVHNAKTKPREEQYNSTYRVVSVLTVLHQDWLNGKEYKCKVSNKA   133
SEQ ID NO: 44   HEDPEVKFNWYVDGVEVHNAKTKPREEQYNSTYRVVSVLTVLHQDWLNGKEYKCKVSNKA   134
SEQ ID NO: 45   HEDPEVKFNWYVDGVEVHNAKTKPREEQYNSTYRVVSVLTVLHQDWLNGKEYKCKVSNKA   132
SEQ ID NO: 46   HEDPEVKFNWYVDGVEVHNAKTKPREEQYNSTYRVVSVLTVLHQDWLNGKEYKCKVSNKA   165
SEQ ID NO: 47   HEDPEVKFNWYVDGVEVHNAKTKPREEQYNSTYRVVSVLTVLHQDWLNGKEYKCKVSNKA   155
                ************************************************************

SEQ ID NO: 40   LPAPIEKTISKAKGQPREPQVYTLPPSRDELTKNQVSLTCLVKGFYPSDIAVEWESNGQP   194
SEQ ID NO: 42   LPAPIEKTISKAKGQPREPQVYTLPPSRDELTKNQVSLTCLVKGFYPSDIAVEWESNGQP   197
SEQ ID NO: 43   LPAPIEKTISKAKGQPREPQVYTLPPSRDELTKNQVSLTCLVKGFYPSDIAVEWESNGQP   193
SEQ ID NO: 44   LPAPIEKTISKAKGQPREPQVYTLPPSRDELTKNQVSLTCLVKGFYPSDIAVEWESNGQP   194
SEQ ID NO: 45   LPAPIEKTISKAKGQPREPQVYTLPPSRDELTKNQVSLTCLVKGFYPSDIAVEWESNGQP   192
SEQ ID NO: 46   LPAPIEKTISKAKGQPREPQVYTLPPSRDELTKNQVSLTCLVKGFYPSDIAVEWESNGQP   225
SEQ ID NO: 47   LPAPIEKTISKAKGQPREPQVYTLPPSRDELTKNQVSLTCLVKGFYPSDIAVEWESNGQP   215
                ************************************************************
```

FIG. 17B

```
SEQ ID NO: 40    ENNYKTTPPVLDSDGSFFLYSKLTVDKSRWQQGNVFSCSVMHEALHNHYTQKSLSLSPG    253
SEQ ID NO: 42    ENNYKTTPPVLDSDGSFFLYSKLTVDKSRWQQGNVFSCSVMHEALHNHYTQKSLSLSPG    256
SEQ ID NO: 43    ENNYKTTPPVLDSDGSFFLYSKLTVDKSRWQQGNVFSCSVMHEALHNHYTQKSLSLSPG    252
SEQ ID NO: 44    ENNYKTTPPVLDSDGSFFLYSKLTVDKSRWQQGNVFSCSVMHEALHNHYTQKSLSLSPG    253
SEQ ID NO: 45    ENNYKTTPPVLDSDGSFFLYSKLTVDKSRWQQGNVFSCSVMHEALHNHYTQKSLSLSPG    251
SEQ ID NO: 46    ENNYKTTPPVLDSDGSFFLYSKLTVDKSRWQQGNVFSCSVMHEALHNHYTQKSLSLSPG    284
SEQ ID NO: 47    ENNYKTTPPVLDSDGSFFLYSKLTVDKSRWQQGNVFSCSVMHEALHNHYTQKSLSLSPG    274
                 ************************************************************
```

FIG. 17C

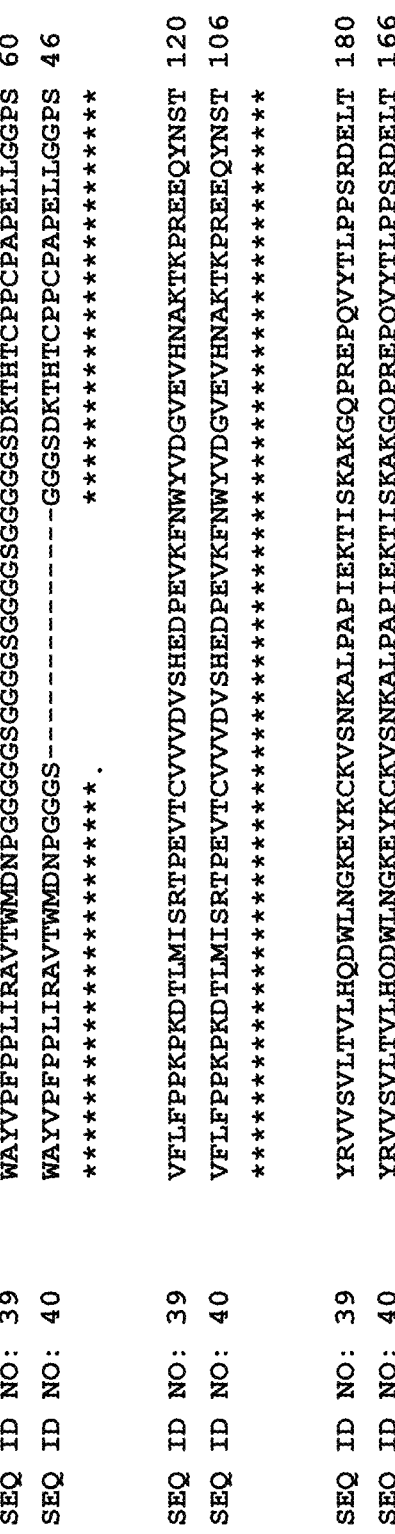

```
SEQ ID NO: 39    WAYVPFPPLIRAVTWMDNPGGGGSGGGGSGGGGSGGGGSDKTHTCPPCPAPELLGGPS    60
SEQ ID NO: 40    WAYVPFPPLIRAVTWMDNPGGGS--------------GGGSDKTHTCPPCPAPELLGGPS    46
                 ********************           ***************************.

SEQ ID NO: 39    VFLFPPKPKDTLMISRTPEVTCVVVDVSHEDPEVKFNWYVDGVEVHNAKTKPREEQYNST   120
SEQ ID NO: 40    VFLFPPKPKDTLMISRTPEVTCVVVDVSHEDPEVKFNWYVDGVEVHNAKTKPREEQYNST   106
                 ************************************************************.

SEQ ID NO: 39    YRVVSVLTVLHQDWLNGKEYKCKVSNKALPAPIEKTISKAKGQPREPQVYTLPPSRDELT   180
SEQ ID NO: 40    YRVVSVLTVLHQDWLNGKEYKCKVSNKALPAPIEKTISKAKGQPREPQVYTLPPSRDELT   166
                 ************************************************************.
```

FIG. 18A

SEQ ID NO: 39    KNQVSLTCLVKGFYPSDIAVEWESNGQPENNYKTTPPVLDSDGSFFLYSKLTVDKSRWQQ 240
SEQ ID NO: 40    KNQVSLTCLVKGFYPSDIAVEWESNGQPENNYKTTPPVLDSDGSFFLYSKLTVDKSRWQQ 226
                 ************************************************************

SEQ ID NO: 39    GNVFSCSVMHEALHNHYTQKSLSLSPG 267
SEQ ID NO: 40    GNVFSCSVMHEALHNHYTQKSLSLSPG 253
                 **************************

FIG. 18B

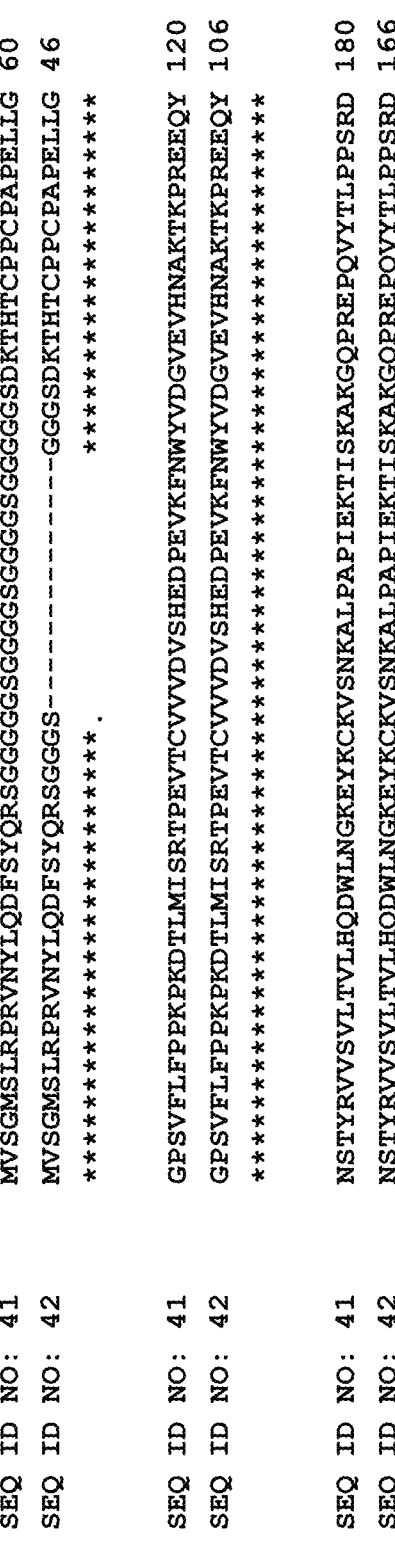

```
SEQ ID NO: 41    MVSGMSLRPRVNYLQDFSYQRSGGGGSGGGGSGGGGSGGGGSDKTHTCPPCPAPELLG   60
SEQ ID NO: 42    MVSGMSLRPRVNYLQDFSYQRSGGGS------------GGGSDKTHTCPPCPAPELLG   46
                 ***********************                ***************

SEQ ID NO: 41    GPSVFLFPPKPKDTLMISRTPEVTCVVVDVSHEDPEVKFNWYVDGVEVHNAKTKPREEQY  120
SEQ ID NO: 42    GPSVFLFPPKPKDTLMISRTPEVTCVVVDVSHEDPEVKFNWYVDGVEVHNAKTKPREEQY  106
                 ***********************************************************

SEQ ID NO: 41    NSTYRVVSVLTVLHQDWLNGKEYKCKVSNKALPAPIEKTISKAKGQPREPQVYTLPPSRD  180
SEQ ID NO: 42    NSTYRVVSVLTVLHQDWLNGKEYKCKVSNKALPAPIEKTISKAKGQPREPQVYTLPPSRD  166
                 ***********************************************************
```

FIG. 19A

SEQ ID NO: 41    ELTKNQVSLTCLVKGFYPSDIAVEWESNGQPENNYKTTPPVLDSDGSFFLYSKLTVDKSR 240

SEQ ID NO: 42    ELTKNQVSLTCLVKGFYPSDIAVEWESNGQPENNYKTTPPVLDSDGSFFLYSKLTVDKSR 226
                 ************************************************************

SEQ ID NO: 41    WQQGNVFSCSVMHEALHNHYTQKSLSLSPG 270

SEQ ID NO: 42    WQQGNVFSCSVMHEALHNHYTQKSLSLSPG 256
                 ******************************

```
SEQ ID NO: 43   ----------CPAKPEEEGMMINISIGYGGGSGGGSDKTHTCPPCPAPELLGGPSVFLFP   50
SEQ ID NO: 44   VWVPGPTDDRCPAKPEEEG---------GGGSGGGSDKTHTCPPCPAPELLGGPSVFLFP   51
SEQ ID NO: 45   --APGCLMPAVQNWLVEVP---------GGGSGGGSDKTHTCPPCPAPELLGGPSVFLFP   49
                           *              ********************

SEQ ID NO: 43   PKPKDTLMISRTPEVTCVVVDVSHEDPEVKFNWYVDGVEVHNAKTKPREEQYNSTYRVVS  110
SEQ ID NO: 44   PKPKDTLMISRTPEVTCVVVDVSHEDPEVKFNWYVDGVEVHNAKTKPREEQYNSTYRVVS  111
SEQ ID NO: 45   PKPKDTLMISRTPEVTCVVVDVSHEDPEVKFNWYVDGVEVHNAKTKPREEQYNSTYRVVS  109
                ***********************************************************

SEQ ID NO: 43   VLTVLHQDWLNGKEYKCKVSNKALPAPIEKTISKAKGQPREPQVYTLPPSRDELTKNQVS  170
SEQ ID NO: 44   VLTVLHQDWLNGKEYKCKVSNKALPAPIEKTISKAKGQPREPQVYTLPPSRDELTKNQVS  171
SEQ ID NO: 45   VLTVLHQDWLNGKEYKCKVSNKALPAPIEKTISKAKGQPREPQVYTLPPSRDELTKNQVS  169
                ***********************************************************
```

FIG. 20A

```
SEQ ID NO: 43    LTCLVKGFYPSDIAVEWESNGQPENNYKTTPPVLDSDGSFFLYSKLTVDKSRWQQGNVFS    230
SEQ ID NO: 44    LTCLVKGFYPSDIAVEWESNGQPENNYKTTPPVLDSDGSFFLYSKLTVDKSRWQQGNVFS    231
SEQ ID NO: 45    LTCLVKGFYPSDIAVEWESNGQPENNYKTTPPVLDSDGSFFLYSKLTVDKSRWQQGNVFS    229
                 ************************************************************

SEQ ID NO: 43    CSVMHEALHNHYTQKSLSLSPG    252
SEQ ID NO: 44    CSVMHEALHNHYTQKSLSLSPG    253
SEQ ID NO: 45    CSVMHEALHNHYTQKSLSLSPG    251
                 **********************
```

FIG. 20B

HERV-K (HML-2) Env ANALOG FUSION PROTEINS FOR ANTIGEN SPECIFIC IMMUNOTHERAPY AND METHODS OF USE

CROSS-REFERENCE TO RELATED APPLICATIONS

The present application claims the priority benefit of International Patent Application Serial No. PCT/US2025/040120, filed Jul. 31, 2025, U.S. Provisional Patent Application Ser. No. 63/678,293, filed Aug. 1, 2024, and U.S. Provisional Patent Application Ser. No. 63/678,337, filed Aug. 1, 2024, each entitled "HERV-K (HML-2) ENV ANALOG FUSION PROTEINS FOR ANTIGEN SPECIFIC IMMUNOTHERAPY AND METHODS OF USE," and each incorporated by reference in its entirety herein.

STATEMENT REGARDING FEDERALLY SPONSORED RESEARCH OR DEVELOPMENT

This invention was made with government support under HT9425-23-1-0564 awarded by the Defense Health Agency, Medical Research and Development Branch. The government has certain rights in the invention.

SEQUENCE LISTING

The following application contains a sequence listing filed electronically as a Standard ST.26 compliant XML file entitled "TWI-001US.xml" created on Jul. 28, 2025, as 51,487 bytes in size, the entire contents of which are incorporated by reference herein.

TECHNICAL FIELD

The present technology relates to fusion proteins comprising human endogenous retrovirus HERV-K (HML-2) envelope (Env) proteins or analogs thereof linked to Fc fragments and their use in the management of HERV-K (HML-2) associated cancers and neurological disorders including amyotrophic lateral sclerosis (ALS) and frontotemporal dementia (FTD).

BACKGROUND

The following description of the background is provided simply as an aid in understanding the present technology and is not admitted to describe or constitute prior art to the present technology.

Fc Fusion Proteins

Fc fusion proteins are comprised of a species-specific immunoglobin Fc domain that is linked to another peptide such as a protein or peptide with therapeutic potential. As used herein, the terms "fusion protein" and "Fc fusion protein" generally mean a protein comprising more than one part, for example from different sources (e.g., different proteins, polypeptides, cells, etc.), that are covalently linked through peptide bonds. Fc fusion proteins are preferably covalently linked by (i) connecting the genes that encode for each part into a single nucleic acid molecule and (ii) expressing in a host cell (e.g., HEK cell or CHO cell) the protein for which the nucleic acid molecule encodes. The fully recombinant synthesis approach is preferred over methods in which the therapeutic protein and Fc fragments are synthesized separately and then chemically conjugated. The chemical conjugation step and subsequent purification process increase the manufacturing complexity, reduce product yield, and increase cost.

The terms "Fc fragment," "Fc portion," "Fc domain," or "Fc polypeptide," are used herein to define a C-terminal portion of an immunoglobulin heavy chain. The Fc fragment, portion, domain, or polypeptide may be a native sequence Fc polypeptide or a variant/mutant Fc polypeptide. Although the boundaries of the Fc portion of an immunoglobulin heavy chain may vary, they generally comprise some or all of the hinge portion of the heavy chain, the CH2 domain of the heavy chain, and the CH3 domain of the heavy chain. The hinge portion of an Fc fragment comprises amino acid sequences that connect the CH1 domain of the heavy chain to the CH2 domain of the heavy chain and contain one or more cysteines that form one or more inter-heavy chain disulfide bridges to form a homodimer of an Fc fusion protein from two identical but separate monomers of the Fc fusion protein. The hinge portion may comprise all or part of a naturally occurring amino acid sequence or a non-naturally occurring amino acid sequence.

The presence of the Fc domain increases the plasma half-life due to its interaction with the neonatal Fc-receptor (FcRn) in addition to slower renal clearance of the Fc fusion protein due to the large molecule size, resulting in in vivo recycling of the molecule achieving prolonged activity of the linked peptide and improved solubility and stability of the Fc fusion protein molecule. The Fc domain also enables Fc fusion proteins to interact with Fc receptors on immune cells. In some examples, the therapeutic protein or peptide is linked to the immunoglobin Fc domain via a linker. The therapeutic protein or peptide and linker replace the variable portion of an antibody while keeping the Fc portion intact.

An Fc receptor (FcR) generally means a receptor that binds to an Fc fragment or to the Fc portion of an antibody. In examples, the FcR is a native sequence of a mammalian FcR, and the FcR is one which binds an Fc fragment or the Fc portion of an IgG antibody (a gamma receptor) and includes without limitation, receptors of the Fc (gamma) receptor I, Fc (gamma) receptor Ia, Fc (gamma) receptor IIb, and Fc (gamma) receptor III subclasses, including allelic variants and alternatively spliced forms of these receptors. "FcR" also includes the neonatal receptor, FcRn, which is responsible for the transfer of maternal IgG molecules to the fetus and is also responsible for the prolonged in vivo elimination half-lives of antibodies and Fc-fusion proteins in vivo. In examples, FcR of human origin are used in vitro (e.g., in an assay) to measure the binding of Fc fusion proteins comprising Fc fragments of any mammalian origin so as to assess their FcR binding properties.

HERV-K

Human Endogenous Retroviruses (HERVs) are genomic sequence remnants from ancient retroviral infections that occurred during primate evolution and constitute 8% of the human genome. Currently, most HERV sequences do not have complete open reading frames (ORFs) due to the accumulation of mutations, so they cannot encode proteins. However, HERV-K (HML-2), which is the most recently acquired HERV, still presents complete ORFs, so it can encode proteins and even form viral-like particles. Expression of HERV-K (HML-2) genes is high during embryonic development but gets mostly silenced in adult tissues. However, aberrant gene expression from HERV-K (HML-2) is rapidly being recognized as a novel disease mechanism in several human cancers and neurological disorders including amyotrophic lateral sclerosis (ALS).

High expression of HERV-K (HML-2) genes has been found in cortical and spinal neurons of ALS patients. Expression of HERV-K (HML-2), or specifically its envelope (Env) protein in human neurons was found to cause retraction and beading of neurites with cell culture exposure to exogenous Env protein being neurotoxic. Moreover, transgenic mice expressing the HERV-K (HML-2) Env gene develop ALS-like progressive motor dysfunction and selective motor cortex volume loss. Decreased synaptic activity with dendritic spine abnormalities, nucleolar dysfunction and DNA damage are also seen in the pyramidal neurons of the HERV-K (HML-2) Env transgenic mice. Injury to spinal cord anterior horn cells occurs as well and manifests as an ALS-like atrophy of nerves and muscles. The expression of HERV-K (HML-2) has been found to be regulated by TAR (transactive response) DNA binding protein 43 (TDP-43), which binds to the long terminal repeat portion of the HERV-K (HML-2) virus. TDP-43 mis-regulation or dysfunction is known to occur in nearly all ALS cases.

Thus, aberrant HERV-K (HML-2) gene expression potentially represents a paradigm-shifting disease mechanism in ALS. There is a differential antibody response against specific epitopes of HERV-K (HML-2) Env in ALS and controls, likely due to persistent antigenic exposure in the affected individuals following reactivation of the viral genes. Low levels of antibodies to HERV-K (HML-2) Env in ALS patients are associated with poor prognosis and decreased survival probability, suggesting a protective role of the antibodies against the disease pathogenesis.

HERV-K (HML-2) was originally identified by its homology to the mouse mammary tumor virus (MMTV) (US20090297530, "HERV-K Antigens, Antibodies, and methods, Feng Wang-Johanning.) Some HERVs, particularly the most recently acquired proviruses of the HERV-K (HML-2), subtype HML-2 family, can express viral proteins and produce viral-like particles (Hohn O, Hanke K, Bannert N. HERV-K (HML-2), *the Best Preserved Family of HERVs: Endogenization, Expression, and Implications in Health and Disease. Front Oncol.* 2013 Sep. 20; 3:246. doi: 10.3389/fonc.2013.00246. PMID: 24066280; PMCID: PMC3778440.)

Human Immunoglobulins

An immunogen or antigen reacts with a B-cell receptor (BCR) on the cell surface of B lymphocytes. A signal is produced which stimulates the synthesis of antibodies which are highly specific for the immunogen that stimulated the B cell. The immune system remembers the antigens that caused a previous reaction (memory) due to the development of memory B cells. These are intermediate, differentiated B cells that can quickly become plasma cells. Circulating antibodies recognize antigens in tissue fluids and serum.

There are four subclasses of human IgG: IgG1, IgG2, IgG3, and IgG4 which are differentiated on the position of interchain disulfide bonds, the size of the hinge region and antigenic differences in structure of the heavy chain. IgG1 is around 65% of the total IgG. IgG2 forms an important host defense against bacteria that are encapsulated. (Justiz Vaillant A A, Jamal Z, Patel P, et al. *Immunoglobulin.* [Updated 2023 Aug. 28]. In: StatPearls [Internet]. Treasure Island (FL): StatPearls Publishing; 2024 January-. Available from: ncbi.nlm.nih.gov/books/NBK513460/.)

The IgG subclasses share more than 90% amino acid sequence homology however they have different antigen binding, immune complex formation, complement activation, effector cell triggering, and half-life. These differences result in significant functional differences. (Sigal L H. 2012. *IgG subclasses. J Clin Rheumatol.* 18 (6): 316-18.) IgG1 and IgG3 are strong mediators of both Fc (gamma) receptors and complement-mediated functions, and are the predominant subclasses involved in the response to protein antigens. IgG2 is a weak mediator of Fc(gamma)R and complement-mediated functions and is involved in the response to polysaccharide antigens. IgG4 has a minimal ability to activate effector cells or fix complement. (Napodano, Cecilia & Marino, Mariapaola & Stefanile, Annunziata & Pocino, Krizia & Scatena, Roberto & Gulli, Francesca & Rapaccini, Gian & Noci, Stefano & Capozio, Giovanna & Rigante, Donato & Basile, Umberto. (2020). *Immunological Role of IgG Subclasses. Immunological Investigations.* 50. 1-18. 10.1080/08820139.2020.1775643.)

SUMMARY OF THE PRESENT TECHNOLOGY

Described herein are fusion proteins, each comprising a respective HERV-K (HML-2) Env analog and an Fc fragment, wherein the HERV-K (HML-2) Env analog and the Fc fragment are connected by a peptide linker. In one or more embodiments, the HERV-K (HML-2) Env analog comprises a HERV-K (HML-2) Env protein comprising a functional fragment, analog, or variant/mutant thereof. In one or more embodiments, the HERV-K (HML-2) Env analog comprises a HERV-K (HML-2) Env analog of SEQ ID NO: 24, or a functional fragment, analog, or variant/mutant thereof.

```
                                        (SEQ ID NO: 24)
GQFYHNCSGQTQSCPSAQVSPAVDSDLTESLDKHKHKKLQSFYPWEWGE
K.
```

In one or more embodiments, the HERV-K (HML-2) Env analog comprises a HERV-K (HML-2) Env analog of SEQ ID NO: 25, or a functional fragment, analog, or variant/mutant thereof.

```
                                        (SEQ ID NO: 25)
SPVSGPEHPELWRLTVASHHIRIWSGNQTLETRDRKPFYT.
```

In one or more embodiments, the Fc fragment comprises a sequence or functional fragment of SEQ ID NO: 1.

```
                                        (SEQ ID NO: 1)
DKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQG
NVFSCSVMHEALHNHYTQKSLSLSPG.
```

In one or more embodiments, the linker comprises the sequence GGGSGGGS (SEQ ID NO: 2).

In one or more embodiments, the fusion protein comprises, consists essentially or even consists of a sequence of SEQ ID NO: 46.

```
                                        (SEQ ID NO: 46)
GQFYHNCSGQTQSCPSAQVSPAVDSDLTESLDKHKHKKLQSFYPWEWGEK
GGGSGGGSDKTHTCPPCPAPELLGGPSVFLFPPKPKDTLMISRTPEVTCV
VVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELTKNQ
```

5

-continued

VSLTCLVKGFYPSDIAVEWESNGQPENNYKTTPPVLDSDGSFFLYSKLTV

DKSRWQQGNVFSCSVMHEALHNHYTQKSLSLSPG.

In one or more embodiments, the fusion protein comprises, consists essentially or even consists of a sequence of SEQ ID NO: 47.

(SEQ ID NO: 47)

SPVSGPEHPELWRLTVASHHIRIWSGNQTLETRDRKPFYTGGGSGGGSDK

THTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNV

FSCSVMHEALHNHYTQKSLSLSPG.

In one or more embodiments, the Fc fragment is glycosylated.

Also described herein are immunogenic compositions which comprise or consist essentially of a fusion protein(s) according to any embodiments or combinations of embodiments described herein and a pharmaceutically acceptable carrier. In one or more embodiments, the fusion protein is dispersed in the carrier. In one or more embodiments, the compositions further comprise an adjuvant. In one or more embodiments, the adjuvant is Sepivac SWE™ (Seppic, Inc. New Jersey, United States). In one or more embodiments, the fusion protein is emulsified with the adjuvant. In one or more embodiments, the emulsification is prepared onsite before administration. In one or more embodiments, the prepared emulsification is refrigerated (4° C.) or room temperature stable for at least 8 hours, preferably up to 24 hours, preferably up to 48 hours or more. In one or more embodiments, the composition is an injectable formulation. In one or more embodiments, the composition is adapted for subcutaneous administration. In one or more embodiments, the composition is adapted for intramuscular administration. In one or more embodiments, the composition is adapted for therapeutic vaccination.

Also described herein are various methods for increasing antibody production in a patient against an antigenic agent, or alternatively or additionally methods of inducing an immune response in a patient against a HERV-K (HML-2) protein. The methods generally comprise administering a therapeutically effective amount of a fusion protein(s) or immunogenic composition(s) according to any embodiments or combinations of embodiments described herein to a patient. In one or more embodiments, the fusion protein or immunogenic composition is administered via injection. In one or more embodiments, the fusion protein or immunogenic composition is administered subcutaneously, intramuscularly, or intranasally. In one or more embodiments, the fusion protein or immunogenic composition is provided as a unit dosage form. In one or more embodiments, the fusion protein or immunogenic composition is co-administered with an adjuvant. In one or more embodiments, the methods further comprise preparing the fusion protein or immunogenic composition for administration, wherein the preparation comprises pre-mixing the fusion protein or immunogenic composition with an adjuvant before administration. In one or more embodiments, pre-mixing comprises emulsifying the adjuvant and fusion protein to yield an emulsion and administering the emulsion to the patient. In one or more embodiments, the adjuvant is Sepivac SWE™ (Seppic, Inc. New Jersey, United States).

Also described herein are methods of producing a fusion protein according to any embodiments or combinations of embodiments described herein. The methods generally comprise transiently transfecting a nucleic acid encoding for the fusion protein into a Chinese Hamster Ovary (CHO) cell, wherein the transfected CHO cell expresses the fusion protein. In one or more embodiments, the fusion protein is secreted by the cells into cell culture media, further comprising purifying or isolating the fusion protein from the media. Advantageously, the yield of the purified or isolated fusion protein is greater than 50 mg/L.

Also described herein are cells engineered to express a fusion protein according to any embodiments or combinations of embodiments described herein. In one or more embodiments, the cell is a CHO cell.

As described herein, the fusion protein(s) or immunogenic composition(s) according to any embodiments or combinations of embodiments described herein can be used in therapy and/or as a medicament.

As described herein, the fusion protein(s) or immunogenic composition(s) according to any embodiments or combinations of embodiments described herein can be used for increasing antibody production in a patient.

As described herein, the fusion protein(s) or immunogenic composition(s) according to any embodiments or combinations of embodiments described herein can be used in treatment of HERV-K-associated cancers and neurological disorders including amyotrophic lateral sclerosis (ALS).

As described herein, the fusion protein(s) or immunogenic composition(s) according to any embodiments or combinations of embodiments described herein can be used as a prophylactic, therapeutic and/or booster vaccine.

Particular embodiments concern the fusion protein consisting of SEQ ID NO: 46, the fusion protein consisting of SEQ ID NO: 47, or pharmaceutical compositions of one of these two fusion proteins for use in treatment of HERV-K-associated cancers and neurological disorders including amyotrophic lateral sclerosis (ALS).

As described herein, the fusion protein(s) or immunogenic composition(s) according to any embodiments or combinations of embodiments described herein can be used in the manufacture of a medicament for the treatment of HERV-K-associated cancers and neurological disorders including amyotrophic lateral sclerosis (ALS).

BRIEF DESCRIPTION OF THE DRAWINGS

FIG. 3A, FIG. 3B, FIG. 3C, and FIG. 3D are a Clustal Omega amino acid sequence comparison showing the alignments of the full-length signal peptide domain (SEQ ID NO: 4), full-length extracellular domain (SEQ ID NO: 5), full-length transmembrane domain (SEQ ID NO: 6), and full-length cytoplasmic domain (SEQ ID NO: 7) of the HERV-K (HML-2) Env consensus sequence with the full-length HERV-K (HML-2) Env consensus sequence (SEQ ID NO: 8).

FIG. 4A, FIG. 4B, FIG. 4C, FIG. 4D, FIG. 4E, and FIG. 4F show a Clustal Omega amino acid sequence comparison of the full-length HERV-K (HML-2) Env consensus sequence (SEQ ID NO: 8), the 6q14.1 K109 full-length HERV-K Env sequence (SEQ ID NO: 9), the 7p22.1 K109 ERK6 full-length HERV-K Env sequence (SEQ ID NO: 10), the 8p23.1a K115 full-length HERV-K Env sequence (SEQ ID NO: 11), the 11q22.1 K118 full-length HERV-K Env sequence (SEQ ID NO: 12), the 12q14.1 K119 full-length HERV-K Env sequence (SEQ ID NO: 13), the 19p12b K113 full-length HERV-K Env sequence (SEQ ID NO: 14), the 19q11 full-length HERV-K Env sequence (SEQ ID NO: 15), and the 1q23.3 full-length HERV-K Env sequence (SEQ ID NO: 16).

FIG. 5A, FIG. 5B, FIG. 5C, FIG. 5D, FIG. 5E, and FIG. 5F are a Clustal Omega amino acid sequence comparison showing the alignment of the full-length HERV-K Env (HML-2) consensus sequence (SEQ ID NO: 8) with eight HERV-K (HML-2) Env analogs (SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25).

FIG. 6A and FIG. 6B are a Clustal Omega amino acid sequence comparison that shows the alignment of the 1q23.3 full-length HERV-K Env sequence (SEQ ID NO: 16) with the HERV-K (HML-2) Env analog of SEQ ID NO: 22.

FIG. 7A, FIG. 7B, and FIG. 7C are a Clustal Omega amino acid sequence comparison showing the alignment of the full-length HERV-K (HML-2) Env consensus sequence (SEQ ID NO: 8) and the G01 epitope (SEQ ID NO: 17).

FIG. 9 is a Clustal Omega amino acid sequence comparison showing the alignment of a HERV-K (HML-2) Env analog (SEQ ID NO: 19) and its corresponding predicted epitope for binding to B-cell receptors (SEQ ID NO: 29).

FIG. 10 is a Clustal Omega amino acid sequence comparison showing the alignment of a HERV-K (HML-2) Env analog (SEQ ID NO: 20) and its corresponding predicted epitope for binding to B-cell receptors (SEQ ID NO: 30).

FIG. 11 is a Clustal Omega amino acid sequence comparison showing the alignment of a HERV-K (HML-2) Env analog (SEQ ID NO: 21) and its corresponding predicted epitope for binding to B-cell receptors (SEQ ID NO: 31).

FIG. 12 is a Clustal Omega amino acid sequence comparison showing the alignment of a HERV-K (HML-2) Env analog (SEQ ID NO: 22) and its corresponding predicted epitope for binding to B-cell receptors (SEQ ID NO: 32).

FIG. 13 is a Clustal Omega amino acid sequence comparison showing the alignment of a HERV-K (HML-2) Env analog (SEQ ID NO: 25) and its corresponding predicted epitopes for binding to B-cell receptors (SEQ ID NO: 34 and SEQ ID NO: 35).

FIG. 15 is a Clustal Omega amino acid sequence comparison showing the alignment of a HERV-K (HML-2) Env analog (SEQ ID NO: 24) and its corresponding recognized epitope (SEQ ID NO: 33).

FIG. 16A and FIG. 16B show a Clustal Omega amino acid sequence comparison of three HERV-K (HML-2) Env analog-Fc fusion proteins (SEQ ID NO: 38, SEQ ID NO: 39, and SEQ ID NO: 41) that each use a long linker (SEQ ID NO: 3).

FIG. 17A, FIG. 17B, and FIG. 17C show a Clustal Omega amino acid sequence comparison of seven HERV-K (HML-2) Env analog-Fc fusion proteins (SEQ ID NO: 40, SEQ ID NO: 42, SEQ ID NO: 43, SEQ ID NO: 44, SEQ ID NO: 45, SEQ ID NO: 46, and SEQ ID NO: 47) that each use a short linker (SEQ ID NO: 2).

FIG. 18A and FIG. 18B show a Clustal Omega amino acid sequence comparison of two HERV-K (HML-2) Env analog Fc-fusion proteins (SEQ ID NO: 39 and SEQ ID NO: 40) that share a common HERV-K (HML-2) Env analog (SEQ ID NO: 19).

FIG. 19A and FIG. 19B show a Clustal Omega amino acid sequence comparison of two HERV-K (HML-2) Env analog-Fc fusion proteins (SEQ ID NO: 41 and SEQ ID NO: 42) that share a common HERV-K (HML-2) Env analog (SEQ ID NO: 20).

FIG. 20A and FIG. 20B show a Clustal Omega amino acid sequence comparison of three HERV-K (HML-2) Env analog-Fc fusion proteins (SEQ ID NO: 43, SEQ ID NO: 44, and SEQ ID NO: 45) that do not share a HERV-K (HML-2) Env analog with any other HERV-K (HML-2) Env analog-Fc fusion protein.

DETAILED DESCRIPTION

Figure 1:
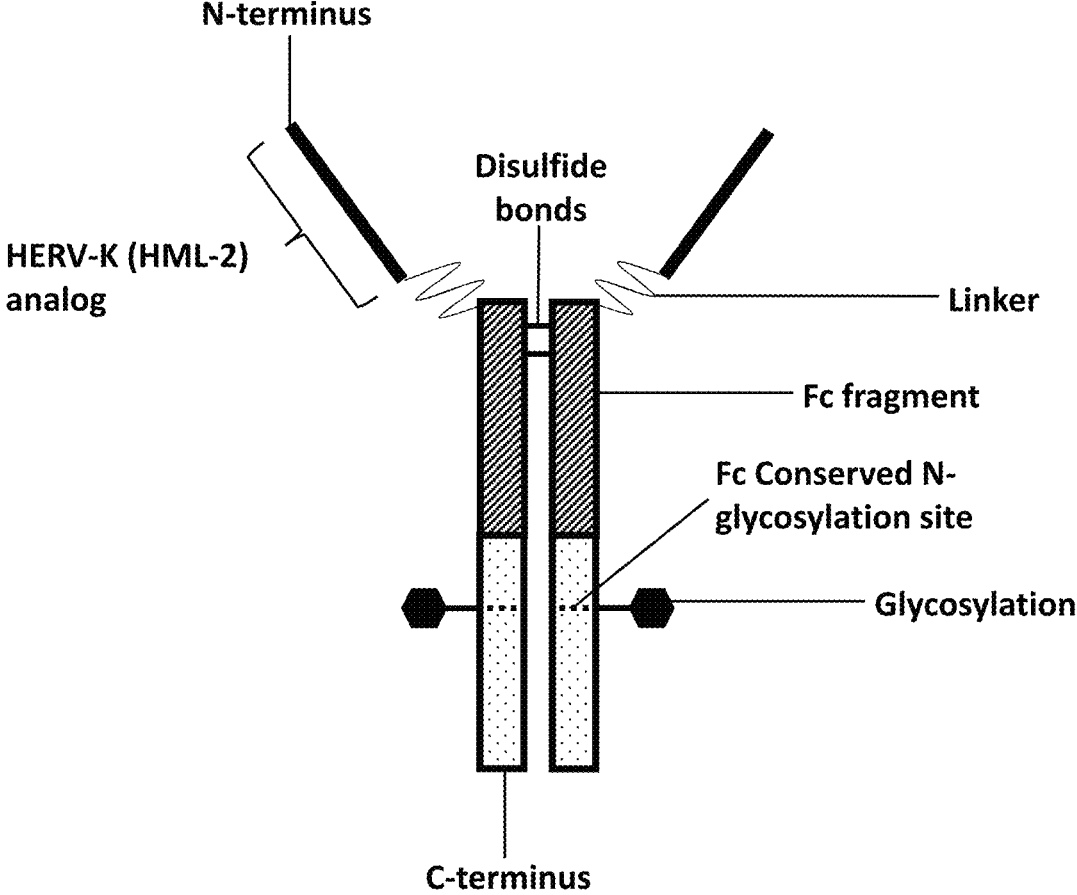
FIG. 1 shows a schematic representation of an HERV-K (HML-2) Env analog-Fc fusion protein homodimer. The glycosylation site shown is the conserved natural glycosylation site on the Fc fragment (glycosylation that may occur on the HERV-K (HML-2) Env analog is not shown).

Retroviruses that have the ability to infect germ line cells can become an integral and inherited part of the host genome. About 8% of the human chromosomal DNA consists of sequences derived from infections by retroviruses that presumably circulated 2-40 million years ago, which are called Human Endogenous Retroviruses (HERVs). Post-insertional recombinations, deletions, and mutations have rendered all known HERVs non-infectious. HERV-K was originally identified by its homology to the mouse mammary tumor virus (MMTV) (US20090297530, "HERV-K Antigens, Antibodies, and methods, Feng Wang-Johanning.) Some HERVs, particularly the most recently acquired proviruses of the HERV-K, subtype HML-2 family, can express viral proteins and produce viral-like particles (Hohn O, Hanke K, Bannert N. HERV-K (HML-2), *the Best Preserved Family of HERVs: Endogenization, Expression, and Implications in Health and Disease. Front Oncol.* 2013 Sep. 20; 3:246. doi: 10.3389/fonc.2013.00246. PMID: 24066280; PMCID: PMC3778440.). HERV-K (HML-2) is transcriptionally active during embryogenesis but gets mostly silenced in differentiated cells.

Aberrant expression of HERV-K (HML-2) in adult tissues has been associated with many types of cancer and with neurodegenerative diseases (Garcia-Montojo M, Doucet-O'Hare T, Henderson L, Nath A. *Human endogenous retrovirus-K (HML-2): a comprehensive review. Crit Rev Microbiol.* 2018 November; 44 (6): 715-738. doi: 10.1080/1040841X.2018.1501345. Epub 2018 Oct. 14. PMID: 30318978; PMCID: PMC6342650). Overexpression of HERV-K (HML-2) has been detected in teratocarcinoma, glioblastoma, breast cancer, germ cell tumors, melanoma, ovarian, and prostate cancer (Lower R, Lower J, Frank H, Harzmann R, Kurth R. 1984. Human teratocarcinomas cultured in vitro produce unique retrovirus-like viruses. *J Gen Virol* 65 (Pt 5): 887-898; Shah A H, Rivas S R, Doucet-O'Hare T T, Govindarajan V, DeMarino C, Wang T, Ampie L, Zhang Y, Banasavadi-Siddegowda Y K, Walbridge S, Maric D, Garcia-Montojo M, Suter R K, Lee M H, Zaghloul K A, Steiner J, Elkahloun A G, Chandar J, Seetharam D, Desgraves J, Li W, Johnson K, Ivan M E, Komotar R J, Gilbert M R, Heiss J D, Nath A. Human endogenous retrovirus K contributes to a stem cell niche in glioblastoma. J Clin Invest. 2023 Jul. 3; 133 (13): e167929. Johanning G L, Malouf G G, Zheng X, Esteva F J, Weinstein J N, Wang-Johanning F, Su X. Expression of human endogenous retrovirus-K is strongly associated with the basal-like breast cancer phenotype. Sci Rep. 2017 Feb. 6; 7:41960. Herbst H, Sauter M, Mueller-Lantzsch N. 1996. *Expression of human endogenous retrovirus K elements in germ cell and trophoblastic tumors. Am J Pathol* 149 (5): 1727-1735.; Muster T, Waltenberger A, Grassauer A, Hirschl S, Caucig P, Romirer I, Fodinger D, Seppele H, Schanab O, Magin-Lachmann C et al. 2003. *An endogenous retrovirus derived from human melanoma cells. Cancer Res* 63 (24): 8735-8741.; Buscher K, Trefzer U, Hofmann M, Sterry W, Kurth R, Denner J. 2005. Expression of human endogenous retrovirus K in melanomas and melanoma cell lines. *Cancer Res* 65 (10): 4172-4180; Buscher K, Hahn S, Hofmann M, Trefzer U, Ozel M, Sterry W, Lower J, Lower R, Kurth R, Denner J. 2006. *Expression of the human endogenous retrovirus-K transmembrane envelope, Rec and Np9 proteins in melanomas and melanoma cell lines. Melanoma Res* 16 (3): 223-234.; Wang-Johanning F, Liu J, Rycaj K, Huang M, Tsai K, Rosen D G, Chen D T, Lu D W, Barnhart K F, Johanning G L. 2007. *Expression of multiple human endogenous retrovirus surface envelope proteins in ovarian cancer. Int J Cancer* 120 (1): 81-90.; Kurth R, Bannert N. 2010. *Beneficial and detrimental effects of human endogenous retroviruses. Int J Cancer* 126 (2): 306-314.), and with various features of malignant cells (Oricchio E, Sciamanna I, Beraldi R, Tolstonog G V, Schumann G G, Spadafora C. 2007. *Distinct roles for LINE-1 and HERV-K retroelements in cell proliferation, differentiation and tumor progression. Oncogene* 26 (29): 4226-4233.; Reis B S, Jungbluth A A, Frosina D, Holz M, Ritter E, Nakayama E, Ishida T, Obata Y, Carver B, Scher H et al. 2013. *Prostate cancer progression correlates with increased humoral immune response to a human endogenous retrovirus GAG protein. Clin Cancer Res* 19 (22): 6112-6125.; Schmitt K, Reichrath J, Roesch A, Meese E, Mayer J. 2013. Transcriptional Profiling of Human Endogenous Retrovirus Group HERV-K (HML-2) Loci in Melanoma. *Genome Biol Evol* 5 (2): 307-328.; Wildschutte J H, Ram D, Subramanian R, Stevens V L, Coffin J M. 2014. *The distribution of insertionally polymorphic endogenous retroviruses in breast cancer patients and cancer-free controls. Retrovirology* 11:62.; Bhardwaj N, Montesion M, Roy F, Coffin J M. 2015. *Differential expression of HERV-K (HML-2) proviruses in cells and virions of the teratocarcinoma cell line Tera-1. Viruses* 7 (3): 939-968.). Even if its contribution to cancer pathogenesis is not entirely clear, HERV-K (HML-2) is consistently over-expressed in certain cancer types. Therefore, immune responses can be directed against HERV-K (HML-2) antigens to eliminate cancer cells. The expression of HERV-K and specifically HML-2 has been associated with many cancer types such as teratocarcinoma, glioblastoma, breast cancer, germ cell tumors, melanoma, ovarian, and prostate cancer (Lower et al. 1984; Herbst et al. 1996; Muster et al. 2003; Buscher et al. 2005; Buscher et al. 2006; Wang-Johanning et al. 2007; Kurth and Bannert 2010), and with various features of malignant cells (Oricchio et al. 2007; Reis et al. 2013; Schmitt et al. 2013; Wildschutte et al. 2014; Bhardwaj et al. 2015).

The evidence for the role of HERV-K (HML-2) in the pathophysiology of sporadic amyotrophic lateral sclerosis (ALS) is strong. Several groups have identified the presence of reverse transcriptase (RT) activity in the blood and cerebrospinal fluid (CSF) of patients with ALS (Viola M V, Frazier M, White L, Brody J, Spiegelman S. 1975. *RNA-instructed DNA polymerase activity in a cytoplasmic particulate fraction in brains from Guamanian patients. J Exp Med* 142 (2): 483-494.; Steele A J, Al-Chalabi A, Ferrante K, Cudkowicz M E, Brown R H Jr., Garson J A. 2005. *Detection of serum reverse transcriptase activity in patients with ALS and unaffected blood relatives. Neurology* 64 (3): 454-458.; McCormick A L, Brown R H Jr., Cudkowicz M E, Al-Chalabi A, Garson J A. 2008. *Quantification of reverse transcriptase in ALS and elimination of a novel retroviral candidate. Neurology* 70 (4): 278-283.). mRNA from HERV-K (HML-2) genes, GAG, POL and ENV can be detected in the brains of ALS patients, and RT and ENV proteins are expressed in cortical neurons in the disease (Douville R, Liu J, Rothstein J, Nath A. 2011. *Identification of active loci of a human endogenous retrovirus in neurons of patients with amyotrophic lateral sclerosis. Ann Neurol* 69 (1): 141-151.; Li W, Lee M H, Henderson L, Tyagi R, Bachani M, Steiner J, Campanac E, Hoffman D A, von Geldern G, Johnson K et al. 2015. *Human endogenous retrovirus-K contributes to motor neuron disease. Sci Transl Med* 7 (307).).

Multiple active HERV-K (HML-2) loci have been identified, although loci in chromosome 7 seem to be differentially expressed in patients and controls (Douville R, Liu J, Rothstein J, Nath A. et al. 2011. *Identification of active loci of a human endogenous retrovirus in neurons of patients with amyotrophic lateral sclerosis. Ann Neurol* 69 (1): 141-151.). Forced expression of HERV-K (HML-2) in neurons, either by transfection with the complete consensus sequence or by activation of the endogenous proviruses with a CRISPR/dCAS9 targeting HERV-K (HML-2) LTRs, lead to neuronal injury and cell death. Transgenic mice in which HERV-K (HML-2) Env (consensus) was expressed under a neuronal promoter developed progressive motor dysfunction, with specific loss of neurons in the motor cortex and the anterior horn of the spinal cord (Li W, Lee M H, Henderson L, Tyagi R, Bachani M, Steiner J, Campanac E, Hoffman D A, von Geldern G, Johnson K et al. 2015. *Human endogenous retrovirus-K contributes to motor neuron disease. Sci Transl Med* 7 (307).). et al. 2015). There is a differential antibody response against specific epitopes of HERV-K (HML-2) Env in ALS and controls, likely due to persistent antigenic exposure in the affected individuals following reactivation of the viral genes. Low levels of antibodies to HERV-K (HML-2) Env in ALS are associated with poor prognosis and decreased survival probability, suggesting a protective role of the antibodies against the disease pathogenesis (Garcia-Montojo, M., Simula, E. R., Fathi, S., McMahan, C., Ghosal, A., Berry, J. D., Cudkowicz, M., Elkahloun, A., Johnson, K., Norato, G., Jensen, P., James, T., Sechi, L. A. and Nath, A. (2022), *Antibody Response to HML-2 May Be Protective in Amyotrophic Lateral Sclerosis. Ann Neurol,* 92:782-792).

Figure 2:
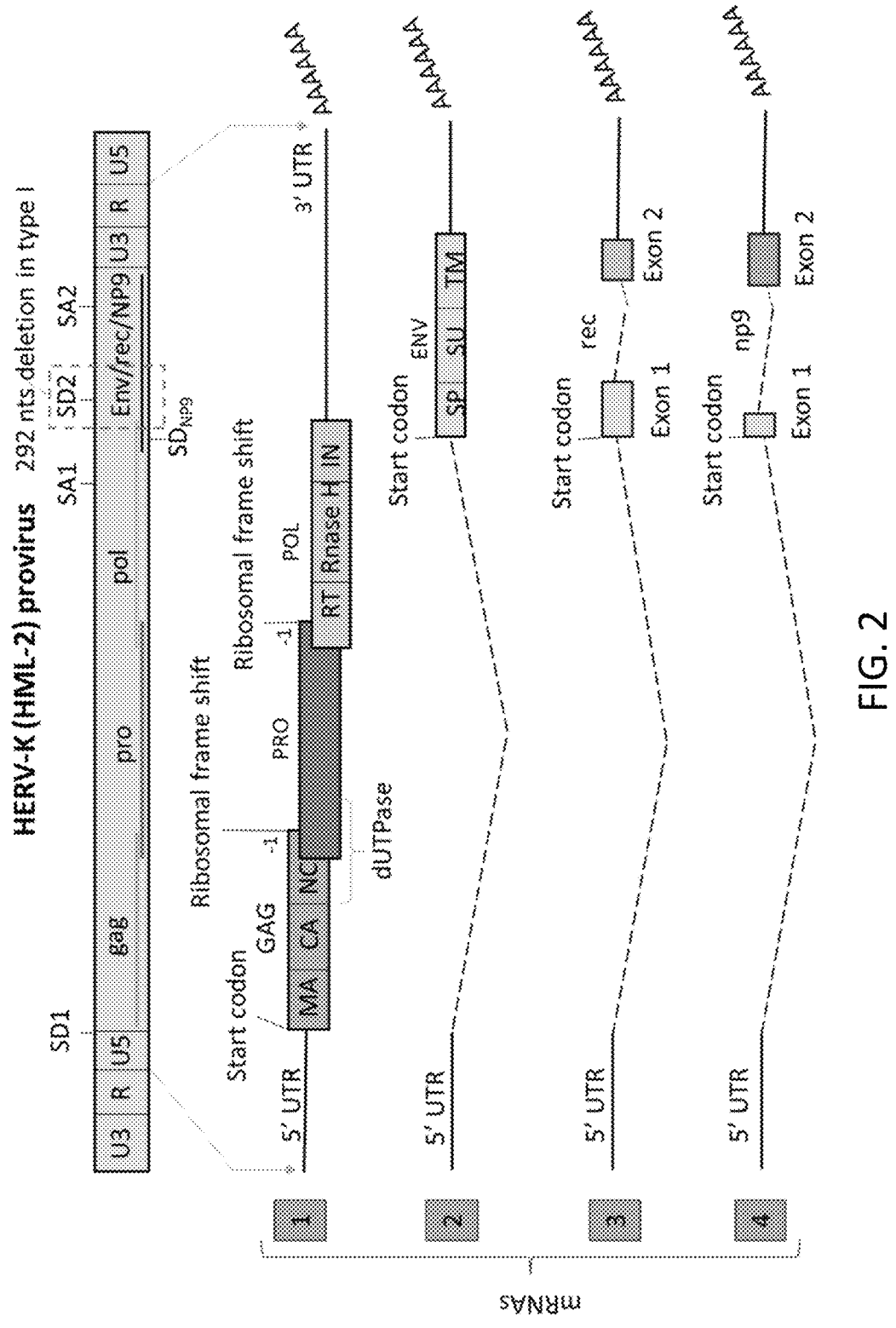
FIG. 2 is a schematic diagram depicting the organization of the HERV-K (HML-2) provirus.
Figure 3C:
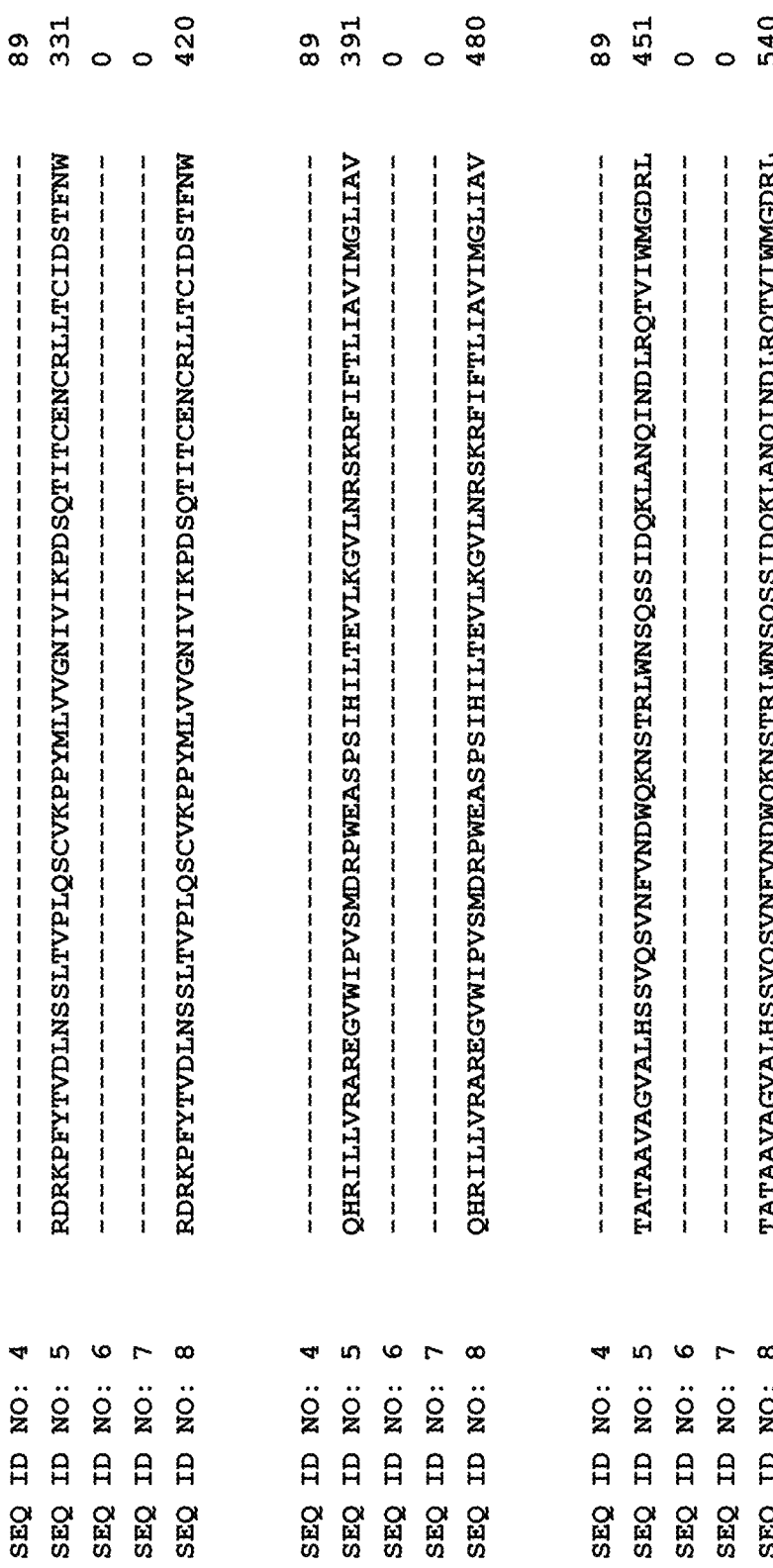
Figure 5A:
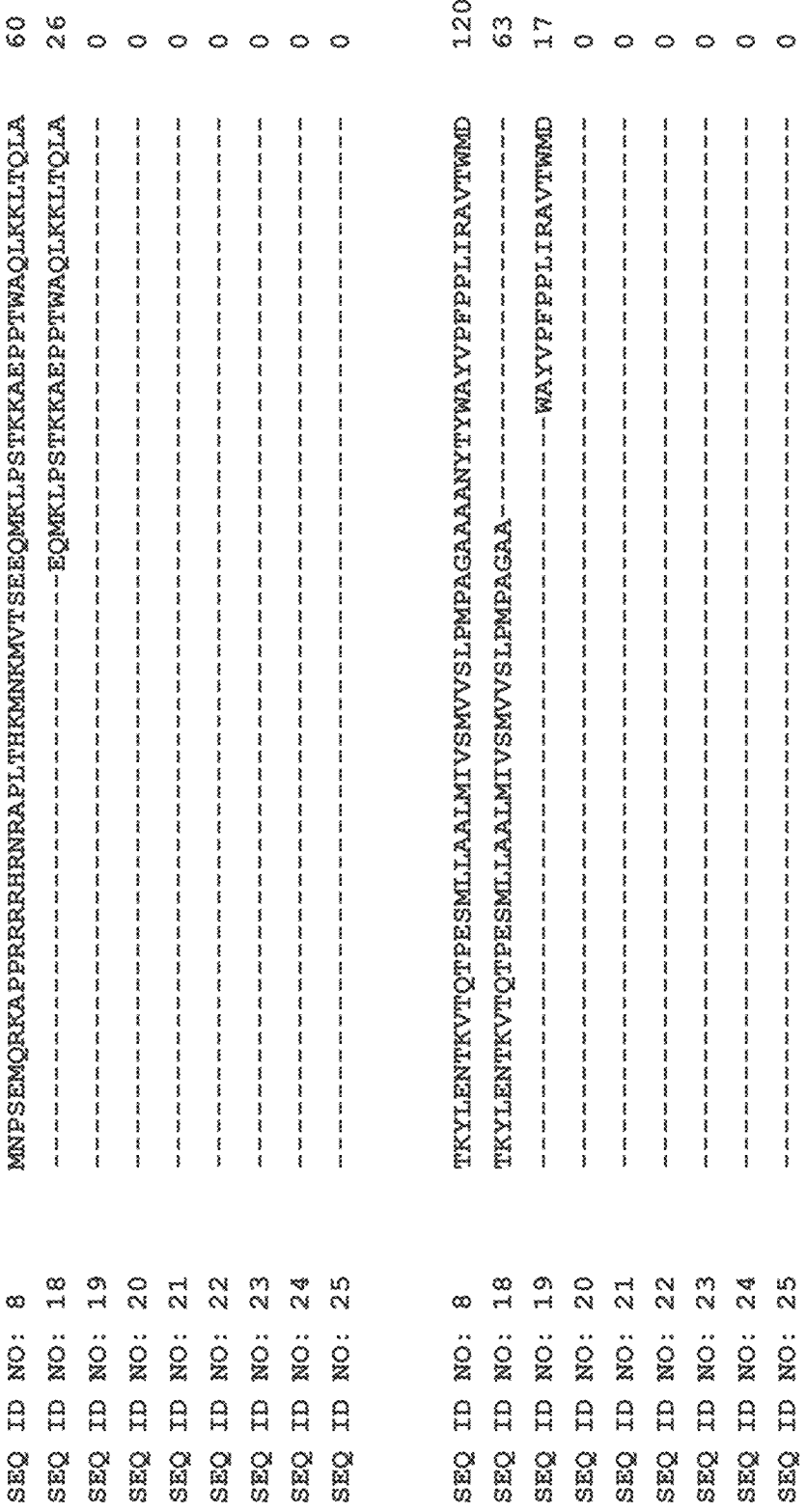
Figure 5B:
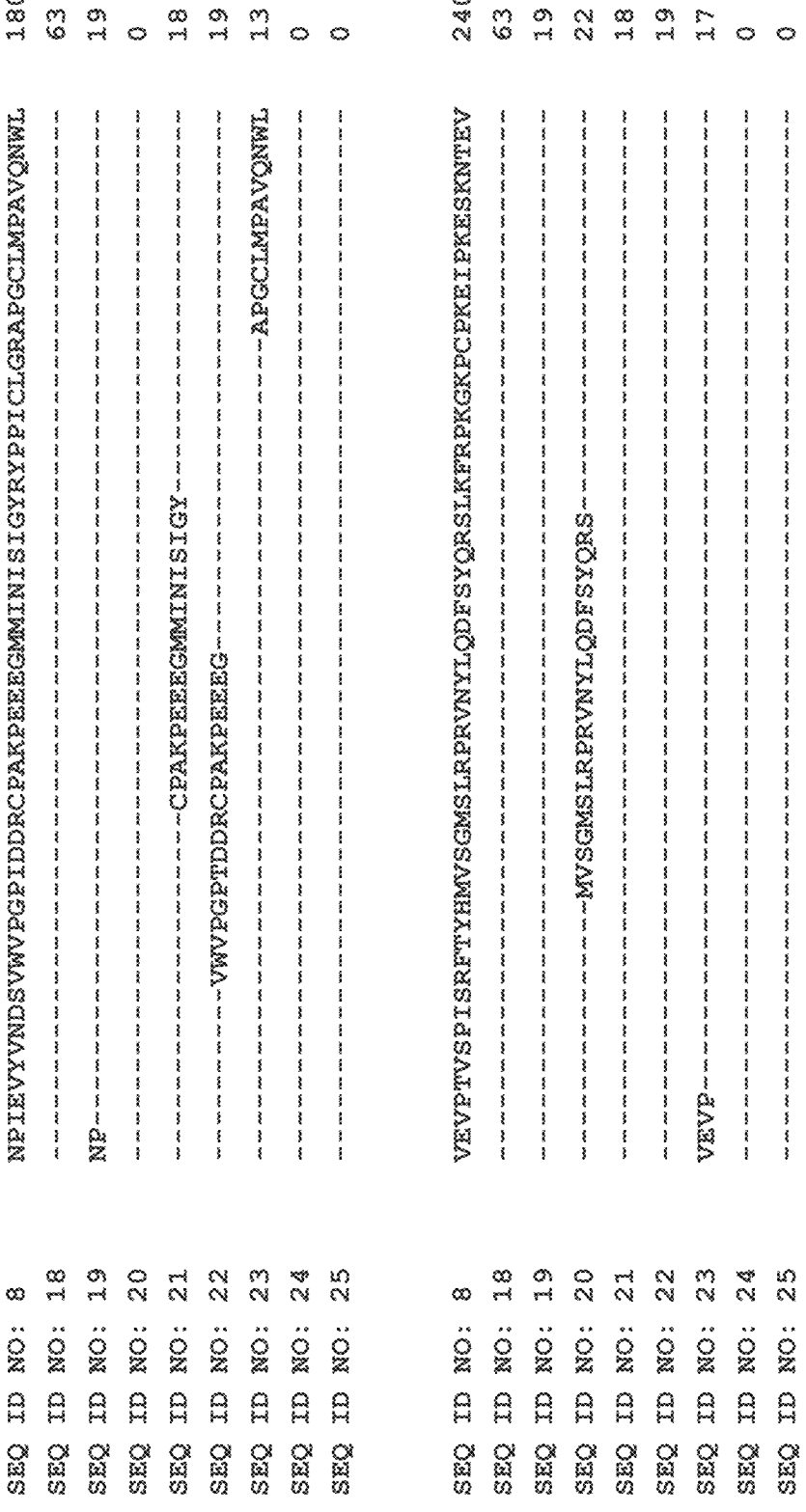
Figure 5D:
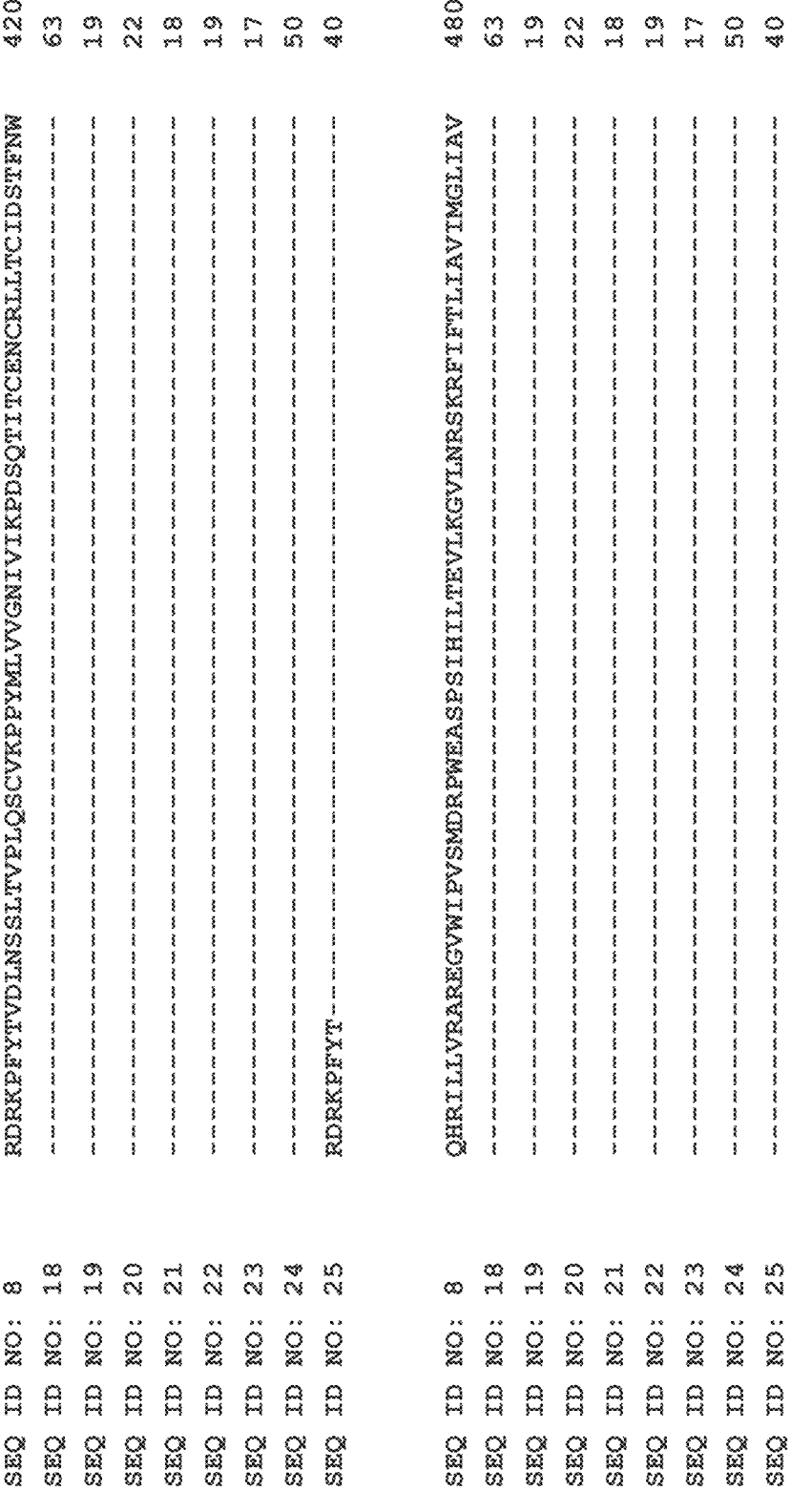
Figure 5E:
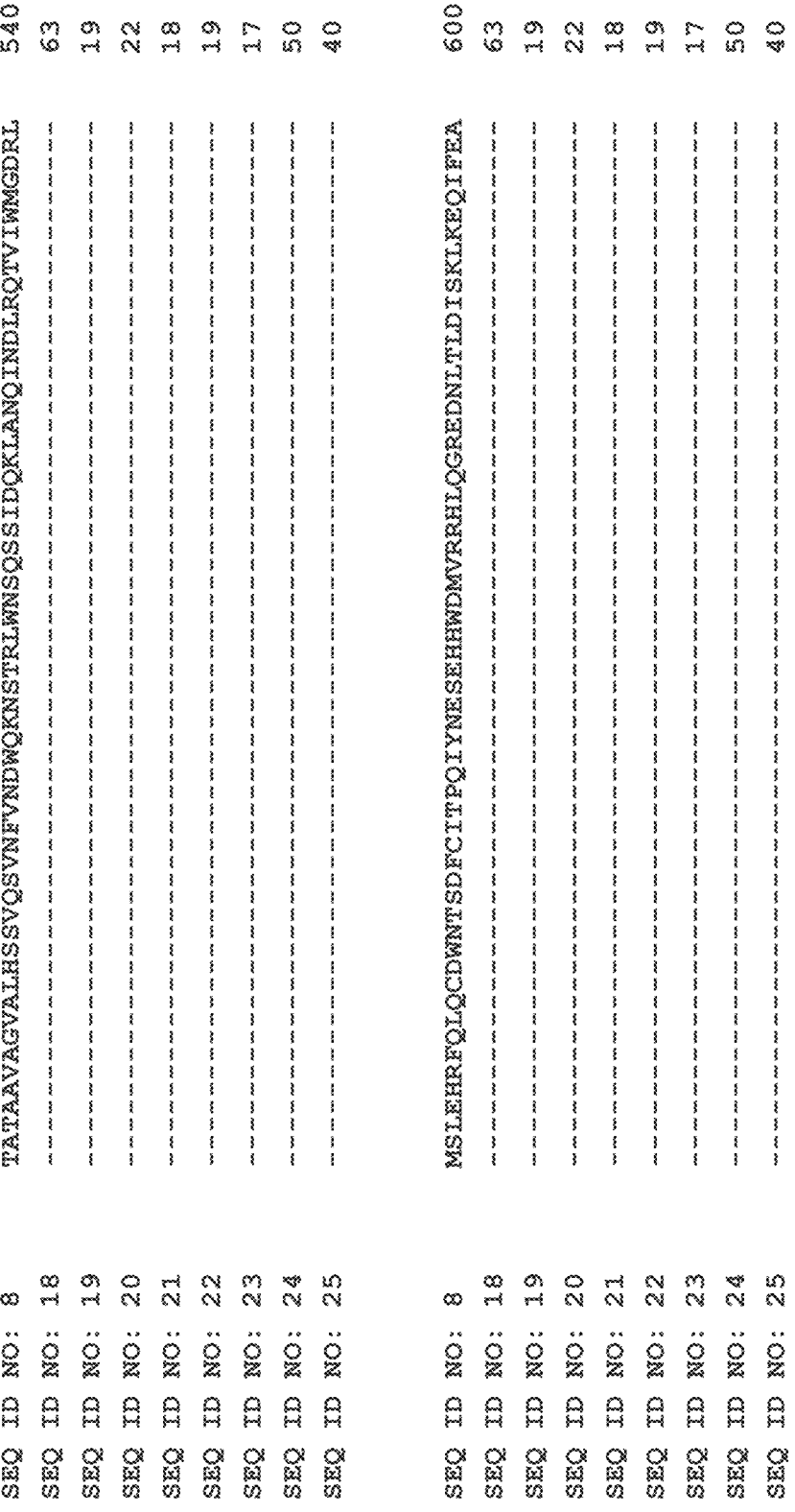
Figure 5F:
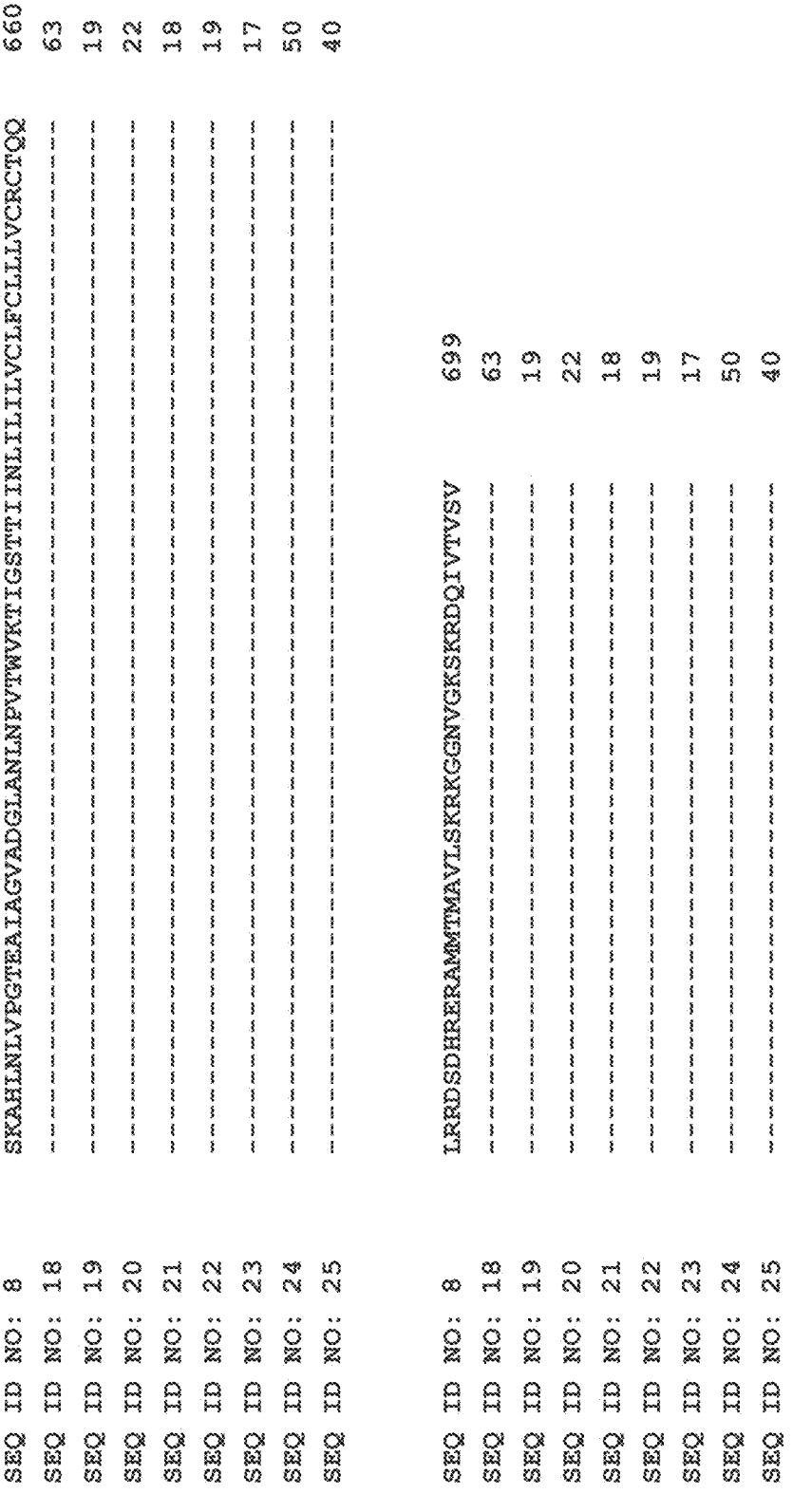

There are multiple HERVs that are implicated in Central Nervous System (CNS) diseases. The organization of the HERV-K (HML-2) provirus is shown in FIG. 2. In the proviral form of HERV-K (HML-2), the sequences of the four ORFs (labelled GAG, PRO, POL, and ENV) overlap. Splice donor (SD) and splice acceptor (SA) sites are shown. LTRs ('Long Terminal Repeat' sequences found at both ends of a retrovirus) are composed of the U3 and U5 regions separated by the R segment. As opposed to canonical retroviruses, which include the R segment in their transcripts, HERV-K (HML-2) transcription starts after the R.

Transcript 1 has 3 ORFs to encode proteins GAG, protease (PRO) and polymerase (POL). In this transcript, only GAG has a start codon (AUG); PRO and POL translation is mediated by 2 ribosomal frame shifts (−1). As a result, and despite having overlapping DNA sequences, the 3 proteins do not have any amino acid sequence in common. The figure also shows the ORFs' organization to encode the different final proteins and domains: matrix (MA), capsid (CA) and nucleocapsid (NC) in GAG, dUTPase in GAG-PRO junction and RT, Rnase H and integrase (IN) in POL). The functional proteins will be formed by proteolysis of the polyproteins GAG, GAG-PRO and GAG-PRO-POL. Transcript 2 encodes the protein ENV, which has 3 different domains: the signal peptide (SP), surface (SU) and transmembrane (TM). Transcript 3 is the product of alternative splicing of the ENV ORF and encodes Rec. This transcript is only produced by type 2 HERV-K (HML-2) proviruses, which do not have the 292 nts deletion. Rec has 87 amino acids in common with ENV, corresponding to its first exon. The second exon starts in a different frame and therefore, the amino acid sequence is not shared with ENV. Transcript 4 is only produced by type 1 proviruses, which present a deletion of 292 nts in the POL-ENV junction. As a result, the SD2 site is lost, and an alternative SD (SDNP9) is used for the splicing. Due to this change only the first 14 amino-acids of NP9 are shared with ENV and Rec. (Garcia-Montojo M, Doucet-O'Hare T, Henderson L, Nath A. *Human endogenous retrovirus-K (HML-2): a comprehensive review. Crit Rev Microbiol.* 2018 November; 44 (6): 715-738).

Although the mechanism of pathogenicity is not entirely clear, it may be partly mediated by TDP-43 which has several putative binding sites on the LTR of HERV-K (HML-2). Signs of nucleolar dysfunction were also observed, as evidenced by redistribution of the nucleolar marker nucleophosmin into the cytoplasm of ENV-expressing neurons (Li W, Lee M H, Henderson L, Tyagi R, Bachani M, Steiner J, Campanac E, Hoffman D A, von Geldern G, Johnson K et al. 2015. *Human endogenous retrovirus-K contributes to motor neuron disease. Sci Transl Med* 7 (307).).

The protein HERV-K (HML-2) Env has shown to be neurotoxic by itself in vivo and in neuronal cultures. In cultures HERV-K (HML-2) Env toxicity to neurons was prevented by incubation with a monoclonal antibody against the protein (Steiner J P, Bachani M, Malik N, DeMarino C, Li W, Sampson K, Lee M H, Kowalak J, Bhaskar M, Doucet-O'Hare T, Garcia-Montojo M, Cowen M, Smith B, Reoma L B, Medina J, Brunel J, Pierquin J, Charvet B, Perron H, Nath A. *Human Endogenous Retrovirus K Envelope in Spinal Fluid of Amyotrophic Lateral Sclerosis Is Toxic. Ann Neurol.* 2022 October; 92 (4): 545-561). The possible neuroprotection shown by the natural immune response against HERV-K (HML-2) Env (Garcia-Montojo, M., Simula, E. R., Fathi, S., McMahan, C., Ghosal, A., Berry, J. D., Cudkowicz, M., Elkahloun, A., Johnson, K., Norato, G., Jensen, P., James, T., Sechi, L. A. and Nath, A. (2022), *Antibody Response to HML-2 May Be Protective in Amyotrophic Lateral Sclerosis. Ann Neurol,* 92:782-792) and the efficacy of monoclonal antibodies anti-HERV-K (HML-2) Env (Steiner J P, Bachani M, Malik N, DeMarino C, Li W, Sampson K, Lee M H, Kowalak J, Bhaskar M, Doucet-O'Hare T, Garcia-Montojo M, Cowen M, Smith B, Reoma L B, Medina J, Brunel J, Pierquin J, Charvet B, Perron H, Nath A. *Human Endogenous Retrovirus K Envelope in Spinal Fluid of Amyotrophic Lateral Sclerosis Is Toxic. Ann Neurol.* 2022 October; 92 (4): 545-561) indicate that triggering or potentiating a humoral response against this neurotoxic protein might be a therapeutic approach to treat ALS. This can be achieved by developing an epitope-specific active immunotherapy against the HERV-K (HML-2) Env protein using an Fc fusion-based vaccine. The vaccine is intended to create Th2 humoral immunity by boosting humoral responses to the HERV-K (HML-2) protein. Antibody against HERV-K (HML-2) Env that targets a conserved region not affected by glycosylation or by native conformation, may be useful in diagnostics and/or in therapy (EP3351265A1, "Anti-HERV-K envelope antibody and uses thereof", U.S. Pat. No. 10,981,977, "Anti-HERV-K envelope protein antibodies and methods for detecting HERV-K envelope protein in patients with sporadic amyotrophic lateral sclerosis", Geneuro & US Department of Health and Human Services).

For example, as shown in the Geneuro references, the murine monoclonal antibody (mAb) named GN_mAb_Env_K01 selectively binds to the SLDKHKHKKLQSFYP (SEQ ID NO: 17) linear epitope on the surface of the HERV-K-ENV protein (also referred to as the G01 epitope) (Steiner J P, Bachani M, Malik N, DeMarino C, Li W, Sampson K, Lee M H, Kowalak J, Bhaskar M, Doucet-O'Hare T, Garcia-Montojo M, Cowen M, Smith B, Reoma L B, Medina J, Brunel J, Pierquin J, Charvet B, Perron H, Nath A. *Human Endogenous Retrovirus K Envelope in Spinal Fluid of Amyotrophic Lateral Sclerosis Is Toxic. Ann Neurol.* 2022 October; 92 (4): 545-561). FIG. 7A, FIG. 7B, and FIG. 7C are a Clustal Omega amino acid sequence comparison showing the alignment of the full-length HERV-K (HML-2) Env consensus sequence (SEQ ID NO: 8) and the G01 epitope (SEQ ID NO: 17). GN_mAb_Env_K01 is a full-length antibody of the IgG2b/kappa murine subclass. GN_mAb_Env_01 biological activity has been confirmed by ELISA and Western Blotting immunoassays. GN_MAB_Env_K01 recognized the native and the denatured HERV-K-ENV protein, as well as the non-glycosylated and the glycosylated forms while a commercial anti-HERV-K-ENV antibody failed to detect the glycosylated form. The targeted epitope appeared to be highly conserved with a stable amino acid sequence encoded by HERV-K Env genes described in the databases which makes the epitope in the GN_mAb_Env_K01 mAb a key binding site useful for targeting HERV-K envelope proteins.

The present disclosure is directed to methods for making and using novel HERV-K (HML-2) Env based Fc fusion proteins (HERV-K (HML-2) Env analog-Fc fusion proteins) which allow for the cost-effective production of vaccines to cause a patient to produce antibodies against HERV-K (HML-2) (e.g., a patient's endogenously produced HERV-K (HML-2) envelope protein) with the effect of reducing the amount of HERV-K (HML-2) envelope protein present, in particular in the brain, spinal cord, and cerebrospinal fluid of the patient. The present disclosure is specifically directed to methods for making and using HERV-K (HML-2) Env analog-Fc fusion proteins for use as a therapeutic vaccine which is efficacious for causing patients to create anti-HERV-K (HML-2) Env antibodies to the HERV-K (HML-2) Env protein, for example to decrease the levels of HERV-K (HML-2) Env protein present, in particular in the brain, spinal cord, and cerebrospinal fluid of the patient or to prevent HERV-K (HML-2) from interacting with the CD98 receptor in order to reduce neurodegeneration symptoms associated with ALS. The present disclosure is directed to the specification of amino acid sequences comprising a HERV-K (HML-2) Env analog linked via a linker to an Fc fragment.

In an example, a pharmaceutical composition of a novel HERV-K (HML-2) Env analog-Fc fusion protein therapeutic or prophylactic vaccine is administered to patients requiring treatment for the pathogenesis of amyotrophic lateral sclerosis (ALS). In examples, the novel HERV-K (HML-2) Env analog-Fc fusion protein has the effect of stimulating the patient to produce humoral immunity, for example generating increased levels of IgG antibodies compared to an untreated patient, where the antibodies bind HERV-K (HML-2) Env protein in the body. When the immune system develops a robust antibody response to HERV-K (HML-2), excess levels of HERV-K (HML-2) are removed and may also be blocked from binding to cell-based HERV-K (HML-2) receptors (e.g., CD98 receptor-linked interactions), thereby alleviating neurodegeneration.

As previously noted, there are drawbacks with existing monoclonal antibody therapy treatments for the pathogenesis of amyotrophic lateral sclerosis (ALS), including side effects and the necessity of frequent administrations by injection. The dose volume can be large, increasing manufacturing costs and costs for patients and insurers. A therapeutic vaccine-based approach to neutralize HERV-K (HML-2) Env protein in the body to reduce levels of HERV-K (HML-2) stimulates the body to generate its own antibodies against the administered HERV-K (HML-2) Env analog-Fc fusion protein, which can then bind and neutralize the endogenously produced HERV-K (HML-2) Env protein. Because antibodies are produced endogenously, the frequency of treatment administration is significantly reduced. The immune system also may generate polyclonal antibodies in response to the vaccine, with the potential of providing a more robust response to endogenously-produced HERV-K (HML-2).

Clarification of Terminology

To aid understanding and provide context, certain terms and phrases are clarified below. These explanations are intended to assist the reader and should not be construed as limiting unless expressly stated otherwise.

As used herein, the articles "a" and "an" refer to one or more than one, e.g., to at least one of the grammatical objects of the article. The use of the words "a" or "an" when used in conjunction with the term "comprising" herein may mean "one," but it is also consistent with the meaning of "one or more," "at least one," and "one or more than one." As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

As used herein, "about" and "approximately" generally mean an acceptable degree of error for the quantity measured given the nature or precision of the measurements.

As used herein, an amount of a molecule, compound, conjugate, or substance effective to treat a disorder (e.g., a disorder described herein), "therapeutically effective amount," or "effective amount" generally means an amount of the molecule, compound, conjugate, or substance which is effective, upon single or multiple dose administration(s) to a patient, in treating a patient, or in curing, alleviating (e.g., alleviating associated symptoms of ALS), relieving or improving a patient with a condition or disorder (e.g., a disorder described herein) beyond that expected in the absence of such treatment.

As used herein, the term "analog" generally means a compound or conjugate (e.g., a compound or conjugate as described herein) having a chemical structure similar to that of another compound or conjugate but differing from it in at least one aspect.

As used herein, the term "antigen" or "antigenic agent" generally means any substance that causes a patient's immune system to produce an immune response (e.g., antibodies and/or T-cell responses) against it. An antigen may be a substance from the environment, such as chemicals, bacteria, viruses, or pollen, or an antigen may also be inside the body. In some cases, the antigen is endogenously-produced (e.g., a self-antigen). An example of a self-antigen is a HERV-K (HML-2) Env protein. An antigen (e.g., HERV-K (HML-2) Env) or an antigen analog (e.g., HERV-K (HML-2) Env analog) may also be covalently linked to another protein (e.g., an Fc fragment).

As used herein, the term "antibody" or "antibody molecule" generally means an immunoglobulin molecule (Ig), or immunologically active portions of an immunoglobulin (Ig) molecule, i.e., a molecule that contains an antigen binding site that specifically binds, e.g., immunoreacts with, an antigen or a self-antigen. As used herein, the term "antibody domain" generally means a variable or constant region of an immunoglobulin. It is documented in the art that antibodies comprise several classes, for example IgA, IgM, or IgG in the case of mammals (e.g., human). Classes of mammalian IgG immunoglobulins can be further classified into different isotypes, such as IgG1, IgG2, IgG3 and IgG4 for humans. Those skilled in the art will recognize that immunoglobulin isotypes of a given immunoglobulin class will comprise different amino acid sequences, structures, and functional properties from one another (e.g., different binding affinities to Fc (gamma) receptors or CD98 receptors). "Specifically binds" or "immunoreacts with" means that the antibody reacts with one or more antigenic determinants of the desired antigen and has a lower affinity for other polypeptides, e.g., does not react with other polypeptides.

As used herein, the term "HERV-K (HML-2) Env analog" includes a protein comprising a peptide derived from or consisting of all or a portion of a HERV-K (HML-2) Env protein locus, which may have none, one, or more than one amino acid deletions, mutations, or additions. For example, a HERV-K (HML-2) Env analog may be a HERV-K (HML-2) Env protein locus with no changes or mutations, a HERV-K (HML-2) Env protein locus comprising an additional peptide sequence combined with the HERV-K (HML-2) Env protein locus, or a HERV-K (HML-2) Env protein locus with none, one, or more than one amino acid deletions, mutations, or additions from the HERV-K (HML-2) Env protein locus.

In examples, a HERV-K (HML-2) Env analog may comprise a portion (e.g., a fragment) or truncated section of a HERV-K (HML-2) Env protein locus, which may have none, one, or more than one amino acid deletions, mutations, or additions. In examples, a HERV-K (HML-2) Env analog may comprise a portion of an artificial consensus sequence created based on two or more HERV-K (HML-2) Env protein loci, whereby the artificial consensus sequence includes common portions of the two or more HERV-K (HML-2) Env protein loci in addition to none, one, or more than one amino acid deletions, mutations, or additions. In examples, the HERV-K (HML-2) Env analog may be linked to an Fc fragment or analog thereof, as illustrated in FIG. 1.

As used herein, the term "dimer" generally means a protein or a fusion protein comprising two polypeptides linked covalently. In embodiments, two identical polypeptides are linked covalently (e.g., via disulfide bonds) forming a "homodimer" (diagrammatically represented in FIG. 1, which is an illustration of a HERV-K (HML-2) Env analog-Fc fusion protein homodimer). Referring to FIG. 1 in more detail, the HERV-K (HML-2) Env analog-Fc fusion protein polypeptide is connected via a linker to an Fc fragment. Disulfide bonds (the total number of disulfide bonds in actuality may be greater or less than the number shown in FIG. 1) create a homodimer from two identical Fc fusion proteins. The novel HERV-K (HML-2) Env analog-Fc fusion protein homodimer may be encoded by a single nucleic acid molecule, wherein the homodimer is made recombinantly inside a cell by first forming novel HERV-K (HML-2) Env analog-Fc fusion protein monomers and by then assembling two identical novel HERV-K (HML-2) Env analog-Fc fusion protein monomers into the homodimer upon further processing inside the cell.

As used herein, the terms "multimer," "multimeric," or "multimeric state" generally mean non-covalent, associated forms of Fc fusion protein dimers that may be in equilibrium with Fc fusion protein dimers or may act as permanently aggregated versions of Fc fusion protein dimers (e.g., dimers of Fc fusion protein homodimers, trimers of Fc fusion protein homodimers, tetramers of Fc fusion protein homodimers, or higher order aggregates containing five or more Fc fusion protein homodimers). It may be expected that multimeric forms of Fc fusion proteins may have different physical, stability, or pharmacologic activities from that of fusion protein homodimers.

As used herein, a "HERV-K (HML-2) Env analog-Fc fusion protein" and a "novel HERV-K (HML-2) Env analog-Fc fusion protein" (which terms may be interchangeably used) generally mean an immunoglobin Fc domain that is linked to a HERV-K (HML-2) Env analog, which is useful in generating antibodies that specifically bind to a HERV-K (HML-2) Env protein. For ease of reference, the term HERV-K (HML-2) Env encompasses protein residues consisting of fragments of one or more native HERV-K (HML-2) Env protein loci. As used herein, the general terms "fusion protein" and "Fc fusion protein" generally mean a protein comprising more than one part, for example from different sources (e.g., different proteins, polypeptides, cells, etc.), that are covalently linked through peptide bonds.

Immunoglobulins (Ig) or antibodies are glycoproteins produced by plasma cells, which have two light chains and two heavy chains in a light-heavy-heavy-light structure arrangement. The heavy chains differ among classes. They have one Fc region that mediates biological functions (e.g., the binding capacity to cellular receptors) and a Fab region containing antigen-binding sites.

B cells are instructed by specific immunogens to differentiate into plasma cells. Plasma cells are protein-making cells participating in humoral immune responses against bacteria, viruses, fungi, parasites, cellular antigens, chemicals, and synthetic substances. Immunoglobulins constitute about 20% of the protein in plasma.

IgG is a type of immunoglobulin in humans that is synthesized mostly in the secondary immune response to pathogens. The IgG antibodies are the main line of acquired defense and the main potentiator of a body's specific humoral response to pathogens in the host extracellular fluids, including blood, lymph and saliva. IgG is the only immunoglobulin that crosses the placenta as its Fc portion binds to the receptors present on the surface of the placenta. There are four subclasses of human IgG: IgG1, IgG2, IgG3, and IgG4 which are differentiated on the position of inter-chain disulfide bonds, the size of the hinge region and antigenic differences in structure of the heavy chain. IgG2 itself has further subclasses, including IgG2a and IgG2b, which have non-identical molecular forms.

The IgG1/IgG2a ratio is calculated as: IgG1 titer/IgG2a titer. A high IgG1/IgG2a ratio (>2) in mice typically means that the immune response will be Th2-biased. Thus, it will be characterized by a predominantly humoral immune response, promoting B cell proliferation and inducing anti-body production, and it will have less cellular immune response, which is promoted by Th1 cells. Reporting of IgG1/IgG2a ratios in mice to predict the type of response is common practice.

As used herein, the term "activity," "biological activity," "potency," "bioactive potency," or "biological potency" generally means the extent to which an Fc fusion protein binds to or activates a cell receptor and/or exerts the pro-duction or reduction of native or foreign substances. As used herein, "in vitro activity" or "receptor activity" generally means the affinity with which an Fc fusion protein binds to a cell receptor and is typically measured by the concentra-tion of an Fc fusion protein that causes the Fc fusion protein to reach half of its maximum binding (i.e., EC50 value).

As used herein, the term "biosynthesis," "recombinant synthesis," or "recombinantly made" generally means the process by which an Fc fusion protein is expressed within a host cell by transfecting the cell with a nucleic acid molecule (e.g., vector) encoding the Fc fusion protein (e.g., where the entire Fc fusion protein is encoded by a single nucleic acid molecule). Exemplary host cells include mammalian cells, e.g., CHO cells or HEK293 cells. The cells can be cultured using standard methods in the art and the expressed Fc fusion protein may be harvested and purified from the cell culture using standard methods in the art.

As used herein, the term "cell surface receptor" generally means a molecule such as a protein, generally found on the external surface of the membrane of a cell and which interacts with soluble molecules, e.g., molecules that circu-late in the blood supply. In some embodiments, a cell surface receptor may include a host cell receptor or an Fc receptor which binds to an Fc fragment or the Fc region of an antibody (e.g., an Fc (gamma) receptor, for example Fc (gamma) receptor I or an Fc neonatal receptor, for example FcRn). As used herein, "in vitro activity" or "Fc (gamma) receptor activity" or "Fc (gamma) receptor binding" or "FcRn receptor activity" or "FcRn binding" generally means the affinity with which an Fc fusion protein binds to the Fc receptor (e.g., Fc (gamma) receptor or FcRn receptor) and is typically measured by the concentration of an Fc fusion protein that causes the Fc fusion protein to reach half of its maximum binding (i.e., EC50 value) as measured on an assay (e.g., an enzyme-linked immunosorbent assay (ELISA) assay) using OD 450 nm values as measured on a microplate reader.

As used herein, the term "immunogenic" or "immunoge-nicity" generally means the capacity for a given molecule or antigen (e.g., an Fc fusion protein of the present invention) to provoke the immune system of a target patient such that after administration of the molecule, the patient develops antibodies capable of binding to all or specific portions of the molecule (i.e., anti-drug antibodies or ADA). In patients, the antibody development may be polyclonal (e.g., a mixture of antibodies capable of binding an Fc fusion protein). As used herein, the terms "neutralizing," "neutralizing antibod-ies", or "neutralizing anti-drug antibodies" generally mean the capacity for antibodies developed against an Fc fusion protein (e.g., an antigen or antigen analog-Fc fusion protein) to cross-react, bind and interfere with all or a portion of the self-antigen's biological activity in the target patient.

For example, in the case of a novel HERV-K (HML-2) Env analog-Fc fusion protein molecule (or a pharmaceutical composition thereof) administered to patients, the immuno-genicity generally means antibodies that bind to the HERV-K (HML-2) Env portion of the HERV-K (HML-2) Env analog-Fc fusion protein but then also cross-react, bind and interfere (e.g., neutralize) with the activity of endog-enously produced HERV-K (HML-2) at a cell surface recep-tor (e.g., a HERV-K (HML-2) receptor, for example a CD98 receptor). Likewise, antibodies generated by the adminis-tration of a novel HERV-K (HML-2) Env analog-Fc fusion protein molecule (or a pharmaceutical composition thereof) are neutralizing when those anti-HERV-K (HML-2) Env antibodies inhibit the binding between an endogenously produced protein (e.g., native HERV-K (HML-2) Env pro-tein) in a patient and a patient's host cells, which is directly related to the bioactivity of endogenously produced HERV-K (HML-2) in the patient.

As used herein, the term "immunogenic composition" generally means a pharmaceutical composition or mixture of substances comprising an immunogenic molecule, antigen or agent, that is suitable for administering to a patient. For example, an immunogenic composition may comprise a HERV-K (HML-2) Env analog-Fc fusion protein and a sterile aqueous solution or adjuvant or another carrier.

As used herein, the term "monomer" generally means a protein or a fusion protein comprising a single polypeptide. In embodiments, the "monomer" is a protein or a fusion protein, e.g., a single polypeptide, comprising a HERV-K (HML-2) Env analog polypeptide and an Fc fragment poly-peptide, wherein the HERV-K (HML-2) Env fragment and Fc fragment polypeptides are joined by peptide bonds via a linker to form the single polypeptide. In embodiments, the monomer is encoded by a single nucleic acid molecule.

As used herein and as illustrated in FIG. 1, "N-terminus" generally means the start of a protein or polypeptide that is initiated by an amino acid containing a free amine group that is the alpha-amino group of the amino acid (e.g., the free amino that is covalently linked to one carbon atom that is located adjacent to a second carbon atom, wherein the second carbon atom is part of the carbonyl group of the amino acid). As used herein and as illustrated in FIG. 1, "C-terminus" generally means the end of a protein or polypeptide that is terminated by an amino acid containing a carboxylic acid group, wherein the carbon atom of the carboxylic acid group is located adjacent to the alpha-amino group of the amino acid.

As used herein, the term "carrier" is used herein to include diluents, excipients, vehicles, and the like, in which the Fc fusion protein(s) may be dispersed, emulsified, or encapsu-lated for administration. Suitable carriers will be pharma-ceutically acceptable. As used herein, the term "pharmaceu-tically acceptable" means not biologically or otherwise undesirable, in that it can be administered to a patient without excessive toxicity, irritation, or allergic response, and does not cause unacceptable biological effects or inter-act in a deleterious manner with any of the other components of the composition in which it is contained. A pharmaceu-tically acceptable carrier would naturally be selected to minimize any degradation of the compound or other agents and to minimize any adverse side effects in the patient, as would be well known to one of skill in the art. Pharmaceutically acceptable ingredients include those acceptable for veterinary use as well as human pharmaceutical use and will depend on the route of administration. Any carrier compatible with the excipient(s) and the Fc fusion protein(s) can be used. In example, an adjuvant may be considered one type or subclass of carrier.

As used herein, "pharmacodynamics" or "PD" generally generally means the biological effects of an Fc fusion protein in a patient. As an example, herein, the PD of a novel HERV-K (HML-2) Env analog-Fc fusion protein generally means the measure of the anti-HERV-K (HML-2) Env antibody titers over time in a patient after the administration of the novel HERV-K (HML-2) Env analog-Fc fusion protein.

As used herein, "pharmacokinetics" or "PK" generally means the characteristic interactions of an Fc fusion protein and the body of the patient in terms of its absorption, distribution, metabolism, and excretion. As an example, herein, the PK generally means the concentration of a novel HERV-K (HML-2) Env analog-Fc fusion protein in the blood or serum of a patient at a given time after the administration of the novel HERV-K (HML-2) Env analog-Fc fusion protein. As used herein, "half-life" generally means the time taken for the concentration of Fc fusion protein in the blood or serum of a patient to reach half of its original value as calculated from a first order exponential decay model for drug elimination. Fc fusion proteins with greater "half-life" values demonstrate greater duration of action in the target patient.

The terms "sequence identity," "sequence homology," "homology," or "identical" in amino acid or nucleotide sequences as used herein describes that the same nucleotides or amino acid residues are found within the variant and reference sequences when a specified, contiguous segment of the nucleotide sequence or amino acid sequence of the variant is aligned and compared to the nucleotide sequence or amino acid sequence of the reference sequence. Methods for sequence alignment and for determining identity between sequences are known in the art, including the use of Clustal Omega, which organizes, aligns, and compares sequences for similarity, wherein the software highlights each sequence position and compares across all sequences at that position and assigns one of the following scores: an "*" (asterisk) for sequence positions which have a single, fully conserved residue, a ":" (colon) indicates conservation between groups of strongly similar properties with scoring greater than 0.5 in the Gonnet PAM 250 matrix, and a "." (period) indicates conservation between groups of weakly similar properties with scoring less than or equal to 0.5 in the Gonnet PAM 250 matrix, a "-" (dash) indicates a sequence gap, meaning that no local homology exists within a particular set of comparisons within a certain range of the sequences, and an empty space " " indicates little or no sequence homology for that particular position across the compared sequences.

With respect to optimal alignment of two nucleotide sequences, the contiguous segment of the variant nucleotide sequence may have additional nucleotides or deleted nucleotides with respect to the reference nucleotide sequence. Likewise, for purposes of optimal alignment of two amino acid sequences, the contiguous segment of the variant amino acid sequence may have additional amino acid residues or deleted amino acid residues with respect to the reference amino acid sequence. In some embodiments, the contiguous segment used for comparison to the reference nucleotide sequence or reference amino acid sequence will comprise at least 6, 10, 15, or 20 contiguous nucleotides, or amino acid residues, and may be 30, 40, 50, 100, or more nucleotides or amino acid residues. Corrections for increased sequence identity associated with inclusion of gaps in the variant's nucleotide sequence or amino acid sequence can be made by assigning gap penalties. Methods of sequence alignment are known in the art.

In embodiments, the determination of percent identity or "homology" between two sequences is accomplished using a mathematical algorithm. For example, the percent identity of an amino acid sequence is determined using the Smith-Waterman homology search algorithm using an affine 6 gap search with a gap open penalty of 12 and a gap extension penalty of 2, BLOSUM matrix 62. In embodiments, the percent identity of a nucleotide sequence is determined using the Smith-Waterman homology search algorithm using a gap open penalty of 25 and a gap extension penalty of 5. Such a determination of sequence identity can be performed using, for example, the DeCypher Hardware Accelerator from TimeLogic.

As used herein, the term "homology" is used to compare two or more proteins by locating common structural characteristics and common spatial distribution of, for instance, beta strands, helices, and folds. Accordingly, homologous protein structures are defined by spatial analyses. Measuring structural homology involves computing the geometric-topological features of a space. One approach used to generate and analyze three-dimensional (3D) protein structures is homology modeling (also called comparative modeling or knowledge-based modeling) which works by finding similar sequences on the basis of the fact that 3D similarity reflects 2D similarity. Homologous structures do not imply sequence similarity as a necessary condition.

As used herein, the terms "subject" and "patient" are intended to include mice, primates and humans. Exemplary human subjects or patients include people having a disease or a disorder, e.g., amyotrophic lateral sclerosis (ALS) or another disease or disorder described herein, or normal subjects.

As used herein, the term "yield" generally means the amount of a fusion protein product (e.g., an Fc fusion protein described herein) resulting from the biosynthesis (e.g., in a mammalian cell, e.g., in a HEK293 cell or CHO cell) per volume of the cell culture. The amount of product may be determined at any step of the production process (e.g., before or after purification), but the yield is always stated per volume of the original cell culture. As used herein, the term "product yield" or "total protein yield" generally means the total amount of Fc fusion protein expressed by cells and purified via at least one affinity chromatography step (e.g., Protein A or Protein G) and includes monomers of Fc fusion protein, homodimers of Fc fusion protein, and higher-order molecular aggregates of homodimers of Fc fusion protein. As used herein, the term "percent homodimer" or "% homodimer" generally means the proportion of a fusion protein product (e.g., an Fc fusion protein described herein) that is the desired homodimer. As used herein, the term "homodimer yield" generally means the product of the % homodimer and the total protein yield after Protein A purification step reported per volume of the cell culture.

As used herein, the terms "treat" or "treating" or "treatment" of a patient having a disease or a disorder generally means an intervention performed with the intention of mitigating or preventing symptoms (for example, by preventing motor neuron degeneration and cell death in ALS) associated with the condition or disease (for example but not limited to muscular weakness, paralysis and respiratory failure), and/or reducing the duration of symptoms associated with the condition or disease. Accordingly, "treatment" generally means both therapeutic treatment and prophylactic or preventative measures. Improvement after treatment may be manifested as a decrease or elimination of such symptoms, e.g., by a decrease or elimination of symptoms associated with ALS, and/or by a decrease in the duration of such symptoms, and/or by affecting the biomarkers associated with the pathology As an example, the compositions described herein are useful in treating symptoms associated with ALS. Treating a patient having a condition or disease may include subjecting the patient with the condition or disease to a treatment regimen, for example the administration of a fusion protein such as a HERV-K (HML-2) Env analog-Fc fusion protein described herein, or a pharmaceutical composition of a fusion protein such as a HERV-K (HML-2) Env analog-Fc fusion protein described herein, such that a symptom or biomarker associated with the condition or disease is reduced, alleviated, relieved, altered, remedied, ameliorated, or improved. Treating includes administering an amount of a fusion protein such as a HERV-K (HML-2) Env analog-Fc fusion protein described herein, or a pharmaceutical composition of a fusion protein such as a HERV-K (HML-2) Env analog-Fc fusion protein described herein that is effective to reduce, alleviate, relieve, alter, remedy, ameliorate, or improve a symptom associated with the condition or disease. Treating includes administering an amount effective to generate antibodies to an antigen (in this case HERV-K (HML-2)) in a patient that has a condition or disease with the intention of generating antibodies targeted to HERV-K (HML-2) (the antigen) to reduce the antigen and hence the severity or duration of a symptom associated with the disease or disorder.

As used herein, a "therapeutic vaccine" generally means a treatment that introduces an antigen or antigen analog into a patient that has a condition or disorder associated with a self-antigen, with the goal that the patient's immune system will create antibodies for the antigen or antigen analog, enabling the patient's body to reduce the level of the self-antigen and have an ameliorating effect on symptoms of the condition or disorder that are associated with the self-antigen (for example, symptoms associated with ALS).

As used herein, a "prophylactic vaccine" or "prophylactic immunization" or "preventative vaccine" generally means the artificial establishment of specific immunity through the introduction of antigens into a patient that is not necessarily suffering with the symptoms of a condition or disorder, with the goal that the patient's immune system will create antibodies against the antigen and thereby prevent any future suffering or increase in suffering with the symptoms of the disorder. The distinction between a prophylactic vaccine and a therapeutic vaccine, is that a therapeutic vaccine is typically administered to a patient that is already suffering from the symptoms that the immunity targets, and a prophylactic vaccine is typically administered to a patient in anticipation of the patient suffering from the symptoms that the immunity targets.

As used herein, "booster vaccine" generally means an extra administration of a vaccine after the patient has previously received an initial administration of a vaccine, or after a patient has acquired antibodies (i.e., has a measurable antibody titer) through having had a previous treatment which introduced antibodies to reduce the symptoms of the condition or disease, or having had previous exposure to the antigen. In some examples, an additional dose of a vaccine is beneficial periodically to "boost" the immunity of a patient to an antigen, by increasing the patient's antigen antibody titer, which in turn ameliorates the symptoms caused by the antigen.

As used herein, the phrase "effective amount" or "therapeutically effective amount" generally means a therapeutic or prophylactic amount of the HERV-K (HML-2) Env analog-Fc fusion protein of the present disclosure or pharmaceutical composition thereof, that elicits the desired therapeutic or prophylactic effect or response in stimulating the immune system of the patient to generate antibodies, as evidenced by the alleviation of some or all of such symptoms of the condition or disease, when administered in accordance with the desired treatment regimen. In examples, where the desired therapeutic or prophylactic effect or response is to alleviate symptoms of a condition or disease, an amount of a HERV-K (HML-2) Env analog-Fc fusion protein of the present disclosure or pharmaceutical composition thereof may be considered therapeutically effective if symptoms and/or effects of the condition or disease are observably reduced in the patient after the treatment regime. The therapeutically effective dosage of a HERV-K (HML-2) Env analog-Fc fusion protein may vary depending on the size and species of the patient, and/or according to the mode of administration.

As used herein, a linker links or connects a HERV-K (HML-2) Env analog to an IgG1 Fc fragment (SEQ ID NO: 1). Either a short linker (an example of which is GGGSGGGS, SEQ ID NO: 2) or a long linker (an example of which is GGGGGSGGGGSGGGGSGGGGGS, SEQ ID NO: 3) is used.

As used herein, when referring to an amino acid in some portion of an amino acid sequence, for example a HERV-K (HML-2) Env analog amino acid sequence, a cited amino acid position is referenced as the position of the amino acid counting from the beginning of the amino acid sequence itself. For example, consider the amino acid sequence of the HERV-K (HML-2) Env consensus sequence of SEQ ID NO: 8.

```
                                              (SEQ ID NO: 8)
MNPSEMQRKAPPRRRRHRNRAPLTHKMNKMVTSEEQMKLPSTKKAEPPTW

AQLKKLTQLATKYLENTKVTQTPESMLLAALMIVSMVVSLPMPAGAAAAN

YTYWAYVPFPPLIRAVTWMDNPIEVYVNDSVWVPGPIDDRCPAKPEEEGM

MINISIGYRYPPICLGRAPGCLMPAVQNWLVEVPTVSPISRFTYHMVSGM

SLRPRVNYLQDFSYQRSLKFRPKGKPCPKEIPKESKNTEVLVWEECVANS

AVILQNNEFGTIIDWAPRGQFYHNCSGQTQSCPSAQVSPAVDSDLTESLD

KHKHKKLQSFYPWEWGEKGISTPRPKIISPVSGPEHPELWRLTVASHHIR

IWSGNQTLETRDRKPFYTVDLNSSLTVPLQSCVKPPYMLVVGNIVIKPDS

QTITCENCRLLTCIDSTFNWQHRILLVRAREGVWIPVSMDRPWEASPSIH

ILTEVLKGVLNRSKRFIFTLIAVIMGLIAVTATAAVAGVALHSSVQSVNF

VNDWQKNSTRLWNSQSSIDQKLANQINDLRQTVIWMGDRLMSLEHRFQLQ

CDWNTSDFCITPQIYNESEHHWDMVRRHLQGREDNLTLDISKLKEQIFEA

SKAHLNLVPGTEAIAGVADGLANLNPVTWVKTIGSTTIINLILILVCLFC

LLLVCRCTQQLRRDSDHRERAMMTMAVLSKRKGGNVGKSKRDQIVTVSV.
```

A mutation of the first serine amino acid of this sequence would be described as a mutation of the 4th amino acid of the sequence. For example, if the first serine amino acid in SEQ ID NO: 8 were mutated to threonine, this could be referred to as an S4T mutation of SEQ ID NO: 8.

As used herein, an "ailment" generally means a HERV-K-(HML-2)-related disease or disorder that is associated with HERV-K (HML-2).

Novel HERV-K (HML-2) Env Analog-Fc Fusion Proteins

Aberrant expression and/or overexpression of HERV-K (HML-2) in adult tissues has been associated with many types of cancer (including, but not limited to, teratocarcinoma, germ cell tumors, melanoma, breast cancer, glioblastoma, ovarian cancer, and prostate cancer), various features of malignant cells (e.g., tumors), and neurodegenerative or central nervous system (CNS) diseases, especially including, but not limited to, amyotrophic lateral sclerosis (ALS) and frontotemporal dementia.

HERV-K (HML-2) envelope (Env) protein has four different domains. The full-length HERV-K (HML-2) Env protein consensus sequence (Dewannieux M, Harper F, Richaud A, Letzelter C, Ribet D, Pierron G, Heidmann T. *Identification of an infectious progenitor for the multiple-copy HERV-K human endogenous retroelements. Genome Res.* 2006 December; 16 (12): 1548-56.) is shown below as SEQ ID NO: 8.

```
                                        (SEQ ID NO: 8)
MNPSEMQRKAPPRRRRHRNRAPLTHKMNKMVTSEEQMKLPSTKKAEPPTW

AQLKKLTQLATKYLENTKVTQTPESMLLAALMIVSMVVSLPMPAGAAAAN

YTYWAYVPFPPLIRAVTWMDNPIEVYVNDSVWVPGPIDDRCPAKPEEEGM

MINISIGYRYPPICLGRAPGCLMPAVQNWLVEVPTVSPISRFTYHMVSGM

SLRPRVNYLQDFSYQRSLKFRPKGKPCPKEIPKESKNTEVLVWEECVANS

AVILQNNEFGTIIDWAPRGQFYHNCSGQTQSCPSAQVSPAVDSDLTESLD

KHKHKKLQSFYPWEWGEKGISTPRPKIISPVSGPEHPELWRLTVASHHIR

IWSGNQTLETRDRKPFYTVDLNSSLTVPLQSCVKPPYMLVVGNIVIKPDS

QTITCENCRLLTCIDSTFNWQHRILLVRAREGVWIPVSMDRPWEASPSIH

ILTEVLKGVLNRSKRFIFTLIAVIMGLIAVTATAAVAGVALHSSVQSVNF

VNDWQKNSTRLWNSQSSIDQKLANQINDLRQTVIWMGDRLMSLEHRFQLQ

CDWNTSDFCITPQIYNESEHHWDMVRRHLQGREDNLTLDISKLKEQIFEA

SKAHLNLVPGTEAIAGVADGLANLNPVTWVKTIGSTTIINLILILVCLFC

LLLVCRCTQQLRRDSDHRERAMMTMAVLSKRKGGNVGKSKRDQIVTVSV.
```

The full-length signal peptide domain of the consensus sequence of SEQ ID NO: 8 is shown below as SEQ ID NO: 4.

```
                                        (SEQ ID NO: 4)
MNPSEMQRKAPPRRRRHRNRAPLTHKMNKMVTSEEQMKLPSTKKAEPPTW

AQLKKLTQLATKYLENTKVTQTPESMLLAALMIVSMVVS.
```

The full-length extracellular domain of the consensus sequence of SEQ ID NO: 8 is shown below as SEQ ID NO: 5.

```
                                        (SEQ ID NO: 5)
LPMPAGAAAANYTYWAYVPFPPLIRAVTWMDNPIEVYVNDSVWVPGPIDD

RCPAKPEEEGMMINISIGYRYPPICLGRAPGCLMPAVQNWLVEVPTVSPI
```

```
-continued
SRFTYHMVSGMSLRPRVNYLQDFSYQRSLKFRPKGKPCPKEIPKESKNTE

VLVWEECVANSAVILQNNEFGTIIDWAPRGQFYHNCSGQTQSCPSAQVSP

AVDSDLTESLDKHKHKKLQSFYPWEWGEKGISTPRPKIISPVSGPEHPEL

WRLTVASHHIRIWSGNQTLETRDRKPFYTVDLNSSLTVPLQSCVKPPYML

VVGNIVIKPDSQTITCENCRLLTCIDSTFNWQHRILLVRAREGVWIPVSM

DRPWEASPSIHILTEVLKGVLNRSKRFIFTLIAVIMGLIAVTATAAVAGV

ALHSSVQSVNFVNDWQKNSTRLWNSQSSIDQKLANQINDLRQTVIWMGDR

LMSLEHRFQLQCDWNTSDFCITPQIYNESEHHWDMVRRHLQGREDNLTLD

ISKLKEQIFEASKAHLNLVPGTEAIAGVADGLANLNPVTWVKT.
```

The full-length transmembrane domain of the consensus sequence of SEQ ID NO: 8 is shown below as SEQ ID NO: 6.

```
                                        (SEQ ID NO: 6)
IGSTTIINLILILVCLFCLLL.
```

The full-length cytoplasmic domain of the consensus sequence of SEQ ID NO: 8 is shown below as SEQ ID NO: 7.

```
                                        (SEQ ID NO: 7)
VCRCTQQLRRDSDHRERAMMTMAVLSKRKGGNVGKSKRDQIVTVSV.
```

FIG. 3A, FIG. 3B, FIG. 3C, and FIG. 3D are a Clustal Omega amino acid sequence comparison showing the alignments of the full-length signal peptide domain (SEQ ID NO: 4), full-length extracellular domain (SEQ ID NO: 5), full-length transmembrane domain (SEQ ID NO: 6), and full-length cytoplasmic domain (SEQ ID NO: 7) of the HERV-K (HML-2) Env consensus sequence with the full-length HERV-K (HML-2) Env consensus sequence (SEQ ID NO: 8). As is apparent from the sequence comparison, SEQ ID NO: 8 is equivalent to the concatenation of SEQ ID NO: 4, SEQ ID NO: 5, SEQ ID NO: 6, and SEQ ID NO: 7.

HERV-K (HML-2) Env has several loci in the human genome that have open reading frames capable of producing an intact Env protein. The sequences that have been identified in practice are listed below.

The 6q14.1 K109 full-length HERV-K Env sequence (UniProt: Q9UKH3) is shown below as SEQ ID NO: 9.

```
                                        (SEQ ID NO: 9)
MNPSEMQRKAPPRRRRHRNRAPLTHKMNKMVTSEEQMKLPSTKKAEPPTW

AQLKKLTQLATKYLENTKVTQTPESMLLAALMIVSMVVSLPMPAGAAAAN

YTNWAYVPFPPLIRAVTWMDNPIEVYVNDSVWVPGPIDDRCPAKPEEEGM

MINISIGYRYPICLGRAPGCLMPAVQNWLVEVPIVSPICRFTYHMVSGMS

LRPRVNYLQDFSYQRSLKFRPKGKPCPKEIPKESKNTEVLVWEECVANSA

VILQNNEFGTIIDWTPQGQFYHNCSGQTQSCPSAQVSPAVDSDLTESLDK

HKHKKLQSFYPWEWGEKGISTPRPKIISPVSGPEHPELWRLTVASHHIRI

WSGNQTLETRDRKPFYTVDLNSSLTLPLQSCVKPPYMLVVGNIVIKPDSQ

TITCENCRLLTCIDSTFNWQHRILLVRAREGVWIPVSMDRPWEASPSIHI

LTEVLKGVLNRSKRFIFTLIAVIMGLIAVTATAAVAGVALHSSVQSVNFV
```

25

-continued

NDGQKNSTRLWNSQSSIDQKLANQINDLRQTVIWMGDRLMSLEHRFQLQC

DWNTSDFCITPQIYNESEHHWDMVRRHLQGREDNLTLDISKLKEQIFEAS

KAHLNLVPGTEAIAGVADGLANLNPVTWVKTIGSTTIINLILILVCLFCL

LLVCRCTQQLRRDSDHRERAMMTMAVLSKRKGGNVGKSKRDQIVTVSV.

The 7p22.1 (ERK6, K108, K (HML.2-HOM), K (C7)) (7p22.1a and 7p22.1b) full-length HERV-K Env sequence (UniProt: Q69384) is shown below as SEQ ID NO: 10.

(SEQ ID NO: 10)
MNPSEMQRKAPPRRRRHRNRAPLTHKMNKMVTSEEQMKLPSTKKAEPPT

WAQLKKLTQLATKYLENTKVTQTPESMLLAALMIVSMVVSLPMPAGAAA

ANYTYWAYVPFPPLIRAVTWMDNPTEVYVNDSVWVPGPIDDRCPAKPEE

EGMMINISIGYHYPPICLGRAPGCLMPAVQNWLVEVPTVSPICRFTYHM

VSGMSLRPRVNYLQDFSYQRSLKFRPKGKPCPKEIPKESKNTEVLVWEE

CVANSAVILQNNEFGTIIDWAPRGQFYHNCSGQTQSCPSAQVSPAVDSD

LTESLDKHKHKKLQSFYPWEWGEKGISTPRPKIVSPVSGPEHPELWRLT

VASHHIRIWSGNQTLETRDRKPFYTIDLNSSLTVPLQSCVKPPYMLVVG

NIVIKPDSQTITCENCRLLTCIDSTFNWQHRILLVRAREGVWIPVSMDR

PWEASPSVHILTEVLKGVLNRSKRFIFTLIAVIMGLIAVTATAAVAGVA

LHSSVQSVNFVNDWQKNSTRLWNSQSSIDQKLANQINDLRQTVIWMGDR

LMSLEHRFQLQCDWNTSDFCITPQIYNESEHHWDMVRRHLQGREDNLTL

DISKLKEQIFEASKAHLNLVPGTEAIAGVADGLANLNPVTWVKTIGSTT

IINLILILVCLFCLLLVCRCTQQLRRDSDHRERAMMTMAVLSKRKGGNV

GKSKRDQIVTVSV.

The 8p23.1a (K27, K115) full-length HERV-K Env sequence (UniProt: Q902F8) is shown below as SEQ ID NO: 11.

(SEQ ID NO: 11)
MNPSEMQRKAPPRRRRHRNRAPLTHKMNKMVTSEEQMKLPSTKKAEPPT

WAQLKKLTQLATKYLENTKVTQTPESMLLAALMIVSMVVSLPMPAGAAV

ANYTNWAYVPFPPLIRAVTWMDNPIEVYVNDSVWVPGPIDDRCPAKPEE

EGMMINISIGYRYPPICLGRAPGCLMPAVQNWLVEVPTVSPISRFTYHM

VSGMSLRPRVNYLQDFSYQRSLKFRPKGKPCPKEIPKESKNTEVLVWEE

CVANSAVILQNNEFGTIIDWAPRGQFYHNCSGQTQSCPSAQVSPAVDSD

LTESLDKHKHKKLQSFYPWEWGEKRISTPRPKIVSPVSGPEHPELWRLT

VASHHIRIWSGNQTLETRDRKPFYTVDLNSSLTLPLQSCVKPPYMLVVG

NIVIKPDSQTITCENCRLLTCIDSTFNWQHRILLVRAREGVWIPVSMDR

PWEASPSVHILTEVLKGVLNRSKRFIFTLIAVIMGLIAVTATAAVAGVA

LHSSVQSVNFVNDGQKNSTRLWNSQSSIDQKLANQINDLRQTVIWMGDR

LMSLEHRFQLQCDWNTSDFCITPQIYNDSEHHWDMVRRHLQGREDNLTL

DISKLKEQIFEASKAHLNLVPGTEAIAGVADGLANLNPVTWVKTIGSTT

IINLILILVCLFCLLLVCRCTQQLRRDSDHRERAMMTMAVLSKRKGGNV

GKSKRDQIVTVSV.

26

The 11q22.1 (K (C11c), K36, K118, ERVK-25) full-length HERV-K Env sequence (UniProt: P61570) is shown below as SEQ ID NO: 12.

(SEQ ID NO: 12)
MNPSEMQRKAPPRRRRHRNRAPLTHKMNKMVTSEEQMKLPSTKKAEPPT

WAQLKKLTQLATKYLENTKVTQTPESMLLAALMIVSMVVSLPMPAGAAA

ANYTYWAYVPFPPLIRAVTWMDNPIEVYVNDSVWVPGPIDDRCPAKPEE

EGMMINISIGYRYPPICLGTAPGCLMPAVQNWLVEVPIVSPISRFTYHM

VSGMSLRPRVNYLQDFSYQRSLKFRPKGKPCPKEIPKESKNTEVLVWEE

CVANSAVILQNNEFGTIIDWAPRGQFYHNCSGQTQSCPSAQVSPAVDSD

LTESLDKHKHKKLQSFYPWEWGEKGISTPRPKIVSPVSGPEHPELWRLT

VASHHIRIWSGNQTLETRDRKPFYTVDLNSSLTVPLQSCVKPPYMLVVG

NIVIKPDSQTITCENCRLLTCIDSTFNWQHRILLVRAREGVWIPVSMDR

PWEASPSIHILTEVLKGVLNRSKRFIFTLIAVIMGLIAVTATGAVAGVA

LHSSVQSVNFVNDWQKNSTRLWNSQSSIDQKLANQINDLRQTVIWMGDR

LMSLEHRFQLQCDWNTSDFCITPQIYNESEHHWDMVRRHLQGREDNLTL

DISKLKEQIFKASKAHLNLVPGTEAIAGVADGLANLNPVTWVKTIGSTT

IINLILILVCLFCLLLVCRCTQQL.

The 12q14.1 (K (C12), K41, K119, ERVK-21) full-length HERV-K Env sequence (UniProt: P61565) is shown below as SEQ ID NO: 13.

(SEQ ID NO: 13)
MHPSEMQRKAPPRRRRHRNRAPLTHKMNKMVTSEQMKLPSTKKAEPPTW

AQLKKLTQLATKYLENTKVTQTPESMLLAALMIVSMVVSLPMPAGAAAA

NYTNWAYVPFPPLIRAVTWMDNPIEVYVNDSVWVHGPIDDRCPAKPEEE

GMMINISIGYHYPPICLGRAPGCLMPAVQNWLVEVPTVSPISRFTYNMV

SGMSLRPRVNYLQDFSYQRSLKFRPKGKPCPKEIPKESKNTEVLVWEEC

VANSVVILQNNEFGTIIDWAPRGQFYHNCSGQTQSCPSAQVSPAVDSDL

TESLDKHKHKKLQSFYPWEWGEKGISTPRPKIISPVSGPEHPELWRLTV

ASHHIRIWSGNQTLETRDRKPFYTVDLNSSLTVPLQSCVKPPYMLVVGN

IVIKPDSQTITCENCRLLTCIDSTFNWQHRILLVRAREGVWIPVSMDRP

WEASPSIHILTEVLKGVLNRSKRFIFTLIAVIMGLIAVTAMAAVAGVAL

HSFVQSVNFVNDWQKNSTRLWNSQSSIDQKLANQINDLRQTVIWMGDRL

MSLEHRFQLQCDWNTSDFCITPQIYNESEHHWDMVRRHLQGREDNLTLD

ISKLKEQIFEASKAHLNLVPGTEAIAGVADGLANLNPVTWVKTIGSTTI

INLILILVCLFCLLLVCRCTQQLRRDSDHRERAMMTMVVLSKRKGGNVG

KSKRDQIVTVSV.

The 19p12b (K113) full-length HERV-K Env sequence (UniProt: Q902F9) is shown below as SEQ ID NO: 14.

(SEQ ID NO: 14)
MNPSEMQRKAPPRRRRHRNRAPLTHKMNKMVTSEEQMKLPSTKKAEPPT

WAQLKKLTQLATKYLENTKVTQTPESMLLAALMIVSMVVSLPMPAGAAA

-continued
ANYTYWAYVPFPPLIRAVTWMDNPIEIYVNDSVWVPGPTDDCCPAKPEE

EGMMINISIGYRYPPICLGRAPGCLMPAVQNWLVEVPTVSPISRFTYHM

VSGMSLRPRVNYLQDFSYQRSLKFRPKGKPCPKEIPKESKNTEVLVWEE

CVANSAVILQNNEFGTLIDWAPRGQFYHNCSGQTQSCPSAQVSPAVDSD

LTESLDKHKHKKLQSFYPWEWGEKGISTARPKIISPVSGPEHPELWRLT

VASHHIRIWSGNQTLETRDRKPFYTIDLNSSLTVPLQSCVKPPYMLVVG

NIVIKPDSQTITCENCRLLTCIDSTFNWQHRILLVRAREGVWIPVSMDR

PWEASPSVHILTEVLKGVLNRSKRFIFTLIAVIMGLIAVTATAAVAGVA

LHSSVQSVNFVNDWQNNSTRLWNSQSSIDQKLANQINDLRQTVIWMGDR

LMSLEHRFQLQCDWNTSDFCITPQIYNESEHHWDMVRCHLQGREDNLTL

DISKLKEQIFEASKAHLNLVPGTEAIAGVADGLANLNTVTWVKTIGSTT

IINLILILVCLFCLLLVYRCTQQLRRDSDHRERAMMTMVVLSKRKGGNV

GKSKRDQIVTVSV.

The 19q11 (K (C19), ERVK-19) full-length HERV-K Env sequence (UniProt: O71037) is shown below as SEQ ID NO: 15.

(SEQ ID NO: 15)
MNPSEMQRKAPPRRRRHRNRAPLTHKMNKMVTSEEQMKLPSTKKAEPPT

WAQLKKLTQLATKYLENTKVTQTPESMLLAALMIVSMVVSLPMPAGAAA

ANYTYWAYVPFPPLIRAVTWMDNPIEVYVNDSVWVPGPTDDHCPAKPEE

EGMMINISIGYRYPPICLGRAPGCLMPAVQNWLVEVPTVSPISRFTYHM

VSGMSLRPRVNYLQDFSYQRSFKFRPKGKPCPKEIPKESKNTEVLVWEE

CVANSAVILQNNEFGTIIDWAPRGQFYHNCSGQTQSCPSAQVSPAVDSD

LTESLDKHKHKKLQSFYPWEWGEKGISTPRPKIISPVSGPEHPELWRLT

VASHHIRIWSGNQTLETRDRKPFYTVDLNSSVTVPLQSCIKPPYMLVVG

NIVIKPDSQTITCENCRLLTCIDSTFNWQHRILLVRAREGVWIPVSMDR

PWETSPSIHTLTEVLKGVLNRSKRFIFTLIAVIMGLIAVTATAAVAGVA

LHSSVQSVNFVNDWQKNSTRLWNSQSSIDQKLANQINDLRQTVIWMGDR

LMSLEHRFQLQCDWNTSDFSITPQIYNESEHHWDMVRRHLQGREDNLTL

DISKLKEQIFEASKAHLNLVPGTEAIAGVADGLANLNPVTWVKTIGSTT

IINLILILVCLFCLLLVCRCTQQLRRDSDHRERAMMTMAVLSKRKGGNV

GKSKRDQIVTVSV.

The 1q23.3 (K110, K18, K (c1A), ERVK-18) full-length HERV-K Env sequence (UniProt: O42043) is shown below as SEQ ID NO: 16.

(SEQ ID NO: 16)
MVTPVTWMDNPIEVYVNDSVWVPGPTDDRCPAKPEEEGMMINISIGYHY

PPICLGRAPGCLMPAVQNWLVEVPTVSPNSRFTYHMVSGMSLRPRVNCL

QDFSYQRSLKFRPKGKTCPKEIPKGSKNTEVLVWEECVANSVVILQNNE

FGTIIDWAPRGQFYHNCSGQTQSCPSAQVSPAVDSDLTESLDKHKHKKL

QSFYLWEWEEKGISTPRPKIISPVSGPEHPELWRLTVASHHIRIWSGNQ

TLETRYRKPFYTIDLNSILTVPLQSCVKPPYMLVVGNIVIKPASQTITC

-continued
ENCRLFTCIDSTFNWQHRILLVRAREGMWIPVSTDRPWEASPSIHILTE

ILKGVLNRSKRFIFTLIAVIMGLIAVTATAAVAGVALHSSVQSVNFVNY

WQKNSTRLWNSQSSIDQKLASQINDLRQTVIWMGDRLMTLEHHFQLQCD

WNTSDFCITPQIYNESEHHWDMVRRHLQGREDNLTLDISKLKEQIFEAS

KAHLNLVPGTEAIAGVADGLANLNPVTWIKTIRSTMIINLILIVVCLFC

LLLVCRCTQQLRRDSDIENGP.

FIG. 4A, FIG. 4B, FIG. 4C, FIG. 4D, FIG. 4E, and FIG. 4F show a Clustal Omega amino acid sequence comparison of the full-length HERV-K (HML-2) Env consensus sequence (SEQ ID NO: 8), the 6q14.1 K109 full-length HERV-K Env sequence (SEQ ID NO: 9), the 7p22.1 K109 ERK6 full-length HERV-K Env sequence (SEQ ID NO: 10), the 8p23.1a K115 full-length HERV-K Env sequence (SEQ ID NO: 11), the 11q22.1 K118 full-length HERV-K Env sequence (SEQ ID NO: 12), the 12q14.1 K119 full-length HERV-K Env sequence (SEQ ID NO: 13), the 19p12b K113 full-length HERV-K Env sequence (SEQ ID NO: 14), the 19q11 full-length HERV-K Env sequence (SEQ ID NO: 15), and the 1q23.3 full-length HERV-K Env sequence (SEQ ID NO: 16). As is apparent from the sequence comparison, the nine sequences have many similarities in terms of amino acid content and order, but there are noticeable differences, including the overall sequence lengths.

Previous work with insulin-Fc fusion proteins, such as is described in WO2018107117A1 and WO2020006529A1, has demonstrated that the choices of the protein sequence, the linker sequence, and the composition of the Fc domain can all potentially influence protein yields, purity, and bioactivity. For example, the application WO2018107117A1 describes a combination of an insulin analog, linker, and Fc domain that yield a non-bioactive insulin-Fc fusion protein. The application WO2020006529A1 describes a combination of a different insulin analog, linker and Fc domain that yield a bioactive insulin-Fc fusion protein. Both the application WO2018107117A1 and the application WO2020006529A1 describe combinations of insulin analogs, linkers and Fc domains that have poor manufacturability or homogeneity.

In choosing the HERV-K (HML-2) Env analog for the novel HERV-K (HML-2) Env analog-Fc fusion protein it is conceivable that one could choose a HERV-K (HML-2) Env analog that includes some portion of the full-length HERV-K (HML-2) Env consensus sequence of SEQ ID NO: 8 or that includes some portion of a full-length HERV-K (HML-2) Env protein locus of SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16. In examples, the HERV-K (HML-2) Env analog for a novel HERV-K (HML-2) Env analog-Fc fusion protein may comprise all or a portion of the signal peptide domain (SEQ ID NO: 4) of the full-length HERV-K (HML-2) Env consensus sequence of SEQ ID NO: 8. In examples, the HERV-K (HML-2) Env analog for a novel HERV-K (HML-2) Env analog-Fc fusion protein may comprise all or a portion of the extracellular domain (SEQ ID NO: 5) of the full-length HERV-K (HML-2) Env consensus sequence of SEQ ID NO: 8. In examples, the HERV-K (HML-2) Env analog for a novel HERV-K (HML-2) Env analog-Fc fusion protein may comprise all or a portion of the transmembrane domain (SEQ ID NO: 6) of the full-length HERV-K (HML-2) Env consensus sequence of SEQ ID NO: 8. In examples, the HERV-K (HML-2) Env analog for a novel HERV-K (HML-2) Env analog-Fc fusion protein may comprise all or a portion of the cytoplasmic domain (SEQ ID NO: 7) of the full-length HERV-K (HML-2) Env consensus sequence of SEQ ID NO: 8. In examples, the HERV-K (HML-2) Env analog for a novel HERV-K (HML-2) Env analog-Fc fusion protein may comprise all or a portion of the signal peptide domain (SEQ ID NO: 4) and all or a portion of the extracellular domain (SEQ ID NO: 5) of the full-length HERV-K (HML-2) Env consensus sequence of SEQ ID NO: 8. In examples, the HERV-K (HML-2) Env analog may comprise additional amino acids or polypeptides, for example at the N-terminus of a HERV-K (HML-2) Env analog sequence (collectively then referred to as the HERV-K (HML-2) Env analog). In examples, one or more amino acids in the HERV-K (HML-2) Env analog of the novel HERV-K (HML-2) Env analog-Fc fusion protein may be deleted or mutated from their native state.

It is expected that different HERV-K (HML-2) Env analog-Fc fusion protein designs will result in different protein yields (see for example, Azadeh Beygmoradi, Ahmad Homaei, Roohullah Hemmati, Pedro Fernandes, *Recombinant protein expression: Challenges in production and folding related matters, International Journal of Biological Macromolecules, Volume* 233, 2023, 123407, ISSN 0141-8130, doi.org/10.1016/j.ijbiomac.2023.123407, and Massimo Stefani, *Protein misfolding and aggregation: new examples in medicine and biology of the dark side of the protein world, Biochimica et Biophysica Acta (BBA)—Molecular Basis of Disease, Volume* 1739, Issue 1, 2004, Pages 5-25, ISSN 0925-4439).

For example, longer or shorter HERV-K (HML-2) Env analog sequences in the HERV-K (HML-2) Env analog, when used to produce the HERV-K (HML-2) Env analog-Fc fusion protein, are expected to result in different protein yields. The resulting protein yield when the selected HERV-K (HML-2) Env analog is attached to an Fc fragment can be experimentally determined. The choice of the Fc fragment that is linked to the selected HERV-K (HML-2) Env analog may impact the manufacturability of the HERV-K (HML-2) Env analog-Fc fusion protein.

The novel HERV-K (HML-2) Env analog-Fc fusion protein may comprise a peptide linker. In examples, the therapeutic protein comprising the HERV-K (HML-2) Env analog is linked to the N-terminal side of the Fc fragment. In examples, the novel HERV-K (HML-2) Env analog-Fc fusion protein comprises domains in the following orientation from N- to C-termini: (N-terminus)-antigen-peptide linker-Fc fragment-(C-terminus) (e.g., (N-terminus)-HERV-K (HML-2) Env analog-peptide linker-Fc fragment-(C-terminus)). The length and composition of the linker connecting the HERV-K (HML-2) Env analog to the Fc fragment may impact the protein yield.

The design goal is to create a HERV-K (HML-2) Env analog-Fc fusion protein with a protein yield, after production in transiently transfected CHO cells and protein A purification, greater than 50 mg/L (e.g., greater than 75 mg/L, greater than 90 mg/L, greater than 100 mg/L).

The choice of a human IgG Fc fragment may also increase immunogenicity of the HERV-K (HML-2) Env analog-Fc fusion protein further resulting in a greater immune reaction which will decrease levels of endogenous HERV-K (HML-2) in the patient through the production of higher levels of antibodies against endogenous HERV-K (HML-2).

The human IgG1 Fc fragment of SEQ ID NO: 1 is shown below.

```
                                            (SEQ ID NO: 1)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPG.
```

In the human IgG1 Fc fragment of SEQ ID NO: 1, the C-terminus lysine on the native human IgG1 Fc fragment was eliminated. The C-terminal lysine that is found in native IgG isotype Fc fragment amino acid sequences (i.e., the lysine that represents the last amino acid of the Fc fragment sequence) is known to result in the accidental production of unwanted amino acid sequence variants during manufacturing (e.g., Fc fragments containing the C-terminal lysine becoming mixed with Fc fragments where the C-terminal lysine is omitted, which can occur during production of the desired protein within cells (Dick, LW., (2008) *Biotechnol Bioeng*. August 15; 100 (6) pp 1132-43). Therefore, it was expected that removing the C-terminal lysine would improve manufacturing yield and purity. In addition, the potential N-glycan site on the human IgG1 Fc fragment was conserved to preserve glycan attachment during fusion protein production in host cells. It has been shown that IgG glycosylation may assist in increased immunogenicity through enhanced antigen presentation via binding to Fc(gamma)R receptors on antigen presenting immune cells present in a patient. Therefore, a HERV-K (HML-2) Env analog-Fc fusion protein comprising a glycosylated Fc fragment is expected to show increased immunogenicity over HERV-K (HML-2) Env analog-Fc fusion protein embodiments without glycosylation (Cobb B A. *The history of IgG glycosylation and where we are now. Glycobiology.* 2020 Mar. 20; 30 (4): 202-213. doi: 10.1093/glycob/cwz065. PMID: 31504525; PMCID: PMC7109348).

As a first attempt in creating a novel HERV-K (HML-2) Env analog-Fc fusion protein, a portion (63 amino acids) of the full-length HERV-K (HML-2) Env consensus sequence of SEQ ID NO: 8 was selected to create the HERV-K (HML-2) Env analog of SEQ ID NO: 18. This length of HERV-K (HML-2) Env analog may potentially incorporate sufficient epitopes which may improve binding and therefore increase immunogenicity. The HERV-K (HML-2) Env analog of SEQ ID NO: 18 is shown below.

```
                                           (SEQ ID NO: 18)
EQMKLPSTKKAEPPTWAQLKKLTQLATKYLENTKVTQTPESMLLAALMI

VSMVVSLPMPAGAA.
```

FIG. 5A, FIG. 5B, FIG. 5C, FIG. 5D, FIG. 5E, and FIG. 5F are a Clustal Omega amino acid sequence comparison that includes the alignment of the full-length HERV-K (HML-2) Env consensus sequence (SEQ ID NO: 8) with the HERV-K (HML-2) Env analog of SEQ ID NO: 18.

The HERV-K (HML-2) Env analog of SEQ ID NO: 18 was created by selecting a section of the signal peptide of SEQ ID NO: 4 and a section of the extracellular domain of SEQ ID NO: 5. This HERV-K (HML-2) Env analog comprises amino acids 35-97 of the full-length HERV-K (HML-2) Env consensus sequence of SEQ ID NO: 8. The signal peptide is highly conserved across all HERV-K Env loci. The signal peptide of HERV-K Env has shown to translocate to the nucleoli (Ruggieri A, Maldener E, Sauter M, Mueller- Lantzsch N, Meese E, Fackler O T, Mayer J. *Human endogenous retrovirus HERV-K (HML-2) encodes a stable signal peptide with biological properties distinct from Rec. Retrovirology.* 2009 Feb. 16; 6:17) and nucleolar dysfunction has been described in the neurons of HERV-K Env transgenic mice (Li W, Lee M H, Henderson L, Tyagi R, Bachani M, Steiner J, Campanac E, Hoffman D A, von Geldern G, Johnson K, Maric D, Morris H D, Lentz M, Pak K, Mammen A, Ostrow L, Rothstein J, Nath A. *Human endogenous retrovirus-K contributes to motor neuron disease. Sci Transl Med.* 2015 Sep. 30; 7 (307): 307ra153), pointing out a mechanism of neurotoxicity of the signal peptide of HERV-K Env in ALS. Thus, targeting this portion of the HERV-K (HML-2) Env protein with a vaccine compound might increase the protective activity of the vaccine.

Figure 8:
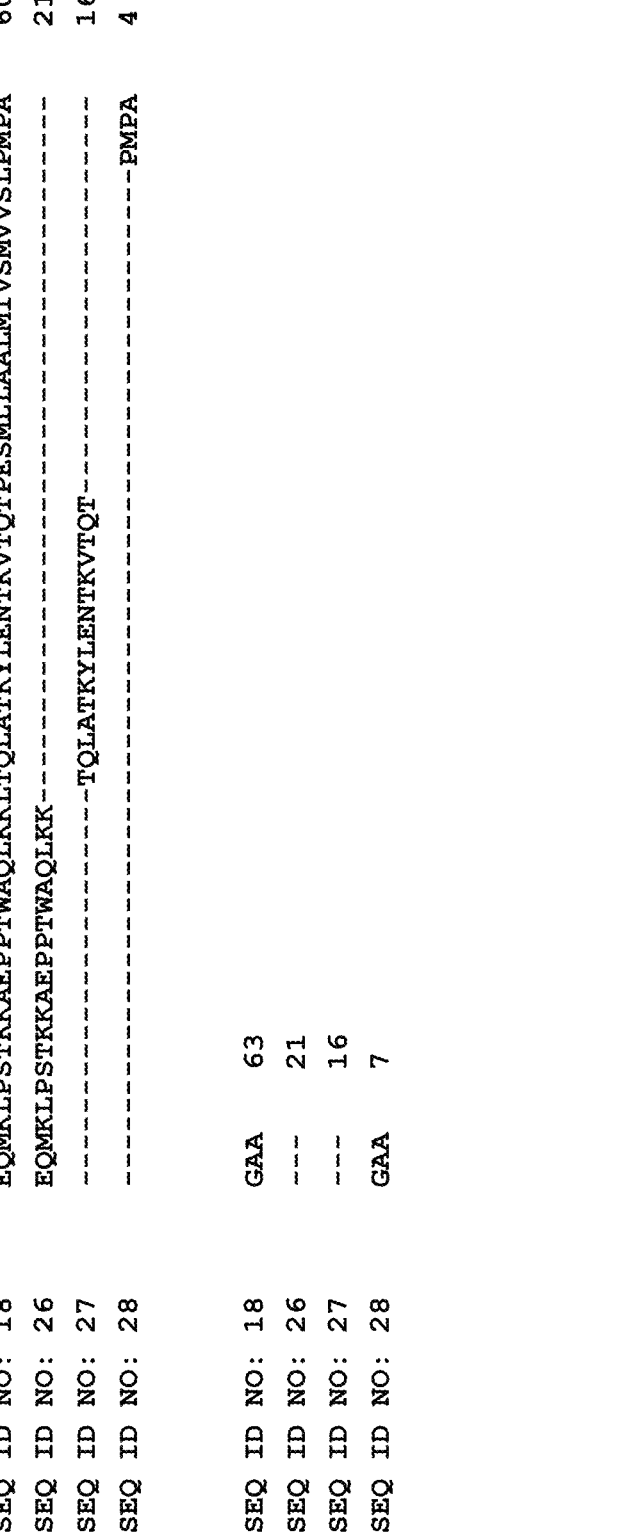
FIG. 8 is a Clustal Omega amino acid sequence comparison showing the alignment of a HERV-K (HML-2) Env analog (SEQ ID NO: 18) and its corresponding predicted epitopes for binding to B-cell receptors (SEQ ID NO: 26, SEQ ID NO: 27, and SEQ ID NO: 28).

The HERV-K (HML-2) Env analog of SEQ ID NO: 18 contains 3 different peptides predicted to bind to B-cell receptors, as analyzed by BepiPred Linear Epitope Prediction 2.0 (Department of Health Technology (DTU) Institute, Lyngby Denmark), which is necessary to induce humoral immunity: 1) EQMKLPSTKKAEPPTWAQLKK (SEQ ID NO: 26); 2) TQLATKYLENTKVTQT (SEQ ID NO: 27); and 3) PMPAGAA (SEQ ID NO: 28). FIG. 8 is a Clustal Omega amino acid sequence comparison showing the alignment of the HERV-K (HML-2) Env analog (SEQ ID NO: 18) and its corresponding predicted epitopes for binding to B-cell receptors (SEQ ID NO: 26, SEQ ID NO: 27, and SEQ ID NO: 28).

The HERV-K (HML-2) Env analog of SEQ ID NO: 18 was linked via the long linker GGGGGSGGGGSGGGGSGGGGGS (SEQ ID NO: 3) to the IgG1 Fc fragment of SEQ ID NO: 1.

```
                                          (SEQ ID NO: 1)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPG.
```

It was expected that the use of a long linker would improve binding, therefore increasing immunogenicity.

The resultant HERV-K (HML-2) Env analog-Fc fusion protein is given below as SEQ ID NO: 38.

```
                                         (SEQ ID NO: 38)
EQMKLPSTKKAEPPTWAQLKKLTQLATKYLENTKVTQTPESMLLAALMI

VSMVVSLPMPAGAAGGGGGSGGGGSGGGGSGGGGGSDKTHTCPPCPAPE

LLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMH

EALHNHYTQKSLSLSPG.
```

The HERV-K (HML-2) Env analog-Fc fusion protein of SEQ ID NO: 38 was manufactured in CHO cells according to Example 4 and was purified according to Example 6. The Fc fusion protein structure of the HERV-K (HML-2) Env analog-Fc fusion protein of SEQ ID NO: 38 was confirmed according to Example 7, and sequence identification is performed according to Example 8. The resultant yield of the HERV-K (HML-2) Env analog-Fc fusion protein of SEQ ID NO: 38 produced was 65 mg/L. SEQ ID NO: 38 did meet the design goal of a HERV-K (HML-2) Env analog-Fc fusion protein with a manufacturing yield greater than 50 mg/L.

Immunization studies to evaluate the effectiveness of the HERV-K (HML-2) Env analog-Fc fusion protein of SEQ ID NO: 38 were performed in 6- to 8-week-old BALB/c mice according to Example 11. Mice were administered three doses of 23 μg of the HERV-K (HML-2) Env analog-Fc fusion protein of SEQ ID NO: 38 with and without adjuvant 4 weeks apart (on Day 0, Day 28 and Day 56) via subcutaneous (s.c.) injection. Blood was obtained from each mouse for antibody titer analysis via ELISA via submandibular venipuncture 21 to 28 days prior to the first injection and then 21 to 28 days after each injection.

The binding capacity of the mice antisera to the HERV-K (HML-2) Env protein and the total levels of IgG anti-HERV-K (HML-2) Env Ab titers in the mice antisera were measured according to Example 12. The resultant total IgG anti-HERV-K (HML-2) Env Ab titers yield in the antisera from mice immunized with the HERV-K (HML-2) Env analog-Fc fusion protein of SEQ ID NO: 38 was 5.34 μg/mL, which was unacceptably low. The IgG1 and IgG2a anti-HERV-K (HML-2) Env Ab titers in the mice antisera were measured according to Example 13, and the ratio of IgG1/IgG2a was calculated as 2.60, which was unacceptably low. It was reasoned that the length of the HERV-K (HML-2) Env sequence may have contributed to acceptable manufacturability. However, the recombinant HERV-K Env used in the ELISA assay to detect antibodies in the mouse sera after immunization with the compounds does not include the signal peptide (which comprises amino acids 0 through 89, i.e., the recombinant HERV-K Env used in the ELISA assay comprises amino acids 90 through 632). Thus, with this assay only the antibodies generated against the extracellular sequence of the HERV-K (HML-2) Env analog portion of SEQ ID NO: 18 may have been detected. Potentially selecting a different analog whose sequence is only located in the extracellular domain could improve antibody production and detection.

As a second attempt in creating a novel HERV-K (HML-2) Env analog-Fc fusion protein, a portion of the extracellular domain (SEQ ID NO: 5) of the full-length HERV-K (HML-2) Env consensus sequence of SEQ ID NO: 8 was selected to create the HERV-K (HML-2) Env analog of SEQ ID NO: 19. It was expected that the short HERV-K (HML-2) Env analog would minimize folding which may result in good binding and therefore good immunogenicity. The HERV-K (HML-2) Env analog of SEQ ID NO: 19 is shown below.

```
                                         (SEQ ID NO: 19)
WAYVPFPPLIRAVTWMDNP.
```

FIG. 5A, FIG. 5B, FIG. 5C, FIG. 5D, FIG. 5E, and FIG. 5F are a Clustal Omega amino acid sequence comparison that includes the alignment of the full-length HERV-K (HML-2) Env consensus sequence (SEQ ID NO: 8) with the HERV-K (HML-2) Env analog of SEQ ID NO: 19.

As this HERV-K (HML-2) Env analog comprising amino acids 104-122 of the HERV-K (HML-2) Env consensus sequence of SEQ ID NO: 8 belongs to the extracellular domain of the Env protein, it was anticipated that endogenous HERV-K (HML-2) Env protein might be accessible to the circulating antibodies generated by the immunization with a HERV-K (HML-2) Env analog-Fc fusion protein using the HERV-K (HML-2) Env analog of SEQ ID NO: 19, facilitating the binding. The HERV-K (HML-2) Env analog of SEQ ID NO: 19 contains a peptide LIRAVTWMDNP (SEQ ID NO: 29) predicted to bind to B-cell receptors, as analyzed by BepiPred Linear Epitope Prediction 2.0 (Department of Health Technology (DTU) Institute, Lyngby Denmark) which is necessary to induce humoral immunity. FIG. 9 is a Clustal Omega amino acid sequence comparison showing the alignment of the HERV-K (HML-2) Env analog (SEQ ID NO: 19) and its corresponding predicted epitope for binding to B-cell receptors (SEQ ID NO: 29).

The HERV-K (HML-2) Env analog of SEQ ID NO: 19 was linked via the long linker GGGGGSGGGGSGGGGSGGGGGS (SEQ ID NO: 3) to the IgG1 Fc fragment of SEQ ID NO: 1.

```
                                          (SEQ ID NO: 1)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPG.
```

It was expected that the use of a long linker would improve binding, therefore increasing immunogenicity.

The resultant HERV-K (HML-2) Env analog-Fc fusion protein is given below as SEQ ID NO: 39.

```
                                         (SEQ ID NO: 39)
WAYVPFPPLIRAVTWMDNPGGGGGSGGGGSGGGGSGGGGGSDKTHTCPP

CPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVFS

CSVMHEALHNHYTQKSLSLSPG.
```

The HERV-K (HML-2) Env analog-Fc fusion protein of SEQ ID NO: 39 was manufactured in CHO cells according to Example 4 and was purified according to Example 6. The Fc fusion protein structure of the HERV-K (HML-2) Env analog-Fc fusion protein of SEQ ID NO: 39 was confirmed according to Example 7, and sequence identification is performed according to Example 8. The resultant yield of the HERV-K (HML-2) Env analog-Fc fusion protein of SEQ ID NO: 39 produced was 37 mg/L. SEQ ID NO: 39 did not meet the design goal of a HERV-K (HML-2) Env analog-Fc fusion protein with a manufacturing yield greater than 50 mg/L.

Immunization studies to evaluate the effectiveness of the HERV-K (HML-2) Env analog-Fc fusion protein of SEQ ID NO: 39 were performed in 6- to 8-week-old BALB/c mice according to Example 11. Mice were administered three doses of 17 μg of the HERV-K (HML-2) Env analog-Fc fusion protein of SEQ ID NO: 39 with and without adjuvant 4 weeks apart (on Day 0, Day 28 and Day 56) via subcutaneous (s.c.) injection. Blood was obtained from each mouse for antibody titer analysis via ELISA via submandibular venipuncture 21 to 28 days prior to the first injection and then 21 to 28 days after each injection.

The binding capacity of the mice antisera to the HERV-K (HML-2) Env protein and the total levels of IgG anti-HERV-K (HML-2) Env Ab titers in the mice antisera were measured according to Example 12. The resultant total IgG anti-HERV-K (HML-2) Env Ab titers yield in the antisera from mice immunized with the HERV-K (HML-2) Env analog-Fc fusion protein of SEQ ID NO: 39 was 11.893 μg/mL, which was unacceptably low. The IgG1 and IgG2a anti-HERV-K (HML-2) Env Ab titers in the mice antisera were measured according to Example 13, and the ratio of IgG1/IgG2a was calculated as 28.30, which was acceptable (greater than 2). Immunogenicity improved over SEQ ID NO: 38 but was still insufficient. Manufacturability could also be improved. It was reasoned that using the same HERV-K (HML-2) Env analog of SEQ ID NO: 19 with the short linker of SEQ ID NO: 2 might improve at least manufacturability.

As a third attempt in creating a novel HERV-K (HML-2) Env analog-Fc fusion protein, the same HERV-K (HML-2) Env analog of SEQ ID NO: 19, comprising a short portion of the extracellular domain (SEQ ID NO: 5) of the full-length HERV-K (HML-2) Env consensus sequence of SEQ ID NO: 8 was again selected. It was expected that the short HERV-K (HML-2) Env analog would minimize folding which may improve binding and therefore improve immunogenicity. The same HERV-K (HML-2) Env analog of SEQ ID NO: 19 is shown below.

```
                                         (SEQ ID NO: 19)
             WAYVPFPPLIRAVTWMDNP.
```

FIG. 5A, FIG. 5B, FIG. 5C, FIG. 5D, FIG. 5E, and FIG. 5F are a Clustal Omega amino acid sequence comparison that includes the alignment of the full-length HERV-K (HML-2) Env consensus sequence (SEQ ID NO: 8) with the HERV-K (HML-2) Env analog of SEQ ID NO: 19.

As this HERV-K (HML-2) Env analog comprising amino acids 104-122 of the HERV-K (HML-2) Env consensus sequence of SEQ ID NO: 8 belongs to the extracellular domain of the Env protein section of the HERV-K (HML-2) it was anticipated that endogenous HERV-K (HML-2) Env protein might be accessible to the circulating antibodies generated by the immunization with a HERV-K (HML-2) Env analog-Fc fusion protein using the HERV-K (HML-2) Env analog of SEQ ID NO: 19, facilitating the binding. The HERV-K (HML-2) Env analog of SEQ ID NO: 19 contains a peptide LIRAVTWMDNP (SEQ ID NO: 29) predicted to bind to B-cell receptors, as analyzed by BepiPred Linear Epitope Prediction 2.0 (Department of Health Technology (DTU) Institute, Lyngby Denmark), which is necessary to induce humoral immunity. FIG. 9 is a Clustal Omega amino acid sequence comparison showing the alignment of the HERV-K (HML-2) Env analog (SEQ ID NO: 19) and its corresponding predicted epitope for binding to B-cell receptors (SEQ ID NO: 29).

The HERV-K (HML-2) Env analog of SEQ ID NO: 19 was linked via the short linker GGGSGGGS (SEQ ID NO: 2) to the IgG1 Fc fragment of SEQ ID NO: 1.

```
                                          (SEQ ID NO: 1)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC
```

-continued

```
LVKGFYPSDIAVEWESNGQPENNYKTTPPVLDSDGSFFLYSKLTVDKSR

WQQGNVFSCSVMHEALHNHYTQKSLSLSPG.
```

It was expected that the use of a short linker would improve manufacturability.

The resultant HERV-K (HML-2) Env analog-Fc fusion protein is given below as SEQ ID NO: 40.

```
                                        (SEQ ID NO: 40)
WAYVPFPPLIRAVTWMDNPGGGSGGGSDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQ

KSLSLSPG.
```

The HERV-K (HML-2) Env analog-Fc fusion protein of SEQ ID NO: 40 was manufactured in CHO cells according to Example 4 and was purified according to Example 6. The Fc fusion protein structure of the HERV-K (HML-2) Env analog-Fc fusion protein of SEQ ID NO: 40 was confirmed according to Example 7, and sequence identification is performed according to Example 8. The resultant yield of the HERV-K (HML-2) Env analog-Fc fusion protein of SEQ ID NO: 40 produced was 60 mg/L.

Immunization studies to evaluate the effectiveness of the HERV-K (HML-2) Env analog-Fc fusion protein of SEQ ID NO: 40 were performed in 6- to 8-week-old BALB/c mice according to Example 11. Mice were administered three doses of 30 µg of the HERV-K (HML-2) Env analog-Fc fusion protein of SEQ ID NO: 40 with and without adjuvant 4 weeks apart (on Day 0, Day 28 and Day 56) via subcutaneous (s.c.) injection. Blood was obtained from each mouse for antibody titer analysis via ELISA via submandibular venipuncture 21 to 28 days prior to the first injection and then 21 to 28 days after each injection.

The binding capacity of the mice antisera to the HERV-K (HML-2) Env protein and the total levels of IgG anti-HERV-K (HML-2) Env Ab titers in the mice antisera were measured according to Example 12. The resultant total IgG anti-HERV-K (HML-2) Env Ab titers yield in the antisera from mice immunized with the HERV-K (HML-2) Env analog-Fc fusion protein of SEQ ID NO: 40 was 4.225 µg/mL, which was unacceptably low. The IgG1 and IgG2a anti-HERV-K (HML-2) Env Ab titers in the mice antisera were measured according to Example 13, and the ratio of IgG1/IgG2a was calculated as 7.10, which was acceptable (greater than 2) but could be improved.

SEQ ID NO: 40 did meet the design goal of a HERV-K (HML-2) Env analog-Fc fusion protein with a manufacturing yield greater than 50 mg/L. Manufacturability improved over SEQ ID NO: 39 (37 mg/L) suggesting that the HERV-K (HML-2) Env analog selection combined with the linker may impact manufacturability. Total IgG titers increased but were still too low. The selected HERV-K (HML-2) Env analog of the extracellular domain may not present the relevant epitopes.

As a fourth attempt in creating a novel HERV-K (HML-2) Env analog-Fc fusion protein a different portion of the extracellular domain (SEQ ID NO: 5) of the full-length HERV-K (HML-2) Env consensus sequence of SEQ ID NO: 8 was selected to create the HERV-K (HML-2) Env analog of SEQ ID NO: 20. It was expected that a short HERV-K (HML-2) Env analog would minimize folding which may improve binding and therefore improve immunogenicity. The HERV-K (HML-2) Env analog of SEQ ID NO: 20 is shown below.

```
                                        (SEQ ID NO: 20)
MVSGMSLRPRVNYLQDFSYQRS.
```

FIG. 5A, FIG. 5B, FIG. 5C, FIG. 5D, FIG. 5E, and FIG. 5F are a Clustal Omega amino acid sequence comparison that includes the alignment of the full-length HERV-K (HML-2) Env consensus sequence (SEQ ID NO: 8) with the HERV-K (HML-2) Env analog of SEQ ID NO: 20.

Figure 10:
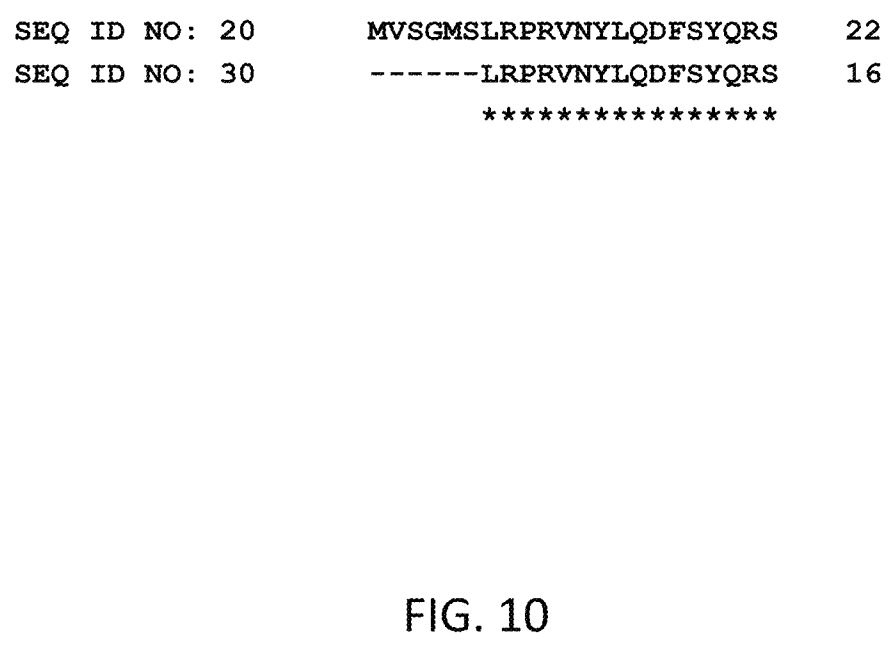

As this HERV-K (HML-2) Env analog comprising amino acids 196-217 of the HERV-K (HML-2) Env consensus sequence of SEQ ID NO: 8 belongs to the extracellular domain of the Env protein, it was anticipated that endogenous HERV-K (HML-2) Env protein might be accessible to the circulating antibodies generated by the immunization with HERV-K (HML-2) Env analog-Fc fusion protein using the HERV-K (HML-2) Env analog of SEQ ID NO: 20, facilitating the binding. The HERV-K (HML-2) Env analog of SEQ ID NO: 20 contains a peptide LRPRV-NYLQDFSYQRS (SEQ ID NO: 30) predicted to bind to B-cell receptors, as analyzed by BepiPred Linear Epitope Prediction 2.0 (Department of Health Technology (DTU) Institute, Lyngby Denmark), which is necessary to induce humoral immunity. FIG. 10 is a Clustal Omega amino acid sequence comparison showing the alignment of the HERV-K (HML-2) Env analog (SEQ ID NO: 20) and its corresponding predicted epitope for binding to B-cell receptors (SEQ ID NO: 30).

The HERV-K (HML-2) Env analog of SEQ ID NO: 20 was linked via the long linker GGGGGSGGGGSGGGGSGGGGGS (SEQ ID NO: 3) to the IgG1 Fc fragment of SEQ ID NO: 1.

```
                                        (SEQ ID NO: 1)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPG.
```

It was expected that the use of a long linker would improve binding, therefore increasing immunogenicity.

The resultant HERV-K (HML-2) Env analog-Fc fusion protein is given below as SEQ ID NO: 41.

```
                                        (SEQ ID NO: 41)
MVSGMSLRPRVNYLQDFSYQRSGGGGGSGGGGSGGGGSGGGGGSDKTHT

CPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKV

SNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGN

VFSCSVMHEALHNHYTQKSLSLSPG.
```

The HERV-K (HML-2) Env analog-Fc fusion protein of SEQ ID NO: 41 was manufactured in CHO cells according to Example 4 and was purified according to Example 6. The Fc fusion protein structure of the HERV-K (HML-2) Env analog-Fc fusion protein of SEQ ID NO: 41 was confirmed according to Example 7, and sequence identification is performed according to Example 8. The resultant yield of the HERV-K (HML-2) Env analog-Fc fusion protein of SEQ ID NO: 41 produced was 46 mg/L. SEQ ID NO: 41 did not meet the design goal of a HERV-K (HML-2) Env analog-Fc fusion protein with a manufacturing yield greater than 50 mg/L.

Immunization studies to evaluate the effectiveness of the HERV-K (HML-2) Env analog-Fc fusion protein of SEQ ID NO: 41 were performed in 6- to 8-week-old BALB/c mice according to Example 11. Mice were administered three doses of 20 μg of the HERV-K (HML-2) Env analog-Fc fusion protein of SEQ ID NO: 41 with and without adjuvant 4 weeks apart (on Day 0, Day 28 and Day 56) via subcutaneous (s.c.) injection. Blood was obtained from each mouse for antibody titer analysis via ELISA via submandibular venipuncture 21 to 28 days prior to the first injection and then 21 to 28 days after each injection.

The binding capacity of the mice antisera to the HERV-K (HML-2) Env protein and the total levels of IgG anti-HERV-K (HML-2) Env Ab titers in the mice antisera were measured according to Example 12. The resultant total IgG anti-HERV-K (HML-2) Env Ab titers yield in the antisera from mice immunized with the HERV-K (HML-2) Env analog-Fc fusion protein of SEQ ID NO: 41 was 4.673 μg/mL, which was unacceptably low. The IgG1 and IgG2a anti-HERV-K (HML-2) Env Ab titers in the mice antisera were measured according to Example 13, and the ratio of IgG1/IgG2a was calculated as 2.27, which was unacceptably low. It was reasoned that a combination of the same HERV-K (HML-2) Env analog (SEQ ID NO: 20) with a shorter linker might improve the results.

As an fifth attempt in creating a novel HERV-K (HML-2) Env analog-Fc fusion protein, the same HERV-K (HML-2) Env analog of SEQ ID NO: 20, comprising a portion of the extracellular domain (SEQ ID NO: 5) of the full-length HERV-K (HML-2) Env consensus sequence of SEQ ID NO: 8 was again selected to create the HERV-K (HML-2) Env analog of SEQ ID NO: 20. It was expected that a short HERV-K (HML-2) Env analog (22 amino acids in length) would minimize folding which may improve binding and therefore improve immunogenicity. The HERV-K (HML-2) Env analog of SEQ ID NO: 20 is shown below.

```
                                      (SEQ ID NO: 20)
          MVSGMSLRPRVNYLQDFSYQRS.
```

FIG. 5A, FIG. 5B, FIG. 5C, FIG. 5D, FIG. 5E, and FIG. 5F are a Clustal Omega amino acid sequence comparison that includes the alignment of the full-length HERV-K (HML-2) Env consensus sequence (SEQ ID NO: 8) with the HERV-K (HML-2) Env analog of SEQ ID NO: 20.

As this section of the HERV-K (HML-2) Env analog comprising amino acids 196-217 of the HERV-K (HML-2) Env consensus sequence of SEQ ID NO: 8 belongs to the extracellular domain of the Env protein it was anticipated that endogenous HERV-K (HML-2) Env protein might be accessible to the circulating antibodies generated by the immunization with the compound, facilitating the binding. It contains a peptide LRPRVNYLQDFSYQRS (SEQ ID NO: 30) predicted to bind to B-cell receptors, as analyzed by BepiPred Linear Epitope Prediction 2.0 (Department of Health Technology (DTU) Institute, Lyngby Denmark), which is necessary to induce humoral immunity. FIG. 10 is a Clustal Omega amino acid sequence comparison showing the alignment of the HERV-K (HML-2) Env analog (SEQ ID NO: 20) and its corresponding predicted epitope for binding to B-cell receptors (SEQ ID NO: 30).

The HERV-K (HML-2) Env analog of SEQ ID NO: 20 was linked via the short linker GGGSGGGS (SEQ ID NO: 2) to the IgG1 Fc fragment of SEQ ID NO: 1.

```
                                      (SEQ ID NO: 1)
DKTHTCPPCPAPELLGGPSVFLFPPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPG.
```

It was expected that the use of a short linker would improve manufacturability.

The resultant HERV-K (HML-2) Env analog-Fc fusion protein is given below as SEQ ID NO: 42.

```
                                      (SEQ ID NO: 42)
MVSGMSLRPRVNYLQDFSYQRSGGGSGGGSDKTHTCPPCPAPELLGGPS

VFLFPPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNH

YTQKSLSLSPG.
```

The HERV-K (HML-2) Env analog-Fc fusion protein of SEQ ID NO: 42 was manufactured in CHO cells according to Example 4 and was purified according to Example 6. The Fc fusion protein structure of the HERV-K (HML-2) Env analog-Fc fusion protein of SEQ ID NO: 42 was confirmed according to Example 7, and sequence identification is performed according to Example 8. The resultant yield of the HERV-K (HML-2) Env analog-Fc fusion protein produced was 130 mg/L.

Immunization studies to evaluate the effectiveness of the HERV-K (HML-2) Env analog-Fc fusion protein of SEQ ID NO: 42 were performed in 6- to 8-week-old BALB/c mice according to Example 11. Mice were administered three doses of 30 μg of the HERV-K (HML-2) Env analog-Fc fusion protein of SEQ ID NO: 42 with and without adjuvant 4 weeks apart (on Day 0, Day 28 and Day 56) via subcutaneous (s.c.) injection. Blood was obtained from each mouse for antibody titer analysis via ELISA via submandibular venipuncture 21 to 28 days prior to the first injection and then 21 to 28 days after each injection.

The binding capacity of the mice antisera to the HERV-K (HML-2) Env protein and the total levels of IgG anti-HERV-K (HML-2) Env Ab titers in the mice antisera were measured according to Example 12. The resultant total IgG anti-HERV-K (HML-2) Env Ab titers yield in the antisera from mice immunized with the HERV-K (HML-2) Env analog-Fc fusion protein of SEQ ID NO: 42 was 2 μg/mL, which was unacceptably low. The IgG1 and IgG2a anti-HERV-K (HML-2) Env Ab titers in the mice antisera were measured according to Example 13, and the ratio of IgG1/IgG2a was calculated as 0.00, which was unacceptably low.

SEQ ID NO: 42 did meet the design goal of a HERV-K (HML-2) Env analog-Fc fusion protein with a manufacturing yield greater than 50 mg/L. Manufacturability improved over SEQ ID NO: 41 (46 mg/L), suggesting that the HERV-K (HML-2) Env analog selection combined with the short linker may impact manufacturability. The total IgG titers and ratio were low. In consequence a different section of the extracellular domain was selected.

As a sixth attempt in creating a novel HERV-K (HML-2) Env analog-Fc fusion protein, a different portion of the extracellular domain (SEQ ID NO: 5) of the full-length HERV-K (HML-2) Env consensus sequence of SEQ ID NO: 8 was selected to create the HERV-K (HML-2) Env analog of SEQ ID NO: 21. It was expected that a short HERV-K (HML-2) Env analog (18 amino acids in length) would minimize folding which may improve binding and therefore improve immunogenicity. The HERV-K (HML-2) Env analog of SEQ ID NO: 21 is shown below.

```
                                    (SEQ ID NO: 21)
          CPAKPEEEGMMINISIGY.
```

FIG. 5A, FIG. 5B, FIG. 5C, FIG. 5D, FIG. 5E, and FIG. 5F are a Clustal Omega amino acid sequence comparison that includes the alignment of the full-length HERV-K (HML-2) Env consensus sequence (SEQ ID NO: 8) with the HERV-K (HML-2) Env analog of SEQ ID NO: 21.

As this HERV-K (HML-2) Env analog comprising amino acids 141-158 of the HERV-K (HML-2) Env consensus sequence of SEQ ID NO: 8 belongs to the extracellular domain of the Env protein it was anticipated that endogenous HERV-K (HML-2) Env protein might be accessible to the circulating antibodies generated by the immunization with the compound, facilitating the binding. It contains a peptide CPAKPEEEGM (SEQ ID NO: 31) predicted to bind to B-cell receptors, as analyzed by BepiPred Linear Epitope Prediction 2.0 (Department of Health Technology (DTU) Institute, Lyngby Denmark), which is necessary to induce humoral immunity. FIG. 11 is a Clustal Omega amino acid sequence comparison showing the alignment of the HERV-K (HML-2) Env analog (SEQ ID NO: 21) and its corresponding predicted epitope for binding to B-cell receptors (SEQ ID NO: 31).

The HERV-K (HML-2) Env analog of SEQ ID NO: 21 was linked via the short linker GGGSGGGS (SEQ ID NO: 2) to the IgG1 Fc fragment of SEQ ID NO: 1.

```
                                    (SEQ ID NO: 1)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPG.
```

It was expected that the use of a short linker would improve manufacturability.

The resultant HERV-K (HML-2) Env analog-Fc fusion protein is given below as SEQ ID NO: 43.

```
                                    (SEQ ID NO: 43)
CPAKPEEEGMMINISIGYGGGSGGGSDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG
```

```
QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPG.
```

The HERV-K (HML-2) Env analog-Fc fusion protein of SEQ ID NO: 43 was manufactured in CHO cells according to Example 4 and was purified according to Example 6. The Fc fusion protein structure of the HERV-K (HML-2) Env analog-Fc fusion protein of SEQ ID NO: 43 was confirmed according to Example 7, and sequence identification is performed according to Example 8. The resultant yield of the HERV-K (HML-2) Env analog-Fc fusion protein produced was 112 mg/L.

Immunization studies to evaluate the effectiveness of the HERV-K (HML-2) Env analog-Fc fusion protein of SEQ ID NO: 43 were performed in 6- to 8-week-old BALB/c mice according to Example 11. Mice were administered three doses of 30 μg of the HERV-K (HML-2) Env analog-Fc fusion protein of SEQ ID NO: 43 with and without adjuvant 4 weeks apart (on Day 0, Day 28 and Day 56) via subcutaneous (s.c.) injection. Blood was obtained from each mouse for antibody titer analysis via ELISA via submandibular venipuncture 21 to 28 days prior to the first injection and then 21 to 28 days after each injection.

The binding capacity of the mice antisera to the HERV-K (HML-2) Env protein and the total levels of IgG anti-HERV-K (HML-2) Env Ab titers in the mice antisera were measured according to Example 12. The resultant total IgG anti-HERV-K (HML-2) Env Ab titers yield in the antisera from mice immunized with the HERV-K (HML-2) Env analog-Fc fusion protein of SEQ ID NO: 43 was 11.2 μg/mL, which was unacceptably low. The IgG1 and IgG2a anti-HERV-K (HML-2) Env Ab titers in the mice antisera were measured according to Example 13, and the ratio of IgG1/IgG2a was calculated as 24.03, which was acceptable.

SEQ ID NO: 43 did meet the design goal of a HERV-K (HML-2) Env analog-Fc fusion protein with a manufacturing yield greater than 50 mg/L. Manufacturability was good, further suggesting that the short linker and IgG1 Fc fragment combination is compatible. Total IgG titers and ratio were higher than other sequences but overall, the immunogenicity was not sufficient, indicating that the HERV-K (HML-2) Env analog selection was not successful. In consequence a different section of the extracellular domain was selected.

As a seventh attempt in creating a novel HERV-K (HML-2) Env analog-Fc fusion protein, a portion of the truncated envelope protein encoded by the 1q23.3 full-length HERV-K (HML-2) Env sequence of SEQ ID NO: 16 was selected to create the HERV-K (HML-2) Env analog of SEQ ID NO: 22. It was expected that a short HERV-K (HML-2) Env analog (19 amino acids in length) would minimize folding which may improve binding and therefore improve immunogenicity. The HERV-K (HML-2) Env analog of SEQ ID NO: 22 is shown below.

```
                                    (SEQ ID NO: 22)
          VWVPGPTDDRCPAKPEEEG.
```

FIG. 6A and FIG. 6B are a Clustal Omega amino acid sequence comparison that shows the alignment of the 1q23.3 full-length HERV-K Env sequence (SEQ ID NO: 16) with the HERV-K (HML-2) Env analog of SEQ ID NO: 22. As shown in the Clustal Omega amino acid sequence comparison of FIG. 5A, FIG. 5B, FIG. 5C, FIG. 5D, FIG. 5E, and FIG. 5F, the HERV-K (HML-2) Env analog of SEQ ID NO: 22 also partially aligns with amino acids 131-149 of the HERV-K (HML-2) Env consensus sequence of SEQ ID NO: 8 which belong to the extracellular domain of the Env protein.

It was anticipated that endogenous HERV-K (HML-2) Env protein might be accessible to the circulating antibodies generated by the immunization with the compound, facilitating the binding. The HERV-K (HML-2) Env analog is from a truncated envelope protein encoded by the locus 1q23.3 (SEQ ID NO: 16, Uniprot: 042043). This was the sequence used in a previous study (Arru G et al. *HERV-K Modulates the Immune Response in ALS Patients. Microorganisms*. 2021 Aug. 23; 9 (8): 1784.) to find immunogenic peptides and they found that this HERV-K (HML-2) Env analog elicited an increased humoral response in ALS patients compared to controls. This was confirmed in a posterior study (Garcia-Montojo et al. *Antibody Response to HML-2 May Be Protective in Amyotrophic Lateral Sclerosis. Ann Neurol.* 2022 November; 92 (5): 782-792.) The HERV-K (HML-2) Env analog of SEQ ID NO: 22 contains a peptide DDRCPAKPEEEG (SEQ ID NO: 32) predicted to bind to B-cell receptors, as analyzed by BepiPred Linear Epitope Prediction 2.0 (Department of Health Technology (DTU) Institute, Lyngby Denmark), which is necessary to induce humoral immunity. FIG. 12 is a Clustal Omega amino acid sequence comparison showing the alignment of the HERV-K (HML-2) Env analog (SEQ ID NO: 22) and its corresponding predicted epitope for binding to B-cell receptors (SEQ ID NO: 32).

The HERV-K (HML-2) Env analog of SEQ ID NO: 22 was linked via the short linker GGGSGGGS (SEQ ID NO: 2) to the IgG1 Fc fragment of SEQ ID NO: 1.

```
                                      (SEQ ID NO: 1)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPG.
```

It was expected that the use of a short linker would improve manufacturability.

The resultant HERV-K (HML-2) Env analog-Fc fusion protein is given below as SEQ ID NO: 44.

```
                                     (SEQ ID NO: 44)
VWVPGPTDDRCPAKPEEEGGGGSGGGSDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQ

KSLSLSPG.
```

The HERV-K (HML-2) Env analog-Fc fusion protein of SEQ ID NO: 44 was manufactured in CHO cells according to Example 4 and was purified according to Example 6. The Fc fusion protein structure of the HERV-K (HML-2) Env analog-Fc fusion protein of SEQ ID NO: 44 was confirmed according to Example 7, and sequence identification is performed according to Example 8. The resultant yield of the HERV-K (HML-2) Env analog-Fc fusion protein produced was 140 mg/L.

Immunization studies to evaluate the effectiveness of the HERV-K (HML-2) Env analog-Fc fusion protein of SEQ ID NO: 44 were performed in 6- to 8-week-old BALB/c mice according to Example 11. Mice were administered three doses of 30 μg of the HERV-K (HML-2) Env analog-Fc fusion protein of SEQ ID NO: 44 with and without adjuvant 4 weeks apart (on Day 0, Day 28 and Day 56) via subcutaneous (s.c.) injection. Blood was obtained from each mouse for antibody titer analysis via ELISA via submandibular venipuncture 21 to 28 days prior to the first injection and then 21 to 28 days after each injection.

The binding capacity of the mice antisera to the HERV-K (HML-2) Env protein and the total levels of IgG anti-HERV-K (HML-2) Env Ab titers in the mice antisera were measured according to Example 12. The resultant total IgG anti-HERV-K (HML-2) Env Ab titers yield in the antisera from mice immunized with the HERV-K (HML-2) Env analog-Fc fusion protein of SEQ ID NO: 44 was 1.1 μg/mL, which was unacceptably low. The IgG1 and IgG2a anti-HERV-K (HML-2) Env Ab titers in the mice antisera were measured according to Example 13, and the ratio of IgG1/IgG2a was calculated as 1.13, which was unacceptably low.

SEQ ID NO: 44 did meet the design goal of a HERV-K (HML-2) Env analog-Fc fusion protein with a manufacturing yield greater than 50 mg/L. Manufacturability was good, further suggesting that the short linker and IgG1 Fc fragment combination is compatible. Total IgG titers and ratio were very low, in spite of the previous study results regarding the increased humoral response in ALS patients (Garcia-Montojo M, Simula E R, Fathi S, McMahan C, Ghosal A, Berry J D, Cudkowicz M, Elkahloun A, Johnson K, Norato G, Jensen P, James T, Sechi L A, Nath A. *Antibody Response to HML-2 May Be Protective in Amyotrophic Lateral Sclerosis. Ann Neurol.* 2022 November; 92 (5): 782-792), indicating that the HERV-K (HML-2) Env analog selection was not successful. In consequence a different portion of the extracellular domain was selected.

As an eighth attempt in creating a novel HERV-K (HML-2) Env analog-Fc fusion protein analog-Fc a different portion of the extracellular domain (SEQ ID NO: 5) of the full-length HERV-K (HML-2) Env consensus sequence of SEQ ID NO: 8 was selected to create the HERV-K (HML-2) Env analog of SEQ ID NO: 23. It was expected that a short HERV-K (HML-2) Env analog (17 amino acids in length) would minimize folding which may improve binding and therefore improve immunogenicity. The HERV-K (HML-2) Env analog of SEQ ID NO: 23 is shown below.

```
                                     (SEQ ID NO: 23)
        APGCLMPAVQNWLVEVP.
```

FIG. 5A, FIG. 5B, FIG. 5C, FIG. 5D, FIG. 5E, and FIG. 5F are a Clustal Omega amino acid sequence comparison that includes the alignment of the full-length HERV-K (HML-2) Env consensus sequence (SEQ ID NO: 8) with the HERV-K (HML-2) Env analog of SEQ ID NO: 23.

As this HERV-K (HML-2) Env analog comprising amino acids 168-184 of the HERV-K (HML-2) Env consensus sequence of SEQ ID NO: 8 belongs to the extracellular domain of the Env protein it was anticipated that endogenous HERV-K (HML-2) Env protein might be accessible to the circulating antibodies generated by the immunization with the compound, facilitating the binding.

The HERV-K (HML-2) Env analog of SEQ ID NO: 23 was linked via the short linker GGGSGGGS (SEQ ID NO: 2) to the IgG1 Fc fragment of SEQ ID NO: 1.

```
                                          (SEQ ID NO: 1)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPG.
```

It was expected that the use of a short linker would improve manufacturability.

The resultant HERV-K (HML-2) Env analog-Fc fusion protein is given below as SEQ ID NO: 45.

```
                                         (SEQ ID NO: 45)
APGCLMPAVQNWLVEVPGGGSGGGSDKTHTCPPCPAPELLGGPSVFLFP

PKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKS

LSLSPG.
```

The HERV-K (HML-2) Env analog-Fc fusion protein of SEQ ID NO: 45 was manufactured in CHO cells according to Example 4 and was purified according to Example 6. The Fc fusion protein structure of the HERV-K (HML-2) Env analog-Fc fusion protein of SEQ ID NO: 45 was confirmed according to Example 7, and sequence identification is performed according to Example 8. The resultant yield of the HERV-K (HML-2) Env analog-Fc fusion protein produced was 81 mg/L.

Immunization studies to evaluate the effectiveness of the HERV-K (HML-2) Env analog-Fc fusion protein of SEQ ID NO: 45 were performed in 6- to 8-week-old BALB/c mice according to Example 11. Mice were administered three doses of 30 µg of the HERV-K (HML-2) Env analog-Fc fusion protein of SEQ ID NO: 45 with and without adjuvant 4 weeks apart (on Day 0, Day 28 and Day 56) via subcutaneous (s.c.) injection. Blood was obtained from each mouse for antibody titer analysis via ELISA via submandibular venipuncture 21 to 28 days prior to the first injection and then 21 to 28 days after each injection.

The binding capacity of the mice antisera to the HERV-K (HML-2) Env protein and the total levels of IgG anti-HERV-K (HML-2) Env Ab titers in the mice antisera were measured according to Example 12. The resultant total IgG anti-HERV-K (HML-2) Env Ab titers yield in the antisera from mice immunized with the HERV-K (HML-2) Env analog-Fc fusion protein of SEQ ID NO: 45 was 1.078 µg/mL, which was unacceptably low. The IgG1 and IgG2a anti-HERV-K (HML-2) Env Ab titers in the mice antisera were measured according to Example 13, and the ratio of IgG1/IgG2a was calculated as 1.27, which was unacceptably low.

SEQ ID NO: 45 did meet the design goal of a HERV-K (HML-2) Env analog-Fc fusion protein with a manufacturing yield greater than 50 mg/L. Manufacturability was good, further suggesting that the short linker and IgG1 Fc fragment combination is compatible. Total IgG titers and ratio were very low indicating that the HERV-K (HML-2) Env analog selection was not successful. This may have been because it does not contain any peptide able to bind to B-cell receptors, as per analysis with BepiPred Linear Epitope Prediction 2.0 (Department of Health Technology (DTU) Institute, Lyngby Denmark). In consequence a different HERV-K (HML-2) Env analog of the extracellular domain was selected which would contain peptides that are predicted to be able to bind to B-cell receptors.

As a ninth attempt in creating a novel HERV-K (HML-2) Env analog-Fc fusion protein, a different portion of the extracellular domain (SEQ ID NO: 5) of the full-length HERV-K (HML-2) Env consensus sequence of SEQ ID NO: 8 was selected to create the HERV-K (HML-2) Env analog of SEQ ID NO: 25. It was expected that a longer HERV-K (HML-2) Env analog (40 amino acids in length) may potentially incorporate more epitopes which may improve binding and therefore increase immunogenicity. The HERV-K (HML-2) Env analog of SEQ ID NO: 25 is shown below.

```
                                         (SEQ ID NO: 25)
  SPVSGPEHPELWRLTVASHHIRIWSGNQTLETRDRKPFYT.
```

FIG. 5A, FIG. 5B, FIG. 5C, FIG. 5D, FIG. 5E, and FIG. 5F are a Clustal Omega amino acid sequence comparison that includes the alignment of the full-length HERV-K (HML-2) Env consensus sequence (SEQ ID NO: 8) with the HERV-K (HML-2) Env analog of SEQ ID NO: 25.

As this HERV-K (HML-2) Env analog comprising amino acids 329-368 of the HERV-K (HML-2) Env consensus sequence of SEQ ID NO: 8 belongs to the extracellular domain of the Env protein it was anticipated that endogenous HERV-K (HML-2) Env protein might be accessible to the circulating antibodies generated by the immunization with the compound, facilitating the binding. The HERV-K (HML-2) Env analog of SEQ ID NO: 25 contains two peptides: SPVSGPEHPE (SEQ ID NO: 34) and IRIWSGNQTLETRDRKPFYT (SEQ ID NO: 35), predicted to bind to B-cell receptors, as analyzed by BepiPred Linear Epitope Prediction 2.0 (Department of Health Technology (DTU) Institute, Lyngby Denmark), which is necessary to induce humoral immunity. FIG. 13 is a Clustal Omega amino acid sequence comparison showing the alignment of the HERV-K (HML-2) Env analog (SEQ ID NO: 25) and its corresponding predicted epitopes for binding to B-cell receptors (SEQ ID NO: 34 and SEQ ID NO: 35).

The HERV-K (HML-2) Env analog of SEQ ID NO: 25 was linked via the short linker GGGSGGGS (SEQ ID NO: 2) to the IgG1 Fc fragment of SEQ ID NO: 1.

```
                                          (SEQ ID NO: 1)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPG.
```

It was expected that the use of a short linker would improve manufacturability.

The resultant HERV-K (HML-2) Env analog-Fc fusion protein is given below as SEQ ID NO: 47.

```
                                    (SEQ ID NO: 47)
SPVSGPEHPELWRLTVASHHIRIWSGNQTLETRDRKPFYTGGGSGGGSD

KTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRW

QQGNVFSCSVMHEALHNHYTQKSLSLSPG.
```

The HERV-K (HML-2) Env analog-Fc fusion protein of SEQ ID NO: 47 was manufactured in CHO cells according to Example 4 and was purified according to Example 6. The Fc fusion protein structure of the HERV-K (HML-2) Env analog-Fc fusion protein of SEQ ID NO: 47 was confirmed according to Example 7, and sequence identification is performed according to Example 8. The resultant yield of the HERV-K (HML-2) Env analog-Fc fusion protein produced was 111 mg/L.

Immunization studies to evaluate the effectiveness of the HERV-K (HML-2) Env analog-Fc fusion protein of SEQ ID NO: 47 were performed in 6- to 8-week-old BALB/c mice according to Example 11. Mice were administered three doses of 30 μg of the HERV-K (HML-2) Env analog-Fc fusion protein of SEQ ID NO: 47 with and without adjuvant 4 weeks apart (on Day 0, Day 28 and Day 56) via subcutaneous (s.c.) injection. Blood was obtained from each mouse for antibody titer analysis via ELISA via submandibular venipuncture 21 to 28 days prior to the first injection and then 21 to 28 days after each injection.

Figure 14:
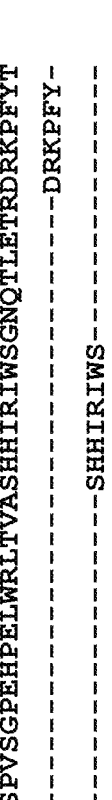
FIG. 14 is a Clustal Omega amino acid sequence comparison showing the alignment of a HERV-K (HML-2) Env analog (SEQ ID NO: 25) and its corresponding recognized epitopes (SEQ ID NO: 36 and SEQ ID NO: 37).

The binding capacity of the mice antisera to the HERV-K (HML-2) Env protein and the total levels of IgG anti-HERV-K (HML-2) Env Ab titers in the mice antisera were measured according to Example 12. The resultant total IgG anti-HERV-K (HML-2) Env Ab titers yield in the antisera from mice immunized with the HERV-K (HML-2) Env analog-Fc fusion protein of SEQ ID NO: 47 was 186 μg/mL, which was unexpectedly high. The IgG1 and IgG2a anti-HERV-K (HML-2) Env Ab titers in the mice antisera were measured according to Example 13, and the ratio of IgG1/IgG2a was calculated as 60.86, which was also unexpectedly high. In addition, epitope mapping according to Example 14 showed recognition of the specific HERV-K (HML-2) Env sequences DRKPFY (SEQ ID NO: 36) and SHHIRIWS (SEQ ID NO: 37) with a sum of fluorescence intensities: 903760 A.U. Fluorescence intensity is the readout of the peptide array assay used for epitope mapping in Example 14 and it is indicative of the level of antibodies binding to a particular region of the protein. FIG. 14 is a Clustal Omega amino acid sequence comparison showing the alignment of the HERV-K (HML-2) Env analog (SEQ ID NO: 25) and its corresponding recognized epitopes (SEQ ID NO: 36 and SEQ ID NO: 37).

SEQ ID NO: 47 met the design goal of a HERV-K (HML-2) Env analog-Fc fusion protein with a manufacturing yield greater than 50 mg/L. In addition, the total anti-HERV-K Env IgG titer and anti-HERV-K Env IgG1/IgG2 ratio were high and met the design goals. The HERV-K (HML-2) Env analog selection combined with the short linker and IgG1 in SEQ ID NO: 47 met the required target criteria for a HERV-K (HML-2) Env analog-Fc fusion protein.

As a tenth attempt in creating a novel HERV-K (HML-2) Env analog-Fc fusion protein, a different portion of the extracellular domain (SEQ ID NO: 5) of the full-length HERV-K (HML-2) Env consensus sequence of SEQ ID NO: 8 was selected to create the HERV-K (HML-2) Env analog of SEQ ID NO: 24. It was expected that a longer HERV-K (HML-2) Env analog (50 amino acids in length) may potentially incorporate more epitopes which may improve binding and therefore increase immunogenicity. The HERV-K (HML-2) Env analog of SEQ ID NO: 24 is shown below.

```
                                    (SEQ ID NO: 24)
GQFYHNCSGQTQSCPSAQVSPAVDSDLTESLDKHKHKKLQSFYPWEWGE

K.
```

FIG. 5A, FIG. 5B, FIG. 5C, FIG. 5D, FIG. 5E, and FIG. 5F are a Clustal Omega amino acid sequence comparison that includes the alignment of the full-length HERV-K (HML-2) Env consensus sequence (SEQ ID NO: 8) with the HERV-K (HML-2) Env analog of SEQ ID NO: 24.

As this HERV-K (HML-2) Env analog comprising amino acids 269-318 of the HERV-K (HML-2) Env consensus sequence of SEQ ID NO: 8 belongs to the extracellular domain of the Env protein it was anticipated that endogenous HERV-K (HML-2) Env protein might be accessible to the circulating antibodies generated by the immunization with the compound, facilitating the binding.

The HERV-K (HML-2) Env analog of SEQ ID NO: 24 includes the G01 binding epitope SLDKHKHKKLQSFYP (SEQ ID NO: 17), which was previously found to be neutralizing (Steiner et al Annals of Neurology, 2022) and was also found in the epitope mapping studies performed on serum samples from individuals with ALS (Example 1). FIG. 7A, FIG. 7B, and FIG. 7C are a Clustal Omega amino acid sequence comparison showing the alignment of the full-length HERV-K (HML-2) Env consensus sequence (SEQ ID NO: 8) and the G01 epitope (SEQ ID NO: 17).

The HERV-K (HML-2) Env analog of SEQ ID NO: 24 is a peptide GQFYHNCSGQTQSCPSAQVSPAV-DSDLTESLDKHKHKKLQSFYPWEWGEK (SEQ ID NO: 24) predicted to bind to B-cell receptors, as analyzed by BepiPred Linear Epitope Prediction 2.0 (Department of Health Technology (DTU) Institute, Lyngby Denmark), which is necessary to induce humoral immunity.

The HERV-K (HML-2) Env analog of SEQ ID NO: 24 was linked via the short linker GGGSGGGS (SEQ ID NO: 2) to the IgG1 Fc fragment of SEQ ID NO: 1.

```
                                    (SEQ ID NO: 1)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPG.
```

It was expected that the use of a short linker would improve manufacturability.

The resultant HERV-K (HML-2) Env analog-Fc fusion protein is given below as SEQ ID NO: 46.

```
                                    (SEQ ID NO: 46)
GQFYHNCSGQTQSCPSAQVSPAVDSDLTESLDKHKHKKLQSFYPWEWGE

KGGGSGGGSDKTHTCPPCPAPELLGGPSVFLFPPKPKDTLMISRTPEVT
```

-continued

```
CVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLY

SKLTVDKSRWQQGNVFSCSVMHEALHNHYTQKSLSLSPG.
```

The HERV-K (HML-2) Env analog-Fc fusion protein of SEQ ID NO: 46 was manufactured in CHO cells according to Example 4 and was purified according to Example 6. The Fc fusion protein structure of the HERV-K (HML-2) Env analog-Fc fusion protein of SEQ ID NO: 46 was confirmed according to Example 7, and sequence identification is performed according to Example 8. The resultant yield of the HERV-K (HML-2) Env analog-Fc fusion protein produced was 125 mg/L.

Immunization studies to evaluate the effectiveness of the HERV-K (HML-2) Env analog-Fc fusion protein of SEQ ID NO: 46 were performed in 6- to 8-week-old BALB/c mice according to Example 11. Mice were administered three doses of 30 μg of the HERV-K (HML-2) Env analog-Fc fusion protein of SEQ ID NO: 46 with and without adjuvant 4 weeks apart (on Day 0, Day 28 and Day 56) via subcutaneous (s.c.) injection. Blood was obtained from each mouse for antibody titer analysis via ELISA via submandibular venipuncture 21 to 28 days prior to the first injection and then 21 to 28 days after each injection.

The binding capacity of the mice antisera to the HERV-K (HML-2) Env protein and the total levels of IgG anti-HERV-K (HML-2) Env Ab titers in the mice antisera were measured according to Example 12. The resultant total IgG anti-HERV-K (HML-2) Env Ab titers yield in the antisera from mice immunized with the HERV-K (HML-2) Env analog-Fc fusion protein of SEQ ID NO: 46 was 2640 μg/mL, which was unexpectedly very high. The IgG1 and IgG2a anti-HERV-K (HML-2) Env Ab titers in the mice antisera were measured according to Example 13, and the ratio of IgG1/IgG2a was calculated as 836.60, which was also unexpectedly very high. In addition, epitope mapping according to Example 14 showed recognition of the specific HERV-K (HML-2) Env sequence SFYPWE (SEQ ID NO: 33) with a sum of fluorescence intensities: 241542 A.U. Fluorescence intensity is the readout of the peptide array assay used for epitope mapping in Example 14 and it is indicative of the level of antibodies binding to a particular region of the protein. FIG. 15 is a Clustal Omega amino acid sequence comparison showing the alignment of the HERV-K (HML-2) Env analog (SEQ ID NO: 24) and its corresponding recognized epitope (SEQ ID NO: 33).

The binding affinity of antisera of mice immunized with the vaccine compound of SEQ ID NO: 46 was evaluated according to Example 15 and Rmax was evaluated as 280.6 for a dilution of 1:100, where Rmax represents the maximum binding capacity of a ligand-analyte interaction, expressed in response units. It is the assessed saturation point of the association rate determined from kinetic evaluations performed by injecting a concentration series of the HERV-K (HML-2) Env recombinant protein (Cusabio), whose sequence comprises the HERV-K Env analog SEQ ID NO: 24 present in HERV-K (HML-2) Env analog-Fc fusion protein SEQ ID NO: 46.

Immunization studies to evaluate the effectiveness of the HERV-K (HML-2) Env analog-Fc fusion protein of SEQ ID NO: 46 were performed in 4 to 6.5 years old male Cynomolgus monkeys according to Example 21. Non-human primates (NHPs) were administered four doses of 90 μg (0.090 mg) of the HERV-K (HML-2) Env analog-Fc fusion protein of SEQ ID NO: 46 with adjuvant on Day 0, Day 14, Day 28 and Day 56 via subcutaneous (s.c.) injection. Blood was obtained from each NHP for antibody titer analysis via ELISA via an appropriate peripheral vein on Day 0, Day 14, Day 28, Day 42 and Day 70. On days where blood samples and immunization injections both occurred, the blood sample was taken first before the immunization injection.

Figure 28:
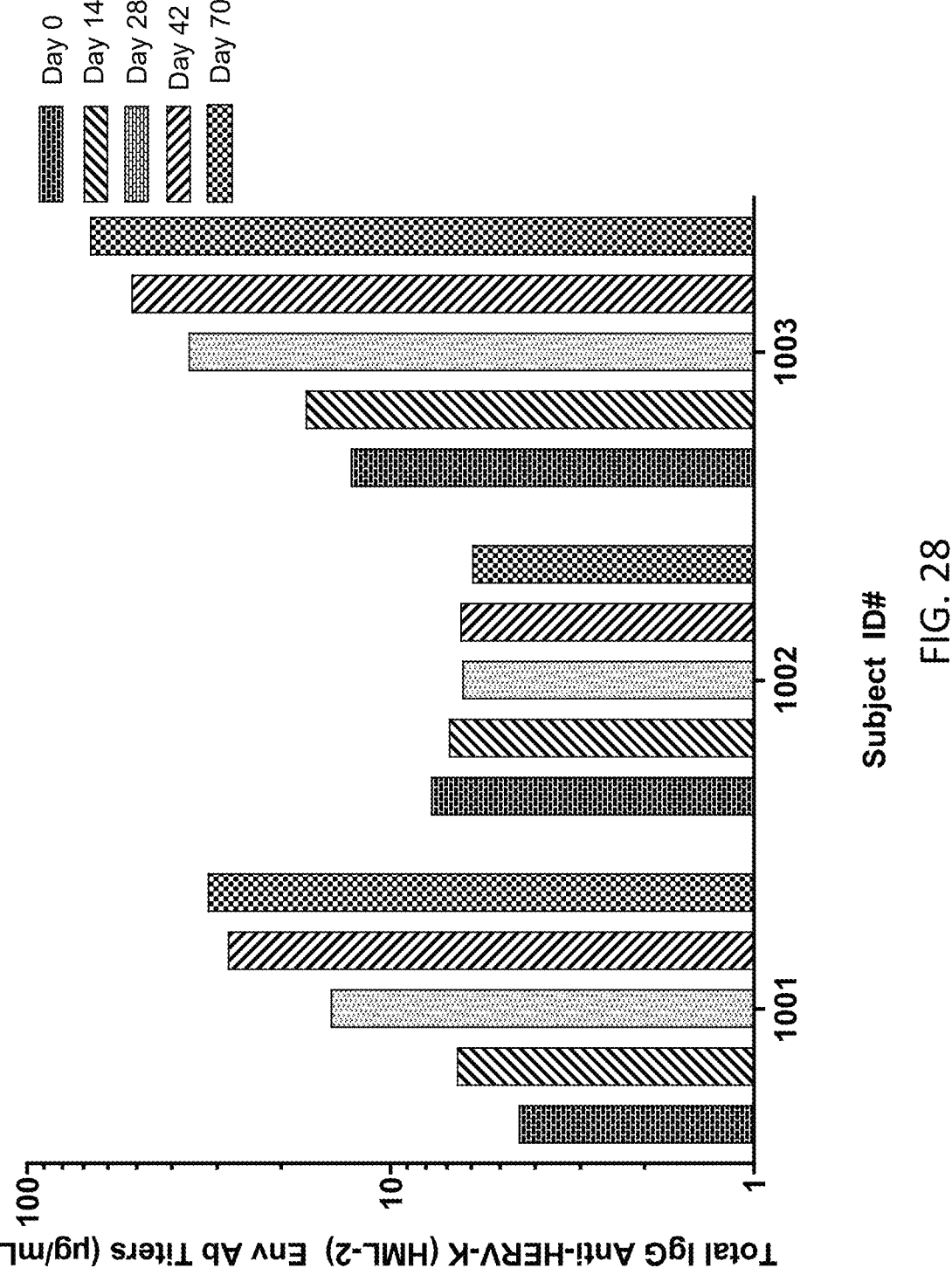
FIG. 28 is a graph showing the measured total anti-HERV-K (HML-2) Env IgG titers measured in serum from monkeys immunized with the HERV-K (HML-2) Env analog-Fc fusion protein of SEQ ID NO: 46.

The total levels of IgG anti-HERV-K (HML-2) Env Ab titers in the NHP antisera were measured according to Example 23. The resultant total IgG anti-HERV-K (HML-2) Env Ab titers yield in the NHP antisera from monkeys immunized with the HERV-K (HML-2) Env analog-Fc fusion protein of SEQ ID NO: 46 are shown in FIG. 28.

Figure 29:
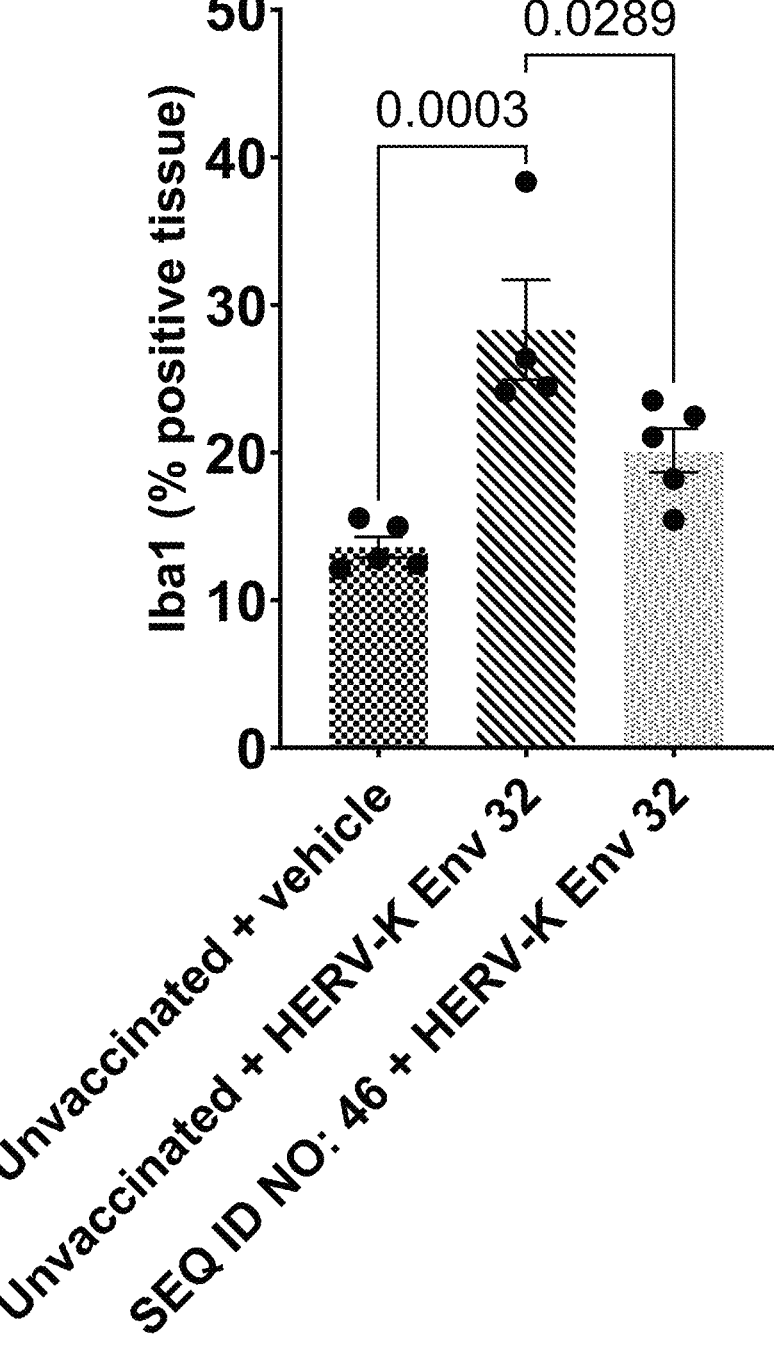
FIG. 29 is a graph showing the percentage of positive tissue for Iba1 stained brain samples from unvaccinated mice that were brain-inoculated with vehicle (2 µL), unvaccinated mice that were brain-inoculated with HERV-K Env 32 ng/µL (2 µL), and mice treated with the HERV-K (HML-2) Env analog-Fc fusion protein of SEQ ID NO: 46 that were brain-inoculated with HERV-K Env 32 ng/µL (2 µL)
Figure 30:
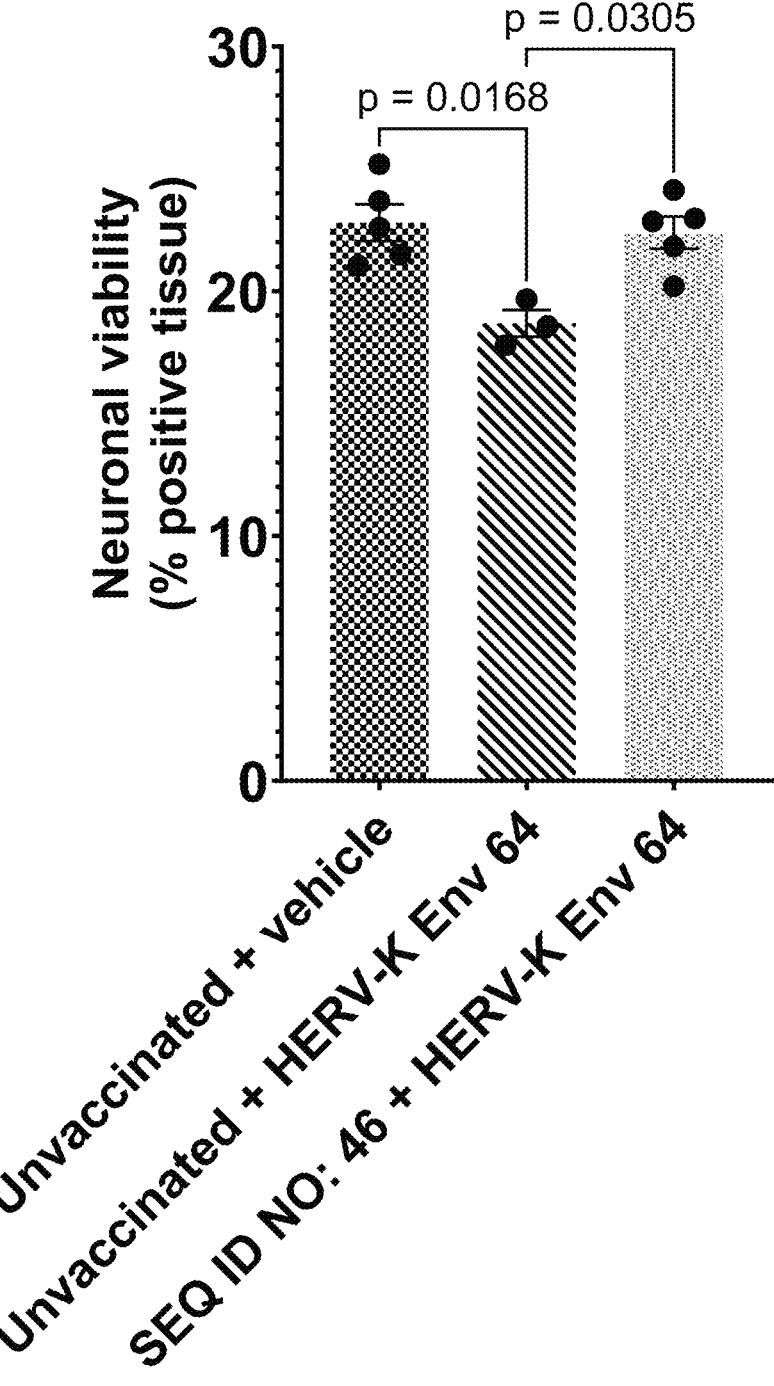
FIG. 30 is a graph showing neuronal viability as the percentage of positive tissue for Nissl staining with Thionine in brain samples from unvaccinated mice that were brain-inoculated with vehicle (2 µL), unvaccinated mice that were brain-inoculated with HERV-K Env 64 ng/µL (2 µL), and mice treated with the HERV-K (HML-2) Env analog-Fc fusion protein of SEQ ID NO: 46 that were brain-inoculated with HERV-K Env 64 ng/µL (2 µL).

The brains from mice immunized with the HERV-K (HML-2) Env analog-Fc fusion protein of SEQ ID NO: 46 were processed according to Example 18. FIG. 29 is a graph showing the percentage of positive tissue for Iba1 stained brain samples from unvaccinated mice that were brain-inoculated with vehicle (2 μL), unvaccinated mice that were brain-inoculated with recombinant HERV-K Env (Cusabio) 32 ng/μL (2 μL), and mice treated with the HERV-K (HML-2) Env analog-Fc fusion protein of SEQ ID NO: 46 that were brain-inoculated with recombinant HERV-K Env (Cusabio) 32 ng/μL (2 μL). FIG. 30 is a graph showing neuronal viability as the percentage of positive tissue for Nissl staining with Thionine in brain samples from unvaccinated mice that were inoculated with vehicle (2 μL), unvaccinated mice that were brain-inoculated with recombinant HERV-K Env (Cusabio) 64 ng/μL (2 μL), and mice treated with the HERV-K (HML-2) Env analog-Fc fusion protein of SEQ ID NO: 46 that were brain-inoculated with HERV-K Env 64 ng/μL (2 μL). The recombinant HERV-K Env (Cusabio) used in the inoculation experiments contains the HERV-K Env analog (SEQ ID NO: 24) present in HERV-K (HML-2) Env analog-Fc fusion protein SEQ ID NO: 46.

SEQ ID NO: 46 met the design goal of a HERV-K (HML-2) Env analog-Fc fusion protein with a manufacturing yield greater than 50 mg/L. In addition, IgG titer and ratio were very high. The HERV-K (HML-2) Env analog selection combined with the short linker and IgG1 in SEQ ID NO: 46 met the required target criteria for a HERV-K (HML-2) Env analog-Fc fusion protein.

Figure 17A:
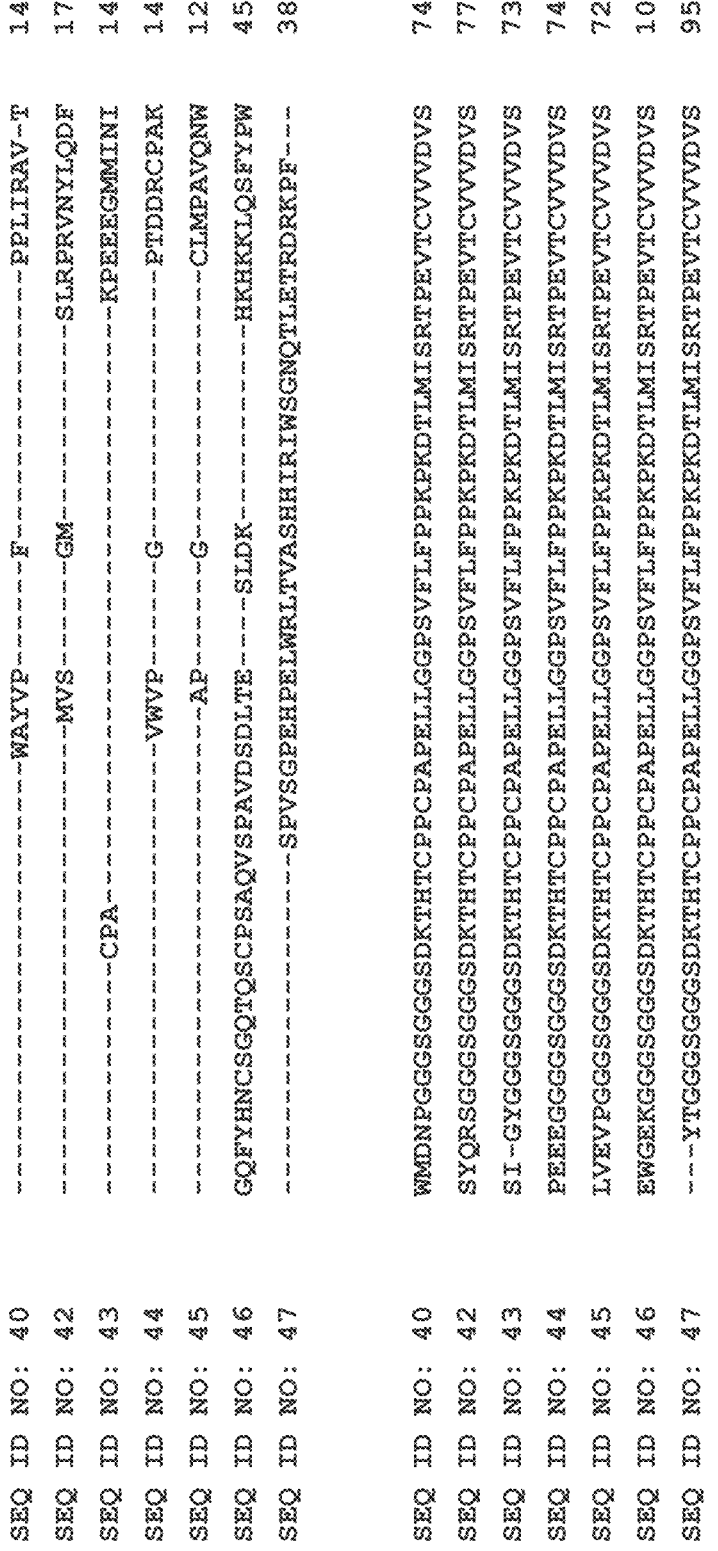
Figure 19B:
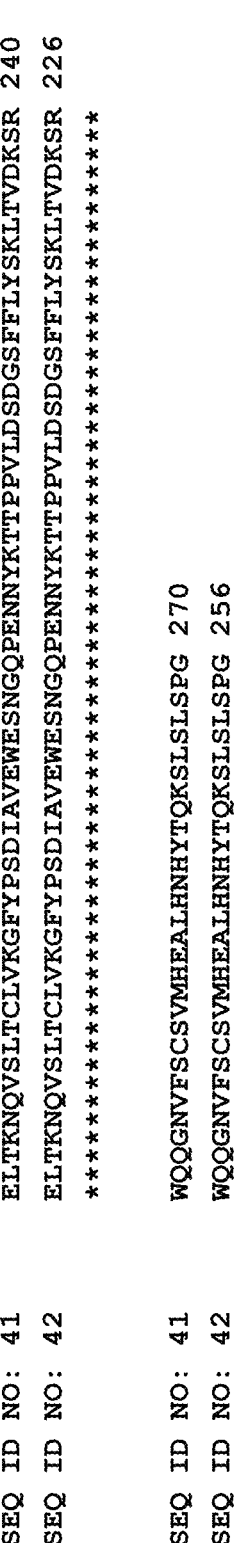

FIG. 5A, FIG. 5B, FIG. 5C, FIG. 5D, FIG. 5E, and FIG. 5F are a Clustal Omega amino acid sequence comparison showing the alignment of the full-length HERV-K (HML-2) Env consensus sequence (SEQ ID NO: 8) with the seven HERV-K (HML-2) Env analogs (SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25). FIG. 16A and FIG. 16B show a Clustal Omega amino acid sequence comparison of the three HERV-K (HML-2) Env analog-Fc fusion proteins (SEQ ID NO: 38, SEQ ID NO: 39, and SEQ ID NO: 41) that use a long linker (SEQ ID NO: 3). FIG. 17A, FIG. 17B, and FIG. 17C show a Clustal Omega amino acid sequence comparison of the seven HERV-K (HML-2) Env analog-Fc fusion proteins (SEQ ID NO: 40, SEQ ID NO: 42, SEQ ID NO: 43, SEQ ID NO: 44, SEQ ID NO: 45, SEQ ID NO: 46, and SEQ ID NO: 47) that use a short linker (SEQ ID NO: 2). FIG. 18A and FIG. 18B show a Clustal Omega amino acid sequence comparison of the two HERV-K (HML-2) Env analog Fc-fusion proteins (SEQ ID NO: 39 and SEQ ID NO: 40) that share a common HERV-K (HML-2) Env analog (SEQ ID NO: 19). FIG. 19A and FIG. 19B show a Clustal Omega amino acid sequence comparison of the two HERV-K (HML-2) Env analog-Fc fusion proteins (SEQ ID NO: 41 and SEQ ID NO: 42) that share a common HERV-K (HML-2) Env analog (SEQ ID NO: 20). FIG. 20A and FIG. 20B show a Clustal Omega amino acid sequence comparison of three HERV-K (HML-2) Env analog-Fc fusion proteins (SEQ ID NO: 43, SEQ ID NO: 44, and SEQ ID NO: 45) that do not share a HERV-K (HML-2) Env analog with any other HERV-K (HML-2) Env analog-Fc fusion protein.

The protein yields of the HERV-K (HML-2) Env analog-Fc fusion proteins of SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 47, and SEQ ID NO: 46 are shown below in Table 1.

TABLE 1

| Manufacturing yields of HERV-K (HML-2) Env analog-Fc fusion proteins | | | | |
|---|---|---|---|---|
| SEQ ID NO: | Calc. MW, without glycan (Da) | Volume Scale (L) | Yield (mg) | Yield (mg/L; rounded to nearest whole mg/L) | Calculated pI, without glycan (Expasy) |
| SEQ ID NO: 38 | 67256.50 | 0.03 | 2.0 | 65 | 8.17 |
| SEQ ID NO: 39 | 58091.40 | 0.03 | 1.1 | 37 | 6.72 |
| SEQ ID NO: 40 | 56373.86 | 0.03 | 1.8 | 60 | 6.72 |
| SEQ ID NO: 41 | 58814.06 | 0.03 | 1.4 | 46 | 7.62 |
| SEQ ID NO: 42 | 57096.52 | 0.03 | 3.9 | 130 | 7.62 |
| SEQ ID NO: 43 | 55789.12 | 0.03 | 3.4 | 112 | 6.19 |
| SEQ ID NO: 44 | 55989.04 | 0.03 | 4.2 | 140 | 6.00 |
| SEQ ID NO: 45 | 55472.86 | 0.03 | 2.4 | 81 | 6.42 |
| SEQ ID NO: 47 | 61227.00 | 0.03 | 3.3 | 111 | 7.12 |
| SEQ ID NO: 46 | 63245.00 | 0.03 | 3.8 | 125 | 6.59 |

Figure 22:
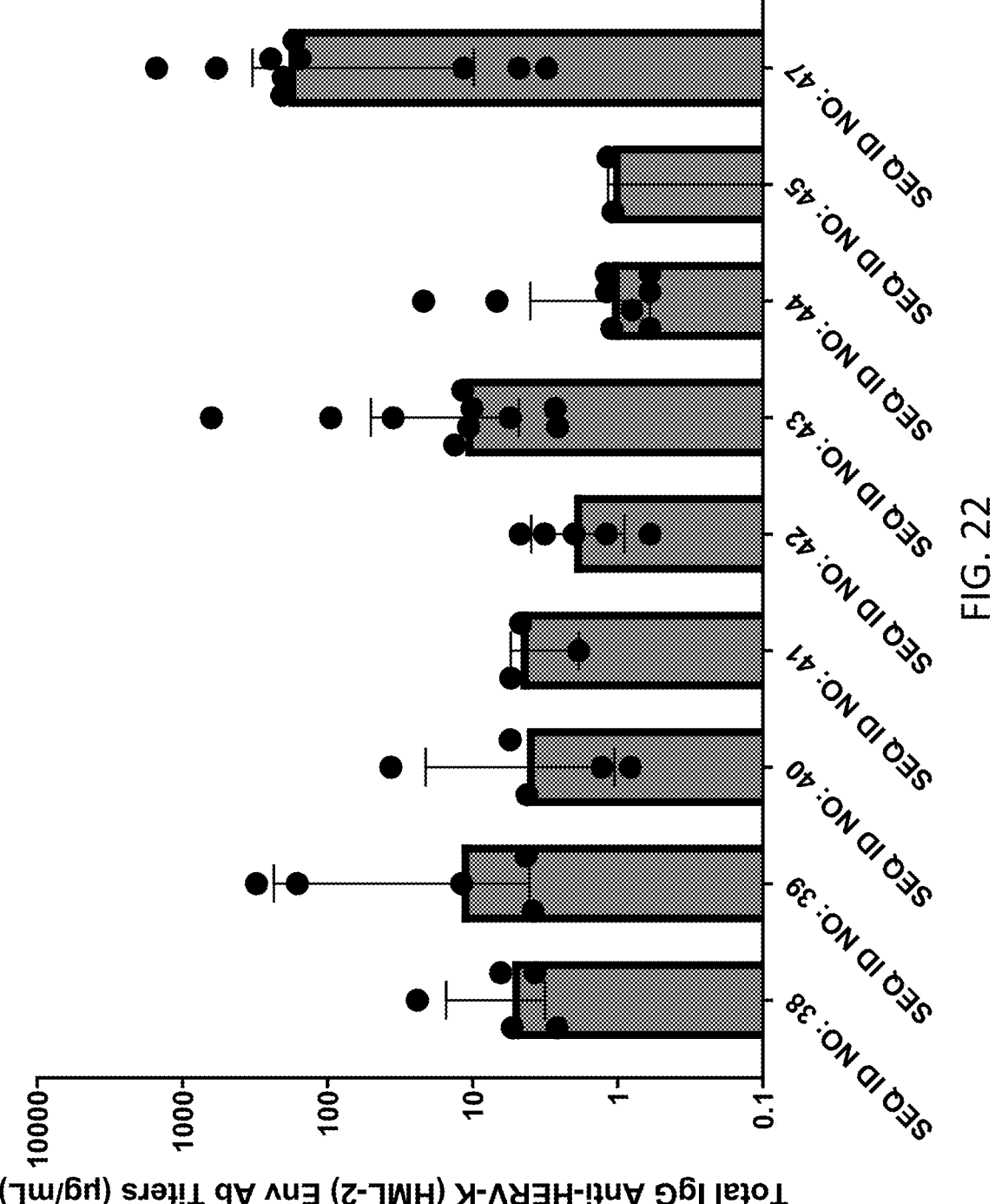
FIG. 22 is a graph showing the measured total anti-HERV-K (HML-2) Env IgG titers (individual and median) measured in serum from mice treated with nine different HERV-K (HML-2) Env analog-Fc fusion proteins (SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, and SEQ ID NO: 47).
Figure 23:
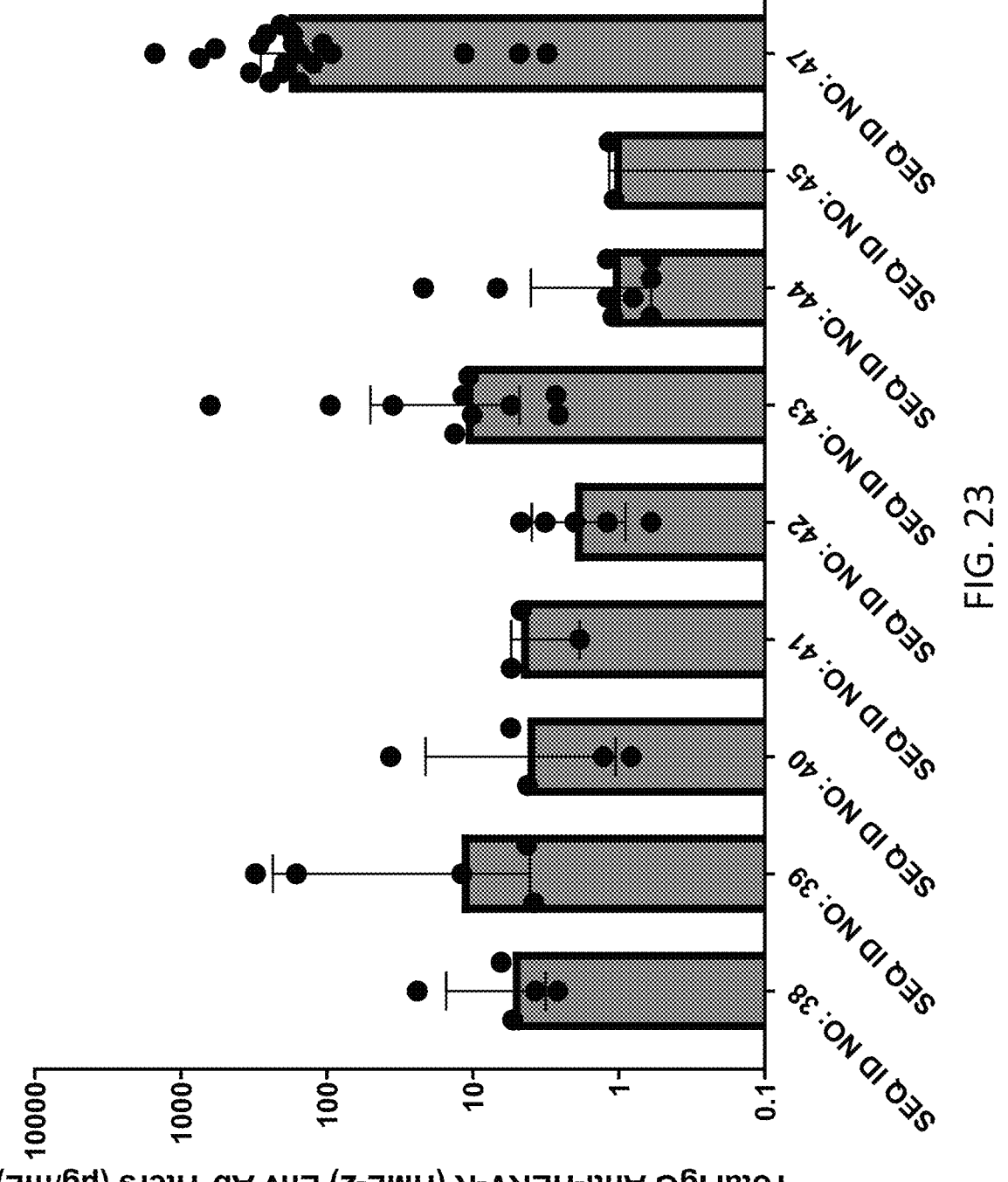
FIG. 23 is a graph showing the measured total anti-HERV-K (HML-2) Env IgG titers (individual and median) measured in serum from mice treated with nine different HERV-K (HML-2) Env analog-Fc fusion proteins (SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, and SEQ ID NO: 47) that includes additional data points for SEQ ID NO: 47 from a second immunogenicity study.
Figure 25:
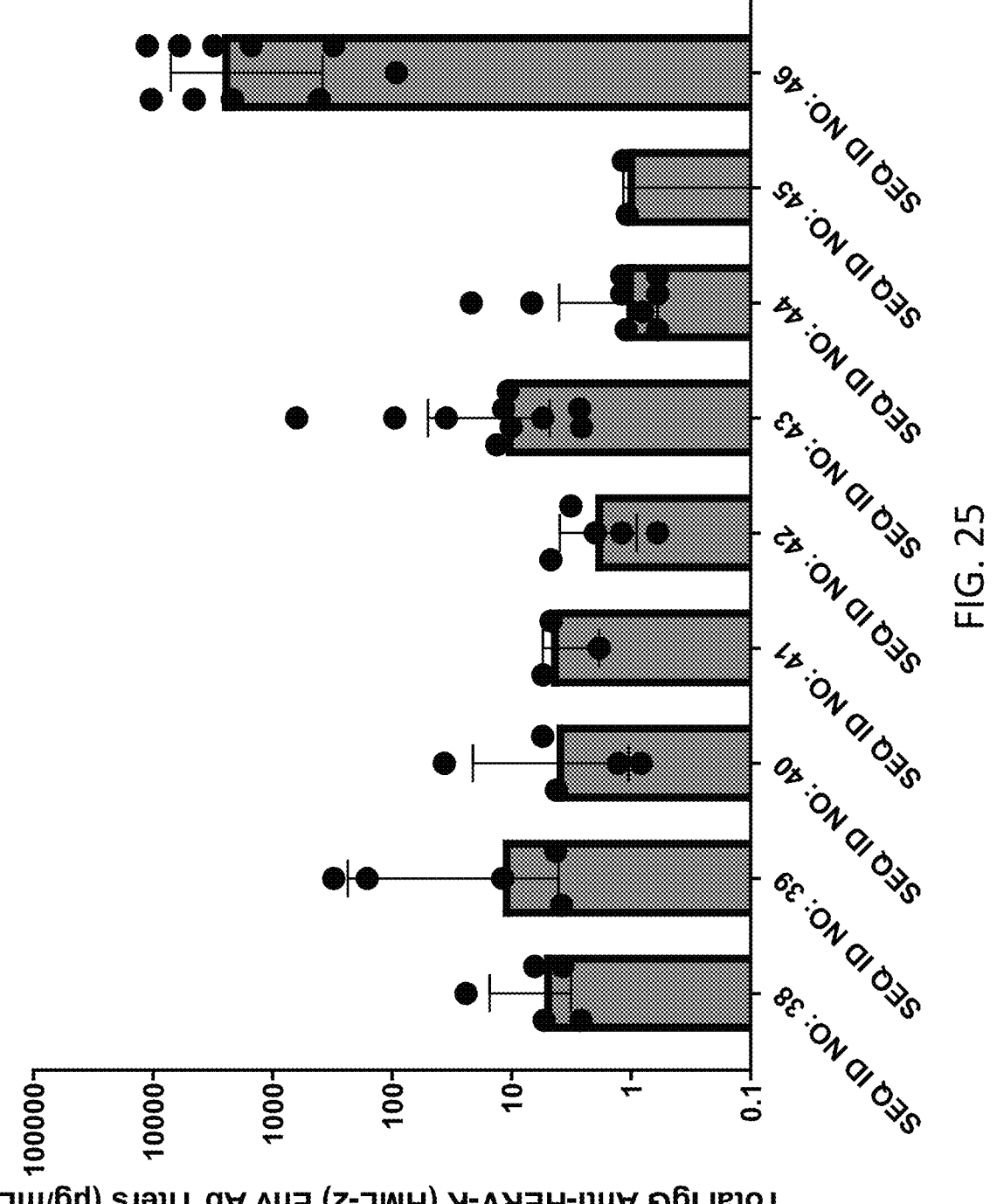
FIG. 25 is a graph showing the measured total anti-HERV-K (HML-2) Env IgG titers (individual and median) measured in serum from mice treated with nine different HERV-K (HML-2) Env analog-Fc fusion proteins (SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 46).
Figure 26:
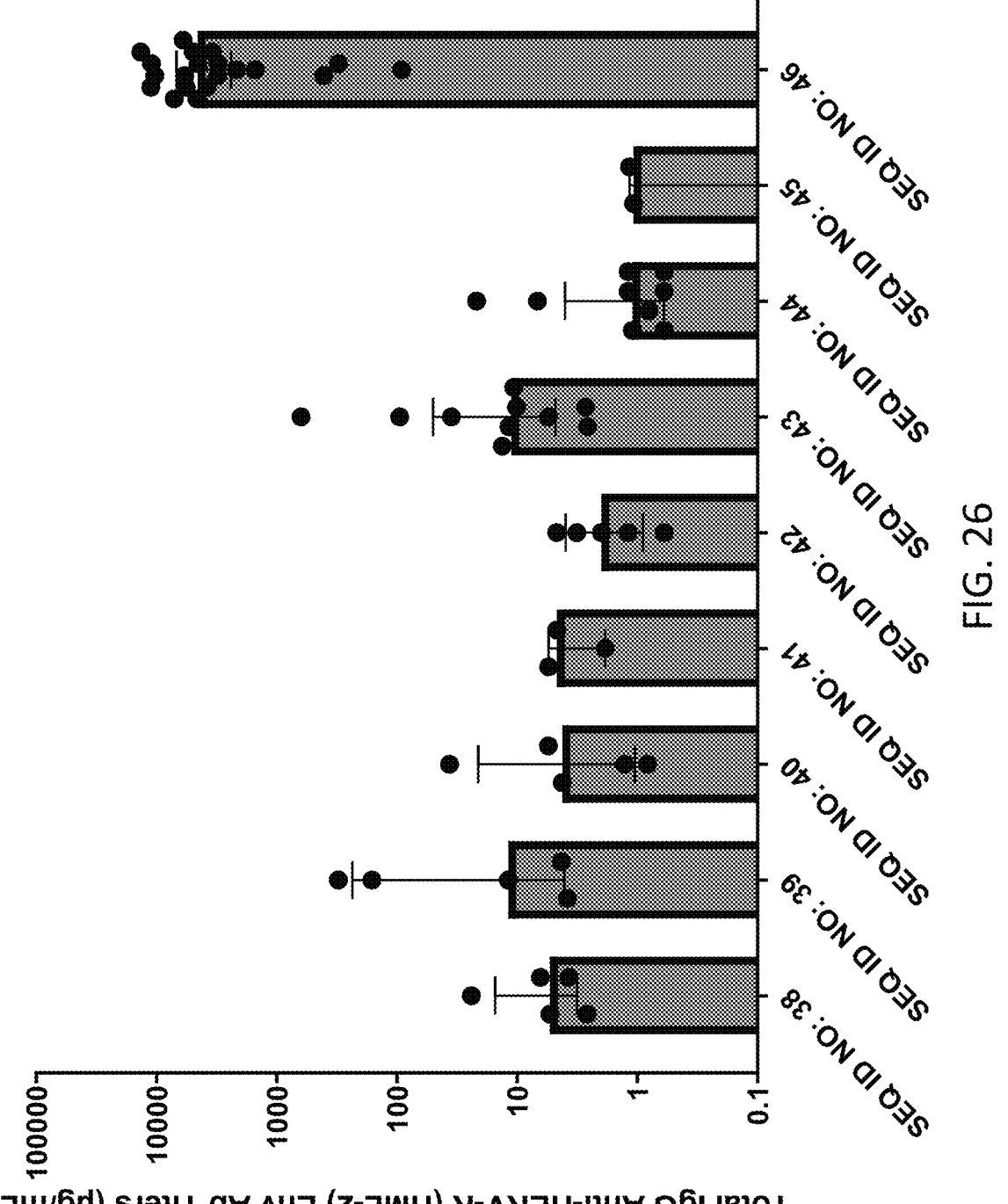
FIG. 26 is a graph showing the measured total anti-HERV-K (HML-2) Env IgG titers (individual and median) measured in serum from mice treated with nine different HERV-K (HML-2) Env analog-Fc fusion proteins (SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, and SEQ ID NO: 46) that includes additional data points for SEQ ID NO: 46 from a second immunogenicity study.

The binding capacity of the mice antisera to the HERV-K (HML-2) Env protein and the total levels of IgG anti-HERV-K (HML-2) Env Ab titers in the mice antisera from mice immunized with one of the ten different HERV-K (HML-2) Env analog-Fc fusion proteins (SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, and SEQ ID NO: 47) were measured according to Example 12. FIG. 22 is a graph showing the measured total anti-HERV-K (HML-2) Env IgG yields (individual and median) for the HERV-K (HML-2) Env analog-Fc fusion proteins of SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, and SEQ ID NO: 47. FIG. 23 is a graph showing the measured total anti-HERV-K (HML-2) Env IgG yields (individual and median) for the HERV-K (HML-2) Env analog-Fc fusion proteins of SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, and SEQ ID NO: 47 that includes additional data points for SEQ ID NO: 47 from a second immunogenicity study. FIG. 25 is a graph showing the measured total anti-HERV-K (HML-2) Env IgG yields (individual and median) for the HERV-K (HML-2) Env analog-Fc fusion proteins of SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, and SEQ ID NO: 46. FIG. 26 is a graph showing the measured total anti-HERV-K (HML-2) Env IgG yields (individual and median) for the HERV-K (HML-2) Env analog-Fc fusion proteins of SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, and SEQ ID NO: 46 that includes additional data points for SEQ ID NO: 46 from a second immunogenicity study. As can be seen from the graphs, SEQ ID NO: 47 had the maximum median anti-HERV-K (HML-2) Env IgG titer across all of the sequences in FIG. 22 and FIG. 23, and SEQ ID NO: 46 had the maximum median anti-HERV-K (HML-2) Env IgG titer across all of the sequences in FIG. 25 and FIG. 26.

Figure 24:
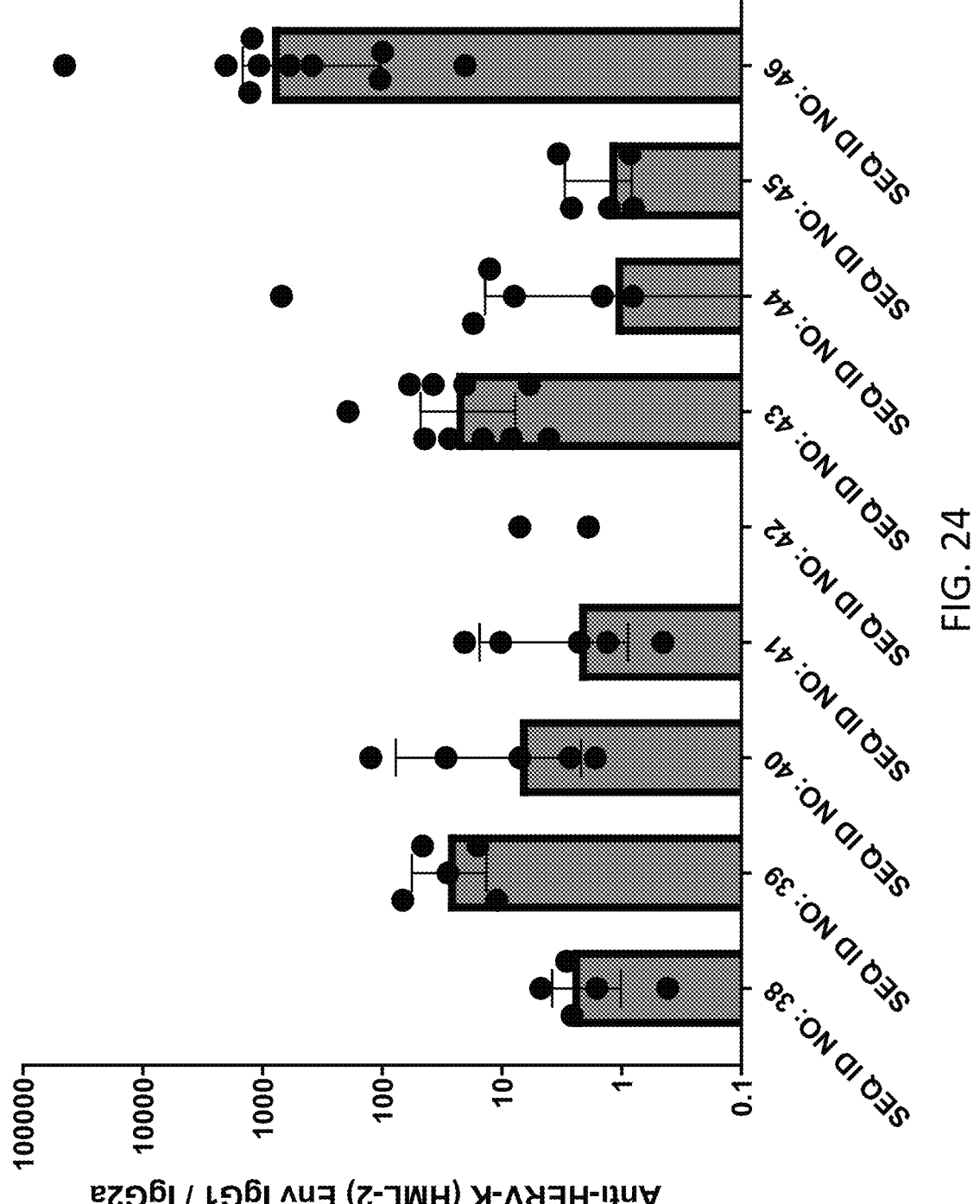
FIG. 24 is a graph showing the measured anti-HERV-K (HML-2) Env IgG1/IgG2a ratios (individual and median) measured in serum from mice treated with nine different HERV-K (HML-2) Env analog-Fc fusion proteins (SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, and SEQ ID NO: 47).
Figure 27:
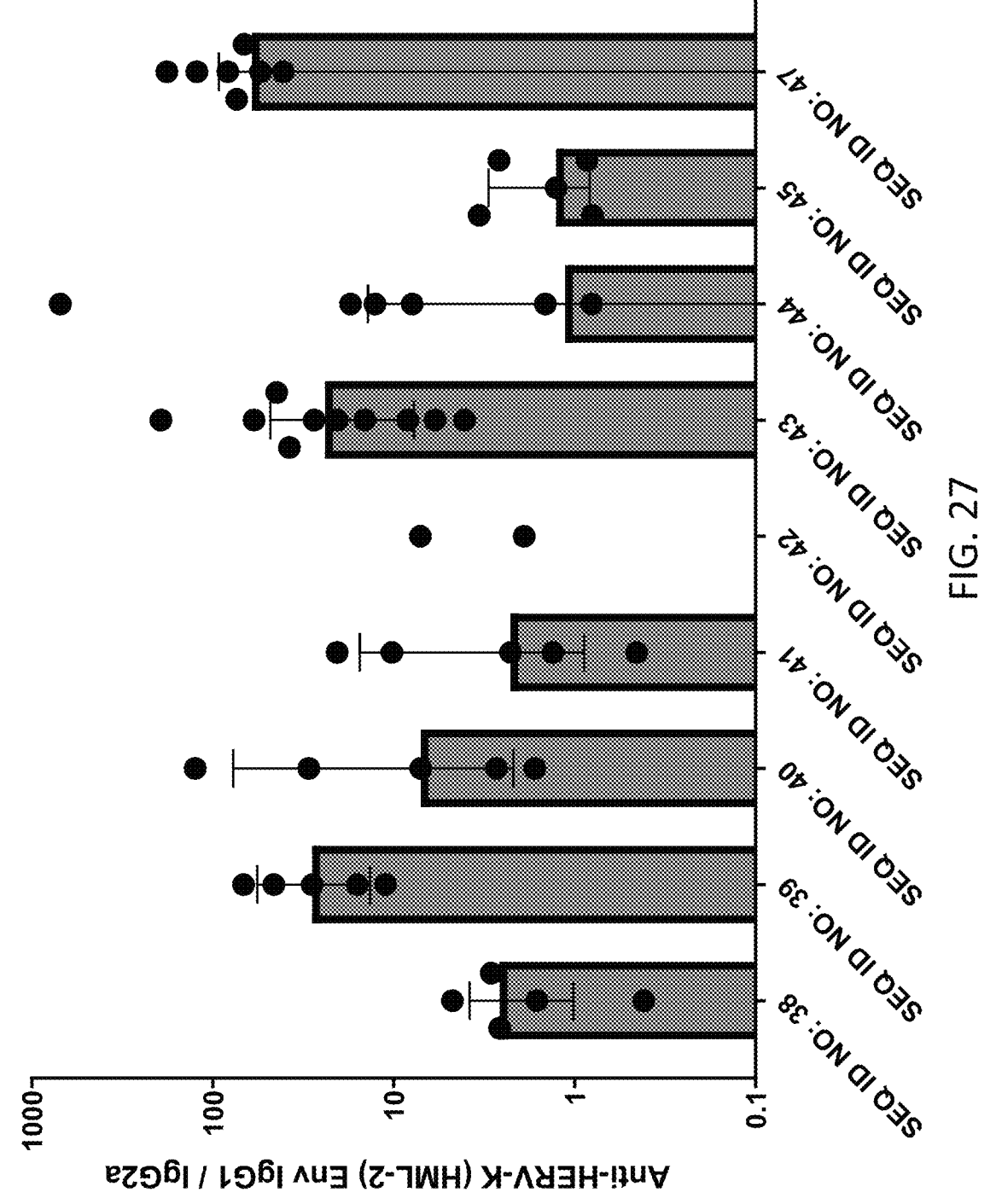
FIG. 27 is a graph showing the measured anti-HERV-K (HML-2) Env IgG1/IgG2a ratios (individual and median) measured in serum from mice treated with nine different HERV-K (HML-2) Env analog-Fc fusion proteins (SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, and SEQ ID NO: 46).

The IgG1 and IgG2a anti-HERV-K (HML-2) Env Ab titers in the mice antisera from mice immunized with one of the ten different HERV-K (HML-2) Env analog-Fc fusion proteins (SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, and SEQ ID NO: 47) were measured according to Example 13. FIG. 24 is a graph showing the measured IgG1/IgG2a ratios (individual and median) for the HERV-K (HML-2) Env analog-Fc fusion proteins SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, and SEQ ID NO: 47. FIG. 27 is a graph showing the measured IgG1/IgG2 ratios (individual and median) for the HERV-K (HML-2) Env analog-Fc fusion proteins SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, and SEQ ID NO: 46. As can be seen from the graphs, SEQ ID NO: 47 had the maximum median IgG1/IgG2 ratio across all of the sequences in FIG. 24 and SEQ ID NO: 46 had the maximum median IgG1/IgG2 ratio across all of the sequences in FIG. 27.

HERV-K (HML-2) Env Analog-Fc Fusion Proteins for Use as a Therapeutic Vaccine

Figure 21:
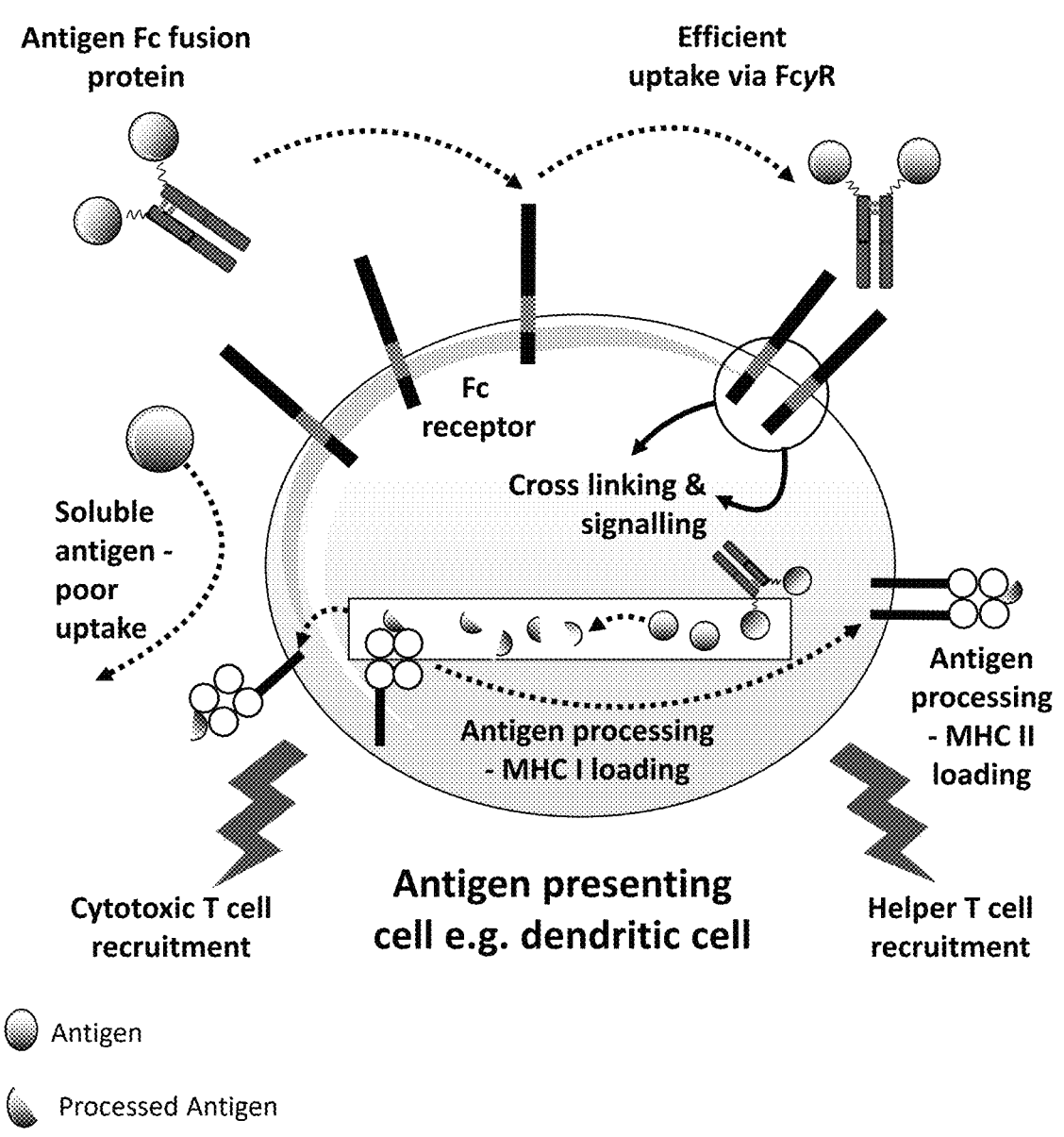
FIG. 21 is a schematic diagram depicting example modes in which an antigen may interact with an antigen presenting cell, e.g., a dendritic cell.

A HERV-K (HML-2) Env analog-Fc fusion protein may be used as a vaccine. In one or more embodiments, the HERV-K (HML-2) Env analog-Fc fusion protein is provided in a pharmaceutical composition. Injection of any protein into a patient (e.g., a human) may induce an immune response, the magnitude and type of which is highly dependent on the "status" of the respective immune system. For example, injection of a foreign antigen (Ag) relative to a self Ag may induce a greater immune response in an immune system that maintains central and peripheral tolerance mechanisms. Moreover, foreign Ag administration to an immune system that has been primed to previous exposure to the respective Ag (e.g., a viral infection) will lodge a more rapid and elevated immune response relative to that of an Ag-naïve system. The immunological basis of this priming is two-fold: 1) an Ag-naïve immune system has naïve B and T lymphocytes that have a much higher threshold of activation than do the Ag-primed "memory" cells of a Ag-primed immune system, such that the antigen-presenting cells (APCs) that present Ag require much less Ag to activate primed memory T cells, and 2) due to expansion of memory T cells during the Ag priming exposure, there are inherently greater numbers of such cells upon re-exposure to an injected Ag, such as an injected self Ag or self Ag analog. Note that dominant APCs are dendritic cells (DCs) and macrophages that present Ag in complex with Major Histocompatibility Complex (MHC) molecules on their surface to T cell Ag receptors. FIG. 21 is a schematic diagram depicting example modes in which an antigen may interact with an antigen presenting cell, e.g., a dendritic cell.

In another example, injection of a self Ag (or self Ag-Fc fusion protein) is designed to induce an immune response against a self Ag (e.g., a patient's endogenously-produced antigen or endogenously-produced protein, e.g., endogenously-produced HERV-K (HML-2)) but needs to overcome immune system central and peripheral tolerance mechanisms. To do so, the antigen is exposed to the immune system to cause an immune response (e.g., generate antibodies against the self Ag) in a manner that overcomes these tolerance mechanisms. In one embodiment, this is done through the use of a carrier (e.g., an adjuvant). In another embodiment, this can be done through linking of the self Ag or a self Ag analog to an Fc fragment in order to increase the antigen presentation of the self Ag via Fc fragment-Fc (gamma)R binding as depicted in FIG. 21. In another embodiment, this is done through linking of the self Ag or self Ag analog to an Fc fragment and using a carrier (e.g., an adjuvant). Generation of an immune response against a self Ag may be done through a priming approach.

Further enhancement of an immune response against a self Ag may be done through a boosting approach. The immunological basis of this boosting is to allow for an expansion of memory T cells during the Ag priming exposure, so as to enhance the numbers of such cells upon re-exposure to an injected self Ag or self Ag analog. Boosting can be done through one or more follow-on injections after a priming injection. Boosting (e.g., booster injections) may contain a carrier (e.g., an adjuvant) or no carrier (no adjuvant). Boosting may increase the level of antibodies against a self Ag, create higher affinity antibodies against a self Ag, or both increase the level and the affinity of antibodies against a self Ag.

Antigen presenting cells (APCs) can influence both the "magnitude" and "type" of response to an Ag. B cells participate in the immune response directly by humoral immunity (antibody production) and also participate in the T cell immune response as specific APCs that selectively capture and present antigens to T cells. Both of these B cell functions are achieved through activation of the surface B cell receptor (BCR), which is essentially a membrane bound antibody that binds specifically to a particular antigen. Multivalent soluble antigens such as the Fc-fusion homodimer containing the specific antigen can be recognized by BCRs and activate them. Thus, the HERV-K (HML-2) Env analog-Fc fusion protein homodimers can 1) activate B cells through antigen-specific BCR activation leading to an increase in antibody production, and 2) through B cell mediated APC activity, increase T cell recognition and reactivity directed specifically against the HERV-K (HML-2) Env epitopes. Thus, these fusion proteins can activate either humoral immunity, cellular immunity or a combination of humoral and cellular immunity after administration.
Adjuvants In some examples, APC activation is the conceptual basis of many immune enhancing substances called adjuvants. Dominant APCs are dendritic cells (DCs) and macrophages that present Ag in complex with Major Histocompatibility Complex (MHC) molecules on their surface to T cell Ag receptors. Some adjuvants are designed to trick the immune system into reacting to the injected vaccine Ag as if it were part of an ongoing infection (i.e., infectious agents provide such natural viral or bacterial adjuvant substances). Therefore, adjuvants activate APCs for greater Ag-presentation capabilities necessary to overcome the high activation threshold of naïve T cells, in addition to shaping their development into the Th1 immune system response, Th2 immune system response, or a mixture of Th1 and Th2 immune system responses. Some T cells provide critical help to B cells that specifically bind the respective Ag to produce Ag-specific antibody (Ab) titers.

The novel HERV-K (HML-2) Env analog-Fc fusion protein used as a vaccine may be co-administered with an adjuvant to enhance or otherwise alter the immune response in the target patient. In examples, known adjuvants may be used in a pharmaceutical composition of the HERV-K (HML-2) Env analog-Fc fusion protein to enhance the induction of anti-HERV-K (HML-2) Env antibodies.

Examples of adjuvants that may be employed in the pharmaceutical compositions disclosed herein include but are not limited to oil-in-water, amorphous aluminum hydroxyphosphate sulfate (AAHS), aluminum hydroxide, aluminum phosphate, potassium aluminum sulfate (Alum), Freund's adjuvant (complete and/or incomplete), squalene, AS01B, AS02, AS03, AS04, MF59, MF59 (Novartis, Basel, Switzerland), QS-21 (SaponiQx, Massachusetts, USA), CpG 1018 (Dynavax, California, USA), Immune Stimulating Complexes (ISCOMS), Montanide™ ISA-51, Montanide™ ISA-720, Montanide™ GEL 01 PR, Montanide™ GEL 02 PR, Sepivac SWE (Seppic, Castres, France), polylactide co-glycolide (PLG), monophosphoryl lipid A (MPL), Detox, AGP [RC-529] (GlaxoSmithKline, London, England, UK), DC_Chol, OM-174 (lipid A derivative), CpG motifs (synthetic oligonucleotides containing immunostimulatory CpG motifs), modified LT and CT, hGM-CSF, hIL-12, Immudaptin, inert vehicles, such as gold particles as well as various experimental adjuvants from sources such as Advax (Vaxine Pvt Ltd., Australia) such as AddaVax (Invivogen) or other Advax-based vaccine adjuvants.

In some examples, the selected adjuvant may be MF59 (Novartis, Basel, Switzerland) and AS-03 (GlaxoSmithKline). A custom formulation of MF59 (Novartis) or an equivalent such as Adda Vax (Invivogen) or other Advax-based vaccine adjuvants from Vaxine Pvt Ltd. (Australia) may be used in a pharmaceutical composition of the HERV-K (HML-2) Env analog-Fc fusion protein. In examples, the HERV-K (HML-2) Env analog-Fc fusion protein is co-administered with the Sepivac SWE (Seppic, Castres, France) adjuvant to enhance or otherwise alter the immune response in the target patient.

In one or more embodiments, the HERV-K (HML-2) Env analog-Fc fusion protein formulation is prepared onsite for administration. In one aspect, the HERV-K (HML-2) Env analog-Fc fusion protein is mixed with an adjuvant onsite under sterile mixing conditions. In one aspect, the HERV-K (HML-2) Env analog-Fc fusion protein and adjuvant are thoroughly mixed and/or emulsified to prepare a homogenous emulsion for administration to the patient. The adjuvanted formulation of the HERV-K (HML-2) Env analog-Fc fusion protein or a pharmaceutical composition thereof is administered to a patient by subcutaneous (s.c.) injection or intramuscular (i.m.) injection, as the s.c. or i.m. injection sites are more likely to induce a strong antibody response due to there being more dendritic cells (DCs) in the subcutaneous and intramuscular spaces.

As described above, in some cases, it may be advantageous to use an adjuvant in the pharmaceutical composition in order to increase the quantity of anti-HERV-K (HML-2) Env antibody titers as measured according to Example 12. The use of an adjuvant may be especially advantageous in older patients who experience altered immune competence with increasing age, so-called immunosenescence, which is the result of changes at multiple levels of the immune system over time. Once a patient has measurable antibodies, upon re-challenge with HERV-K (HML-2) or a HERV-K (HML-2) Env analog-Fc fusion protein, the patient will exhibit rapid development of anti-HERV-K (HML-2) Env antibodies.

Immunogenicity of HERV-K (HML-2) Env Analog-Fc Fusion Protein Vaccines Evaluated in Mice The efficacy of exemplary HERV-K (HML-2) Env analog-Fc fusion proteins of this disclosure or pharmaceutical compositions thereof may be initially evaluated in mice immunization studies for their capacity to induce anti-HERV-K (HML-2) Env protein IgG titers when administered according to the procedure in Example 11. BALB/c mice are a relevant animal model that has been extensively used for preclinical immunogenicity assessment of vaccines. This strain generates robust Ab responses when immunized with adjuvanted and non-adjuvanted vaccine candidates. Moreover, mouse-specific reagents are widely available for evaluating the kinetics and characteristics of a variety of immune responses to vaccination, including relevant Ab isotypes and T helper cell responses (e.g., Th1 vs. Th2 responses). Therefore, the BALB/c mouse model was selected to evaluate the immunogenicity of HERV-K (HML-2) Env analog-Fc fusion protein vaccines with respect to dose, potentiation by adjuvants, routes of administration, and dosing frequency required to achieve optimal Ab responses.

Briefly, target mice (e.g., BALB/c mice) were injected three times at predetermined intervals (e.g., on Day 0, Day 21 and Day 42) with an exemplary HERV-K (HML-2) Env analog-Fc fusion protein (with or without Sepivac SWE adjuvant) or pharmaceutical composition thereof. Serum was collected before the first injection and then at regular intervals following the first injection (e.g., every 7-14 days beginning at Day 14).

After administering one or more than one treatment of the HERV-K (HML-2) Env analog-Fc fusion protein to BALB/c mice according to Example 11, anti-HERV-K (HML-2) Env IgG antibody titers were measured according to Example 12.

As previously discussed, adjuvants activate APCs for greater Ag-processing and Ag-presentation capabilities which are necessary to overcome the high activation threshold of naïve T cells. It is expected that when a HERV-K (HML-2) Env analog-Fc fusion protein is combined with Sepivac SWE adjuvant (50%/50% v/v), the anti-HERV-K (HML-2) Env protein antibody titers at approximately 21 to 28 days after the first injection on Day 0 will be greater compared to the HERV-K (HML-2) Env analog-Fc fusion protein without adjuvant.

The kinetic response, that is the duration of response, to dose levels varying from 1 μg to 100 μg after 1, 2, and 3 doses is expected to demonstrate increasing anti-HERV-K (HML-2) Env protein antibody titers at all dose levels up to at least 56 days post vaccination.

HERV-K (HML-2) Env Analog-Fc Fusion Proteins for Use as a Booster Vaccine

In examples, an exemplary HERV-K (HML-2) Env analog-Fc fusion protein of this disclosure, for example the HERV-K (HML-2) Env analog-Fc fusion protein of SEQ ID NO: 46 or the HERV-K (HML-2) Env analog-Fc fusion protein of SEQ ID NO: 47, may be used as a booster vaccine. Administration of the HERV-K (HML-2) Env analog-Fc fusion protein to patients that already have low but measurable antibody levels to the HERV-K (HML-2) Env self-antigen (e.g., after a primary vaccination with an HERV-K (HML-2) Env analog-Fc fusion protein) may amplify their antibody titers and increase their neutralization against endogenously produced HERV-K (HML-2). HERV-K (HML-2) Env analogs are synthesized to maximize antigenicity and overall manufacturability, while the Fc region prolongs antigen residence time and/or binding to Fc(gamma)R receptors present on APCs. Without wishing to be bound to any particular theory of mechanism, it is believed that during the longer in vivo residence time, the naturally glycosylated Fc fragment will help bind Fc (gamma) receptors on antigen-presenting cells (APCs), which will in turn cause greater presentation of the HERV-K (HML-2) Env analog antigen to T-cells and/or B-cells, which is expected to produce a strong immune response (e.g., antibody titers) to the HERV-K (HML-2) Env antigen present on the HERV-K (HML-2) Env analog-Fc fusion protein, and that these antibody titers will be able to bind and neutralize the endogenously produced target protein (e.g., the HERV-K (HML-2) Env protein). Specifically, the APCs can internalize the HERV-K (HML-2) Env antigen via Fc (gamma) receptors (the Fc portion of the vaccine compound will bind to the Fc receptor on the membrane of APCs) or through B-cell receptors (BCRs) (the HERV-K (HML-2) Env analog can be recognized by BCRs), and then process and present HERV-K (HML-2) Env fragments to CD4+Th cells that in turn promote ("help") B cell activation and anti-HERV-K (HML-2) Env IgG (i.e., Ab) production.

Antigen-presenting cells may be, for example, dendritic cells (DCs), monocytes or macrophages that can internalize the molecules of the HERV-K (HML-2) Env analog-Fc fusion protein of SEQ ID NO: 46 or the molecules of the HERV-K (HML-2) Env analog-Fc fusion protein of SEQ ID NO: 47 via Fc-receptor mediated phagocytosis or endocytosis (e.g., through the Fc region of the HERV-K (HML-2) Env analog-Fc fusion protein binding to the Fc (gamma) receptors in immune cells). After Fc-mediated uptake of the HERV-K (HML-2) Env analog-Fc fusion protein by APCs, the antigen will be processed and presented on the MHC II complex where it can be recognized by T-cell receptors (TCRs) specific for the same antigen of naïve CD4 T-helper cells, which can get differentiated into Th2 or Th1.

B-cells that have recognized the HERV-K (HML-2) Env will also process and present the antigen on the MHC II complex, where it can be recognized by Th2 cells specific to the same antigen. The TCR of the helper T cell recognizes the antigen, and the T cell's CD4 molecule interacts with MHC II on the B cell. The coordination between B cells and helper T cells that are specific to the same antigen is referred to as linked recognition.

Once activated by linked recognition, Th2 cells produce and secrete cytokines, such as IL-4, IL-5 and IL-6, that activate the B cells and cause proliferation into clonal cells. After several rounds of proliferation, additional cytokines provided by the Th2 cells stimulate the differentiation of activated B cell clones into memory B cells, which will quickly respond to subsequent exposures to the same protein epitope, and plasma cells, which will secrete anti-HERV-K (HML-2) Env antibodies.

The HERV-K (HML-2) Env analog-Fc fusion protein of SEQ ID NO: 46 or the HERV-K (HML-2) Env analog-Fc fusion protein of SEQ ID NO: 47 may increase exposure of the HERV-K (HML-2) Env analog to APCs over a protracted period of time due to the presence of the Fc fragment and the Fc-FcRn receptor interactions that enable the HERV-K (HML-2) Env analog-Fc fusion protein to have a prolonged in vivo pharmacokinetic half-life. Furthermore, and as previously described, the glycosylated Fc fragment in the HERV-K (HML-2) Env analog-Fc fusion protein of SEQ ID NO: 46 or in the HERV-K (HML-2) Env analog-Fc fusion protein of SEQ ID NO: 47 is expected to help induce a strong immune response directed to the therapeutic or antigen portion of the fusion protein through binding of the Fc to Fc(gamma)R receptors on immune cells, thereby increasing HERV-K (HML-2) Env analog uptake and processing in a manner described in FIG. 21. These properties in combination are expected to significantly increase the amount of anti-HERV-K (HML-2) Env antibodies while also decreasing the amount of antigen necessary to produce the required immune response.

In examples, a therapy comprising treatment of a patient with the HERV-K (HML-2) Env analog-Fc fusion protein of SEQ ID NO: 46, the HERV-K (HML-2) Env analog-Fc fusion protein of SEQ ID NO: 47, or a pharmaceutical composition of one of these two fusion proteins, may consist of a booster vaccine administered to patients that are already antibody-positive to HERV-K (e.g., patients that may already have received an initial dose of HERV-K (HML-2) Env analog-Fc fusion protein vaccine), as a means to amplify their antibody titers and affinity. Furthermore, a therapy comprising a treatment of a patient with the HERV-K (HML-2) Env analog-Fc fusion protein of SEQ ID NO: 46, the HERV-K (HML-2) Env analog-Fc fusion protein of SEQ ID NO: 47, or a pharmaceutical composition of one of these two fusion proteins, may be administered as a booster vaccine to patients that have been previously immunized with a vaccine against HERV-K (HML-2) as a means to amplify their antibody titers and affinity specifically against HERV-K (HML-2). Such a therapy is important in cases where priming vaccines are not 100% effective and/or where the induced antibody titers wane over time. In examples, the HERV-K (HML-2) Env analog-Fc fusion protein of SEQ ID NO: 46, the HERV-K (HML-2) Env analog-Fc fusion protein of SEQ ID NO: 47, or a pharmaceutical composition of one of these two fusion proteins may be administered to a patient by subcutaneous injection (s.c.) or intramuscularly (i.m.), as the s.c. or i.m. injection sites are more likely to induce a strong antibody response with minimal side effects.

Fc Fusion Protein Production

In embodiments, a fusion protein can be expressed by a cell as described in more detail in the Examples section.

Expression and Purification

A HERV-K (HML-2) Env analog-Fc fusion protein can be expressed recombinantly, e.g., in a eukaryotic cell, e.g., mammalian cell or non-mammalian cell. Exemplary mammalian cells used for expression include CHO cells or HEK293 cells. CHO cells can be subdivided into various strains or subclasses, (e.g., CHO DG44, CHO-M, CHO-SE™ and CHO-K1), and some of these cell strains may be genetically engineered for optimal use with a particular type of nucleic acid molecule (e.g., a vector comprising DNA) or a particular cell growth media composition as described in the Examples section. Cells may be transfected with a nucleic acid molecule (e.g., vector) encoding the HERV-K (HML-2) Env analog-Fc fusion protein (e.g., where the entire HERV-K (HML-2) Env analog-Fc fusion protein is encoded by a single nucleic acid molecule). CHO cells may be transfected with a vector that encodes for the HERV-K (HML-2) Env analog-Fc fusion protein, but this process only results in temporary expression of the HERV-K (HML-2) Env analog-Fc fusion protein for a period of time (e.g., 3 days, 4 days, 5, days, 7 days, 10 days, 12 days, 14 days, or more) before the host cell stops expressing appreciable levels of the HERV-K (HML-2) Env analog-Fc fusion protein (i.e., transient transfection). CHO cells that are transiently transfected with nucleic acid sequences encoding for HERV-K (HML-2) Env analog-Fc fusion proteins often allow for more rapid production of recombinant proteins which facilitates making and screening multiple HERV-K (HML-2) Env analog-Fc fusion protein candidates. CHO cells may be transfected with a vector that is permanently incorporated into the host cell DNA and leads to consistent and permanent expression (i.e., stable transfection) of the HERV-K (HML-2) Env analog-Fc fusion protein as long as the cells are cultured appropriately. CHO cells and CHO cell lines that are stably transfected with nucleic acids encoding for HERV-K (HML-2) Env analog-Fc fusion proteins often take longer to develop, but they often produce higher protein yields and are more amenable to manufacturing low-cost products (e.g., products for use in the pharmaceutical market). Cells and cell lines can be cultured using standard methods known in the art. Synthesis and methods of making an HERV-K (HML-2) Env analog-Fc fusion protein in transiently transfected CHO cells is described in Example 4, and synthesis and methods of making a HERV-K (HML-2) Env analog-Fc fusion protein in stably transfected CHO cells is described in Example 5.

In examples, the HERV-K (HML-2) Env analog-Fc fusion protein may be purified or isolated from the cells (e.g., by lysis of the cells). The HERV-K (HML-2) Env analog-Fc fusion protein is secreted by the cells and may be purified or isolated from the cell culture media in which the cells were grown. Purification of the HERV-K (HML-2) Env analog-Fc fusion protein can include using column chromatography (e.g., affinity chromatography) or using other separation methods based on differences in size, charge, and/or affinity for certain molecules. Purification of the HERV-K (HML-2) Env analog-Fc fusion protein involves selecting or enriching for proteins containing an Fc fragment, e.g., by using Protein A beads or a Protein A column that cause proteins containing an Fc fragment to become bound with affinity at neutral solution pH to the Protein A covalently conjugated to the Protein A beads. The bound HERV-K (HML-2) Env analog-Fc fusion protein may then be eluted from the Protein A beads by a change in a solution variable (e.g., a decrease in the solution pH). Other separation methods such as ion exchange chromatography and/or gel filtration chromatography can also be employed alternatively or additionally. Purification of the HERV-K (HML-2) Env analog-Fc fusion protein may further comprise filtering or centrifuging the protein preparation, diafiltration, ultrafiltration, and filtration through porous membranes of various sizes, as well as final formulation with excipients. Purification of an HERV-K (HML-2) Env analog-Fc fusion protein is described in Example 6.

The purified HERV-K (HML-2) Env analog-Fc fusion protein can be characterized, e.g., for purity, protein yield, structure, and/or activity, using a variety of methods, e.g., absorbance at 280 nm (e.g., to determine protein yield), size exclusion or capillary electrophoresis (e.g., to determine the molecular weight, percent aggregation, and/or purity), mass spectrometry (MS) and/or liquid chromatography (LC-MS) (e.g., to determine purity and/or glycosylation), and/or ELISA (e.g., to determine extent of binding, e.g., affinity, to a HERV-K (HML-2) Env antibody or a cell receptor such as a CD98 cell receptor). Exemplary methods of characterization are also described in Example 7 and Example 8.

The protein yield of a HERV-K (HML-2) Env analog-Fc fusion protein after production in transiently transfected CHO cells and protein A purification may be greater than 50 mg/L (e.g., greater than 60 mg/L, greater than 70 mg/L, greater than 80 mg/L, greater than 90 mg/L, greater than 100 mg/L).

Pharmaceutical Compositions and Routes of Administration

The amount and concentration of the HERV-K (HML-2) Env analog-Fc fusion protein in the pharmaceutical compositions, as well as the quantity of the pharmaceutical composition administered to a patient, can be selected based on clinically relevant factors, such as medically relevant characteristics of the patient (e.g., age, weight, gender, other medical conditions, and the like), the solubility of compounds in the pharmaceutical compositions, the potency and activity of the compounds, and the manner of administration of the pharmaceutical compositions.

Formulations of the present disclosure include those suitable for parenteral administration. The phrases "parenteral administration" and "administered parenterally" as used herein means modes of administration other than enteral and topical administration, usually by intravenous, intramuscular, or subcutaneous injection or by intranasal administration.

Examples of suitable aqueous and non-aqueous carriers that may be employed in the pharmaceutical compositions of the disclosure include water, saline, ethanol, salts, polyols (such as glycerol, propylene glycol, polyethylene glycol, and the like), and suitable mixtures thereof, vegetable oils, such as olive oil, and injectable organic esters, such as ethyl oleate, buffering agents, such as potassium and/or sodium phosphates, pH buffers, such as hydrochloric acid and/or sodium hydroxide, and the like. Proper fluidity can be maintained, for example, by the use of coating or emulsifier materials, such as lecithin, by the maintenance of the required particle size in the case of dispersions, and by the use of surfactants, e.g., Tween-like surfactants. In some examples, the pharmaceutical composition (e.g., as described herein) comprises a Tween-like surfactant, e.g., polysorbate-20, Tween-20 or Tween-80. In some examples, the pharmaceutical composition (e.g., as described herein) comprises a Tween-like surfactant, e.g., Tween-80, at a concentration between about 0.001% and about 2%, or between about 0.005% and about 0.1%, or between about 0.01% and about 0.5%.

The HERV-K (HML-2) Env analog-Fc fusion protein may be administered as a bolus, infusion, or an intravenous push, or administered through syringe injection, pump, pen, needle, or indwelling catheter. The HERV-K (HML-2) Env analog-Fc fusion protein may be administered by a subcutaneous bolus injection. In examples, the HERV-K (HML-2) Env analog-Fc fusion protein or a pharmaceutical composition thereof is administered to a patient by subcutaneous injection (s.c.) or intramuscularly (i.m.), as the s.c. or i.m. injection sites are more likely to induce a strong antibody response with minimal side effects. Methods of introduction may also be provided by rechargeable or biodegradable devices. Various slow-release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site. Additional pharmaceutically acceptable ingredients for use in the compositions include buffering agents, salts, stabilizing agents, diluents, preservatives, antibiotics, isotonic agents, and the like.

Dosages

In use, a therapeutically effective amount of the HERV-K (HML-2) Env analog-Fc fusion protein is administered to a patient in need thereof. Administration of the HERV-K (HML-2) Env analog-Fc fusion protein elicits an immune response in the patient, and more specifically an immune response against HERV-K (HML-2), relieving symptoms and conditions associated with ALS (e.g., motor neuron degeneration and cell death, muscular weakness, paralysis, and respiratory failure). The immune response is demonstrated by a lack of observable clinical symptoms, or reduction of clinical symptoms or disease biomarkers normally displayed by an afflicted patient. In another embodiment, a method of activating immune cells at a site of infection or disease is provided comprising administering a therapeutically effective amount of the HERV-K (HML-2) Env analog-Fc fusion protein to a patient. In another aspect, a method of increasing antibody production in a patient is provided comprising administering a therapeutically effective amount of the HERV-K (HML-2) Env analog-Fc fusion protein to a patient.

Actual dosage levels of the HERV-K (HML-2) Env analog-Fc fusion protein can be varied so as to obtain an amount of the active ingredient that is effective to achieve the desired therapeutic response for a particular patient. The selected dosage level will depend upon a variety of factors including the activity of the particular fusion protein employed, or the ester, salt or amide thereof, the route of administration, the time of administration, the rate of excretion of the particular compound being employed, the duration of the treatment, other drugs, compounds and/or materials used in combination with the particular fusion protein employed, the age, sex, weight, condition, general health and prior medical history of the patient being treated, and like factors well known in the medical arts. In general, a suitable dose of a HERV-K (HML-2) Env analog-Fc fusion protein will be the amount that is the lowest dose effective to produce a therapeutic effect. Such an effective dose will generally depend upon the factors described above.

The immunogenic formulation is provided, in various aspects, in unit dosage form for ease of administration and uniformity of dosage. "Unit dosage form" as used herein generally means physically discrete units suited as unitary dosages for the patient to be treated, each unit containing a predetermined quantity of the HERV-K (HML-2) Env analog-Fc fusion protein calculated to produce the desired therapeutic effect in association with the required pharmaceutical carrier. The specification for the dosage unit forms is dictated by and are directly dependent on the unique characteristics of the excipient(s) and therapeutic agent(s) and the particular biological effect to be achieved. In one or more embodiments, the formulation is provided in a kit of components for administration of the HERV-K (HML-2) Env analog-Fc fusion protein to the patient. In one or more embodiments, a pharmaceutical composition comprising the HERV-K (HML-2) Env analog-Fc fusion protein dispersed in a suitable carrier is provided in a unit dosage form (e.g., vial). In one or more embodiments, the kit further comprises a discrete unit dosage form (e.g., vial) containing an adjuvant and/or other carrier system for onsite mixing of the HERV-K (HML-2) Env analog-Fc fusion protein for administration. In one or more embodiments, the kit comprises one or more emulsifying needles and syringes for onsite mixing of the immunogenic formulation for administration. In one or more embodiments, the kit comprises one or more dosing syringes for administering the prepared immunological composition to the patient. In one or more embodiments, the kit further comprises instructions for preparing the immunogenic composition and/or administering the immunogenic composition.

The present disclosure contemplates formulation of a HERV-K (HML-2) Env analog-Fc fusion protein in any of the aforementioned pharmaceutical compositions and preparations. Furthermore, the present disclosure contemplates administration via any of the foregoing routes of administration. One of skill in the art can select the appropriate formulation, dose level and route of administration based on the condition being treated and the overall health, age, and size of the patient being treated.

EXAMPLES

The present technology is further illustrated by the following Examples. It is to be understood, however, that these examples are provided by way of illustration, and nothing therein should be taken as a limitation upon the overall scope of the technology.

General Examples for Synthesis, Purification and Validation of HERV-K (HML-2) Env Analog-Fc Fusion Proteins

Examples for Identification of Key HERV-K (HML-2) Env Epitopes in ALS Patients

Example 1: Epitope Mapping to HERV-K (HML-2) Env Using Peptide Microarrays

Analysis of serum samples from 66 individuals with ALS and 46 HDs was performed using an enzyme-linked immunosorbent (ELISA) assay to detect antibodies against a recombinant HERV-K (HML-2) Env protein (MyBioSource; catalogue number MBS1391552_a0). Serum samples from 10 ALS and 8 age- and sex-matched controls that showed reactivity to the protein were selected.

Epitope mapping of the antibodies to HERV-K (HML-2) Env was performed by using peptide microarrays (PEPperCHIP Immunoassay, PEPperPRINT, Heidelberg, Germany) covering the complete sequence of the protein (SEQ ID NO: 10, Uniprot ID: Q69384). The elongated 699 amino acids antigen sequence was converted into 15 amino acid peptides with a peptide-peptide overlap of 14 amino acids in duplicate. The assay was performed following the manufacturer's instructions. To discriminate secondary antibody background, the microarray was pre-stained with the secondary antibody and the background signal was subtracted from the final measurement.

The peptide microarrays were incubated in washing buffer (phosphate-buffered saline (PBS) with 0.05% Tween20, pH 7.4) for 15 min at room temperature (RT) and in blocking buffer (Rockland Blocking Buffer MB-070) for 30 min at RT, followed by incubation with secondary antibody diluted 1:5000 in staining buffer (PBS with 0.05% Tween20 and 10% blocking buffer, pH 7.4) for 45 min. Then, microarrays were washed three times in washing buffer for 1 min each and in dipping buffer (1 mM Tris buffer, pH 7.4) three times until all visible contamination was removed. The microarrays were dried in a pressurized air stream from top to bottom and scanned (GenePix 4300A, Molecular Devices LLC, CA, USA).

Serum samples were diluted 1:200 in staining buffer and 200 μL were added to each array, which were incubated overnight at 4° C. on an orbital shaker (85 rpm). Peptide microarrays were washed three times for 1 min in washing buffer and stained with the secondary antibody (1:5000 in staining buffer) for 45 min. Then, the microarrays were dipped three times in dipping buffer, dried in a pressurized air stream and scanned. The same process was performed with an anti-hemagglutinin control antibody. Finally, the scanned images were analyzed with MAPIX analyzer.

Since the total amount of antibodies against HERV-K (HML-2) Env was variable among individuals, to map the epitopes of HERV-K (HML-2) Env recognized by ALS and control sera, the total OD of HERV-K (HML-2) Env in each sample was first calculated as the sum of ODs of all HERV-K (HML-2) Env peptides (Total OD=PODpeptides). Next, the percentage of the total OD that corresponded to each peptide in each sample (% ODpeptide=100×[ODpeptide/total OD]) was calculated and the percentages for each peptide were compared between ALS and control samples by Wilcoxon signed-rank test with correction for the number of comparisons. Next, the means of these percentages in ALS and control samples were calculated, generating a value for each peptide which was called epitope recognition score (ERS). The ERS for all peptides was compared between ALS and controls by Mann-Whitney test. The median ERS of the controls was defined as a positivity threshold: peptides above this value were considered positive in eliciting a humoral response. The percentage of positive peptides was compared between ALS and controls by Fisher's exact test. To search for the actual epitopes eliciting a differential response in ALS sera compared to controls, adjacent peptides were analyzed to find a common sequence between 4 and 12 amino acids.

Example 2: PEPperMAP IgG Epitope Mapping of Mouse Sera Samples Against the Envelope Protein of HERV-K (HML-2)

The sequence of the envelope protein of HERV-K (HML-2) (SEQ ID NO: 10, UniProtKB: Q69384) was elongated with neutral GSGSGSG linkers at the C- and N-terminus to avoid truncated peptides. The elongated antigen sequence was converted into linear 15 amino acid peptides with a peptide-peptide overlap of 14 amino acids. The resulting HERV-K (HML-2) Env peptide microarrays contained 699 different peptides printed in duplicate (1,398 spots) and were framed by additional HA (YPYDVPDYAG, 90 spots) control peptides.

One hundred and twenty (120) mouse sera samples comprised pre- and post-treatment pairs of animals treated with a HERV-K (HML-2) Env analog-Fc fusion protein, with or without adjuvant and at doses of 1 μg, 10 μg or 30 μg.

The washing buffer used was PBS, pH 7.4 with 0.005% Tween 20; washing for 2×10 sec after each incubation step. The blocking buffer used was Rockland blocking buffer MB-070; for 30 min before first assay. The incubation buffer used was washing buffer with 10% blocking buffer.

Assay conditions include serum dilution of 1:200 in incubation buffer; incubation for 16 h at 4° C. and orbital shaking at 140 rpm.

A HERV-K (HML-2) Env peptide microarray was pre-stained with the secondary antibody (goat anti-mouse IgG (Fc) DyLight680 (0.2 μg/mL)) in incubation buffer for 45 min at RT to investigate background interactions with the antigen-derived peptides that could interfere with the main assays. Incubation of further HERV-K (HML-2) Env peptide microarrays with the mouse serum samples at a dilution of 1:200 was followed by staining with the secondary antibody and read-out with an Innopsys InnoScan 710-IR Microarray Scanner (Innopsys, Carbonne, France) at scanning gains of 20/10 (red/green). The additional HA peptides framing the peptide microarrays were subsequently stained (45 min staining in incubation buffer at RT) with the control antibody (mouse monoclonal anti-HA (12CA5) DyLight800 (0.2 μg/mL)) as internal quality control to confirm the assay performance and the peptide microarray integrity.

Quantification of spot intensities and peptide annotation were based on the 16-bit gray scale TIFF files that exhibit a higher dynamic range than the 24-bit colorized TIFF files. Microarray image analysis was done with PepSlide® Analyzer (SICASYS Software GmbH, Heidelberg, Germany) and summarized in Excel files. A software algorithm broke down fluorescence intensities of each spot into raw, foreground and background signals, and calculated averaged median foreground intensities and spot-to-spot deviations of spot duplicates. Based on averaged median foreground intensities, intensity maps were generated and interactions in the peptide maps highlighted by an intensity color code with red for high and white for low spot intensities. A maximum spot-to-spot deviation of 40% was tolerated, otherwise the corresponding intensity value was zeroed. This could be bypassed by manual flagging of peptides as "Artifact" or "Valid".

Averaged spot intensities of the assays with the mouse serum samples were plotted against the microarray content from the N- to the C-terminus of the envelope protein of HERV-K (HML-2) of SEQ ID NO: 10 to visualize overall spot intensities and signal-to-noise ratios. The intensity plots were correlated with peptide and intensity maps as well as with visual inspection of the microarray scans to identify epitopes of the mouse serum samples. In case it was not clear if a certain amino acid contributed to antibody binding, the corresponding letter was written in gray. For a better data overview, the baselines of the intensity plots were shifted up.

To facilitate comparison of overall response levels across the individual IgG responses of all samples treated with a HERV-K (HML-2) Env analog-Fc fusion protein, the sum of all intensities for all fifteen amino acid length peptides in the epitope area was calculated; within each group, the mean values of Pre and Post samples of the intensity sums in the epitope area were also calculated.

Examples for Identification of Appropriate Cell Types for Neutralization Studies

Example 3: Determination of Optimal Concentration of HERV-K (HML-2) Env Protein, Neuronal Type and Time Points to be Used in the Neutralization Study iPSC derived (control line WC-30, male) spinal motor neurons and cortical GABAergic neurons were thawed and cultured for seven days. Cells were seeded at 30K cells/well onto 96-well PDL coated plates for use in determining the toxicity of HERV-K (HML-2) Env protein. Cells were treated with different concentrations of recombinant HERV-K (HML-2) Env (MyBiosource (MBS1391552) diluted in cell culture media: 0, 20, 40, 80, 160, 320, 640 and 1280 nM. Cellular viability was measured at 4 different time points: 24, 48, 72, 96 hours in triplicate using the CellTiter-Glo2® (Promega; G9241). Conditions for the neutralization study were selected according to the results: 1) 1 cell type, 2) 1 HERV-K (HML-2) Env concentration and 3) 2 time points.

General Examples for Synthesis, Purification and Validation of HERV-K (HML-2) Env Analog-Fc Fusion Proteins

Example 4: Synthesis and Methods of Making a HERV-K (HML-2) Env Analog-Fc Fusion Protein in Transiently Transfected CHO Cells HERV-K (HML-2) Env analog-Fc fusion proteins were synthesized as follows. A gene sequence of interest was constructed using proprietary software (Curia, Belmont, CA) and was cloned into a high expression mammalian vector. CHO cells were seeded in a shake flask 24 hours before transfection and were grown using serum-free chemically defined media. A DNA expression construct that encodes the HERV-K (HML-2) Env analog-Fc fusion protein of interest was transiently transfected into a suspension of CHO cells using the (Curia, Belmont, CA) standard operating procedure for transient transfection. After 20 hours, the cells were counted to determine the viability and viable cell count, and the titer was measured by FortéBio® Octet® (Pall FortéBio LLC, Fremont, CA). Additional readings were taken throughout the transient transfection production run. The culture was harvested on or after Day 14.

Example 5: Synthesis and Methods of Making a HERV-K (HML-2) Env Analog-Fc Fusion Protein by Integration of a Stable Expression Vector in CHO Cells A CHO cell line is originally derived from CHO-K1 (Curia, Belmont, CA), and the endogenous glutamine synthetase (GS) genes are knocked out by recombinant technology using methods known in the art. Stable expression DNA vectors are designed and optimized for CHO expression and GS selection and are incorporated into a high expression mammalian vector (Curia, Belmont, CA). The sequence of each completed construct is confirmed prior to initiating scale up experiments. The suspension-adapted CHO cells are cultured in a humidified 5% CO2 incubator at 37° C. in a chemically defined media (CD OptiCHO; Invitrogen, Carlsbad, CA). No serum or other animal-derived products are used in culturing the CHO cells.

Approximately 80 million suspension-adapted CHO cells, growing in CD OptiCHO media during the exponential growth phase, are transfected by electroporation using MaxCyte® STX® system (MaxCyte, Inc., Gaithersburg, MD) with 80 µg DNA to a create a stable CHO cell line for each HERV-K (HML-2) Env analog-Fc fusion protein (DNA construct contained the full-length sequence of the HERV-K (HML-2) Env analog-Fc fusion protein.) After twenty-four hours, the transfected cells are counted and placed under selection for stable integration of the HERV-K (HML-2) Env analog-Fc fusion genes. The transfected cells are seeded into CD OptiCHO selection media containing between 0-100 µM methionine sulfoximine (MSX) at a cell density of $0.5 \times 10^6$ cells/mL in a shaker flask and are incubated at 37° C. with 5% CO2. During the selection process, the cells are spun down and resuspended in fresh selection media every 2-3 days until the CHO stable pool recovers its growth rate and viability. The cell culture is monitored for growth and titer.

The cells are grown to $2.5 \times 10^6$ cells per mL. At the time of harvest for cell banking, the viability is expected to be above 95%. The cells are then centrifuged, and the cell pellet is resuspended in the CD OptiCHO media with 7.5% dimethyl sulfoxide (DMSO) to a cell count of $15 \times 10^6$ cells per mL per vial. Vials are cryopreserved for storage in liquid nitrogen.

A small-scale-up production is performed using the CHO cells as follows. The cells are scaled up for production in CD OptiCHO growth medium containing 100 µM MSX at 37° C. and are fed every 2-4 days as needed, with CD OptiCHO growth medium supplemented with glucose and additional amino acids as necessary for approximately 14-21 days. The conditioned media supernatant harvested from the stable pool production run is clarified by centrifuge spinning. The protein is run over a Protein A (MabSelect, GE Healthcare, Little Chalfont, United Kingdom) column pre-equilibrated with binding buffer. Washing buffer is then passed through the column until the OD280 value (NanoDrop, Thermo Scientific) is measured to be at or near background levels. The HERV-K (HML-2) Env analog-Fc fusion protein is eluted using a low pH buffer, elution fractions are collected, and the OD280 value of each fraction is recorded. Fractions containing the target HERV-K (HML-2) Env analog-Fc fusion protein are pooled and optionally further filtered using a 0.2 μm membrane filter.

The cell line is optionally further subcloned to monoclonality and is optionally further selected for high titer HERV-K (HML-2) Env analog-Fc-fusion protein-expressing clones using the method of limiting dilution, a method known to those skilled in the art. After obtaining a high titer, monoclonal HERV-K (HML-2) Env analog-Fc fusion protein-expressing cell line, production of the HERV-K (HML-2) Env analog-Fc fusion protein is accomplished as described above in growth medium without MSX, or optionally in growth medium containing MSX, to obtain a cell culture supernatant containing the recombinant, CHO-made, HERV-K (HML-2) Env analog-Fc fusion protein. The MSX concentration is optionally increased over time to exert additional selectivity for clones capable of yielding higher product titers.

Example 6: Purification of a HERV-K (HML-2) Env Analog-Fc Fusion Protein Manufactured in CHO Cells Purification of a HERV-K (HML-2) Env analog-Fc fusion protein was performed as follows. Conditioned media supernatants containing the secreted HERV-K (HML-2) Env analog-Fc fusion protein were harvested from the CHO production runs and were clarified by centrifugation. The supernatant containing the desired HERV-K (HML-2) Env analog-Fc fusion protein was run over a Protein A column, washed and eluted using a low pH gradient. Afterwards, the eluted fractions containing the desired protein were pooled and buffer exchanged into 200 mM HEPES, 100 mM NaCl, 50 mM NaOAc, pH 7.0 buffer. A final filtration step was performed using a 0.2 μm membrane filter. The final protein concentration was calculated from the solution optical density at 280 nm. Capillary Electrophoresis using Sodium Dodecyl Sulfate (CE-SDS) Analysis of the size and purity of the target protein was performed using a LabChip GXII (Perkin Elmer). Further optional purification by ion-exchange chromatography (e.g., using an anion exchange bead resin or a cation exchange bead resin), gel filtration chromatography, or other methods were performed as necessary.

Example 7: HERV-K (HML-2) Env Analog-Fc Fusion Protein Structure Confirmation by Non-Reducing and Reducing SDS-PAGE A HERV-K (HML-2) Env analog-Fc fusion protein sample for analysis was prepared in loading buffer (±reductant; e.g., beta-mercaptoethanol) and denatured at 70° C. for 10 min before being loaded into the NuPAGE™ Gel system (ThermoFisher Scientific). After electrophoresis, the gel was stained with SimplyBlue™ SafeStain. Under non-reducing conditions, the sample was run against known molecular weight (MW) protein standards, and the eluting peak represented the 'apparent' MW of the fusion protein homodimer.

Under reducing conditions (e.g., using beta-mercaptoethanol to break disulfide bonds of the HERV-K (HML-2) Env analog-Fc fusion protein homodimer), the apparent MW of the resulting HERV-K (HML-2) Env analog-Fc fusion protein monomer was compared against half the molecular weight of the HERV-K (HML-2) Env analog-Fc fusion protein homodimer as a way of determining that the structural purity of the HERV-K (HML-2) Env analog-Fc fusion protein was likely to be correct. The results of the fusion protein structure confirmation for SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 47, and SEQ ID NO: 46 are given in Table 2.

TABLE 2

CE-SDS Non-Reducing and Reducing Main Peak for HERV-K (HML-2) Env analog-Fc fusion proteins synthesized in CHO cells

| Sequence | Non-reducing (kDa) Peak 1 | Reducing (kDa) Peak 1 | $\dfrac{MW_{homodimer}}{2 \times MW_{monomer}}$ |
|---|---|---|---|
| SEQ ID NO: 38 | 94.44 | 49.63 | 1.0 |
| SEQ ID NO: 39 | 82.38 | 42.82 | 1.0 |
| SEQ ID NO: 40 | 77.53 | 39.45 | 1.0 |
| SEQ ID NO: 41 | 82.38 | 43.12 | 1.0 |
| SEQ ID NO: 42 | 75.62 | 38.88 | 1.0 |
| SEQ ID NO: 43 | 118.92 | 58.25 | 1.0 |
| SEQ ID NO: 44 | 82.97 | 45.3 | 0.9 |
| SEQ ID NO: 45 | 71.74 | 36.91 | 1.0 |
| SEQ ID NO: 47 | 107.65 | 54.2 | 1.0 |
| SEQ ID NO: 46 | 115.87 | 57.57 | 1.0 |

Example 8: HERV-K (HML-2) Env Analog-Fc Fusion Protein Sequence Identification by LC-MS with Glycan Removal To obtain an accurate estimate of the HERV-K (HML-2) Env analog-Fc fusion protein mass via mass spectroscopy (MS), the sample is first treated to remove naturally occurring glycan that might interfere with the MS analysis. 100 μL of a 2.5 mg/mL HERV-K (HML-2) Env analog-Fc fusion protein dissolved in 200 mM HEPES, 100 mM NaCl, 50 mM NaOAc, pH 7.0 buffer solution is first buffer exchanged into 0.1 M Tris, pH 8.0 buffer containing 5 mM EDTA using a Zeba desalting column (Pierce, ThermoFisher Scientific, Waltham, MA). 1.67 μL of PNGase F enzyme (Prozyme N-glycanase) is added to this solution to remove N-linked glycan present in the fusion protein (e.g., glycan linked to the side chain of the asparagine located at the N glycosylation site on the Fc fragment), and the mixture is incubated at 37° C. overnight in an incubator. The sample is then analyzed via LC-MS (NovaBioassays, Woburn, MA) resulting in a molecular mass of the molecule which corresponds to the desired homodimer without the glycan. This mass is then further corrected since the enzymatic process used to cleave the glycan from the N glycosylation site also deaminates the asparagine side chain to form an aspartic acid, and in doing so the enzymatically treated homodimer gains 2 Da overall, corresponding to a mass of 1 Da for each chain present in the homodimer. Therefore, the actual molecular mass is the measured mass minus 2 Da to correct for each of the enzymatic modifications of the HERV-K (HML-2) Env analog-Fc fusion protein structure in the analytical sample.

Example 9: % Homodimer by Size-Exclusion Chromatography for a HERV-K (HML-2) Env Analog-Fc Fusion Protein Size-exclusion chromatography (SEC-HPLC) of HERV-K (HML-2) Env analog-Fc fusion proteins is carried out using a Waters 2795HT HPLC (Waters Corporation, Milford, MA) connected to a 2998 Photodiode array at a wavelength of 280 nm. 100 μL or less of a sample containing a HERV-K (HML-2) Env analog-Fc fusion protein of interest is injected into a MAbPac SEC-1, 5 μm, 4×300 mm column (ThermoFisher Scientific, Waltham, MA) operating at a flow rate of 0.2 mL/min and with a mobile phase comprising 50 mM sodium phosphate, 300 mM NaCl, and 0.05% w/v sodium azide, pH 6.2. The MAbPac SEC-1 column operates on the principle of molecular size separation. Therefore, larger soluble HERV-K (HML-2) Env analog-Fc aggregates (e.g., multimers of HERV-K (HML-2) Env analog-Fc fusion protein homodimers) elute at earlier retention times, and the non-aggregated homodimers elute at later retention times. In separating the mixture of homodimers from aggregated multimeric homodimers via analytical SEC-HPLC, the purity of the HERV-K (HML-2) Env analog-Fc fusion protein solution in terms of the percentage of non-aggregated homodimer is ascertained.

Example 10: In Vitro Fc (Gamma) and FcRn Receptor Binding Affinity for a HERV-K (HML-2) Env Analog-Fc Fusion Protein The binding of a HERV-K (HML-2) Env analog-Fc fusion protein to Fc (gamma) receptors at pH 7.4 is conducted using an ELISA assay as follows. Human Fc (gamma) receptors I, IIa, IIb, III and the FcRn receptor are used as mammalian receptors. A HERV-K (HML-2) Env analog-Fc fusion protein is diluted to 10 μg/mL in sodium bicarbonate buffer at pH 9.6 and coated on Maxisorp (Nunc) microtiter plates overnight at 4° C., after which the microplate strips are washed 5 times with PBST (PBS/0.05% Tween-20) buffer and blocked with Superblock blocking reagent (ThermoFisher). Serial dilutions of biotinylated rhFc (gamma) receptors (recombinant human Fc(gamma)RI, Fc(gamma) RIIa, Fc(gamma)RIIb, Fc(gamma)RIII, FcRn; R&D Systems) are prepared in PBST/10% Superblock buffer from 6000 ng/mL to 8.2 ng/ml and are loaded at 100 μL/well onto the microplate strips coated with the HERV-K (HML-2) Env analog-Fc fusion protein. The microtiter plate is incubated for 1 hour at room temperature after which the microplate strips are washed 5 times with PBST and then are loaded with 100 μL/well of streptavidin-HRP diluted 1:10000 in PBST/10% Superblock buffer. After incubating for 45 min, the microplate strips are washed again 5 times with PBST. Trimethylbenzidine (TMB) is added to reveal the bound Fc (gamma) or FcRn receptor proteins and is stopped with ELISA stop reagent (Boston Bioproducts). The plate is read in an ELISA plate reader at 450 nm, and the OD values (proportional to the binding of each rhFc (gamma) or FcRn receptor to the HERV-K (HML-2) Env analog-Fc fusion protein) are plotted against log concentrations of each rhFc (gamma) receptor or FcRn receptor added to each well to generate binding curves using GraphPad Prism software.

Examples for General Preclinical Evaluation of the Effectiveness of HERV-K (HML-2) Env Analog-Fc Fusion Proteins in Inducing an Anti-HERV-K (HML-2) Env Titer in Mice Example 11: General Vaccination Protocol of HERV-K (HML-2) Env Analog-Fc Fusion Proteins in Mice Immunization studies to evaluate the effectiveness of different vaccine formulations were performed in 6- to 8-week-old BALB/c mice purchased from Jackson Laboratories that were acclimatized for a week before being assigned into study groups for immunization. The animal studies were carried out with protocols approved by the IACUC committee in a vivarium which has a capacity to hold 3,000 mice in individually ventilated cages. BALB/c mice were randomly assigned to 10 animals per study group, were housed 5 per cage in ventilated housing racks, and were given standard irradiated feed and filtered water ad libitum. Mice were ear tagged individually for identification, the study cages were labeled with animal IDs, study name, and study group identification, and the study records including individual and group immunization sheets, blood/serum collection sheets, weight measurement, and health observation records were maintained per standard operating procedures (SOPs) and specific study protocols.

HERV-K (HML-2) Env analog-Fc fusion proteins were administered at doses ranging from 0.1 μg to 100 μg with and without an adjuvant. This allowed selection of optimal vaccine formulation(s) based on antibody titer responses. For example, if 100 μg dose formulation without an adjuvant gave the same level and quality of antibody response as the 10 μg dose with an adjuvant, this provided an opportunity of producing 10 times more doses of vaccine from the same amount of available HERV-K (HML-2) Env analog-Fc fusion proteins.

All mice were weighed at the beginning of the study and were randomly assigned into study groups. Mice were given three doses of vaccines at 4 weeks apart (Day 0, Day 28 and Day 56) via subcutaneous (s.c.) injection. For s.c. injections, mice were restrained at the neck scruff with the thumb and forefinger such that a tent of skin was formed over the scruff. The needle was inserted parallel to the skin and was directed toward the posterior of the animal. Injections were administered with a 23-gauge needle and injection volumes did not exceed 2 mL. Mice were observed for 1-3 hrs after administration for any immediate reactions and then daily for general health. Blood was obtained from each mouse via submandibular venipuncture 21-28 days prior to the first test article injection and then 21 to 28 days after each injection. Fresh blood was collected in micro-vacutainer tubes and allowed to clot, and then serum was separated by centrifugation and was stored frozen in aliquots for antibody titer analysis via ELISA.

After the last serum collection at 21 to 28 days post the third immunization (i.e., Days 77 to 84), groups of mice that showed substantial antibody responses and the unimmunized control group may be kept for an additional 60-90 days until their antibody levels wane down to baseline/minimum levels, and then given an additional booster injection to evaluate the recall (memory) immune response. This would require up to three additional serum collections at 60 and 90 days after the last serum collection (i.e., Days 144 and 174, respectively), and then at 28 days after the final booster injection. Equal volumes of HERV-K (HML-2) Env analog-Fc fusion protein and adjuvant (50 to 100 μL) would be mixed immediately prior to immunization of 50 to 100 μL injections.

Example 12: Evaluation of Binding Capability of Mice Antisera to the HERV-K (HML-2) Env Protein and the Total Levels of IgG Anti-HERV-K (HML-2) Env Ab Titers in Mice Antisera In this ELISA anti-HERV-K (HML-2) Env IgG antibodies present in mouse serum samples (antisera) taken from mice immunized with a HERV-K (HML-2) Env analog-Fc fusion protein were captured by recombinant HERV-K (HML-2) (Catalog #CBS EP724336HUaO; Cusabio) coated on microtiter plate strip wells (coating buffer: 0.05 M Carb/Bicarb Buffer pH9.6 (#C3041; Sigma)), overnight at 2-8° C. Soluble antibody standards were included in the assay for quantitating an IgG titer. Soluble standards (prepared from diluting anti-HERV-K (HML-2) rabbit anti-human HERV-K (HML-2) (Catalog #CSB PA724336LA01HU; Cusabio) in SDB), assay controls, and study serum samples, diluted at 1:100 or higher in Sample Dilution Buffer (SDB: PBST+ 10% SB, 10% HS, 2 mM EDT, 0.05% Na Azide), were added to the protein coated strip wells for analysis. Plates were incubated for 14-21 hours at 4° C. The next day plates were washed with PBS/tween (PBST) buffer to remove all unbound molecules, and HRP-conjugated Goat anti-mouse IgG Fc (#1013-05; Southern Biotech) was added and incubated for 60 minutes. Following washes with PBST buffer and deionized water, TMB reagent was added and incubated for 25 minutes. The enzyme substrate reaction was then stopped by the addition of Stop Reagent (1% H2SO4) and the color intensity (optical density, OD) was measured in a microplate reader at 450 nm wavelength. For quantitating the antibody titers, a standard curve was created by serial dilutions of anti-HERV-K (HML-2) antibody added to recombinant HERV-K (HML-2) coated wells. Antibody titers in the samples were analyzed by interpolating on the 4-PL standard curve fitting using SoftMax software.

Example 13: ELISA for Measurement of IgG1 and IgG2 Anti-HERV-K (HML-2) Env Ab Titers in Mice Antisera In this ELISA anti-IgG1, IgG2a, IgG2b, or IgG3 antibodies present in mouse serum samples (antisera) were captured by recombinant HERV-K (HML-2) Env (Catalog #CBS-EP724336HUaO; Cusabio) coated on microtiter plate strip wells (coating buffer: 0.05 M Carb/Bicarb Buffer pH9.6 (Catalog #C3041; Sigma)). Recombinant IgG subclass antibodies (Monoclonal Mouse IgG1 Isotype Control (Catalog #NBP1-97005; Novus Biologicals), Mouse IgG2a isotype control antibody (Catalog #NBP1-96778; Novus Biologicals), Mouse G2b isotype control antibody (Catalog #NBP1-96969; Novus Biologicals), Recomb. Mouse IgG3 isotype control antibody (Catalog #MAB007; R&D Systems)) were serially diluted in sample dilution buffer (SBD) (PBST+10% SB, 10% HS, 2 mM EDTA, NaAzide) and were immobilized on 96-well plates for final quantitation of mouse antibody titers. Assay controls made from the same recombinant IgG subclass antibodies were also included to ensure assay reproducibility.

Study serum samples diluted at 1:100 or higher in SDB were added to the antigen coated strip wells for analysis. Plate strips were incubated for 14-21 hours at 4° C. The next day, incubated plates were washed with PBS/tween (PBST) buffer to remove all unbound molecules. Plates coated with antibody standard and controls were assembled and HRP-conjugated anti-mouse IgG1, IgG2a, IgG2b, or IgG3 detection antibody (Goat anti-mouse IgG1 Fc-HRP (Catalog #1073-05; Southern Biotech), goat anti-mouse IgG2a Fc-HRP (Catalog #1083-05; Southern Biotech), goat anti-mouse IgG2b Fc-HRP (Catalog #1093-05; Southern Biotech), goat anti-mouse IgG3 Fc-HRP (Catalog #1100-05; Southern Biotech)) was added to appropriate wells (standards, controls, and serum incubated) and was incubated for 60 minutes. Following washing with PBST buffer and deionized water, TMB reagent was added and incubated for 25 minutes. The enzyme substrate reaction was then stopped by the addition of Stop Reagent (1% H2SO4) and the color intensity (optical density, OD) was measured in a microplate reader at 450 nm wavelength. Antibody titers in the samples were analyzed by interpolating on the 4-PL standard curve fitting using SoftMax software.

Example 14: Epitope Mapping to Analyze Specific HERV-K (HML-2) Env Epitope Recognition Using Mice Antisera A HERV-K (HML-2) Env peptide microarray was pre-stained with the secondary antibody in incubation buffer to investigate background interactions with the antigen-derived peptides that could interfere with the main assays. The microarray content was the sequence of the envelope protein of HERV-K (HML-2) (UniProtKB: Q69384) elongated with neutral GSGSGSG linkers at the C- and N-terminus to avoid truncated peptides. The elongated antigen sequence was converted into linear 15 amino acid peptides with a peptide-peptide overlap of 14 amino acids. The resulting HERV-K (HML-2) Env peptide microarrays contained 699 different peptides printed in duplicate (1,398 spots) and were framed by additional HA (YPYDVPDYAG, 90 spots) control peptides.

Incubation of further HERV-K (HML-2) Env peptide microarrays with the mouse serum (antisera) samples at a dilution of 1:200 in incubation buffer (PBS, pH 7.4 with 0.005% Tween 20+10% Rockland blocking buffer MB-070) for 16 h at 4° C. and orbital shaking at 140 rpm was followed by washing twice in washing buffer (PBS, pH 7.4 with 0.005% Tween 20) for 10 sec. Then, microarrays were stained with the secondary antibody goat anti-mouse IgG (Fc) DyLight680 (0.2 μg/mL) for 45 min in incubation buffer at RT, followed by washing twice in washing buffer (PBS, pH 7.4 with 0.005% Tween 20) for 10 sec. Then, microarrays were read-out with an Innopsys InnoScan 710-IR Microarray Scanner (Innopsys, Carbonne, France) at scanning gains of 50/10 (red/green). The additional HA peptides framing the peptide microarrays were subsequently stained with the control antibody (mouse monoclonal anti-HA (12CA5) DyLight800 (0.2 μg/mL)) for 45 min in incubation buffer at RT, as internal quality control to confirm the assay performance and the peptide microarray integrity.

Quantification of spot intensities and peptide annotation were based on the 16-bit gray scale TIFF files that exhibit a higher dynamic range than the 24-bit colorized TIFF files. Microarray image analysis was done with PepSlide® Analyzer (SICASYS Software GmbH, Heidelberg, Germany) and was summarized in Excel files. A software algorithm broke down fluorescence intensities of each spot into raw, foreground and background signals and calculated averaged median foreground intensities and spot-to-spot deviations of spot duplicates. Based on averaged median foreground intensities, intensity maps were generated and interactions in the peptide maps were highlighted by an intensity color code with red for high and white for low spot intensities. A maximum spot-to-spot deviation of 40% was tolerated, otherwise the corresponding intensity value was zeroed.

Averaged spot intensities of the assays with the mouse serum samples against the microarray content from the N- to the C-terminus of the envelope protein of HERV-K (HML-2) were further plotted to visualize overall spot intensities and signal-to-noise ratios. The intensity plots were correlated with peptide and intensity maps as well as with visual inspection of the microarray scans to identify epitopes of the mouse serum samples.

Example 15: Evaluation of Binding Affinity of
Mice Antisera to the HERV-K (HML-2) Env
Protein by Surface Plasmon Resonance Antisera of mice immunized with vaccine compounds
were analyzed with a Surface Plasmon Resonance assay
(Carterra) to measure their binding affinity to recombinant
HERV-K Env protein. For the experiment a HC30M (Poly-
carboxylate hydrogel, medium charge density, 30 nm coat-
ing thickness) chip was used. Goat Anti-Mouse IgG Fc
UNLB was covalently immobilized at 0.070 mg/ml to
capture the antibodies from the mouse sera. Up to four
dilutions of mice sera (1:100, 1:1000, 1:10000, 1:100000) in
HBSTE+0.5 g/L BSA were applied to the chip in duplicate.
Anti-human Endogenous Retrovirus type K (HERV-K)
envelope protein antibody from Austral Biologicals was
used as a positive control. Six concentrations (1 μM-0.00412
μM) and (0.65 μM-0.0025 μM) of HERV-K Env recombi-
nant protein from Cusabio were injected into the chips.
These were made with 1:3 dilutions to determine binding
kinetics using non-regenerative kinetics. The Kinetics pro-
tocol was:

Capture: 5 minutes
Baseline: 1 minute
Association: 5 minutes
Dissociation: 5 minutes
Data Analysis: Performed using Carterra kinetics soft-
ware The data analysis quantities in Table 3 are defined as
follows. n represents the number of replicates used for the
mean calculations. ka is the on-rate and kd is the off-rate, as
determined from a 1:1 Langmuir binding model to which
direct observations of binding association and dissociation
have been fit. KD is the equilibrium dissociation rate con-
stant (typically referred to as the binding affinity) and is
calculated as KD=kd/ka. Kinetic evaluations were per-
formed by injecting a concentration series of the analyte
(i.e., the HERV-K (HML-2) Env analog-Fc fusion protein)
and Rmax is the assessed saturation point of the association
rate. RU is an acronym corresponding to Response Unit or
Resonance Unit.

source; MBS1391552) (80 nM and 320 nM), as determined
according to Example 3, was preincubated for 1 hour at RT
with: Only culture media, four different dilutions of mice
antisera in culture media: 1:1, 1:10, 1:100, 1:1000, a com-
mercial HERV-K (HML-2) Env antibody (Austral Biologi-
cals, HERM-1811-5; 3 μg/mL) as positive control and a
mouse IgG isotype control (Invitrogen, #31903, 3 μg/mL) as
a negative control. Cellular viability was measured at 96
hours in triplicate using the CellTiter-Glo2® (Promega;
G9241).

Example 17: Generation of Acute Lesions by
Injecting HERV-K (HML-2) Env Protein in the
Motor Cortex Through Stereotaxia Adult mice (3 months or older) previously immunized
with a HERV-K (HML-2) Env analog-Fc fusion protein and
non-immunized mice were stereotaxically injected in the
motor cortex with recombinant HERV-K (HML-2) Env (32
ng or 64 ng), or vehicle and brains were collected for further
immunohistochemistry analysis, according to the following
protocol. Body weights were collected from all mice and
animals' health status was recorded. Recombinant HERV-K
(HML-2) Env protein (Catalog #CBS-EP724336HUaO;
Cusabio) was diluted to a final injection dosage of 32 ng or
64 ng per mouse (2 μL were injected per animal) in vehicle
(TE Buffer (10 mM tris-HCl pH 8.0; 1 mM EDTA (Qiagen
1018499)) with 10% glycerol). Mice were anesthetized
with ketamine (100 mg/kg) and xylazine (10 mg/kg). Using
a stereotaxic apparatus, the left motor cortex was injected
with 2 μL of HERV-K (HML-2) Env in vehicle or only
vehicle at a rate of 0.1 μL/min using a microinjector.
Coordinates: (A-P, anterior-posterior to Bregma; ML,

TABLE 3

| | | | Mean ka (M−1 s−1) | ka Std. Dev. | Mean kd (s−1) | kd Std. Dev. | Mean KD | KD Std. Dev. | Mean Rmax (RU) | Rmax Std. Dev. |
|---|---|---|---|---|---|---|---|---|---|---|
| Sequence | Dilution | n | | | | | | | | |
| SEQ ID NO: 46 | 1:100 | 2 | 1.8e4 | 8.5e0 | 1.0e−5 | 0.0e0 | 5.5e−10 | 2.6e−13 | 280.6 | 35.2 |
| | 1:1000 | 2 | 2.3e4 | 3.4e3 | 1.0e−5 | 0.0e0 | 4.4e−10 | 6.6e−11 | 214.1 | 31.3 |
| | 1:10000 | 2 | 1.5e4 | 3.0e2 | 1.0e−5 | 0.0e0 | 6.7e−10 | 1.4e−11 | 148.9 | 30.5 |
| | 1:100000 | 2 | 2.0e4 | 9.4e2 | 1.0e−5 | 2.9e−7 | 5.3e−10 | 2.9e−11 | 34.9 | 1.9 |

Examples for General Preclinical Evaluation of the
Effectiveness of HERV-K (HML-2) Env Analog-Fc
Fusion Proteins in Neutralizing the Toxic Effect of
HERV-K (HML-2) Env Example 16: In Vitro HERV-K (HML-2) Env
Protein Neutralizing Activity of Mice Antisera iPSC derived motor neuronal lines were thawed and
cultured for seven days. Cells were seeded at 30K cells/well
onto 96-well PDL coated plates. The selected concentration
of HERV-K (HML-2) Env recombinant protein (MyBiomedio-lateral to midline; DV, dorso-ventral, in mm): motor
cortex, left hemisphere, 1.5 mm AP, 1.5 mm ML, 1.3 mm
DV. Mice were euthanized 1 week after the injection. Before
euthanasia, mice were weighed and had terminal bleeding.
Blood was processed to serum or plasma and aliquots were
sent for antibody analysis. Animals were cardiac punctuated,
perfused with PBS and fixed with 4% PFA for 16 hours.
Brains were rinsed with PBS 3 times 1 hour each. Brains
were collected and transferred to a 10% sucrose in PBS
solution for 2 hours. Brains were transferred to a 20%
sucrose in PBS solution and were left overnight. Then,
brains were transferred to a 30% sucrose in PBS solution
stored at 4° C. until further analysis.

Example 18: Assessment of In Vivo Protection Against Acute Lesions Caused by Stereotaxic Injection of HERV-K (HML-2) Env Protein in the Motor Cortex of Mice Vaccinated with a HERV-K (HML-2) Env Analog-Fc Fusion Protein To determine the neuroprotective effect of a vaccine compound against the acute toxic effect of HERV-K (HML-2) Env protein stereotaxically injected in the motor cortex of mice (Coordinates: (A-P, anterior-posterior to Bregma; ML, medio-lateral to midline; DV, dorso-ventral, in mm): motor cortex, right hemisphere, 1.5 mm AP, 1.5 mm ML, 1.3 mm DV, the following procedure was followed.

The mouse brains were examined, hemisected, then the right hemisphere of each brain was treated overnight with 20% glycerol and 2% dimethylsulfoxide to prevent freeze-artifacts. The specimens were embedded, with up to 40 brain hemispheres per block, arranged for coronal sectioning in a gelatin matrix using MultiBrain® Technology (NeuroScience Associates, Knoxville, TN). After curing with a form-aldehyde solution, the blocks were rapidly frozen by immersion in 2-methylbutane chilled with crushed dry ice and mounted on a freezing stage of an AO 860 microtome. The MultiBrain® blocks were sectioned in the coronal plane with a setting on the microtome of 35 μm. All sections were cut through the entire hemisphere of the brain and collected sequentially into a series of 24 cups. All cups contained Antigen Preserve solution (50-parts PBS pH7.0, 50-parts ethylene glycol, 1-part polyvinyl pyrrolidone); no sections were discarded.

Thionine Nissl Stain—A set of every twelfth section (at an interval of 420 microns) was mounted on gelatin coated glass slides, air dried and carried through the following sequence: 95% ethanol, 95% ethanol/Formaldehyde; 95% ethanol, Chloroform/Ether/absolute ethanol (8:1:1), 95% ethanol; 10% HCl/ethanol, 95% ethanol, 70% ethanol, dH$_2$O, Thionine (0.05% Thionine/acetate buffer, pH 4.5), dH$_2$O, 70% ethanol, 95% ethanol, Acetic Acid/ethanol, 95% ethanol, 100% ethanol, 100% ethanol, 1:1 100% ethanol/xylene, xylene, xylene, coverslip.

Immunohistochemistry—For immunohistochemistry (IHC), a set of every twelfth section (an interval of 420 microns) for Iba1, NeuN and Caspase-3, were stained free-floating. All incubation solutions from the primary antibody onward used Tris buffered saline (TBS) with Triton X100 as the vehicle; all rinses were with TBS.

After a hydrogen peroxide treatment and rinses, each set of sections were immunostained with the primary antibodies as shown below, overnight at room temperature. Vehicle solutions contained Triton X100 for permeabilization. Following rinses, a biotinylated secondary antibody (anti IgG of host animal in which the primary antibody was produced) was applied. After further rinses Vector Lab's ABC solution Catalog #PK-6100 (avidin-biotin-HRP complex; details in instruction for VECTASTAIN® Elite ABC, Vector, Burlingame, CA) at a dilution specified in the tables below was applied. The sections were again rinsed, then treated with a chromagen: diaminobenzidine tetrahydrochloride (DAB) and hydrogen peroxide, nickel (II) sulfate to create a visible reaction product. Following further rinses, the sections were mounted on gelatin coated glass slides, then air dried. The mounted Caspase-3 slides were counterstained with Neutral Red counterstain. The Iba1 and NeuN stained slides were dehydrated in alcohols, cleared in xylene and coverslipped.

Iba1 IHC Stain:

| Primary Antibody: | Iba1 IHC | Secondary Antibody: | Anti-Rabbit Biotinylated |
|---|---|---|---|
| Source: | Abcam | Source: | Vector |
| Catalog #: | ab178846 | Catalog #: | BA-1000 |
| Host: | Rabbit | Host: | Goat |
| Dilutions: | 150,000 | Dilution: | 1:1,000 |
| | | VECTASTAIN ® Dilution: | 1:222 |
| | | Chromagen: | Ni(II)-DAB |
| | | Color: | Black |

NeuN IHC Stain:

| Primary Antibody: | NeuN IHC | Secondary Antibody: | Anti-Rabbit Biotinylated |
|---|---|---|---|
| Source: | Abcam | Source: | Vector |
| Catalog #: | ab177487 | Catalog #: | BA-1000 |
| Host: | Rabbit | Host: | Goat |
| Dilutions: | 150,000 | Dilution: | 1:1,000 |
| | | VECTASTAIN ® Dilution: | 1:222 |
| | | Chromagen: | Ni(II)-DAB |
| | | Color: | Black |

Caspase-3 IHC Stain:

| Primary Antibody: | Caspase-3 IHC | Secondary Antibody: | Anti-Rabbit Biotinylated |
|---|---|---|---|
| Source: | Cell Signaling | Source: | Vector |
| Catalog #: | 9661 | Catalog #: | BA-1000 |
| Host: | Rabbit | Host: | Goat |
| Dilutions: | 5,000 | Dilution: | 1:1,000 |
| | | VECTASTAIN ® Dilution: | 1:222 |
| | | Chromagen: | Ni(II)-DAB |
| | | Color: | Black |

Neutral Red Counterstain (N.R.)—The Caspase-3 IHC stained mounted slides were carried through the following sequence: deionized water (dH$_2$O), neutral red solution made in an acetate buffer; pH4.5, dH$_2$O rinses, differentiated in 70% ethanol, 95% ethanol, 100% ethanol, 1:1 100% ethanol/xylene, xylene, then coverslipped with Permount as a bonding medium.

All slides were scanned at 20× resolution (0.137 μm/pixel) using an Evident (formerly Olympus) VS200 scanning system.

The following variables were measured for each one of the markers: Total area stained (μm$^2$), percentage of positive tissue, average optical density and percentage of negative tissue.

Example 19: Assessment of In Vivo Protection Against Acute Lesions Caused by Stereotaxic Injection of HERV-K (HML-2) Env Protein in the Motor Cortex of Mice Vaccinated with a HERV-K (HML-2) Env Analog-Fc Fusion Protein To determine the neuroprotective effect of a vaccine compound against the acute toxic effect of HERV-K (HML-2) Env protein stereotaxically injected in the motor cortex of mice (Coordinates: (A-P, anterior-posterior to Bregma; ML, medio-lateral to midline; DV, dorso-ventral, in mm): motor cortex, right hemisphere, 1.5 mm AP, 1.5 mm ML, 1.3 mm DV, the following procedure is followed.

The mouse brains are examined, hemisected, then the right hemisphere of each brain is treated overnight with 20% glycerol and 2% dimethylsulfoxide to prevent freeze-artifacts. The specimens are embedded, with up to 40 brain hemispheres per block, arranged for coronal sectioning in a gelatin matrix using MultiBrain® Technology (NeuroScience Associates, Knoxville, TN). After curing with a formaldehyde solution, the blocks are rapidly frozen by immersion in 2-methylbutane chilled with crushed dry ice and are mounted on a freezing stage of an AO 860 microtome. The MultiBrain® blocks are sectioned in the coronal plane with a setting on the microtome of 35 µm. All sections are cut through the entire hemisphere of the brain and collected sequentially into a series of 24 cups. All cups contain Antigen Preserve solution (50-parts PBS pH7.0, 50-parts ethylene glycol, 1-part polyvinyl pyrrolidone); no sections are discarded.

Thionine Nissl Stain—A set of every twelfth section (at an interval of 420 microns) is mounted on gelatin coated glass slides, air dried and carried through the following sequence: 95% ethanol, 95% ethanol/Formaldehyde; 95% ethanol, Chloroform/Ether/absolute ethanol (8:1:1), 95% ethanol; 10% HCl/ethanol, 95% ethanol, 70% ethanol, $dH_2O$, Thionine (0.05% Thionine/acetate buffer, pH 4.5), $dH_2O$, 70% ethanol, 95% ethanol, Acetic Acid/ethanol, 95% ethanol, 100% ethanol, 100% ethanol, 1:1 100% ethanol/xylene, xylene, xylene, coverslip.

Immunohistochemistry—For immunohistochemistry (IHC), a set of every twelfth section (an interval of 420 microns) for Iba1, NeuN and Caspase-3 is stained free-floating. All incubation solutions from the primary antibody onward use Tris buffered saline (TBS) with Triton X100 as the vehicle; all rinses are with TBS.

After a hydrogen peroxide treatment and rinses, each set of sections is immunostained with the primary antibodies as shown below, overnight at room temperature. Vehicle solutions contain Triton X100 for permeabilization. Following rinses, a biotinylated secondary antibody (anti IgG of host animal in which the primary antibody is produced) is applied. After further rinses, Vector Lab's ABC solution Catalog #PK-6100 (avidin-biotin-HRP complex; details in instruction for VECTASTAIN® Elite ABC, Vector, Burlingame, CA) at a dilution specified in the tables below is applied. The sections are again rinsed, then treated with a chromagen: diaminobenzidine tetrahydrochloride (DAB) and hydrogen peroxide, nickel (II) sulfate to create a visible reaction product. Following further rinses, the sections are mounted on gelatin coated glass slides, then air dried. The mounted Caspase-3 slides are counterstained with Neutral Red counterstain. The Iba1 and NeuN stained slides are dehydrated in alcohols, cleared in xylene and coverslipped.

Iba1 IHC Stain:

| Primary Antibody: | Iba1 IHC | Secondary Antibody: | Anti-Rabbit Biotinylated |
|---|---|---|---|
| Source: | Abcam | Source: | Vector |
| Catalog #: | ab178846 | Catalog #: | BA-1000 |
| Host: | Rabbit | Host: | Goat |
| Dilutions: | 150,000 | Dilution: | 1:1,000 |
| | | VECTASTAIN ® Dilution: | 1:222 |
| | | Chromagen: | Ni(II)-DAB |
| | | Color: | Black |

NeuN IHC Stain:

| Primary Antibody: | NeuN IHC | Secondary Antibody: | Anti-Rabbit Biotinylated |
|---|---|---|---|
| Source: | Abcam | Source: | Vector |

-continued

| Catalog #: | ab177487 | Catalog #: | BA-1000 |
|---|---|---|---|
| Host: | Rabbit | Host: | Goat |
| Dilutions: | 150,000 | Dilution: | 1:1,000 |
| | | VECTASTAIN ® Dilution: | 1:222 |
| | | Chromagen: | Ni(II)-DAB |
| | | Color: | Black |

Caspase-3 IHC Stain:

| Primary Antibody: | Caspase-3 IHC | Secondary Antibody: | Anti-Rabbit Biotinylated |
|---|---|---|---|
| Source: | Cell Signaling | Source: | Vector |
| Catalog #: | 9661 | Catalog #: | BA-1000 |
| Host: | Rabbit | Host: | Goat |
| Dilutions: | 5,000 | Dilution: | 1:1,000 |
| | | VECTASTAIN ® Dilution: | 1:222 |
| | | Chromagen: | Ni(II)-DAB |
| | | Color: | Black |

Neutral Red Counterstain (N.R.)—The Caspase-3 IHC stained mounted slides are carried through the following sequence: deionized water ($dH_2O$), neutral red solution made in an acetate buffer; pH4.5, $dH_2O$ rinses, differentiated in 70% ethanol, 95% ethanol, 100% ethanol, 1:1 100% ethanol/xylene, xylene, then coverslipped with Permount as a bonding medium.

All slides are scanned at 20× resolution (0.137 µm/pixel) using an Evident (formerly Olympus) VS200 scanning system.

The following variables are measured for each one of the markers: total area stained ($µm^2$), percentage of positive tissue, average optical density and percentage of negative tissue.

Example 20: Assessment of In Vivo Protection in HERV-K (HML-2) Env Transgenic Mice (HEMI) Vaccinated with HERV-K (HML-2) Env Analog-Fc Fusion Proteins The HERV-K Env transgenic mouse developed by Nath's lab is an accurate model of motor neuronal disease. These animals show weight loss, motor-neuronal symptoms, grouping of muscle fibers characteristic of ALS and short life span. Moreover, these animals show signs of TDP-43 proteinopathy in the brain, the hallmark of ALS. The appearance of symptoms starts very early, at around 1.5 months of age thus, vaccination against HERV-K Env to prevent the disease should be done at neonatal age. However, the neonatal immune system in mice and humans is still immature and, compared to the adult one, it is switched towards immune tolerance to prevent autoimmunity. Thus, it is first necessary to test whether the neonatal transgenic mice can mount an appropriate humoral response after vaccination with the compounds.

The suitability of the model is determined by analyzing the evolution of HERV-K Env antibody titers following immunization as measured by ELISA. If an appropriate immune response is confirmed, the animals are followed up to evaluate the protective effect of the vaccine against the appearance of clinical symptoms, neuropathology, and neurodegeneration biomarkers.

Twenty (20) mixed sex hemizygous C57BL/6-Tg (Thy1-env) E337Nath/J (JAX Stock #28326) and twenty (20) mixed sex non-transgenic littermates are generated by IVF.

Mice are enrolled in the study at 1 month-old as described in Table 4 below.

TABLE 4

Study Design

| Group | N | Geno-type | Test Articles | Frequency and Duration | Bleeds |
|---|---|---|---|---|---|
| 1 | 10 | WT | Adjuvant | Starting at 1-month-old: SC injection at D 0, D 21, D 42 and D 105 | Non-terminal bleed before each injection, 2 weeks after the final SC injection (D 119) and at D 150. Terminal bleed at D 180. |
| 2 | 10 | WT | Test article + adjuvant | | |
| 3 | 10 | HEMI | Adjuvant | | |
| 4 | 10 | HEMI | Test article + adjuvant | | |

Groups 2 and 4 of mice receive 4 subcutaneous (SC) injections of the test article at Day 0, at Day 21, at Day 42 and at Day 105 of the study. Groups 1 and 3 receive injections of only adjuvant on the same days. Before each injection and two weeks after the final injection (D119) non-terminal bleeds are collected and processed to serum. Terminal bleeds are conducted at Day 180. Blood is processed to serum for analysis of HERV-K Env antibody titers by ELISA and for Neuron-derived exosome isolation and biomarker analysis. If an appropriate humoral response against HERV-K Env in the vaccinated mice is observed, the animals continue to be followed up to assess neuroprotection of the vaccines.

Body weights, Neuroscore and clinical observations are recorded weekly from 1 to 25 weeks. Motor function tests, such as rotarod, open field and tail suspension are applied at the investigator discretion.

Mice are euthanized by CO2 narcosis at Day 180 after birth and terminal bleeds are collected. Plasma or serum collected from cardiocentesis blood, and 2 skeletal muscles, the brain and spinal cord are collected and are preserved frozen or in fixative for analyses. For mice humanely euthanized before the scheduled necropsy, reasonable effort is made to collect tissues as described but necropsies are not guaranteed.

NDEs are isolated from serum collected from the animals at each time point at Neurodex. Levels of HERV-K nucleic acids and proteins and levels of neurodegenerative proteins (TDP-43, Aβ, α-synuclein, tau and phospho-tau) are measured in the NDEs by qPCR and sensitive immunoassays (ELISA, Luminex and MSD). A statistical comparison of the levels of HERV-K and neurodegenerative proteins is performed between WT and transgenic mice and between vaccinated and unvaccinated mice. The levels are also correlated with the clinical symptoms and other established markers of neurodegeneration such as Nfl and GFAP levels in serum, as measured by Luminex.

Brain and muscle tissue collected from the study mice are analyzed for neuropathological changes by IHC.

Mice brains and spinal cord are stained by IHC for:

HERV-K Env protein, to assess whether the vaccination affects the expression of the antigen.

Neuronal and motor neuronal markers, to assess whether the vaccination rescues from neuronal and motor neuronal death caused by the target protein.

Inflammatory markers, such as Iba1, to assess whether the vaccination rescues from brain inflammation caused by the target protein.

TDP-43, to assess if the vaccination protects against the formation of TDP-43 cytoplasmic aggregates.

Proteins of the TDP-43 pathway, such as UNC13A and stathmin-2, to assess whether the vaccination protects against the loss of TDP-43 functionality.

Sections of the tibialis anterior muscle from the mice are stained for myosin heavy chain, to assess whether the vaccines protect against the fiber grouping in skeletal muscle characteristic of motor neuronal disease.

Examples for General Preclinical Evaluation of the Effectiveness of HERV-K (HML-2) Env Analog-Fc Fusion Proteins in Inducing an Anti-HERV-K (HML-2) Env Titer in Non-Human Primates Example 21: General Vaccination Protocol of HERV-K (HML-2) Env Analog-Fc Fusion Proteins in Cynomolgus Monkeys (*Macaca fascicularis*)

Immunization studies to evaluate the effectiveness of different vaccine formulations were performed in 4 to 6.5 years-old male Cynomolgus monkeys from Cambodia at AltaScience. Animals were acclimatized for a week before being assigned into study groups for immunization. The animal studies were carried out with protocols approved by the IACUC committee. Animals were socially housed (same dosing group together). The primary enclosure complied with the Animal Welfare Act and recommendations set forth in the Guide for the Care and Use of Laboratory Animals (National Research Council 2011). Housing conditions were maintained except when animals were separated for study-specific procedures or as required for monitoring and/or health purposes, as deemed appropriate by Study Director and/or Clinical Veterinarian. Animals were housed in a temperature and humidity-controlled environment. An automatic lighting system was set to provide a 12-hour light/dark cycle, except during designated procedures. PMI LabDiet® Fiber-Plus® Monkey Diet 5049 biscuits were provided at an appropriate daily ration. The diet was routinely analyzed by the manufacturer for contaminants to be within Testing Facility's specifications. Drinking water was provided ad libitum. The water was routinely analyzed for contaminants. Fruits, vegetables, treats, as well as enrichment devices (such as perches, music, movies, floor toys, and/or foraging/hanging devices) were provided throughout the course of the study. Veterinary care was available throughout the course of the study and animals were examined by veterinary staff as warranted by clinical signs or other changes.

Animals were transferred to the study from a Testing Facility stock colony. Animals were acclimated to the laboratory housing conditions over a minimum period of 7 days prior to initiation of dosing. Animals were randomly assigned to groups at study transfer.

Doses were prepared using the HERV-K (HML-2) Env analog-Fc fusion protein to be evaluated. The dose level was 0.090 mg/animal, the dose concentration was 0.3 mg/mL, and the dose volume was 0.3 mL/animal. The dose formulations of the HERV-K (HML-2) Env analog-Fc fusion protein were administered to appropriate animals by subcutaneous injection into the interscapular area once on Days 0, 14, 28, and 56. Formulation was vortexed for 10-20 sec prior to injection.

Experimental observations and measurements listed in the subsequent sections were conducted for all animals

| Procedure Details | |
|---|---|
| Mortality/ moribundity check | At least twice daily (AM and PM) To assess general animal health and wellness (except on the first and last day of the study where it was conducted at least once). |
| Food Evaluation | Visual inspection for overall appetite was conducted concomitantly with the mortality/moribundity checks. |
| Cage side Observations | Once daily, beginning of the second day of acclimation, and 1 hour (±0.5 hour) after dosing on dosing days. Additional cage side observations were conducted as necessary to properly monitor the animal's health condition. |
| Body Weight | Twice during acclimation, including on Day −1, then once weekly thereafter throughout the study, including the day prior to return to colony. |

Blood was collected from an appropriate peripheral vein before each dose on Days 0, 14, 28, and then on Day 70. CSF was collected on Day 0. Blood was processed to serum, for measurement of anti-HERV-K Env antibody titers, and to PBMCs, to conduct ELISpot.

After the completion of in-life procedures on Day 70, animals were transferred to a stock colony.

Example 22: General Vaccination Protocol of HERV-K (HML-2) Env Analog-Fc Fusion Proteins in Cynomolgus Monkeys (*Macaca fascicularis*)

Immunization studies to evaluate the effectiveness of different vaccine formulations are performed in 4 to 6.5 years-old male Cynomolgus monkeys from Cambodia at AltaScience. Animals are acclimatized for a week before being assigned into study groups for immunization. The animal studies are carried out with protocols approved by the IACUC committee. Animals are socially housed (same dosing group together). The primary enclosure complies with the Animal Welfare Act and recommendations set forth in the Guide for the Care and Use of Laboratory Animals (National Research Council 2011). Housing conditions are maintained except when animals are separated for study-specific procedures or as required for monitoring and/or health purposes, as deemed appropriate by Study Director and/or Clinical Veterinarian. Animals are housed in a temperature and humidity-controlled environment. An automatic lighting system is set to provide a 12-hour light/dark cycle, except during designated procedures. PMI LabDiet® Fiber-Plus® Monkey Diet 5049 biscuits are provided at an appropriate daily ration. The diet is routinely analyzed by the manufacturer for contaminants to be within Testing Facility's specifications. Drinking water is provided ad libitum. The water is routinely analyzed for contaminants. Fruits, vegetables, treats, as well as enrichment devices (such as perches, music, movies, floor toys, and/or foraging/hanging devices) are provided throughout the course of the study. Veterinary care is available throughout the course of the study and animals are examined by veterinary staff as warranted by clinical signs or other changes.

Animals are transferred to the study from a Testing Facility stock colony. Animals are acclimated to the laboratory housing conditions over a minimum period of 7 days prior to initiation of dosing. Animals are randomly assigned to groups at study transfer.

Doses are prepared using the HERV-K (HML-2) Env analog-Fc fusion protein to be evaluated. The dose level is 0.090 mg/animal, the dose concentration is 0.3 mg/mL, and the dose volume is 0.3 mL/animal. The dose formulations of the HERV-K (HML-2) Env analog-Fc fusion protein are administered to appropriate animals by subcutaneous injection into the interscapular area once on Days 0, 14, 28, and 56. Formulation is vortexed for 10-20 sec prior to injection.

Experimental observations and measurements listed in the subsequent sections are conducted for all animals

| Procedure Details | |
|---|---|
| Mortality/ moribundity check | At least twice daily (AM and PM) To assess general animal health and wellness (except on the first and last day of the study where it is conducted at least once). |
| Food Evaluation | Visual inspection for overall appetite is conducted concomitantly with the mortality/moribundity checks. |
| Cage side Observations | Once daily, beginning of the second day of acclimation, and 1 hour (±0.5 hour) after dosing on dosing days. Additional cage side observations are conducted as necessary to properly monitor the animal's health condition. |
| Body Weight | Twice during acclimation, including on Day −1, then once weekly thereafter throughout the study, including the day prior to return to colony. |

Blood is collected from an appropriate peripheral vein before each dose on Days 0, 14, 28, and then on Day 70. CSF is collected on Day 0. Blood is processed to serum, for measurement of anti-HERV-K Env antibody titers, and to PBMCs, to conduct ELISpot.

After the completion of in-life procedures on Day 70, animals are transferred to a stock colony.

Example 23: Evaluation of the Total Levels of IgG Anti-HERV-K (HML-2) Env Ab Titers in Cynomolgus Monkeys' Antisera In this ELISA, anti-HERV-K (HML-2) Env IgG antibodies present in serum samples (antisera) taken from monkeys immunized with a HERV-K (HML-2) Env analog-Fc fusion protein were captured by recombinant HERV-K (HML-2) (Catalog #CBS EP724336HUaO; Cusabio) coated on microtiter plate strip wells (coating buffer: 0.05 M Carb/Bicarb Buffer pH9.6 (#C3041; Sigma)), overnight at 2-8° C. Soluble antibody standards were included in the assay for quantitating an IgG titer. Soluble standards (prepared from diluting anti-HERV-K (HML-2) rabbit anti-human HERV-K (HML-2) (Catalog #CSB PA724336LA01HU; Cusabio) in SDB), assay controls, and study serum samples, diluted at 1:100 or higher in Sample Dilution Buffer (SDB: PBST+ 10% SB, 10% HS, 2 mM EDT, 0.05% Na Azide), were added to the protein coated strip wells for analysis. Plates were incubated for 14-21 hours at 4° C. The next day plates were washed with PBS/tween (PBST) buffer to remove all unbound molecules, and Mouse Anti-Monkey IgG-HRP (SB108a; Southern Biotech) was added and incubated for 60 minutes. Following washes with PBST buffer and deionized water, TMB reagent was added and incubated for 25 minutes. The enzyme substrate reaction was then stopped by the addition of Stop Reagent (1% H2SO4) and the color intensity (optical density, OD) was measured in a microplate reader at 450 nm wavelength. For quantitating the antibody titers, a standard curve was created by serial dilutions of anti-HERV-K (HML-2) antibody added to recombinant HERV-K (HML-2) coated wells. Antibody titers in the samples were analyzed by interpolating on the 4-PL standard curve fitting using SoftMax software.

Example 24: Evaluation of the Total Levels of IgG Anti-HERV-K (HML-2) Env Ab Titers in Cynomolgus Monkeys' Antisera In this ELISA, anti-HERV-K (HML-2) Env IgG antibodies present in serum samples (antisera) taken from monkeys immunized with a HERV-K (HML-2) Env analog-Fc fusion protein are captured by recombinant HERV-K (HML-2) (Catalog #CBS EP724336HUaO; Cusabio) coated on microtiter plate strip wells (coating buffer: 0.05 M Carb/Bicarb Buffer pH9.6 (#C3041; Sigma)), overnight at 2-8° C. Soluble antibody standards are included in the assay for quantitating an IgG titer. Soluble standards (prepared from diluting anti-HERV-K (HML-2) rabbit anti-human HERV-K (HML-2) (Catalog #CSB PA724336LA01HU; Cusabio) in SDB), assay controls, and study serum samples, diluted at 1:100 or higher in Sample Dilution Buffer (SDB: PBST+ 10% SB, 10% HS, 2 mM EDT, 0.05% Na Azide), are added to the protein coated strip wells for analysis. Plates are incubated for 14-21 hours at 4° C. The next day plates are washed with PBS/tween (PBST) buffer to remove all unbound molecules, and Mouse Anti-Monkey IgG-HRP (SB108a; Southern Biotech) is added and incubated for 60 minutes. Following washes with PBST buffer and deionized water, TMB reagent is added and incubated for 25 minutes. The enzyme substrate reaction is then stopped by the addition of Stop Reagent (1% H2SO4) and the color intensity (optical density, OD) is measured in a microplate reader at 450 nm wavelength. For quantitating the antibody titers, a standard curve is created by serial dilutions of anti-HERV-K (HML-2) antibody added to recombinant HERV-K (HML-2) coated wells. Antibody titers in the samples are analyzed by interpolating on the 4-PL standard curve fitting using Soft-Max software.

It is expected that anti-HERV-K Env antibody titers measured in serum from animals immunized with the HERV-K (HML-2) Env analog-Fc fusion protein of SEQ ID NO: 47 will increase following each dose.

Example 25: Epitope Mapping to Analyze Specific HERV-K (HML-2) Env Epitope Recognition Using Non-Human Primate Antisera A HERV-K (HML-2) Env peptide microarray is pre-stained with the secondary antibody in incubation buffer to investigate background interactions with the antigen-derived peptides that could interfere with the main assays. The microarray content is the sequence of the envelope protein of HERV-K (HML-2) (UniProtKB: Q69384) elongated with neutral GSGSGSG linkers at the C- and N-terminus to avoid truncated peptides. The elongated antigen sequence is converted into linear 15 amino acid peptides with a peptide-peptide overlap of 14 amino acids. The resulting HERV-K (HML-2) Env peptide microarrays contain 699 different peptides printed in duplicate (1,398 spots) and are framed by additional HA (YPYDVPDYAG, 90 spots) control peptides. Incubation of further HERV-K (HML-2) Env peptide microarrays with the monkey serum (antisera) samples at a dilution of 1:200 in incubation buffer (PBS, pH 7.4 with 0.005% Tween 20+10% Rockland blocking buffer MB-070) for 16 h at 4° C. and orbital shaking at 140 rpm is followed by washing twice in washing buffer (PBS, pH 7.4 with 0.005% Tween 20) for 10 sec. Next, microarrays are stained with the secondary antibody goat anti-monkey IgG (Fc) DyLight680 (0.2 µg/mL) for 45 min in incubation buffer at RT, followed by washing twice in washing buffer (PBS, pH 7.4 with 0.005% Tween 20) for 10 sec. Then, microarrays are read out with an Innopsys InnoScan 710-IR Microarray Scanner (Innopsys, Carbonne, France) at scanning gains of 50/10 (red/green). The additional HA peptides framing the peptide microarrays are subsequently stained with the control antibody (mouse monoclonal anti-HA (12CA5) DyLight800 (0.2 µg/mL)) for 45 min in incubation buffer at RT, as internal quality control to confirm the assay performance and the peptide microarray integrity.

Quantification of spot intensities and peptide annotation are based on the 16-bit gray scale TIFF files that exhibit a higher dynamic range than the 24-bit colorized TIFF files. Microarray image analysis is done with PepSlide® Analyzer (SICASYS Software GmbH, Heidelberg, Germany) and is summarized in Excel files. A software algorithm breaks down fluorescence intensities of each spot into raw, foreground and background signals and calculates averaged median foreground intensities and spot-to-spot deviations of spot duplicates. Based on averaged median foreground intensities, intensity maps are generated and interactions in the peptide maps are highlighted by an intensity color code with red for high and white for low spot intensities. A maximum spot-to-spot deviation of 40% is tolerated, otherwise the corresponding intensity value is zeroed.

Averaged spot intensities of the assays with the monkey serum samples against the microarray content from the N- to the C-terminus of the envelope protein of HERV-K (HML-2) are further plotted to visualize overall spot intensities and signal-to-noise ratios. The intensity plots are correlated with peptide and intensity maps as well as with visual inspection of the microarray scans to identify epitopes of the monkey serum samples.

It is expected that epitope mapping of serum from animals immunized with the HERV-K (HML-2) Env analog-Fc fusion protein of SEQ ID NO: 46 or the HERV-K (HML-2) Env analog-Fc fusion protein of SEQ ID NO: 47 will show recognition of one or more specific HERV-K (HML-2) Env sequences contained in SEQ ID NO: 46 or SEQ ID NO: 47, respectively.

Example 26: ELISpot to Analyze Type of Th Immune Response in Immunized Non-Human Primates ELISpot is a technique related to ELISA that was developed for the detection of secreted proteins, such as cytokines and growth factors. It is also called enzyme-linked immunospot.

ELISpot is performed using a PVDF or nitrocellulose membrane 96-well plate pre-coated with an antibody specific to the secreted protein. Cells are added to the plate, where they attach to the coated membrane. Cells are then stimulated, and the secreted protein binds to the antibody. Next, a detection antibody is added that binds specifically to the bound protein.

The resulting antibody complex is detected either through enzymatic action to produce a colored substrate or with fluorescent tags. An advantage to using fluorescence is the ability to identify more than one secreted protein at a time.

The membrane is analyzed by manually counting the spots or with an automated reader designed for this purpose. Each secreting cell appears as a spot of color or fluorescence; thus this is a quantitative method for evaluating protein secretion.

PVDF membranes are prepared in 96-well plates by incubating in 35% ethanol for 30 seconds and then washing thoroughly with PBS. Any remaining ethanol can affect cell viability, as well as antibody binding. Each 96-well plate is coated with capture antibody (anti-IL4, anti-IL-5 and anti-IFN gamma) diluted in phosphate buffered saline (PBS). Approximately 0.5-1 µg per well of antibody is used for well-defined spots. Kits are optimized with capture concentrations for best performance (100 µL per well). Plates are incubated overnight at 4° C. and then are washed manually with PBS. A plate washer is not used at this stage. One hundred (100) μL of 2% dry skim milk is added per well to block non-specific binding to the membrane. Plates are incubated for 2 h at room temperature and then are washed 3 times in PBS.

Most ELISpot experiments are done with isolated PBMCs (peripheral blood mononuclear cells). Both freshly prepared and cryopreserved cells may be used in the assay. However, frozen cells are left to rest at least 1 hour after thawing to allow the removal of cell debris before addition to the plate. Cells are counted using a viability dye like trypan blue and should be over 95% viable. Cells are diluted to the required concentration and the cell suspension is added to wells. Typically, cell numbers should usually range from between $2\times10^5$ to $4\times10^5$ PBMC cells per well. Serum-free media is used since serum contains many proteins which may affect the results. Cells are cultured overnight at 37° C. in CO2 incubator without shaking the plates. During the overnight incubation, the cells secrete cytokine, which binds to the primary antibody. Cells are stimulated with peptide pools of the target HERV-K Env protein and with PMA/Ionomycin as positive controls to stimulate IL-4 and IL-5 and PHA to stimulate IFN gamma. Cells are washed and the unbound cytokine is washed away by incubating with PBS 0.1% Tween 20 for 10 min. For the detection of antibodies, the secondary conjugated-antibody is diluted in PBS 1% BSA, added to the wells and incubated for 1-2 h at room temperature. Plates are washed 3 times with PBS 0.1% Tween 20 to remove non-specific detection antibody binding. For enzymatic detection, the base is taken off the bottom of the plate to enable thorough washing of the membrane before substrate/chromogen is added. The enzyme substrate (TMB (3,3',5,5'-tetramethylbenzidine) is added to each well and is incubated with gentle agitation on a plate shaker, as directed by the manufacturer. After the base is replaced and the substrate is added, spot formation is carefully monitored. Reaction is stopped by gently washing the plate with PBS 0.1% Tween 20 once development appears to slow. Both sides of the membrane are washed with distilled water to stop the spot formation and membranes are dried at room temperature.

For readout and analysis, the number of spots corresponds to the number of cells that secreted the protein, allowing for quantification of the immune response.

Each plate is read 3 times and results are averaged in order to minimize errors in the measurements.

It is expected that the number of cells secreting IL-4 and IL-5 will be higher than the number of cells secreting IFN gamma, which would be indicative of a Th2 response induced by the vaccine.

EQUIVALENTS

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprise(s)," "comprising," "contain(s)," and "containing" are intended to be open and the use thereof permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

Additional advantages of the various embodiments of the technology will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments but is not necessarily included. Thus, the present invention encompasses a variety of combinations and/or integrations of the specific embodiments described herein.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

SEQUENCE LISTING

```
Sequence total quantity: 47
SEQ ID NO: 1            moltype = AA  length = 226
FEATURE                 Location/Qualifiers
```

```
source                     1..226
                           mol_type = protein
                           organism = Homo sapiens
SEQUENCE: 1
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPG              226

SEQ ID NO: 2                moltype = AA   length = 8
FEATURE                    Location/Qualifiers
source                     1..8
                           mol_type = protein
                           organism = synthetic construct
SEQUENCE: 2
GGGSGGGS                                                         8

SEQ ID NO: 3                moltype = AA   length = 22
FEATURE                    Location/Qualifiers
source                     1..22
                           mol_type = protein
                           organism = synthetic construct
SEQUENCE: 3
GGGGGSGGGG SGGGGSGGGG GS                                         22

SEQ ID NO: 4                moltype = AA   length = 89
FEATURE                    Location/Qualifiers
source                     1..89
                           mol_type = protein
                           organism = synthetic construct
SEQUENCE: 4
MNPSEMQRKA PPRRRRHRNR APLTHKMNKM VTSEEQMKLP STKKAEPPTW AQLKKLTQLA   60
TKYLENTKVT QTPESMLLAA LMIVSMVVS                                  89

SEQ ID NO: 5                moltype = AA   length = 543
FEATURE                    Location/Qualifiers
source                     1..543
                           mol_type = protein
                           organism = synthetic construct
SEQUENCE: 5
LPMPAGAAAA NYTYWAYVPF PPLIRAVTWM DNPIEVYVND SVWVPGPIDD RCPAKPEEEG   60
MMINISIGYR YPPICLGRAP GCLMPAVQNW LVEVPTVSPI SRFTYHMVSG MSLRPRVNYL  120
QDFSYQRSLK FRPKGKPCPK EIPKESKNTE VLVWEECVAN SAVILQNNEF GTIIDWAPRG  180
QFYHNCSGQT QSCPSAQVSP AVDSDLTESL DKHKHKKLQS FYPWEWGEKG ISTPRPKIIS  240
PVSGPEHPEL WRLTVASHHI RIWSGNQTLE TRDRKPFYTV DLNSSLTVPL QSCVKPPYML  300
VVGNIVIKPD SQTITCENCR LLTCIDSTFN WQHRILLVRA REGVWIPVSM DRPWEASPSI  360
HILTEVLKGV LNRSKRFIFT LIAVIMGLIA VTATAAVAGV ALHSSVQSVN FVNDWQKNST  420
RLWNSQSSID QKLANQINDL RQTVIWMGDR LMSLEHRFQL QCDWNTSDFC ITPQIYNESE  480
HHWDMVRRHL QGREDNLTLD ISKLKEQIFE ASKAHLNLVP GTEAIAGVAD GLANLNPVTW  540
VKT                                                             543

SEQ ID NO: 6                moltype = AA   length = 21
FEATURE                    Location/Qualifiers
source                     1..21
                           mol_type = protein
                           organism = synthetic construct
SEQUENCE: 6
IGSTTIINLI LILVCLFCLL L                                          21

SEQ ID NO: 7                moltype = AA   length = 46
FEATURE                    Location/Qualifiers
source                     1..46
                           mol_type = protein
                           organism = synthetic construct
SEQUENCE: 7
VCRCTQQLRR DSDHRERAMM TMAVLSKRKG GNVGKSKRDQ IVTVSV              46

SEQ ID NO: 8                moltype = AA   length = 699
FEATURE                    Location/Qualifiers
source                     1..699
                           mol_type = protein
                           organism = synthetic construct
SEQUENCE: 8
MNPSEMQRKA PPRRRRHRNR APLTHKMNKM VTSEEQMKLP STKKAEPPTW AQLKKLTQLA   60
TKYLENTKVT QTPESMLLAA LMIVSMVVSL PMPAGAAAAA YTYWAYVPFP PLIRAVTWMD  120
NPIEVYVNDS VWVPGPIDDR CPAKPEEEGM MINISIGYRY PPICLGRAPG CLMPAVQNWL  180
VEVPTVSPIS RFTYHMVSGM SLRPRVNYLQ DFSYQRSLKF RPKGKPCPKE IPKESKNTEV  240
LVWEECVANS AVILQNNEFG TIIDWAPRGQ FYHNCSGQTQ SCPSAQVSPA VDSDLTESLD  300
KHKHKKLQSF YPWEWGEKGI STPRPKIISP VSGPEHPELW RLTVASHHIR IWSGNQTLET  360
```

-continued

```
RDRKPFYTVD LNSSLTVPLQ SCVKPPYMLV VGNIVIKPDS QTITCENCRL LTCIDSTFNW   420
QHRILLVRAR EGVWIPVSMD RPWEASPSIH ILTEVLKGVL NRSKRFIFTL IAVIMGLIAV   480
TATAAAVGVA LHSSVQSVNF VNDWQKNSTR LWNSQSSIDQ KLANQINDLR QTVIWMGDRL   540
MSLEHRFQLQ CDWNTSDFCI TPQIYNESEH HWDMVRRHLQ GREDNLTLDI SKLKEQIFEA   600
SKAHLNLVPG TEAIAGVADG LANLNPVTWV KTIGSTTIIN LILILVCLFC LLLVCRCTQQ   660
LRRDSDHRER AMMTMAVLSK RKGGNVGKSK RDQIVTVSV                         699
```

SEQ ID NO: 9                    moltype = AA   length = 698
FEATURE                         Location/Qualifiers
source                          1..698
                                mol_type = protein
                                organism = synthetic construct
SEQUENCE: 9

```
MNPSEMQRKA PPRRRHRNR APLTHKMNKM VTSEEQMKLP STKKAEPPTW AQLKKLTQLA   60
TKYLENTKVT QTPESMLLAA LMIVSMVVSL PMPAGAAAAN YTNWAYVPFP PLIRAVTWMD   120
NPIEVYVNDS VWVPGPIDDR CPAKPEEEGM MINISIGYRY PICLGRAPGC LMPAVQNWLV   180
EVPIVSPICR FTYHMVSGMS LRPRVNYLQD FSYQRSLKFR PKGKPCPKEI PKESKNTEVL   240
VWEECVANSA VILQNNEFGT IIDWTPQGQF YHNCSGQTQS CPSAQVSPAV DSDLTESLDK   300
HKHKKLQSFY PWEWGEKGIS TPRPKIISPV SGPEHPELWR LTVASHHIRI WSGNQTLETR   360
DRKPFYTVDL NSSLTLPLQS CVKPPYMLVV GNIVIKPDSQ TITCENCRLL TCIDSTFNWQ   420
HRILLVRARE GVWIPVSMDR PWEASPSIHI LTEVLKGVLN RSKRFIFTLI AVIMGLIAVT   480
ATAAVGVAL HSSVQSVNFV NDGQKNSTRL WNSQSSIDQ LANQINDLRQ TVIWMGDRLM   540
SLEHRFQLQC DWNTSDFCIT PQIYNESEHH WDMVRRHLQG REDNLTLDIS KLKEQIFEAS   600
KAHLNLVPGT EAIAGVADGL ANLNPVTWVK TIGSTTIINL ILILVCLFCL LLVCRCTQQL   660
RRDSDHRERA MMTMAVLSKR KGGNVGKSKR DQIVTVSV                          698
```

SEQ ID NO: 10                   moltype = AA   length = 699
FEATURE                         Location/Qualifiers
source                          1..699
                                mol_type = protein
                                organism = synthetic construct
SEQUENCE: 10

```
MNPSEMQRKA PPRRRHRNR APLTHKMNKM VTSEEQMKLP STKKAEPPTW AQLKKLTQLA   60
TKYLENTKVT QTPESMLLAA LMIVSMVVSL PMPAGAAAAN YTYWAYVPFP PLIRAVTWMD   120
NPTEVYVNDS VWVPGPIDDR CPAKPEEEGM MINISIGYHY PPICLGRAPG CLMPAVQNWL   180
VEVPTVSPIC RFTYHMVSGM SLRPRVNYLQ DFSYQRSLKF RPKGKPCPKE IPKESKNTEV   240
LVWEECVANS AVILQNNEFG TIIDWAPRGQ FYHNCSGQTQ SCPSAQVSPA VDSDLTESLD   300
KHKHKKLQSF YPWEWGEKGI STPRPKIVSP VSGPEHPELW RLTVASHHIR IWSGNQTLET   360
RDRKPFYTID LNSSLTVPLQ SCVKPPYMLV VGNIVIKPDS QTITCENCRL LTCIDSTFNW   420
QHRILLVRAR EGVWIPVSMD RPWEASPSVH ILTEVLKGVL NRSKRFIFTL IAVIMGLIAV   480
TATAAAVGVA LHSSVQSVNF VNDWQKNSTR LWNSQSSIDQ KLANQINDLR QTVIWMGDRL   540
MSLEHRFQLQ CDWNTSDFCI TPQIYNESEH HWDMVRRHLQ GREDNLTLDI SKLKEQIFEA   600
SKAHLNLVPG TEAIAGVADG LANLNPVTWV KTIGSTTIIN LILILVCLFC LLLVCRCTQQ   660
LRRDSDHRER AMMTMAVLSK RKGGNVGKSK RDQIVTVSV                         699
```

SEQ ID NO: 11                   moltype = AA   length = 699
FEATURE                         Location/Qualifiers
source                          1..699
                                mol_type = protein
                                organism = synthetic construct
SEQUENCE: 11

```
MNPSEMQRKA PPRRRHRNR APLTHKMNKM VTSEEQMKLP STKKAEPPTW AQLKKLTQLA   60
TKYLENTKVT QTPESMLLAA LMIVSMVVSL PMPAGAAVAN YTNWAYVPFP PLIRAVTWMD   120
NPIEVYVNDS VWVPGPIDDR CPAKPEEEGM MINISIGYRY PPICLGRAPG CLMPAVQNWL   180
VEVPTVSPIS RFTYHMVSGM SLRPRVNYLQ DFSYQRSLKF RPKGKPCPKE IPKESKNTEV   240
LVWEECVANS AVILQNNEFG TIIDWAPRGQ FYHNCSGQTQ SCPSAQVSPA VDSDLTESLD   300
KHKHKKLQSF YPWEWGEKRI STPRPKIVSP VSGPEHPELW RLTVASHHIR IWSGNQTLET   360
RDRKPFYTVD LNSSLTLPLQ SCVKPPYMLV VGNIVIKPDS QTITCENCRL LTCIDSTFNW   420
QHRILLVRAR EGVWIPVSMD RPWEASPSVH ILTEVLKGVL NRSKRFIFTL IAVIMGLIAV   480
TATAVAGVA LHSSVQSVNF VNDGQKNSTR LWNSQSSIDQ KLANQINDLR QTVIWMGDRL   540
MSLEHRFQLQ CDWNTSDFCI TPQIYNDSEH HWDMVRRHLQ GREDNLTLDI SKLKEQIFEA   600
SKAHLNLVPG TEAIAGVADG LANLNPVTWV KTIGSTTIIN LILILVCLFC LLLVCRCTQQ   660
LRRDSDHRER AMMTMAVLSK RKGGNVGKSK RDQIVTVSV                         699
```

SEQ ID NO: 12                   moltype = AA   length = 661
FEATURE                         Location/Qualifiers
source                          1..661
                                mol_type = protein
                                organism = synthetic construct
SEQUENCE: 12

```
MNPSEMQRKA PPRRRHRNR APLTHKMNKM VTSEEQMKLP STKKAEPPTW AQLKKLTQLA   60
TKYLENTKVT QTPESMLLAA LMIVSMVVSL PMPAGAAAAN YTYWAYVPFP PLIRAVTWMD   120
NPIEVYVNDS VWVPGPIDDR CPAKPEEEGM MINISIGYRY PPICLGTAPG CLMPAVQNWL   180
VEVPIVSPIS RFTYHMVSGM SLRPRVNYLQ DFSYQRSLKF RPKGKPCPKE IPKESKNTEV   240
LVWEECVANS AVILQNNEFG TIIDWAPRGQ FYHNCSGQTQ SCPSAQVSPA VDSDLTESLD   300
KHKHKKLQSF YPWEWGEKGI STPRPKIVSP VSGPEHPELW RLTVASHHIR IWSGNQTLET   360
RDRKPFYTVD LNSSLTVPLQ SCVKPPYMLV VGNIVIKPDS QTITCENCRL LTCIDSTFNW   420
QHRILLVRAR EGVWIPVSMD RPWEASPSIH ILTEVLKGVL NRSKRFIFTL IAVIMGLIAV   480
TATGAVAGVA LHSSVQSVNF VNDWQKNSTR LWNSQSSIDQ KLANQINDLR QTVIWMGDRL   540
```

-continued

```
MSLEHRFQLQ CDWNTSDFCI TPQIYNESEH HWDMVRRHLQ GREDNLTLDI SKLKEQIFKA    600
SKAHLNLVPG TEAIAGVADG LANLNPVTWV KTIGSTTIIN LILILVCLFC LLLVCRCTQQ    660
L                                                                   661

SEQ ID NO: 13            moltype = AA  length = 698
FEATURE                  Location/Qualifiers
source                   1..698
                         mol_type = protein
                         organism = synthetic construct
SEQUENCE: 13
MHPSEMQRKA PPRRRHRNR APLTHKMNKM VTSEQMKLPS TKKAEPPTWA QLKKLTQLAT    60
KYLENTKVTQ TPESMLLAAL MIVSMVVSLP MPAGAAAANY TNWAYVPFPP LIRAVTWMDN    120
PIEVYVNDSV WVHGPIDDRC PAKPEEEGMM INISIGYHYP PICLGRAPGC LMPAVQNWLV    180
EVPTVSPISR FTYNMVSGMS LRPRVNYLQD FSYQRSLKFR PKGKPCPKEI PKESKNTEVL    240
VWEECVANSV VILQNNEFGT IIDWAPRGQF YHNCSGQTQS CPSAQVSPAV DSDLTESLDK    300
HKHKKLQSFY PWEWGEKGIS TPRPKIISPV SGPEHPELWR LTVASHHIRI WSGNQTLETR    360
DRKPFYTVDL NSSLTVPLQS CVKPPYMLVV GNIVIKPDSQ TITCENCRLL TCIDSTFNWQ    420
HRILLVRARE GVWIPVSMDR PWEASPSIHI LTEVLKGVLN RSKRFIFTLI AVIMGLIAVT    480
AMAAVAGVAL HSFVQSVNFV NDWQKNSTRL WNSQSSIDQK LANQINDLRQ TVIWMGDRLM    540
SLEHRFQLQC DWNTSDFCIT PQIYNESEHH WDMVRRHLQG REDNLTLDIS KLKEQIFEAS    600
KAHLNLVPGT EAIAGVADGL ANLNPVTWVK TIGSTTIINL ILILVCLFCL LLVCRCTQQL    660
RRDSDHRERA MMTMVVLSKR KGGNVGKSKR DQIVTVSV                            698

SEQ ID NO: 14            moltype = AA  length = 699
FEATURE                  Location/Qualifiers
source                   1..699
                         mol_type = protein
                         organism = synthetic construct
SEQUENCE: 14
MNPSEMQRKA PPRRRHRNR APLTHKMNKM VTSEEQMKLP STKKAEPPTW AQLKKLTQLA    60
TKYLENTKVT QTPESMLLAA LMIVSMVVSL PMPAGAAAAN YTYWAYVPFP PLIRAVTWMD    120
NPIEIYVNDS VWVPGPTDDC CPAKPEEEGM MINISIGYRY PPICLGRAPG CLMPAVQNWL    180
VEVPTVSPIS RFTYHMVSGM SLRPRVNYLQ DFSYQRSLKF RPKGKPCPKE IPKESKNTEV    240
LVWEECVANS AVILQNNEFG TLIDWAPRGQ FYHNCSGQTQ SCPSAQVSPA VDSDLTESLD    300
KHKHKKLQSF YPWEWGEKGI STARPKIISP VSGPEHPELW RLTVASHHIR IWSGNQTLET    360
RDRKPFYTID LNSSLTVPLQ SCVKPPYMLV VGNIVIKPDS QTITCENCRL LTCIDSTFNW    420
QHRILLVRAR EGVWIPVSMD RPWEASPSVH ILTEVLKGVL NRSKRFIFTL IAVIMGLIAV    480
TATAAVAGVA LHSSVQSVNF VNDWQNNSTR LWNSQSSIDQ KLANQINDLR QTVIWMGDRL    540
MSLEHRFQLQ CDWNTSDFCI TPQIYNESEH HWDMVRCHLQ GREDNLTLDI SKLKEQIFEA    600
SKAHLNLVPG TEAIAGVADG LANLNTVTWV KTIGSTTIIN LILILVCLFC LLLVYRCTQQ    660
LRRDSDHRER AMMTMVVLSK RKGGNVGKSK RDQIVTVSV                           699

SEQ ID NO: 15            moltype = AA  length = 699
FEATURE                  Location/Qualifiers
source                   1..699
                         mol_type = protein
                         organism = synthetic construct
SEQUENCE: 15
MNPSEMQRKA PPRRRHRNR APLTHKMNKM VTSEEQMKLP STKKAEPPTW AQLKKLTQLA    60
TKYLENTKVT QTPESMLLAA LMIVSMVVSL PMPAGAAAAN YTYWAYVPFP PLIRAVTWMD    120
NPIEVYVNDS VWVPGPTDDH CPAKPEEEGM MINISIGYRY PPICLGRAPG CLMPAVQNWL    180
VEVPTVSPIS RFTYHMVSGM SLRPRVNYLQ DFSYQRSFKF RPKGKPCPKE IPKESKNTEV    240
LVWEECVANS AVILQNNEFG TIIDWAPRGQ FYHNCSGQTQ SCPSAQVSPA VDSDLTESLD    300
KHKHKKLQSF YPWEWGEKGI STPRPKIISP VSGPEHPELW RLTVASHHIR IWSGNQTLET    360
RDRKPFYTVD LNSSVTVPLQ SCIKPPYMLV VGNIVIKPDS QTITCENCRL LTCIDSTFNW    420
QHRILLVRAR EGVWIPVSMD RPWETSPSIH TLTEVLKGVL NRSKRFIFTL IAVIMGLIAV    480
TATAAVAGVA LHSSVQSVNF VNDWQKNSTR LWNSQSSIDQ KLANQINDLR QTVIWMGDRL    540
MSLEHRFQLQ CDWNTSDFSI TPQIYNESEH HWDMVRRHLQ GREDNLTLDI SKLKEQIFEA    600
SKAHLNLVPG TEAIAGVADG LANLNPVTWV KTIGSTTIIN LILILVCLFC LLLVCRCTQQ    660
LRRDSDHRER AMMTMAVLSK RKGGNVGKSK RDQIVTVSV                           699

SEQ ID NO: 16            moltype = AA  length = 560
FEATURE                  Location/Qualifiers
source                   1..560
                         mol_type = protein
                         organism = synthetic construct
SEQUENCE: 16
MVTPVTWMDN PIEVYVNDSV WVPGPTDDRC PAKPEEEGMM INISIGYHYP PICLGRAPGC    60
LMPAVQNWLV EVPTVSPNSR FTYHMVSGMS LRPRVNCLQD FSYQRSLKFR PKGKTCPKEI    120
PKGSKNTEVL VWEECVANSV VILQNNEFGT IIDWAPRGQF YHNCSGQTQS CPSAQVSPAV    180
DSDLTESLDK HKHKKLQSFY LWEWEEKGIS TPRPKIISPV SGPEHPELWR LTVASHHIRI    240
WSGNQTLETR YRKPFYTIDL NSILTVPLQS CVKPPYMLVV GNIVIKPASQ TITCENCRLF    300
TCIDSTFNWQ HRILLVRARE GMWIPVSTDR PWEASPSIHI LTEILKGVLN RSKRFIFTLI    360
AVIMGLIAVT ATAAVAGVAL HSSVQSVNFV NYWQKNSTRL WNSQSSIDQK LASQINDLRQ    420
TVIWMGDRLM TLEHHFQLQC DWNTSDFCIT PQIYNESEHH WDMVRRHLQG REDNLTLDIS    480
KLKEQIFEAS KAHLNLVPGT EAIAGVADGL ANLNPVTWIK TIRSTMIINL ILIVVCLFCL    540
LLVCRCTQQL RRDSDIENGP                                               560

SEQ ID NO: 17            moltype = AA  length = 15
```

-continued

```
FEATURE              Location/Qualifiers
source               1..15
                     mol_type = protein
                     organism = synthetic construct
SEQUENCE: 17
SLDKHKHKKL QSFYP                                                        15

SEQ ID NO: 18        moltype = AA  length = 63
FEATURE              Location/Qualifiers
source               1..63
                     mol_type = protein
                     organism = synthetic construct
SEQUENCE: 18
EQMKLPSTKK AEPPTWAQLK KLTQLATKYL ENTKVTQTPE SMLLAALMIV SMVVSLPMPA    60
GAA                                                                    63

SEQ ID NO: 19        moltype = AA  length = 19
FEATURE              Location/Qualifiers
source               1..19
                     mol_type = protein
                     organism = synthetic construct
SEQUENCE: 19
WAYVPFPPLI RAVTWMDNP                                                    19

SEQ ID NO: 20        moltype = AA  length = 22
FEATURE              Location/Qualifiers
source               1..22
                     mol_type = protein
                     organism = synthetic construct
SEQUENCE: 20
MVSGMSLRPR VNYLQDFSYQ RS                                                22

SEQ ID NO: 21        moltype = AA  length = 18
FEATURE              Location/Qualifiers
source               1..18
                     mol_type = protein
                     organism = synthetic construct
SEQUENCE: 21
CPAKPEEEGM MINISIGY                                                     18

SEQ ID NO: 22        moltype = AA  length = 19
FEATURE              Location/Qualifiers
source               1..19
                     mol_type = protein
                     organism = synthetic construct
SEQUENCE: 22
VWVPGPTDDR CPAKPEEG                                                     19

SEQ ID NO: 23        moltype = AA  length = 17
FEATURE              Location/Qualifiers
source               1..17
                     mol_type = protein
                     organism = synthetic construct
SEQUENCE: 23
APGCLMPAVQ NWLVEVP                                                      17

SEQ ID NO: 24        moltype = AA  length = 50
FEATURE              Location/Qualifiers
source               1..50
                     mol_type = protein
                     organism = synthetic construct
SEQUENCE: 24
GQFYHNCSGQ TQSCPSAQVS PAVDSDLTES LDKHKHKKLQ SFYPWEWGEK                 50

SEQ ID NO: 25        moltype = AA  length = 40
FEATURE              Location/Qualifiers
source               1..40
                     mol_type = protein
                     organism = synthetic construct
SEQUENCE: 25
SPVSGPEHPE LWRLTVASHH IRIWSGNQTL ETRDRKPFYT                            40

SEQ ID NO: 26        moltype = AA  length = 21
FEATURE              Location/Qualifiers
source               1..21
                     mol_type = protein
                     organism = synthetic construct
SEQUENCE: 26
EQMKLPSTKK AEPPTWAQLK K                                                 21
```

-continued

```
SEQ ID NO: 27              moltype = AA   length = 16
FEATURE                    Location/Qualifiers
source                     1..16
                           mol_type = protein
                           organism = synthetic construct
SEQUENCE: 27
TQLATKYLEN TKVTQT                                                        16

SEQ ID NO: 28              moltype = AA   length = 7
FEATURE                    Location/Qualifiers
source                     1..7
                           mol_type = protein
                           organism = synthetic construct
SEQUENCE: 28
PMPAGAA                                                                  7

SEQ ID NO: 29              moltype = AA   length = 11
FEATURE                    Location/Qualifiers
source                     1..11
                           mol_type = protein
                           organism = synthetic construct
SEQUENCE: 29
LIRAVTWMDN P                                                             11

SEQ ID NO: 30              moltype = AA   length = 16
FEATURE                    Location/Qualifiers
source                     1..16
                           mol_type = protein
                           organism = synthetic construct
SEQUENCE: 30
LRPRVNYLQD FSYQRS                                                        16

SEQ ID NO: 31              moltype = AA   length = 10
FEATURE                    Location/Qualifiers
source                     1..10
                           mol_type = protein
                           organism = synthetic construct
SEQUENCE: 31
CPAKPEEEGM                                                               10

SEQ ID NO: 32              moltype = AA   length = 12
FEATURE                    Location/Qualifiers
source                     1..12
                           mol_type = protein
                           organism = synthetic construct
SEQUENCE: 32
DDRCPAKPEE EG                                                            12

SEQ ID NO: 33              moltype = AA   length = 6
FEATURE                    Location/Qualifiers
source                     1..6
                           mol_type = protein
                           organism = synthetic construct
SEQUENCE: 33
SFYPWE                                                                   6

SEQ ID NO: 34              moltype = AA   length = 10
FEATURE                    Location/Qualifiers
source                     1..10
                           mol_type = protein
                           organism = synthetic construct
SEQUENCE: 34
SPVSGPEHPE                                                               10

SEQ ID NO: 35              moltype = AA   length = 20
FEATURE                    Location/Qualifiers
source                     1..20
                           mol_type = protein
                           organism = synthetic construct
SEQUENCE: 35
IRIWSGNQTL ETRDRKPFYT                                                    20

SEQ ID NO: 36              moltype = AA   length = 6
FEATURE                    Location/Qualifiers
source                     1..6
                           mol_type = protein
                           organism = synthetic construct
SEQUENCE: 36
```

```
DRKPFY                                                              6

SEQ ID NO: 37          moltype = AA   length = 8
FEATURE                Location/Qualifiers
source                 1..8
                       mol_type = protein
                       organism = synthetic construct
SEQUENCE: 37
SHHIRIWS                                                            8

SEQ ID NO: 38          moltype = AA   length = 311
FEATURE                Location/Qualifiers
source                 1..311
                       mol_type = protein
                       organism = synthetic construct
SEQUENCE: 38
EQMKLPSTKK AEPPTWAQLK KLTQLATKYL ENTKVTQTPE SMLLAALMIV SMVVSLPMPA   60
GAAGGGGGSG GGGSGGGGSG GGGGSDKTHT CPPCPAPELL GGPSVFLFPP KPKDTLMISR   120
TPEVTCVVVD VSHEDPEVKF NWYVDGVEVH NAKTKPREEQ YNSTYRVVSV LTVLHQDWLN   180
GKEYKCKVSN KALPAPIEKT ISKAKGQPRE PQVYTLPPSR DELTKNQVSL TCLVKGFYPS   240
DIAVEWESNG QPENNYKTTP PVLDSDGSFF LYSKLTVDKS RWQQGNVFSC SVMHEALHNH   300
YTQKSLSLSP G                                                        311

SEQ ID NO: 39          moltype = AA   length = 267
FEATURE                Location/Qualifiers
source                 1..267
                       mol_type = protein
                       organism = synthetic construct
SEQUENCE: 39
WAYVPFPPLI RAVTWMDNPG GGGGSGGGGS GGGGSGGGGG SDKTHTCPPC PAPELLGGPS   60
VFLFPPKPKD TLMISRTPEV TCVVVDVSHE DPEVKFNWYV DGVEVHNAKT KPREEQYNST   120
YRVVSVLTVL HQDWLNGKEY KCKVSNKALP APIEKTISKA KGQPREPQVY TLPPSRDELT   180
KNQVSLTCLV KGFYPSDIAV EWESNGQPEN NYKTTPPVLD SDGSFFLYSK LTVDKSRWQQ   240
GNVFSCSVMH EALHNHYTQK SLSLSPG                                       267

SEQ ID NO: 40          moltype = AA   length = 253
FEATURE                Location/Qualifiers
source                 1..253
                       mol_type = protein
                       organism = synthetic construct
SEQUENCE: 40
WAYVPFPPLI RAVTWMDNPG GGSGGGSDKT HTCPPCPAPE LLGGPSVFLF PPKPKDTLMI   60
SRTPEVTCVV VDVSHEDPEV KFNWYVDGVE VHNAKTKPRE EQYNSTYRVV SVLTVLHQDW   120
LNGKEYKCKV SNKALPAPIE KTISKAKGQP REPQVYTLPP SRDELTKNQV SLTCLVKGFY   180
PSDIAVEWES NGQPENNYKT TPPVLDSDG FFLYSKLTVD KSRWQQGNVF SCSVMHEALH   240
NHYTQKSLSL SPG                                                      253

SEQ ID NO: 41          moltype = AA   length = 270
FEATURE                Location/Qualifiers
source                 1..270
                       mol_type = protein
                       organism = synthetic construct
SEQUENCE: 41
MVSGMSLRPR VNYLQDFSYQ RSGGGGGSGG GGSGGGGSGG GGGSDKTHTC PPCPAPELLG   60
GPSVFLFPPK PKDTLMISRT PEVTCVVVDV SHEDPEVKFN WYVDGVEVHN AKTKPREEQY   120
NSTYRVVSVL TVLHQDWLNG KEYKCKVSNK ALPAPIEKTI SKAKGQPREP QVYTLPPSRD   180
ELTKNQVSLT CLVKGFYPSD IAVEWESNGQ PENNYKTTPP VLDSDGSFFL YSKLTVDKSR   240
WQQGNVFSCS VMHEALHNHY TQKSLSLSPG                                    270

SEQ ID NO: 42          moltype = AA   length = 256
FEATURE                Location/Qualifiers
source                 1..256
                       mol_type = protein
                       organism = synthetic construct
SEQUENCE: 42
MVSGMSLRPR VNYLQDFSYQ RSGGGSGGGS DKTHTCPPCP APELLGGPSV FLFPPKPKDT   60
LMISRTPEVT CVVVDVSHED PEVKFNWYVD GVEVHNAKTK PREEQYNSTY RVVSVLTVLH   120
QDWLNGKEYK CKVSNKALPA PIEKTISKAK GQPREPQVYT LPPSRDELTK NQVSLTCLVK   180
GFYPSDIAVE WESNGQPENN YKTTPPVLDS DGSFFLYSKL TVDKSRWQQG NVFSCSVMHE   240
ALHNHYTQKS LSLSPG                                                   256

SEQ ID NO: 43          moltype = AA   length = 252
FEATURE                Location/Qualifiers
source                 1..252
                       mol_type = protein
                       organism = synthetic construct
SEQUENCE: 43
CPAKPEEEGM MINISIGYGG GSGGGSDKTH TCPPCPAPEL LGGPSVFLFP PKPKDTLMIS   60
RTPEVTCVVV DVSHEDPEVK FNWYVDGVEV HNAKTKPREE QYNSTYRVVS VLTVLHQDWL   120
```

-continued

```
NGKEYKCKVS NKALPAPIEK TISKAKGQPR EPQVYTLPPS RDELTKNQVS LTCLVKGFYP    180
SDIAVEWESN GQPENNYKTT PPVLDSDGSF FLYSKLTVDK SRWQQGNVFS CSVMHEALHN    240
HYTQKSLSLS PG                                                        252

SEQ ID NO: 44            moltype = AA  length = 253
FEATURE                  Location/Qualifiers
source                   1..253
                         mol_type = protein
                         organism = synthetic construct
SEQUENCE: 44
VWVPGPTDDR CPAKPEEEGG GGSGGGSDKT HTCPPCPAPE LLGGPSVFLF PPKPKDTLMI    60
SRTPEVTCVV VDVSHEDPEV KFNWYVDGVE VHNAKTKPRE EQYNSTYRVV SVLTVLHQDW    120
LNGKEYKCKV SNKALPAPIE KTISKAKGQP REPQVYTLPP SRDELTKNQV SLTCLVKGFY    180
PSDIAVEWES NGQPENNYKT TPPVLDSDGS FFLYSKLTVD KSRWQQGNVF SCSVMHEALH    240
NHYTQKSLSL SPG                                                       253

SEQ ID NO: 45            moltype = AA  length = 251
FEATURE                  Location/Qualifiers
source                   1..251
                         mol_type = protein
                         organism = synthetic construct
SEQUENCE: 45
APGCLMPAVQ NWLVEVPGGG SGGGSDKTHT CPPCPAPELL GGPSVFLFPP KPKDTLMISR    60
TPEVTCVVVD VSHEDPEVKF NWYVDGVEVH NAKTKPREEQ YNSTYRVVSV LTVLHQDWLN    120
GKEYKCKVSN KALPAPIEKT ISKAKGQPRE PQVYTLPPSR DELTKNQVSL TCLVKGFYPS    180
DIAVEWESNG QPENNYKTTP PVLDSDGSFF LYSKLTVDKS RWQQGNVFSC SVMHEALHNH    240
YTQKSLSLSP G                                                         251

SEQ ID NO: 46            moltype = AA  length = 284
FEATURE                  Location/Qualifiers
source                   1..284
                         mol_type = protein
                         organism = synthetic construct
SEQUENCE: 46
GQFYHNCSGQ TQSCPSAQVS PAVDSDLTES LDKHKHKKLQ SFYPWEWGEK GGGSGGGSDK    60
THTCPPCPAP ELLGGPSVFL FPPKPKDTLM ISRTPEVTCV VVDVSHEDPE VKFNWYVDGV    120
EVHNAKTKPR EEQYNSTYRV VSVLTVLHQD WLNGKEYKCK VSNKALPAPI EKTISKAKGQ    180
PREPQVYTLP PSRDELTKNQ VSLTCLVKGF YPSDIAVEWE SNGQPENNYK TTPPVLDSDG    240
SFFLYSKLTV DKSRWQQGNV FSCSVMHEAL HNHYTQKSLS LSPG                     284

SEQ ID NO: 47            moltype = AA  length = 274
FEATURE                  Location/Qualifiers
source                   1..274
                         mol_type = protein
                         organism = synthetic construct
SEQUENCE: 47
SPVSGPEHPE LWRLTVASHH IRIWSGNQTL ETRDRKPFYT GGGSGGGSDK THTCPPCPAP    60
ELLGGPSVFL FPPKPKDTLM ISRTPEVTCV VVDVSHEDPE VKFNWYVDGV EVHNAKTKPR    120
EEQYNSTYRV VSVLTVLHQD WLNGKEYKCK VSNKALPAPI EKTISKAKGQ PREPQVYTLP    180
PSRDELTKNQ VSLTCLVKGF YPSDIAVEWE SNGQPENNYK TTPPVLDSDG SFFLYSKLTV    240
DKSRWQQGNV FSCSVMHEAL HNHYTQKSLS LSPG                                274
```

We claim:

1. A fusion protein comprising a human endogenous retrovirus K (HERV-K) subgroup human endogenous mouse mammary tumor virus-like type 2 (HML-2) envelope protein (Env) analog ("HERV-K (HML-2) Env analog") and an Fc fragment, wherein the HERV-K (HML-2) Env analog and the Fc fragment are connected by a peptide linker, wherein the HERV-K (HML-2) Env analog consists of the following sequence:

```
                                    (SEQ ID NO: 24)
GQFYHNCSGQTQSCPSAQVSPAVDSDLTESLDKHKHKKLQSFYPWEWGE

K.
```

2. The fusion protein of claim 1, wherein the Fc fragment comprises the following sequence:

```
                                    (SEQ ID NO: 1)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE
```

-continued

```
YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPG.
```

3. The fusion protein of claim 1, wherein the linker comprises the following sequence:

```
                                    (SEQ ID NO: 2)
GGGSGGGS.
```

4. The fusion protein of claim 1, wherein the fusion protein comprises the following sequence:

```
                                    (SEQ ID NO: 46)
GQFYHNCSGQTQSCPSAQVSPAVDSDLTESLDKHKHKKLQSFYPWEWGE

KGGGSGGGSDKTHTCPPCPAPELLGGPSVFLFPPKPKDTLMISRTPEVT
```

-continued

CVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLY

SKLTVDKSRWQQGNVFSCSVMHEALHNHYTQKSLSLSPG.

5. The fusion protein of claim 1, wherein the Fc fragment is glycosylated.

6. An immunogenic composition comprising the fusion protein of claim 1 and a pharmaceutically acceptable carrier.

7. The immunogenic composition of claim 6, further comprising an adjuvant.

8. A method for increasing antibody production in a subject against an antigenic agent comprising a HERV-K (HML-2) Env analog, the method comprising administering a therapeutically effective amount of the fusion protein of claim 1 to said subject.

9. The method of claim 8, wherein the subject is antibody naïve to the antigenic agent prior to administration of the fusion protein.

10. The method of claim 8, wherein the subject has a measurable antibody titer against said antigenic agent prior to administration of the fusion protein.

11. The method of claim 8, wherein the fusion protein is administered via injection.

12. The method of claim 8, wherein the fusion protein is administered subcutaneously or intramuscularly.

13. The method of claim 8, wherein the fusion protein is co-administered with an adjuvant.

14. A method of producing the fusion protein of claim 1, said method comprising transiently transfecting a nucleic acid encoding for the fusion protein into a Chinese hamster ovary (CHO) cell expression system, wherein the transfected CHO cell expression system expresses the fusion protein, and wherein the yield of the purified or isolated fusion protein from the transfected CHO cell expression system is greater than 50 mg/L.

15. An isolated cell engineered to express the fusion protein of claim 1.

16. A cDNA encoding the fusion protein of claim 1.

17. A fusion protein comprising a human endogenous retrovirus K (HERV-K) subgroup human endogenous mouse mammary tumor virus-like type 2 (HML-2) envelope protein (Env) analog ("HERV-K (HML-2) Env analog") and an Fc fragment, wherein the HERV-K (HML-2) Env analog and the Fc fragment are connected by a peptide linker, wherein the HERV-K (HML-2) Env analog consists of the following sequence:

(SEQ ID NO: 25)
SPVSGPEHPELWRLTVASHHIRIWSGNQTLETRDRKPFYT.

18. The fusion protein of claim 17, wherein the Fc fragment comprises the following sequence:

(SEQ ID NO: 1)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPG.

19. The fusion protein of claim 17, wherein the fusion protein comprises the following sequence:

(SEQ ID NO: 47)
SPVSGPEHPELWRLTVASHHIRIWSGNQTLETRDRKPFYTGGGSGGGSD

KTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRW

QQGNVFSCSVMHEALHNHYTQKSLSLSPG.

20. A fusion protein consisting of the sequence of SEQ ID NO: 46 or SEQ ID NO:47 or pharmaceutical composition thereof.

* * * * *